United States Patent
Wagner et al.

(10) Patent No.: US 8,686,022 B2
(45) Date of Patent: Apr. 1, 2014

(54) 7-(PIPERAZINE-1-YMETHYL)-1H-INDOLE-2-CARBOXYLIC ACID (PHENYL)-AMIDE DERIVATIVES AND ALLIED COMPOUNDS AS P38 MAP KINASE INHIBITORS FOR THE TREATMENT OF RESPIRATORY DISEASES

(75) Inventors: Holger Wagner, Mettenberg (DE); Birgit Jung, Laupheim (DE); Frank Himmelsbach, Mittelbiberach (DE); Rolf Goeggel, Ulm (DE); Georg Dahmann, Attenweiler (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 319 days.

(21) Appl. No.: 13/060,504

(22) PCT Filed: Aug. 26, 2009

(86) PCT No.: PCT/EP2009/061025
§ 371 (c)(1), (2), (4) Date: Apr. 6, 2011

(87) PCT Pub. No.: WO2010/026096
PCT Pub. Date: Mar. 11, 2010

(65) Prior Publication Data
US 2011/0269737 A1    Nov. 3, 2011

(30) Foreign Application Priority Data
Sep. 2, 2008 (EP) .................................. 08163526

(51) Int. Cl.
*A61K 31/40* (2006.01)
*A61K 31/405* (2006.01)

(52) U.S. Cl.
USPC ............................ 514/414; 514/415; 548/468

(58) Field of Classification Search
None
See application file for complete search history.

(56) References Cited

U.S. PATENT DOCUMENTS

2012/0108572 A1    5/2012   Wagner et al.

FOREIGN PATENT DOCUMENTS

| CA | 2557302 A1 | 9/2005 |
| WO | 0147897 A1 | 7/2001 |
| WO | 2005085202 A1 | 9/2005 |
| WO | 2006026235 A1 | 3/2006 |
| WO | 2008057775 A2 | 5/2008 |
| WO | 2010026095 A1 | 3/2010 |
| WO | 2010026096 A1 | 3/2010 |

OTHER PUBLICATIONS

Coulthard. Trends in Molecular Medicine, 2009, 15(8), 369-79.*
International Search Report and Written Opinion or PCT/EP2009/061025 mailed Oct. 28, 2009.
U.S. Appl. No. 13/060,504, filed Feb. 24, 2011, Inventor: Holger Wagner.
U.S. Appl. No. 13/060,761, filed Feb. 25, 2011, Inventor: Holger Wagner.

* cited by examiner

*Primary Examiner* — Noble Jarrell
(74) *Attorney, Agent, or Firm* — Michael P. Morris; Anthony P. Bottino

(57) ABSTRACT

The present invention provides compounds according to general formula (I)

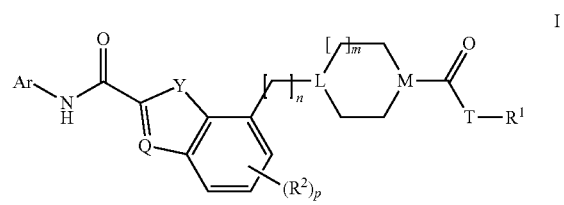

which are proposed for the treatment of respiratory complaints, particularly asthma and COPD.

27 Claims, No Drawings

7-(PIPERAZINE-1-YMETHYL)-1H-INDOLE-2-CARBOXYLIC ACID (PHENYL)-AMIDE DERIVATIVES AND ALLIED COMPOUNDS AS P38 MAP KINASE INHIBITORS FOR THE TREATMENT OF RESPIRATORY DISEASES

The present invention relates to new substituted heteroarylcarboxamide derivatives of general formula

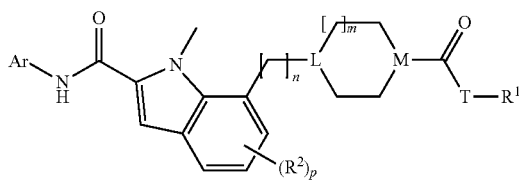

wherein the groups Ar, L, M, T, m, n, p, $R^1$, and $R^2$ are as hereinafter defined, including the tautomers, the stereoisomers, the mixtures and the salts thereof. This invention further relates to medicaments containing a compound of formula I according to the invention and the use of a compound according to the invention for preparing a medicament for the treatment of respiratory complaints. This invention further relates to processes for preparing a medicament.

In the literature, compounds that have an inhibitory effect on the enzyme p38 mitogen-activated protein (MAP) kinase (also p38 MAP-kinase or p38-Kinase) are proposed, inter alia, for the treatment of respiratory complaints, particularly COPD and asthma (cf. P. J. Barnes, *Journal of Allergy and Clinical Immunology* 2007, 119 (5), 1055-1062 and M. F. Fitzgerald, J. C. Fox, *Drug Discovery Today* 2007, 12 (11/12), 479-486, and the literature cited therein).

Substituted heteroarylcarboxamides and the preparation thereof and their possible activity as p38 MAP-kinase inhibitors are known from published International Applications WO 2003/087085; WO 2005/016918; WO 2005/108387 and WO 2006/026235.

AIM OF THE INVENTION

The aim of the present invention is to disclose new substituted heteroarylcarboxamides, particularly those that have an effect on the enzyme p38 MAP-kinase. A further aim of the present invention is to indicate substituted heteroarylcarboxamides that have an inhibitory effect on the enzyme p38 MAP-kinase, in vitro and/or in vivo, and have suitable pharmacological and/or pharmacokinetic and/or physicochemical properties, in order to be able to use them as medicaments.

A further aim of the present invention is to provide new pharmaceutical compositions which are suitable for the prevention and/or treatment of respiratory complaints, particularly COPD and asthma.

Other objectives of the present invention will be apparent to the skilled man directly from the foregoing remarks and those that follow.

SUBJECT-MATTER OF THE INVENTION

In a first aspect the present invention relates to heteroarylcarboxamides of general formula I

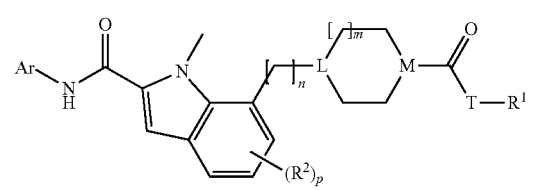

wherein
Ar denotes a substituent of formula (II), (III) or (IV)

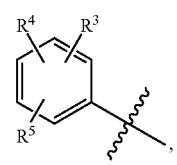

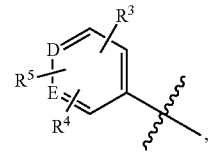

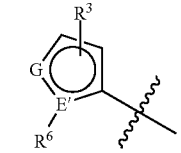

wherein $R^3$ denotes $C_{1-6}$-alkyl, $C_{3-6}$-cycloalkyl, $C_{1-4}$-alkoxy, $C_{1-2}$-perfluoroalkyl, 3-methyl-oxetan-3-yl, $C_{1-2}$-perfluoroalkoxy, morpholinyl, wherein the cycloalkyl group may optionally be substituted by $C_{1-3}$-alkyl, wherein $R^4$ denotes H, $C_{1-4}$-alkyl, $C_{1-4}$-alkoxy, wherein $R^5$ denotes H, $C_{1-5}$-alkyl-sulphonyl-amino, $C_{3-6}$-cycloalkyl-sulphonyl-amino, ($C_{1-5}$-alkyl-sulphonyl)-(methyl)-amino, ($C_{3-6}$-cycloalkyl-sulphonyl)-(methyl)-amino, $C_{1-5}$-alkyl-carbonyl-amino, $C_{3-6}$-cycloalkyl-carbonyl-amino, ($C_{1-5}$-alkyl-carbonyl)-(methyl)-amino, ($C_{3-6}$-cycloalkyl-carbonyl)-(methyl)-amino, aminocarbonyl, $C_{1-5}$-alkyl-amino-carbonyl, $C_{3-6}$-cycloalkyl-amino-carbonyl, di-($C_{1-3}$-alkyl)-amino-carbonyl, di-($C_{1-3}$-alkyl)-amino-$C_{1-2}$-alkyl, di-($C_{1-3}$-alkyl)-amino-pyrrolidin-1-yl-$C_{1-2}$-alkyl, 4-$C_{1-5}$-alkyl-piperazin-1-yl-$C_{1-2}$-alkyl, 4-di-($C_{1-3}$-alkyl)-amino-piperidin-1-yl-$C_{1-2}$-alkyl, 3-di-($C_{1-3}$-alkyl)-amino-piperidin-1-yl-$C_{1-2}$-alkyl, $C_{1-5}$-alkyl-sulphinyl, $C_{3-6}$-cycloalkyl-sulphinyl, $C_{1-5}$-alkyl-sulphonyl, $C_{3-6}$-cycloalkyl-sulphonyl, hydroxy-$C_{1-2}$-alkyl, $C_{1-5}$-alkyl-sulphinyl-methyl, $C_{1-5}$-alkyl-sulphonyl-methyl, wherein $R^6$ denotes $C_{1-3}$-alkyl or phenyl,
wherein the $C_{1-3}$-alkyl group may optionally be substituted by hydroxy
or
di-($C_{1-3}$-alkyl)-amino and
the phenyl group may optionally be substituted by fluorine or $C_{1-3}$-alkyl.
wherein D or E represents nitrogen,
wherein G and E' independently of one another represent nitrogen or oxygen,
wherein $R^6$ is only bound to E' if E' denotes nitrogen,
$R^1$ denotes a $C_{4-6}$-cycloalkyl system, which contains 1 to 2 nitrogen atoms that may optionally be 1- to 2-substituted by $R^7$,
wherein $R^7$ may be $C_{1-3}$-alkyl, hydroxy, $C_{1-3}$-alkoxy, amino, $C_{1-3}$-alkyl-amino, di-($C_{1-3}$-alkyl)-amino.
$R^2$ denotes hydrogen, halogen or $C_{1-4}$-alkyl,
L denotes —C(H)< or —N<,
M denotes —C(H)< or —N<,
T denotes a bond or $C_{1-4}$-alkylene,
while the $C_{1-4}$-alkylene group may be substituted by $C_{1-2}$-alkyl,
m denotes 0, 1, 2 or 3,
n denotes 1, 2 or 3,
p denotes 0, 1, 2 or 3,
while, unless stated otherwise, the above-mentioned alkyl groups may be straight-chain or branched,
the tautomers, the stereoisomers, the mixtures and the salts thereof, particularly the physiologically acceptable salts thereof.

In a preferred embodiment the present invention relates to compounds of general formula (I),
wherein
Ar is a substituent according to general formula (II')

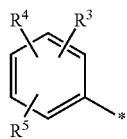

(II')

wherein $R^3$ denotes —$C_1$-$C_6$-alkyl, —$C_3$-$C_6$-cycloalkyl, —$CF_3$, —$CF_2CF_3$ or

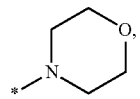

while the —$C_3$-$C_6$-cycloalkyl group may be substituted by —$C_1$-$C_3$-alkyl,
wherein $R^4$ denotes —H, —$C_1$-$C_4$-alkyl or —O—$C_1$-$C_4$-alkyl,
wherein $R^5$ is selected from
—NH—S(O)$_2$—$C_1$-$C_4$-alkyl;
—NH—S(O)$_2$—$C_3$-$C_5$-cycloalkyl;
—N(CH$_3$)—S(O)$_2$—$C_1$-$C_4$-alkyl;
—N(CH$_3$)—S(O)$_2$—$C_3$-$C_5$-cycloalkyl;
—NH—C(O)—$C_1$-$C_4$-alkyl;
—NH—C(O)—$C_3$-$C_5$-cycloalkyl;
—N(CH$_3$)—C(O)—$C_1$-$C_4$-alkyl;
—N(CH$_3$)—C(O)—$C_3$-$C_5$-cycloalkyl;
—C(O)—NH$_2$;
—C(O)—NH—$C_1$-$C_4$-alkyl;
—C(O)—N(di-$C_1$-$C_4$-alkyl);
—C(O)—NH—$C_3$-$C_5$-cycloalkyl;
—C(O)—N($C_1$-$C_4$-alkyl)($C_3$-$C_5$-cycloalkyl);
—S(O)—$C_1$-$C_4$-alkyl;
—S(O)—$C_3$-$C_5$-cycloalkyl;
—S(O)$_2$—$C_1$-$C_4$-alkyl;
—S(O)$_2$—$C_3$-$C_5$-cycloalkyl;
—$C_1$-$C_4$-alkyl-OH
—CH$_2$—S(O)—$C_1$-$C_4$-alkyl;
—CH$_2$—S(O)—$C_3$-$C_5$-cycloalkyl;
—CH$_2$—S(O)$_2$—$C_1$-$C_4$-alkyl;
—CH$_2$—S(O)$_2$—$C_3$-$C_5$-cycloalkyl;
—$C_1$-$C_4$-alkylene-N($R^8$,$R^{8'}$);
wherein $R^1$ denotes —$C_4$-$C_6$-cycloalkyl, which contains 1 to 2 nitrogen atoms in the ring,
wherein $R^1$ is optionally substituted by a group selected from —$C_1$-$C_4$-alkyl,
—OH, —O—$C_1$-$C_4$-alkyl, and —N($R^9$,$R^{9'}$),
wherein $R^2$ is selected from —H, -halogen and $C_1$-$C_4$-alkyl,
wherein in each case $R^8$, $R^{8'}$, $R^9$ and $R^{9'}$ independently of one another are selected from —H and —$C_1$-$C_5$-alkyl,
wherein the two groups $R^8$ and $R^{8'}$ together with the nitrogen to which they are bound, may form a 4- to 6-membered ring system, which may be substituted by —OH or —N($R^{10}$, $R^{10'}$),
wherein in each case $R^{10}$ and $R^{10'}$ independently of one another are selected from —H and —$C_1$-$C_5$-alkyl,
wherein L and M independently of one another are selected from —CH< and —N<,
wherein T is selected from a bond and —$C_1$-$C_3$-alkylene,
while the $C_{1-3}$-alkylene group may be substituted by methyl,
wherein m may be 0-3,
wherein n may be 1-3,
wherein p may be 0-3,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I),
wherein
Ar is a substituent according to general formula (II")

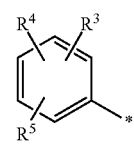

(II")

wherein $R^3$ is selected from —CH$_3$, —C$_2$H$_5$, -n-C$_3$H$_7$, -i-C$_3$H$_7$, —C(CH$_3$)$_3$, -n-C$_4$H$_9$, —CH$_2$-i-C$_3$H$_7$, —CH(CH$_3$)(C$_2$H$_5$), -n-C$_5$H$_{11}$, —CH$_2$—CH$_2$-i-C$_3$H$_7$, —CH$_2$—C(CH$_3$)$_3$, —CF$_3$, —CF$_2$CF$_3$ or

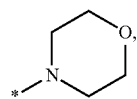

wherein R⁴ is selected from H, —O—CH₃, —O—C₂H₅,
wherein R⁵ is selected from H, —NH—S(O)₂—CH₃, —NH—S(O)₂—C₂H₅, —NH—S(O)₂-n-C₃H₇, —NH—S(O)₂-i-C₃H₇, NH—S(O)₂-c-C₃H₅, —NH—S(O)₂-n-C₄H₉, —NH—S(O)₂—CH₂-i-C₃H₇, —NH—S(O)₂—C(CH₃)₃, —NH—S(O)₂-c-C₄H₇, —NH—S(O)₂-n-C₅H₁₁, —NH—S(O)₂—(CH₂)₂-i-C₃H₇, —NH—S(O)₂—CH₂—C(CH₃)₃, —NH—S(O)₂-c-C₅H₉, —NH—C(O)—CH₃, —NH—C(O)—C₂H₅, —NH—C(O)-n-C₃H₇, —NH—C(O)-i-C₃H₇, —NH—C(O)-c-C₃H₅, —NH—C(O)-n-C₄H₉, —NH—C(O)—CH₂-i-C₃H₇, —NH—C(O)—C(CH₃)₃, —NH—C(O)-c-C₄H₇, —NH—C(O)-n-C₅H₁₁, —NH—C(O)—(CH₂)₂-i-C₃H₇, —NH—C(O)—CH₂—C(CH₃)₃, —NH—C(O)-c-C₅H₉, —C(O)—NH₂, —C(O)—NH—CH₃, —C(O)—N(CH₃)₂, —C(O)—NH—C₂H₅, —C(O)—N(C₂H₅)₂, —C(O)—NH-n-C₃H₇, —C(O)—N(C₃H₇)₂, —C(O)—NH-i-C₃H₇, —C(O)—N(i-C₃H₇)₂, —C(O)—NH-c-C₃H₅, —C(O)—NH-n-C₄H₉, —C(O)—N(n-C₄H₉)₂, —C(O)—NH—CH₂-i-C₃H₇, —C(O)—N(CH₂-i-C₃H₇)₂, —C(O)—NH-c-C₄H₇, —CH₂—N(CH₃)₂, —CH₂—N(C₂H₅)₂, —CH₂—N(n-C₃H₇)₂, —CH₂—N(i-C₃H₇)₂, —CH₂—N(n-C₄H₉)₂, —CH₂—N(CH₂-i-C₃H₇)₂,

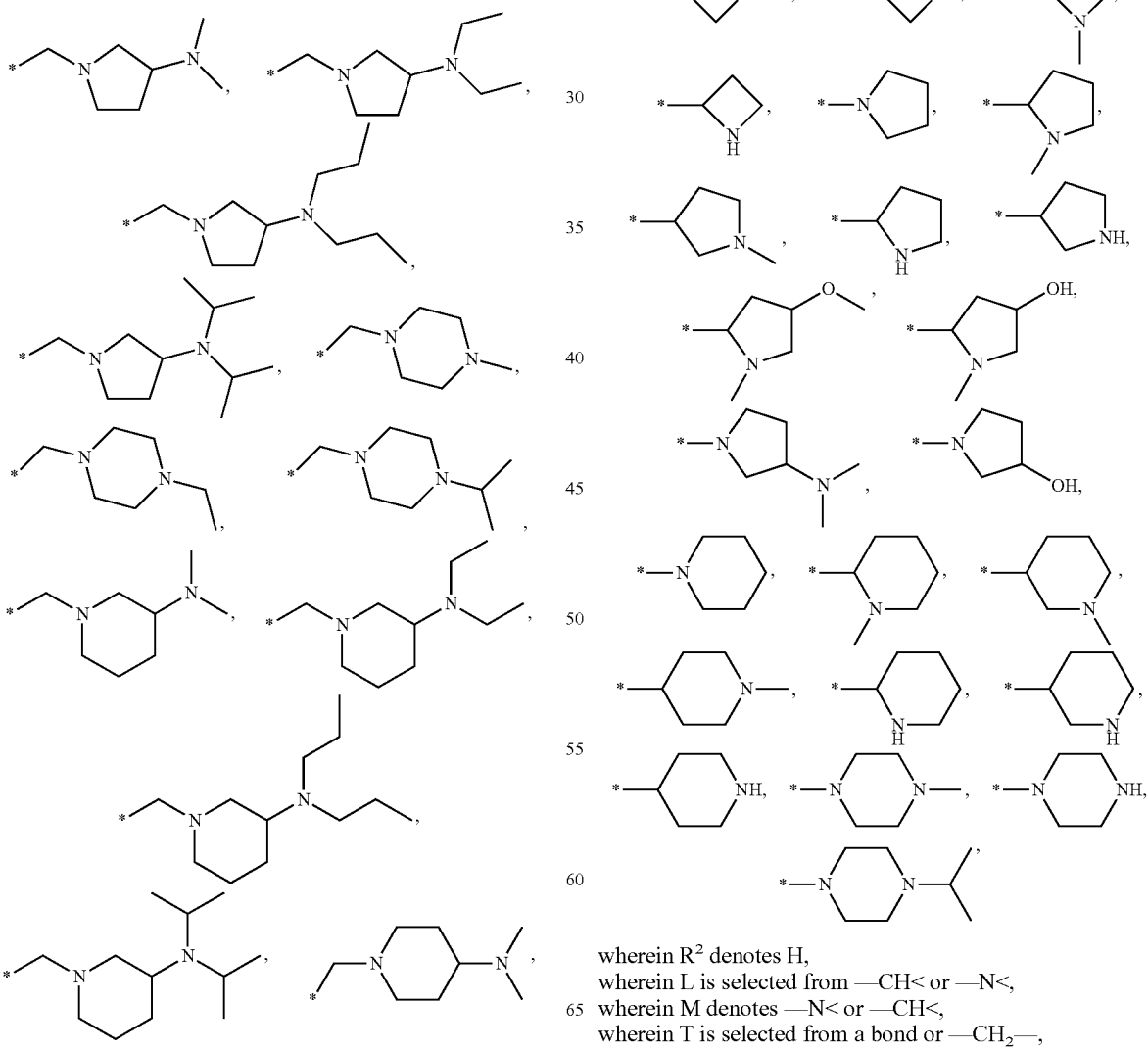

—S(O)—CH₃, —S(O)₂—CH₃, —S(O)—C₂H₅, —S(O)₂—C₂H₅, —CH₂—OH, —CH₂—S(O)—CH₃, —CH₂—S(O)₂—CH₃, —CH₂—S(O)—C₂H₅ or —CH₂—S(O)₂—C₂H₅, wherein R¹ is selected from

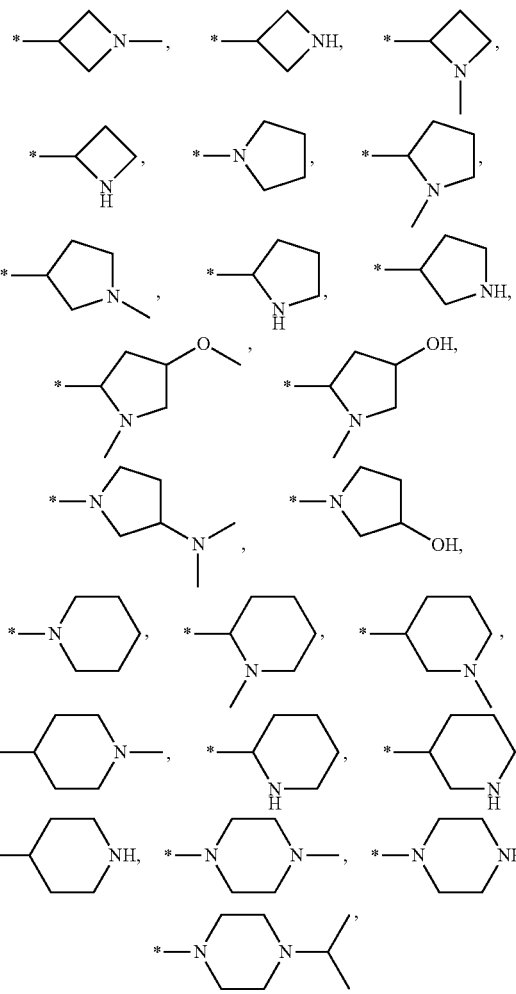

wherein R² denotes H,
wherein L is selected from —CH< or —N<,
wherein M denotes —N< or —CH<,
wherein T is selected from a bond or —CH₂—,
    while the —CH₂— group may be substituted by methyl, wherein m may be 1 or 2
wherein n may be 1 or 2,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I),
wherein
Ar is a substituent according to general formula (II''')

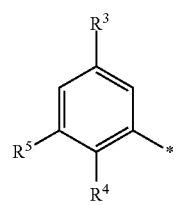

(II''')

wherein R³ denotes —C(CH₃)₃, —CH(CH₃)(C₂H₅), -i-C₃H₇, —CH₂-i-C₃H₇, —CF₃ or —CF₂CF₃,
wherein R⁴ denotes —O—CH₃ or —O—C₂H₅,
wherein R⁵ is selected from —NH—S(O)₂—CH₃, —NH—S(O)₂-n-C₃H₇, —NH—S(O)₂-c-C₃H₅, —NH—C(O)—CH₃, —NH—C(O)—C₂H₅, —NH—C(O)-n-C₃H₇, —NH—C(O)-i-C₃H₇, —NH—C(O)-c-C₃H₅, —C(O)—NH₂, —C(O)—NH—CH₃, —C(O)—NH—C₂H₅, —C(O)—NH-i-C₃H₇, —C(O)—NH-c-C₃H₅, —C(O)—N(CH₃)₂, —CH₂—N(CH₃)₂, —CH₂—N(C₂H₅)₂, —CH₂—N(i-C₃H₇)₂,

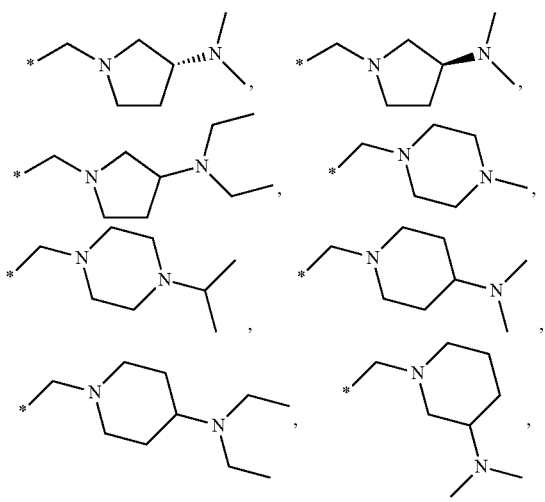

—S(O)—CH₃, —S(O)₂—CH₃, —CH₂—OH, —CH₂—S(O)—CH₃ or —CH₂—S(O)₂—CH₃,
wherein R¹ is selected from,

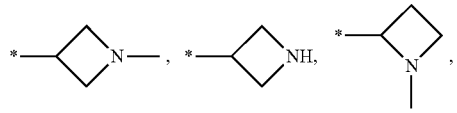

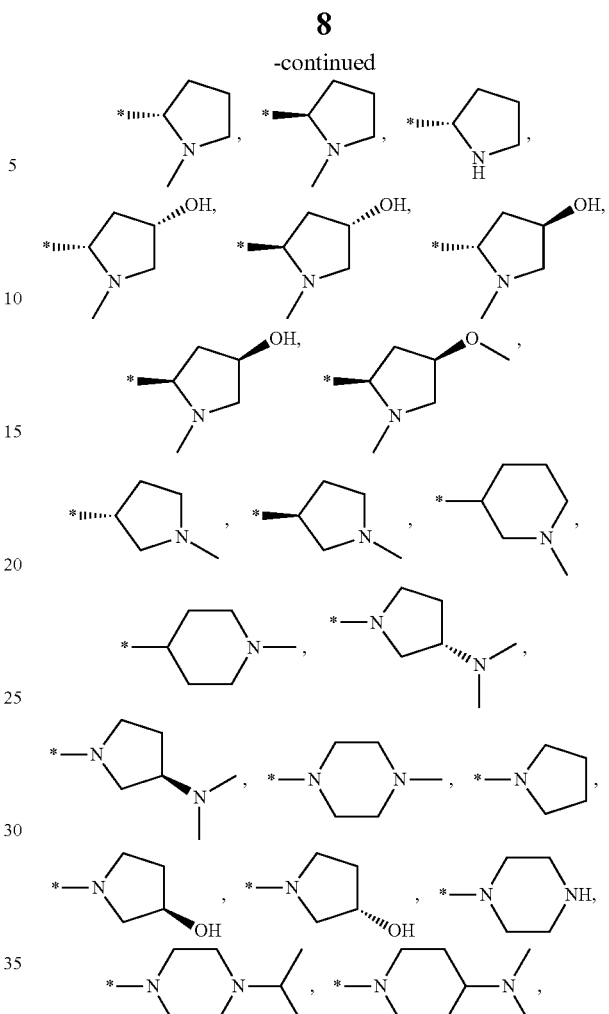

wherein R² denotes —H,
wherein L is selected from —CH< and —N<,
wherein M denotes —N<,
wherein T denotes a bond,
wherein m denotes 1,
wherein n denotes 1,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
Ar is a substituent according to one of general formulae (IIa), (IIIa) or (IVa),

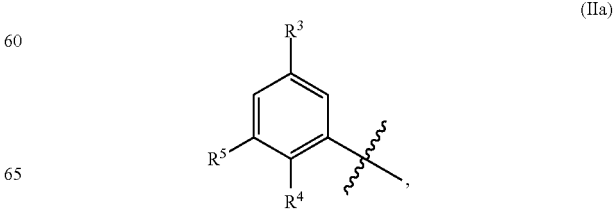

(IIa)

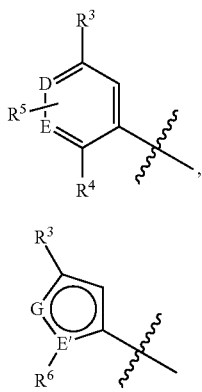

wherein R³ denotes C₁₋₆-alkyl, C₃₋₆-cycloalkyl, C₁₋₄-alkoxy, C₁₋₂-perfluoroalkyl, 3-methyl-oxetan-3-yl, C₁₋₂-perfluoroalkoxy, morpholinyl,
 wherein the cycloalkyl group may optionally be substituted by C₁₋₃-alkyl,
wherein R⁴ denotes H, C₁₋₄-alkyl, C₁₋₄-alkoxy,
wherein R⁵ denotes H, C₁₋₅-alkyl-sulphonyl-amino, C₃₋₆-cycloalkyl-sulphonyl-amino, (C₁₋₅-alkyl-sulphonyl)-(methyl)-amino, (C₃₋₆-cycloalkyl-sulphonyl)-(methyl)-amino, C₁₋₅-alkyl-carbonyl-amino, C₃₋₆-cycloalkyl-carbonyl-amino, (C₁₋₅-alkyl-carbonyl)-(methyl)-amino, (C₃₋₆-cycloalkyl-carbonyl)-(methyl)-amino, aminocarbonyl, C₁₋₅-alkyl-amino-carbonyl, C₃₋₆-cycloalkyl-amino-carbonyl, di-(C₁₋₃-alkyl)-amino-carbonyl, di-(C₁₋₃-alkyl)-amino-C₁₋₂-alkyl, di-(C₁₋₃-alkyl)-amino-pyrrolidin-1-yl-C₁₋₂-alkyl, 4-C₁₋₅-alkyl-piperazin-1-yl-C₁₋₂-alkyl, 4-di-(C₁₋₃-alkyl)-amino-piperidin-1-yl-C₁₋₂-alkyl, 3-di-(C₁₋₃-alkyl)-amino-piperidin-1-yl-C₁₋₂-alkyl, C₁₋₅-alkyl-sulphinyl, C₃₋₆-cycloalkyl-sulphinyl, C₁₋₅-alkyl-sulphonyl, C₃₋₆-cycloalkyl-sulphonyl, hydroxy-C₁₋₂-alkyl, C₁₋₅-alkyl-sulphinyl-methyl, C₁₋₅-alkyl-sulphonyl-methyl,
wherein R⁶ denotes C₁₋₃-alkyl or phenyl,
 while the C₁₋₃-alkyl group may optionally be substituted by hydroxy or di-(C₁₋₃-alkyl)-amino and
 the phenyl group may optionally be substituted by fluorine or C₁₋₃-alkyl,
wherein D or E represents nitrogen,
wherein G and E' independently of one another represent nitrogen or oxygen,
wherein R⁶ is only bound to E' if E' denotes nitrogen,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein Ar denotes a substituent of formula (IIa) or (IIIa),

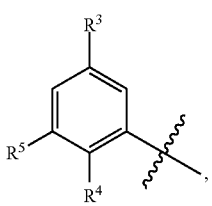

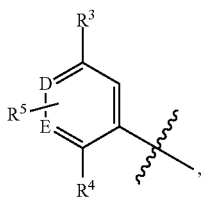

wherein R³ denotes methyl, ethyl, n-propyl, i-propyl, n-butyl, i-butyl, sec.-butyl, tert-butyl, n-pentyl, i-pentyl, neopentyl, 1-methyl-cyclopropyl, methoxy, trifluoromethyl, pentafluoroethyl, 3-methyl-oxetan-3-yl, trifluoromethoxy, morpholin-4-yl,
wherein R⁴ denotes H, methyl, ethyl, n-propyl, methoxy, ethoxy, n-propyloxy, i-propyloxy,
wherein R⁵ denotes H, methyl-sulphonyl-amino, ethyl-sulphonyl-amino, n-propyl-sulphonyl-amino, i-propyl-sulphonyl-amino, n-butyl-sulphonyl-amino, i-butyl-sulphonyl-amino, sec-butyl-sulphonyl-amino, tert.-butyl-sulphonyl-amino, n-pentyl-sulphonyl-amino, i-pentyl-sulphonyl-amino, neo-pentyl-sulphonyl-amino, cyclopropyl-sulphonyl-amino, cyclobutyl-sulphonyl-amino, cyclopentyl-sulphonyl-amino, acetyl-amino, ethyl-carbonyl-amino, n-propyl-carbonyl-amino, i-propyl-carbonyl-amino, cyclopropyl-carbonyl-amino, n-butyl-carbonyl-amino, i-butyl-carbonyl-amino, sec-butyl-carbonyl-amino, tert.-butyl-carbonyl-amino, cyclobutyl-carbonyl-amino, n-pentyl-carbonyl-amino, i-pentyl-carbonyl-amino, neo-pentyl-carbonyl-amino, cyclopentyl-carbonyl-amino, amino-carbonyl, methylamino-carbonyl, ethylamino-carbonyl, n-propylamino-carbonyl, i-propylamino-carbonyl, n-butylamino-carbonyl, i-butylamino-carbonyl, sec-butylamino-carbonyl, tert.-butylamino-carbonyl, n-pentylamino-carbonyl, i-pentylamino-carbonyl, neo-pentylamino-carbonyl, cyclopropylamino-carbonyl, cyclobutylamino-carbonyl, cyclopentylamino-carbonyl, dimethylamino-carbonyl, diethylamino-carbonyl, di-n-propylamino-carbonyl, di-i-propylamino-carbonyl, dimethylamino-methyl, diethylamino-methyl, di-n-propylamino-methyl, di-i-propylamino-methyl, 3-dimethylamino-pyrrolidin-1-yl-methyl, 3-diethylamino-pyrrolidin-1-yl-methyl, 3-di-n-propylamino-pyrrolidin-1-yl-methyl, 3-di-i-propylamino-pyrrolidin-1-yl-methyl, 4-methyl-piperazin-1-yl-methyl, 4-ethyl-piperazin-1-yl-methyl, 4-n-propyl-piperazin-1-yl-methyl, 4-i-propyl-piperazin-1-yl-methyl, 4-n-butyl-piperazin-1-yl-methyl, 4-sec-but-yl-piperazin-1-yl-methyl, 4-i-butyl-piperazin-1-yl-methyl, 4-tert-butyl-piperazin-1-yl-methyl, 4-dimethylamino-piperidin-1-yl-methyl, 4-diethylamino-piperidin-1-yl-methyl, 4-di-n-propylamino-piperidin-1-yl-methyl, 4-di-i-propylamino-piperidin-1-yl-methyl, 3-dimethylamino-piperidin-1-yl-methyl, 3-diethylamino-piperidin-1-yl-methyl, 3-di-n-propylamino-piperidin-1-yl-methyl, 3-di-i-propylamino-piperidin-1-yl-methyl, methyl-sulphinyl, ethyl-sulphinyl, n-propyl-sulphinyl, i-propyl-sulphinyl, cyclopropyl-sulphinyl, methyl-sulphonyl, ethyl-sulphonyl, n-propyl-sulphonyl, i-propyl-sulphonyl, cyclopropyl-sulphonyl, hydroxy-methyl, methyl-sulphinyl-methyl, methyl-sulphonyl-methyl,
wherein D or E represents nitrogen, optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
Ar denotes a substituent of formula (IIa),

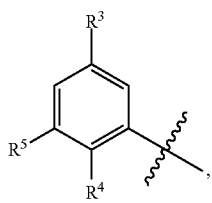
(IIa)

wherein $R^3$ denotes i-propyl, i-butyl, sec.-butyl, tert.-butyl, 1-methyl-cyclopropyl, methoxy, trifluoromethyl, pentafluoroethyl, trifluoromethoxy,
wherein $R^4$ denotes methoxy, ethoxy,
wherein $R^5$ denotes methyl-sulphonyl-amino, ethyl-sulphonyl-amino, n-propyl-sulphonyl-amino, i-propyl-sulphonyl-amino, cyclopropyl-sulphonyl-amino, acetyl-amino, ethyl-carbonyl-amino, n-propyl-carbonyl-amino, i-propyl-carbonyl-amino, cyclopropyl-carbonyl-amino, amino-carbonyl, methylamino-carbonyl, ethylamino-carbonyl, i-propylamino-carbonyl, cyclopropylamino-carbonyl, dimethylamino-carbonyl, diethylamino-carbonyl, di-n-propylamino-carbonyl, di-i-propylamino-carbonyl, dimethylamino-methyl, diethylamino-methyl, di-n-propylamino-methyl, di-i-propylamino-methyl, 3-dimethylamino-pyrrolidin-1-yl-methyl, 3-diethylamino-pyrrolidin-1-yl-methyl, 3-di-n-propylamino-pyrrolidin-1-yl-methyl, 3-di-i-propylamino-pyrrolidin-1-yl-methyl, 4-methyl-piperazin-1-yl-methyl, 4-ethyl-piperazin-1-yl-methyl, 4-n-propyl-piperazin-1-yl-methyl, 4-i-propyl-piperazin-1-yl-methyl, 4-dimethylamino-piperidin-1-yl-methyl, 4-diethylamino-piperidin-1-yl-methyl, 4-di-n-propylamino-piperidin-1-yl-methyl, 4-di-i-propylamino-piperidin-1-yl-methyl, 3-dimethylamino-piperidin-1-yl-methyl, 3-diethylamino-piperidin-1-yl-methyl, 3-di-n-propylamino-piperidin-1-yl-methyl, 3-di-i-propylamino-piperidin-1-yl-methyl, methyl-sulphinyl, ethyl-sulphinyl, n-propyl-sulphinyl, i-propyl-sulphinyl, cyclopropyl-sulphinyl, methyl-sulphonyl, ethyl-sulphonyl, n-propyl-sulphonyl, i-propyl-sulphonyl, cyclopropyl-sulphonyl, hydroxy-methyl, methyl-sulphinyl-methyl, methyl-sulphonyl-methyl,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
Ar denotes a substituent of formula (IIa),

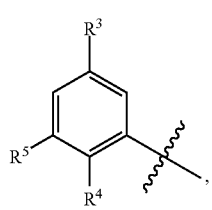
(IIa)

wherein $R^3$ denotes tert.-butyl, sec-butyl, i-propyl, i-butyl, trifluoromethyl, pentafluoroethyl,
wherein $R^4$ denotes methoxy, ethoxy,
wherein $R^5$ denotes methyl-sulphonyl-amino, n-propyl-sulphonyl-amino, cyclopropyl-sulphonyl-amino, acetyl-amino, ethyl-carbonyl-amino, n-propyl-carbonyl-amino, i-propyl-carbonyl-amino, cyclopropyl-carbonyl-amino, amino-carbonyl, methylamino-carbonyl, ethylamino-carbonyl, i-propylamino-carbonyl, cyclopropylamino-carbonyl, dimethylamino-carbonyl, dimethylamino-methyl, diethylamino-methyl, di-i-propylamino-methyl, (R)-3-dimethylamino-pyrrolidin-1-yl-methyl, (S)-3-dimethylamino-pyrrolidin-1-yl-methyl, 3-diethylamino-pyrrolidin-1-yl-methyl, 4-methyl-piperazin-1-yl-methyl, 4-i-propyl-piperazin-1-yl-methyl, 4-dimethylamino-piperidin-1-yl-methyl, 4-diethylamino-piperidin-1-yl-methyl, 3-dimethylamino-piperidin-1-yl-methyl, methyl-sulphinyl, methyl-sulphonyl, hydroxy-methyl, methyl-sulphinyl-methyl, methyl-sulphonyl-methyl,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
Ar is a substituent according to general formula (II')

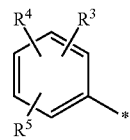
(II')

wherein $R^3$ denotes —$C_1$-$C_6$-alkyl, —$C_3$-$C_6$-cycloalkyl, —$CF_3$, —$CF_2CF_3$ or

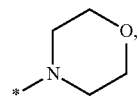

while the —$C_3$-$C_6$-cycloalkyl group may be substituted by —$C_1$-$C_3$-alkyl,
wherein $R^4$ denotes —H, —$C_1$-$C_4$-alkyl or —O—$C_1$-$C_4$-alkyl,
wherein $R^5$ is selected from
—NH—S(O)$_2$—$C_1$-$C_4$-alkyl;
—NH—S(O)$_2$—$C_3$-$C_5$-cycloalkyl;
—N(CH$_3$)—S(O)$_2$—$C_1$-$C_4$-alkyl;
—N(CH$_3$)—S(O)$_2$—$C_3$-$C_5$-cycloalkyl;
—NH—C(O)—$C_1$-$C_4$-alkyl;
—NH—C(O)—$C_3$-$C_5$-cycloalkyl;
—N(CH$_3$)—C(O)—$C_1$-$C_4$-alkyl;
—N(CH$_3$)—C(O)—$C_3$-$C_5$-cycloalkyl;
—C(O)—NH$_2$;
—C(O)—NH—$C_1$-$C_4$-alkyl;
—C(O)—N(di-$C_1$-$C_4$-alkyl);
—C(O)—NH—$C_3$-$C_5$-cycloalkyl;
—C(O)—N($C_1$-$C_4$-alkyl)($C_3$-$C_5$-cycloalkyl);
—S(O)—$C_1$-$C_4$-alkyl;
—S(O)—$C_3$-$C_5$-cycloalkyl;
—S(O)$_2$—$C_1$-$C_4$-alkyl;

—S(O)$_2$—C$_3$-C$_5$-cycloalkyl;
—C$_1$-C$_4$-alkyl-OH
—CH$_2$—S(O)—C$_1$-C$_4$-alkyl;
—CH$_2$—S(O)—C$_3$-C$_5$-cycloalkyl;
—CH$_2$—S(O)$_2$—C$_1$-C$_4$-alkyl;
—CH$_2$—S(O)$_2$—C$_3$-C$_5$-cycloalkyl;
—C$_1$-C$_4$-alkylene-N(R$^8$,R$^{8'}$);
wherein R$^8$ and R$^{8'}$ are each selected independently of one another from —H and —C$_1$-C$_5$-alkyl,
wherein the two groups R$^8$ and R$^{8'}$ together with the nitrogen to which they are bound may form a 4- to 6-membered ring system, which may be substituted by —OH or —N(R$^{10}$, R$^{10'}$),
wherein R$^{10}$ and R$^{10'}$ are each selected independently of one another from —H and —C$_1$-C$_5$-alkyl,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
Ar is a substituent according to general formula (II″)

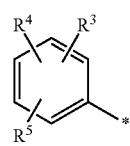
(II″)

wherein R$^3$ is selected from —CH$_3$, —C$_2$H$_5$, -n-C$_3$H$_7$, -i-C$_3$H$_7$, —C(CH$_3$)$_3$, -n-C$_4$H$_9$, —CH$_2$-i-C$_3$H$_7$, —CH(CH$_3$)(C$_2$H$_5$), -n-C$_5$H$_{11}$, —CH$_2$—CH$_2$-i-C$_3$H$_7$, —CH$_2$—C(CH$_3$)$_3$, —CF$_3$, —CF$_2$CF$_3$ or

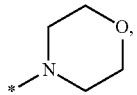

wherein R$^4$ is selected from H, —O—CH$_3$ or —O—C$_2$H$_5$,
wherein R$^5$ is selected from H, —NH—S(O)$_2$—CH$_3$, —NH—S(O)$_2$—C$_2$H$_5$, —NH—S(O)$_2$-n-C$_3$H$_7$, —NH—S(O)$_2$-i-C$_3$H$_7$, NH—S(O)$_2$-c-C$_3$H$_5$, —NH—S(O)$_2$-n-C$_4$H$_9$, —NH—S(O)$_2$—CH$_2$-i-C$_3$H$_7$, —NH—S(O)$_2$—C(CH$_3$)$_3$, —NH—S(O)$_2$-c-C$_4$H$_7$, —NH—S(O)$_2$-n-C$_5$H$_{11}$, —NH—S(O)$_2$—(CH$_2$)$_2$-i-C$_3$H$_7$, —NH—S(O)$_2$—CH$_2$—C(CH$_3$)$_3$, —NH—S(O)$_2$-c-C$_5$H$_9$, —NH—C(O)—CH$_3$, —NH—C(O)—C$_2$H$_5$, —NH—C(O)-n-C$_3$H$_7$, —NH—C(O)-i-C$_3$H$_7$, —NH—C(O)-c-C$_3$H$_5$, —NH—C(O)-n-C$_4$H$_9$, —NH—C(O)—CH$_2$-i-C$_3$H$_7$, —NH—C(O)—C(CH$_3$)$_3$, —NH—C(O)-c-C$_4$H$_7$, —NH—C(O)-n-C$_5$H$_{11}$, —NH—C(O)—(CH$_2$)$_2$-i-C$_3$H$_7$, —NH—C(O)—CH$_2$—C(CH$_3$)$_3$, —NH—C(O)-c-C$_5$H$_9$, —C(O)—NH$_2$, —C(O)—NH—CH$_3$, —C(O)—N(CH$_3$)$_2$, —C(O)—NH—C$_2$H$_5$, —C(O)—N(C$_2$H$_5$)$_2$, —C(O)—NH-n-C$_3$H$_7$, —C(O)—N(C$_3$H$_7$)$_2$, —C(O)—NH-i-C$_3$H$_7$, —C(O)—N(i-C$_3$H$_7$)$_2$, —C(O)—NH-c-C$_3$H$_5$, —C(O)—NH-n-C$_4$H$_9$, —C(O)—N(n-C$_4$H$_9$)$_2$, —C(O)—NH—CH$_2$-i-C$_3$H$_7$, —C(O)—N(CH$_2$-i-C$_3$H$_7$)$_2$, —C(O)—NH-c-C$_4$H$_7$, —CH$_2$—N(CH$_3$)$_2$, —CH$_2$—N(C$_2$H$_5$)$_2$, —CH$_2$—N(n-C$_3$H$_7$)$_2$, —CH$_2$—N(i-C$_3$H$_7$)$_2$, —CH$_2$—N(n-C$_4$H$_9$)$_2$, —CH$_2$—N(CH$_2$-i-C$_3$H$_7$)$_2$,

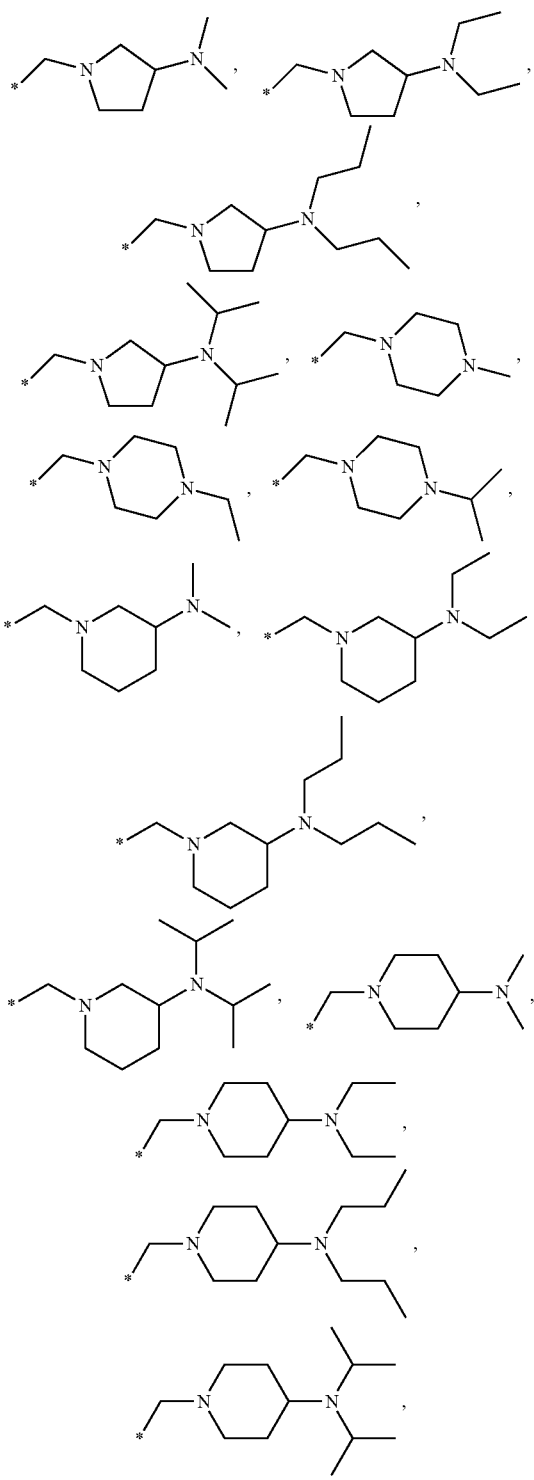

—S(O)—CH$_3$, —S(O)$_2$—CH$_3$, —S(O)—C$_2$H$_5$, —S(O)$_2$—C$_2$H$_5$, —CH$_2$—OH, —CH$_2$—S(O)—CH$_3$, —CH$_2$—S(O)$_2$—CH$_3$, —CH$_2$—S(O)—C$_2$H$_5$ or —CH$_2$—S(O)$_2$—C$_2$H$_5$, optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
Ar is a substituent according to general formula (II''')

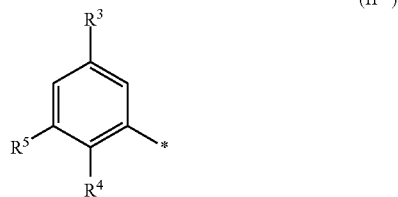

(II''')

wherein $R^3$ denotes —C(CH$_3$)$_3$, —CH(CH$_3$)(C$_2$H$_5$), -i-C$_3$H$_7$, —CH$_2$-i-C$_3$H$_7$, —CF$_3$ or —CF$_2$CF$_3$,
wherein $R^4$ denotes —O—CH$_3$ or —O—C$_2$H$_5$,
wherein $R^5$ is selected from —NH—S(O)$_2$—CH$_3$, —NH—S(O)$_2$-n-C$_3$H$_7$, —NH—S(O)$_2$-c-C$_3$H$_5$, —NH—C(O)—CH$_3$, —NH—C(O)—C$_2$H$_5$, —NH—C(O)-n-C$_3$H$_7$, —NH—C(O)-i-C$_3$H$_7$, —NH—C(O)-c-C$_3$H$_5$, —C(O)—NH$_2$, —C(O)—NH—CH$_3$, —C(O)—NH—C$_2$H$_5$, —C(O)—NH-i-C$_3$H$_7$, —C(O)—NH-c-C$_3$H$_5$, —C(O)—N(CH$_3$)$_2$, —CH$_2$—N(CH$_3$)$_2$, —CH$_2$—N(C$_2$H$_5$)$_2$, —CH$_2$—N(i-C$_3$H$_7$)$_2$,

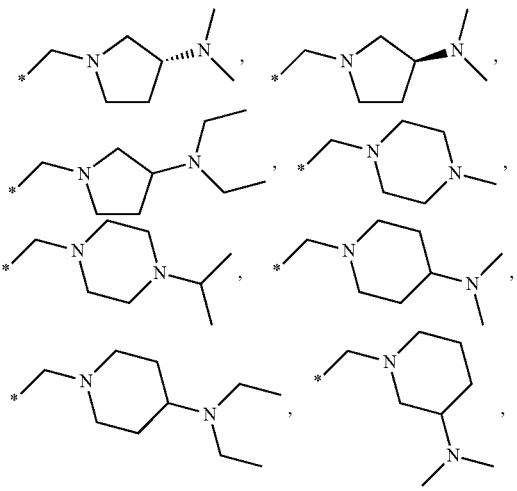

—S(O)—CH$_3$, —S(O)$_2$—CH$_3$, —CH$_2$—OH, —CH$_2$—S(O)—CH$_3$ or —CH$_2$—S(O)$_2$—CH$_3$,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein $R^1$ denotes a C$_{4-6}$-cycloalkyl system, which contains 1 to 2 nitrogen atoms that may optionally be 1- to 2-substituted by $R^7$,
wherein $R^7$ may be C$_{1-3}$-alkyl, hydroxy, C$_{1-3}$-alkoxy, amino, C$_{1-3}$-alkyl-amino, di-(C$_{1-3}$-alkyl)-amino,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein $R^1$ denotes azetidin-2-yl, azetidin-3-yl, 1-methyl-azetidin-2-yl, 1-methyl-azetidin-3-yl, 1-ethyl-azetidin-2-yl, 1-ethyl-azetidin-3-yl, pyrrolidin-1-yl, pyrrolidin-2-yl, pyrrolidin-3-yl, 3-hydroxy-pyrrolidin-1-yl, 3-amino-pyrrolidin-1-yl, 3-methylamino-pyrrolidin-1-yl, 3-dimethylamino-pyrrolidin-1-yl, 3-ethylamino-pyrrolidin-1-yl, 3-diethylamino-pyrrolidin-1-yl, 1-methyl-pyrrolidin-2-yl, 1-methyl-pyrrolidin-3-yl, 1-ethyl-pyrrolidin-2-yl, 1-ethyl-pyrrolidin-3-yl, 1-methyl-4-hydroxy-pyrrolidin-2-yl, 1-methyl-4-methoxy-pyrrolidin-2-yl, piperidin-1-yl, piperidin-2-yl, piperidin-3-yl, piperidin-4-yl, 4-amino-piperidin-1-yl, 4-methylamino-piperidin-1-yl, 4-dimethylamino-piperidin-1-yl, 4-ethylamino-piperidin-1-yl, 4-diethylamino-piperidin-1-yl, 1-methyl-piperidin-2-yl, 1-methyl-piperidin-3-yl, 1-methyl-piperidin-4-yl, 1-ethyl-piperidin-2-yl, 1-ethyl-piperidin-3-yl, 1-ethyl-piperidin-4-yl, piperazin-1-yl, 4-methyl-piperazin-1-yl, 4-ethyl-piperazin-1-yl, 4-isopropyl-piperazin-1-yl,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein $R^1$ denotes 1-methyl-azetidin-3-yl, azetidin-3-yl, (2RS)-1-methyl-azetidin-2-yl, (2S)-1-methyl-pyrrolidin-2-yl, (2R)-1-methyl-pyrrolidin-2-yl, (2S)-pyrrolidin-2-yl, (2S,4S)-1-methyl-4-hydroxy-pyrrolidin-2-yl, (2R,4S)-1-methyl-4-hydroxy-pyrrolidin-2-yl, (2S,4R)-1-methyl-4-hydroxy-pyrrolidin-2-yl, (2R,4R)-1-methyl-4-hydroxy-pyrrolidin-2-yl, (2R,4R)-1-methyl-4-methoxy-pyrrolidin-2-yl, (3S)-1-methyl-pyrrolidin-3-yl, (3R)-1-methyl-pyrrolidin-3-yl, 1-methyl-piperidin-3-yl, 1-methyl-piperidin-4-yl, (3S)-3-dimethylamino-pyrrolidin-1-yl, (3R)-3-dimethylamino-pyrrolidin-1-yl, 4-methyl-piperazin-1-yl, pyrrolidin-1-yl, (3R)-3-hydroxy-pyrrolidin-1-yl, (3S)-3-hydroxy-pyrrolidin-1-yl, piperazin-1-yl, 4-isopropyl-piperazin-1-yl, 4-dimethylamino-piperidin-1-yl,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
$R^1$ is selected from —C$_4$-C$_6$-cycloalkyl, which contains 1 to 2 nitrogen atoms in the ring, while $R^1$ is optionally substituted by a group selected from —C$_1$-C$_4$-alkyl, —OH, —O—C$_1$-C$_4$-alkyl, and —N(R$^9$,R$^{9'}$),
wherein $R^9$,$R^{9'}$ have the meanings given above,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
$R^1$ is selected from

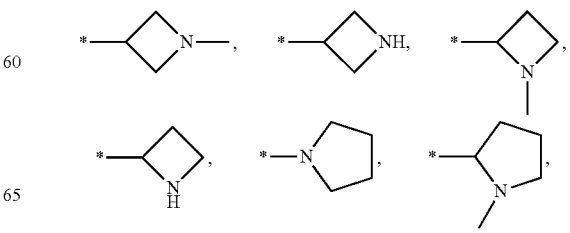

-continued

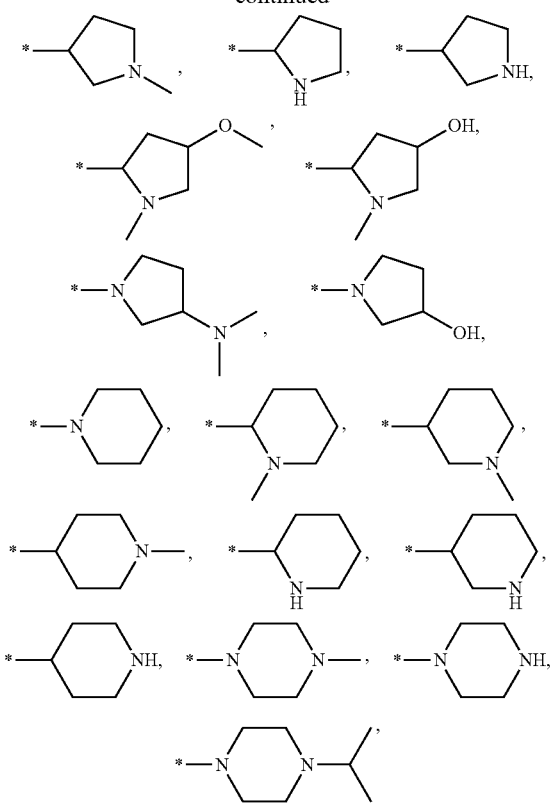

optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
$R^1$ is selected from -continued

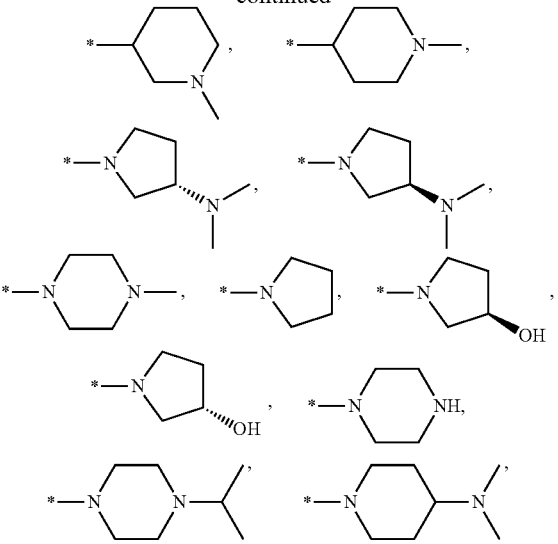

optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
$R^2$ is selected from —H, —F, —Cl and —$CH_3$,
and wherein
p is selected from 0, 1, 2 or 3,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
$R^2$ is H,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
L and M are selected independently of one another from —CH< and —N<,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
L is selected from —CH< or —N<,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
M denotes —N<,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
T is selected from a bond and —C$_1$-C$_3$-alkylene,
while the —C$_1$-C$_3$-alkylene group may be substituted by methyl,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
T is selected from a bond, and —CH$_2$—,
while the —CH$_2$— group may be substituted by methyl,
optionally in the form of the individual optical isomers thereof, mixtures of these isomers, racemates, optionally in the form of the acid addition salts thereof with pharmacologically acceptable acids.

In another preferred embodiment the present invention relates to compounds of general formula (I), wherein
T denotes a bond,
optionally in the form of the individual optical isomers thereof, mixtures of these isomers, racemates, optionally in the form of the acid addition salts thereof with pharmacologically acceptable acids.

Another preferred embodiment relates to the compounds of general formula (I) described above for the treatment of diseases selected from asthma or COPD.

Another preferred embodiment relates to the use of the compounds of general formula (I) described above for preparing a medicament for the treatment of diseases selected from asthma or COPD.

The compounds according to the invention of general formula I and the physiologically acceptable salts thereof have valuable pharmacological properties, particularly an inhibitory effect on the enzyme p38 MAP-kinase.

The present invention also relates to the physiologically acceptable salts of the compounds according to the invention with inorganic or organic acids. The invention relates to the respective compounds of formula I in the form of the pharmacologically acceptable salts thereof. These pharmacologically acceptable salts of the compounds of formula I may also be present in the form of their respective hydrates (e.g. monohydrates, dehydrates, etc.) as well as in the form of their respective solvates.

By a hydrate of the compound according to formula I is meant, within the scope of the invention, a crystalline salt of the compound according to formula I containing water of crystallisation. By a solvate of the compound according to formula I is meant within the scope of the invention a crystalline salt of the compound according to formula I that contains molecules of solvent (e.g. ethanol, methanol, etc) in the crystal lattice. The skilled man will be familiar with standard methods of obtaining hydrates and solvates (e.g. recrystallisation from the corresponding solvent or from water).

Therefore the use of the compounds according to the invention, including the physiologically acceptable salts, as pharmaceutical compositions is also an object of this invention.

This invention further relates to medicaments containing at least one compound according to the invention or a physiologically acceptable salt according to the invention, optionally together with one or more inert carriers and/or diluents.

The invention also relates to the use of at least one compound according to the invention or a physiologically acceptable salt of such a compound for preparing a medicament that is suitable for the treatment or prevention of diseases or conditions that can be influenced by inhibiting the enzyme p38 MAP-kinase.

This invention further relates to the use of at least one compound according to the invention for preparing a pharmaceutical composition for inhibiting the enzyme p38 MAP-kinase.

This invention also relates to a process for preparing a medicament according to the invention, characterised in that a compound according to the invention is incorporated in one or more inert carriers and/or diluents by a non-chemical method.

The following compounds Va, Vb and Vc are explicitly not a part of the present invention:

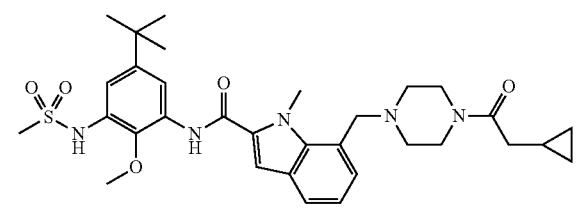

Va

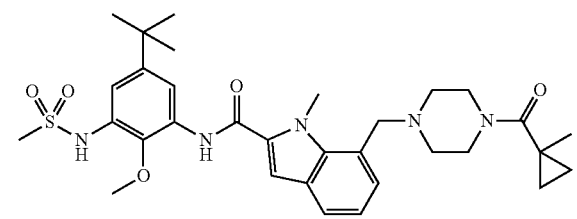

Vb

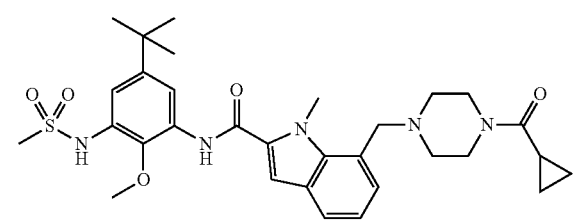

Vc

DETAILED DESCRIPTION OF THE INVENTION

Unless stated otherwise, the groups, residues and substituents, particularly Ar, R$^1$ to R$^7$, L, M, T, m, n and p have the meanings stated hereinbefore and hereinafter.

If residues, substituents or groups occur several times in a compound, they may have the same or different meanings.

Preferred embodiments of the invention are indicated by the following definitions:

a) The definitions (a$^i$) for Ar in increasing order of preference, starting with preferably (a$^1$) through particularly preferably (a$^2$), most particularly preferably (a$^3$) to most preferably of all (a$^4$) are as follows:

(a$^1$): Preferably Ar denotes a substituent of formula (IIa), (IIIa) or (IVa),

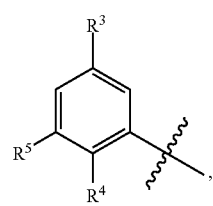

(IIa)

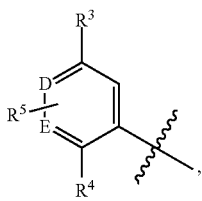
(IIIa)

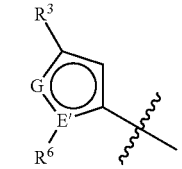
(IVa)

wherein R³ denotes C₁₋₆-alkyl, C₃₋₆-cycloalkyl, C₁₋₄-alkoxy, C₁₋₂-perfluoroalkyl, 3-methyl-oxetan-3-yl, C₁₋₂-perfluoroalkoxy, morpholinyl,
  wherein the cycloalkyl group may optionally be substituted by C₁₋₃-alkyl,
wherein R⁴ denotes H, C₁₋₄-alkyl, C₁₋₄-alkoxy,
wherein R⁵ denotes H, C₁₋₅-alkyl-sulphonyl-amino, C₃₋₆-cycloalkyl-sulphonyl-amino, (C₁₋₅-alkyl-sulphonyl)-(methyl)-amino, (C₃₋₆-cycloalkyl-sulphonyl)-(methyl)-amino, C₁₋₅-alkyl-carbonyl-amino, C₃₋₆-cycloalkyl-carbonyl-amino, (C₁₋₅-alkyl-carbonyl)-(methyl)-amino, (C₃₋₆-cycloalkyl-carbonyl)-(methyl)-amino, aminocarbonyl, C₁₋₅-alkyl-amino-carbonyl, C₃₋₆-cycloalkyl-amino-carbonyl, di-(C₁₋₃-alkyl)-amino-carbonyl, di-(C₁₋₃-alkyl)-amino-C₁₋₂-alkyl, di-(C₁₋₃-alkyl)-amino-pyrrolidin-1-yl-C₁₋₂-alkyl, 4-C₁₋₅-alkyl-piperazin-1-yl-C₁₋₂-alkyl, 4-di-(C₁₋₃-alkyl)-amino-piperidin-1-yl-C₁₋₂-alkyl, 3-di-(C₁₋₃-alkyl)-amino-piperidin-1-yl-C₁₋₂-alkyl, C₁₋₅-alkyl-sulphinyl, C₃₋₆-cycloalkyl-sulphinyl, C₁₋₅-alkyl-sulphonyl, C₃₋₆-cycloalkyl-sulphonyl, hydroxy-C₁₋₂-alkyl, C₁₋₅-alkyl-sulphinyl-methyl, C₁₋₅-alkyl-sulphonyl-methyl,
wherein R⁶ denotes C₁₋₃-alkyl or phenyl,
  while the C₁₋₃-alkyl group may optionally be substituted by hydroxy or di-(C₁₋₃-alkyl)-amino and
  the phenyl group may optionally be substituted by fluorine or C₁₋₃-alkyl,
wherein D or E represents nitrogen,
wherein G and E' independently of one another represent nitrogen or oxygen,
wherein R⁶ is only bound to E' if E' denotes nitrogen,
(a²): particularly preferably Ar denotes a substituent of formula (IIa) or (IIIa)

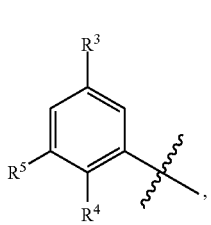
(IIa)

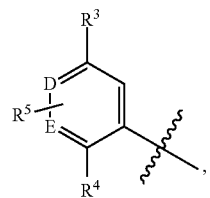
(IIIa)

wherein R³ demotes methyl, ethyl, n-propyl, i-propyl, n-butyl, i-butyl, sec.-butyl, tert-butyl, n-pentyl, i-pentyl, neo-pentyl, 1-methyl-cyclopropyl, methoxy, trifluoromethyl, pentafluoroethyl, 3-methyl-oxetan-3-yl, trifluoromethoxy, morpholin-4-yl,
wherein R⁴ denotes H, methyl, ethyl, n-propyl, methoxy, ethoxy, n-propyloxy, i-propyloxy,
wherein R⁵ denotes H, methyl-sulphonyl-amino, ethyl-sulphonyl-amino, n-propyl-sulphonyl-amino, i-propyl-sulphonyl-amino, n-butyl-sulphonyl-amino, i-butyl-sulphonyl-amino, sec-butyl-sulphonyl-amino, tert.-butyl-sulphonyl-amino, sulphonyl-amino, cyclopropyl-sulphonyl-amino, cyclobutyl-sulphonyl-amino, cyclopentyl-sulphonyl-amino, acetyl-amino, ethyl-carbonyl-amino, n-propyl-carbonyl-amino, i-propyl-carbonyl-amino, cyclopropyl-carbonyl-amino, n-butyl-carbonyl-amino, i-butyl-carbonyl-amino, sec-butyl-carbonyl-amino, tert.-butyl-carbonyl-amino, cyclobutyl-carbonyl-amino, n-pentyl-carbonyl-amino, i-pentyl-carbonyl-amino, neo-pentyl-carbonyl-amino, cyclopentyl-carbonyl-amino, amino-carbonyl, methylamino-carbonyl, ethylamino-carbonyl, n-propylamino-carbonyl, i-propylamino-carbonyl, n-butylamino-carbonyl, i-butylamino-carbonyl, sec-butylamino-carbonyl, tert.-butylamino-carbonyl, n-pentylamino-carbonyl, i-pentylamino-carbonyl, neo-pentylamino-carbonyl, cyclopropylamino-carbonyl, cyclobutylamino-carbonyl, cyclopentylamino-carbonyl, dimethylamino-carbonyl, diethylamino-carbonyl, di-n-propylamino-carbonyl, di-i-propylamino-carbonyl, dimethylamino-methyl, diethylamino-methyl, di-n-propylamino-methyl, di-i-propylamino-methyl, 3-dimethylamino-pyrrolidin-1-yl-methyl, 3-diethylamino-pyrrolidin-1-yl-methyl, 3-di-n-propylamino-pyrrolidin-1-yl-methyl, 3-di-i-propylamino-pyrrolidin-1-yl-methyl, 4-methyl-piperazin-1-yl-methyl, 4-ethyl-piperazin-1-yl-methyl, 4-n-propyl-piperazin-1-yl-methyl, 4-i-propyl-piperazin-1-yl-methyl, 4-n-butyl-piperazin-1-yl-methyl, 4-sec-but-yl-piperazin-1-yl-methyl, 4-i-butyl-piperazin-1-yl-methyl, 4-tert.-butyl-piperazin-1-yl-methyl, 4-dimethylamino-piperidin-1-yl-methyl, 4-diethylamino-piperidin-1-yl-methyl, 4-di-n-propylamino-piperidin-1-yl-methyl, 4-di-i-propylamino-piperidin-1-yl-methyl, 3-dimethylamino-piperidin-1-yl-methyl, 3-diethylamino-piperidin-1-yl-methyl, 3-di-n-propylamino-piperidin-1-yl-methyl, 3-di-i-propylamino-piperidin-1-yl-methyl, methyl-sulphinyl, ethyl-sulphinyl, n-propyl-sulphinyl, i-propyl-sulphinyl, cyclopropyl-sulphinyl, methyl-sulphonyl, ethyl-sulphonyl, n-propyl-sulphonyl, i-propyl-sulphonyl, cyclopropyl-sulphonyl, hydroxy-methyl, methyl-sulphinyl-methyl, methyl-sulphonyl-methyl.
wherein D or E represents nitrogen, (a³): Most particularly preferably Ar denotes a substituent of formula (IIa),

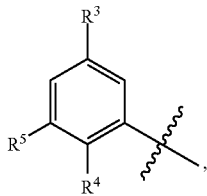

wherein R³ denotes i-propyl, i-butyl, sec.-butyl, tert.-butyl, 1-methyl-cyclopropyl, methoxy, trifluoromethyl, pentafluoroethyl, trifluoromethoxy, wherein R⁴ denotes methoxy, ethoxy, wherein R⁵ denotes methyl-sulphonyl-amino, ethyl-sulphonyl-amino, n-propyl-sulphonyl-amino, i-propyl-sulphonyl-amino, cyclopropyl-sulphonyl-amino, acetyl-amino, ethyl-carbonyl-amino, n-propyl-carbonyl-amino, i-propyl-carbonyl-amino, cyclopropyl-carbonyl-amino, amino-carbonyl, methylamino-carbonyl, ethylamino-carbonyl, i-propylamino-carbonyl, cyclopropylamino-carbonyl, dimethylamino-carbonyl, diethylamino-carbonyl, di-n-propylamino-carbonyl, di-i-propylamino-carbonyl, dimethylamino-methyl, diethylamino-methyl, di-n-propylamino-methyl, di-i-propylamino-methyl, 3-dimethylamino-pyrrolidin-1-yl-methyl, 3-diethylamino-pyrrolidin-1-yl-methyl, 3-di-n-propylamino-pyrrolidin-1-yl-methyl, 3-di-i-propylamino-pyrrolidin-1-yl-methyl, 4-methyl-piperazin-1-yl-methyl, 4-ethyl-piperazin-1-yl-methyl, 4-n-propyl-piperazin-1-yl-methyl, 4-i-propyl-piperazin-1-yl-methyl, 4-dimethylamino-piperidin-1-yl-methyl, 4-diethylamino-piperidin-1-yl-methyl, 4-di-n-propylamino-piperidin-1-yl-methyl, 4-di-i-propylamino-piperidin-1-yl-methyl, 3-dimethylamino-piperidin-1-yl-methyl, 3-diethylamino-piperidin-1-yl-methyl, 3-di-n-propylamino-piperidin-1-yl-methyl, 3-di-i-propylamino-piperidin-1-yl-methyl, methyl-sulphinyl, ethyl-sulphinyl, n-propyl-sulphinyl, i-propyl-sulphinyl, cyclopropyl-sulphinyl, methyl-sulphonyl, ethyl-sulphonyl, n-propyl-sulphonyl, i-propyl-sulphonyl, cyclopropyl-sulphonyl, hydroxy-methyl, methyl-sulphinyl-methyl, methyl-sulphonyl-methyl.

(a⁴): Most preferably of all, Ar denotes a substituent of formula (IIa),

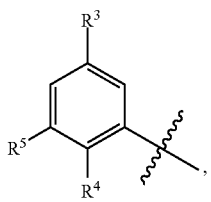

wherein R³ denotes tert.-butyl, sec-butyl, i-propyl, i-butyl, trifluoromethyl, pentafluoroethyl, wherein R⁴ denotes methoxy, ethoxy, wherein R⁵ denotes methyl-sulphonyl-amino, n-propyl-sulphonyl-amino, cyclopropyl-sulphonyl-amino, acetyl-amino, ethyl-carbonyl-amino, n-propyl-carbonyl-amino, i-propyl-carbonyl-amino, cyclopropyl-carbonyl-amino, amino-carbonyl, methylamino-carbonyl, ethylamino-carbonyl, i-propylamino-carbonyl, cyclopropylamino-carbonyl, dimethylamino-carbonyl, dimethylamino-methyl, diethylamino-methyl, di-i-propylamino-methyl, (R)-3-dimethylamino-pyrrolidin-1-yl-methyl, (S)-3-dimethylamino-pyrrolidin-1-yl-methyl, 3-diethylamino-pyrrolidin-1-yl-methyl, 4-methyl-piperazin-1-yl-methyl, 4-i-propyl-piperazin-1-yl-methyl, 4-dimethylamino-piperidin-1-yl-methyl, 4-diethylamino-piperidin-1-yl-methyl, 3-dimethylamino-piperidin-1-yl-methyl, methyl-sulphinyl, methyl-sulphonyl, hydroxy-methyl, methyl-sulphinyl-methyl, methyl-sulphonyl-methyl.

b) The definitions (bⁱ) for R¹ in increasing order of preference, starting with preferably (b¹) through particularly preferably (b²) to most particularly preferably (b³), are as follows:

(b¹): Preferably R¹ denotes a $C_{4-6}$-cycloalkyl system, which contains 1 to 2 nitrogen atoms that may optionally be 1- to 2-substituted by R⁷, wherein R⁷ may be $C_{1-3}$-alkyl, hydroxy, $C_{1-3}$-alkoxy, amino, $C_{1-3}$-alkyl-amino, di-($C_{1-3}$-alkyl)-amino.

(b²): Particularly preferably R¹ denotes azetidin-2-yl, azetidin-3-yl, 1-methyl-azetidin-2-yl, 1-methyl-azetidin-3-yl, 1-ethyl-azetidin-2-yl, 1-ethyl-azetidin-3-yl, pyrrolidin-1-yl, pyrrolidin-2-yl, pyrrolidin-3-yl, 3-hydroxy-pyrrolidin-1-yl, 3-amino-pyrrolidin-1-yl, 3-methylamino-pyrrolidin-1-yl, 3-dimethylamino-pyrrolidin-1-yl, 3-ethylamino-pyrrolidin-1-yl, 3-diethylamino-pyrrolidin-1-yl, 1-methyl-pyrrolidin-2-yl, 1-methyl-pyrrolidin-3-yl, 1-ethyl-pyrrolidin-2-yl, 1-ethyl-pyrrolidin-3-yl, 1-methyl-4-hydroxy-pyrrolidin-2-yl, 1-methyl-4-methoxy-pyrrolidin-2-yl, piperidin-1-yl, piperidin-2-yl, piperidin-3-yl, piperidin-4-yl, 4-amino-piperidin-1-yl, 4-methylamino-piperidin-1-yl, 4-dimethylamino-piperidin-1-yl, 4-ethylamino-piperidin-1-yl, 4-diethylamino-piperidin-1-yl, 1-methyl-piperidin-2-yl, 1-methyl-piperidin-3-yl, 1-methyl-piperidin-4-yl, 1-ethyl-piperidin-2-yl, 1-ethyl-piperidin-3-yl, 1-ethyl-piperidin-4-yl, piperazin-1-yl, 4-methyl-piperazin-1-yl, 4-ethyl-piperazin-1-yl, 4-isopropyl-piperazin-1-yl.

(b³): Most particularly preferably R¹ is 1-methyl-azetidin-3-yl, azetidin-3-yl, (2RS)-1-methyl-azetidin-2-yl, (2S)-1-methyl-pyrrolidin-2-yl, (2R)-1-methyl-pyrrolidin-2-yl, (2S)-pyrrolidin-2-yl, (2S,4S)-1-methyl-4-hydroxy-pyrrolidin-2-yl, (2R,4S)-1-methyl-4-hydroxy-pyrrolidin-2-yl, (2S,4R)-1-methyl-4-hydroxy-pyrrolidin-2-yl, (2R,4R)-1-methyl-4-hydroxy-pyrrolidin-2-yl, (2R,4R)-1-methyl-4-methoxy-pyrrolidin-2-yl, (3S)-1-methyl-pyrrolidin-3-yl, (3R)-1-methyl-pyrrolidin-3-yl, 1-methyl-piperidin-3-yl, 1-methyl-piperidin-4-yl, (3S)-3-dimethylamino-pyrrolidin-1-yl, (3R)-3-dimethylamino-pyrrolidin-1-yl, 4-methyl-piperazin-1-yl, pyrrolidin-1-yl, (3R)-3-hydroxy-pyrrolidin-1-yl, (3S)-3-hydroxy-pyrrolidin-1-yl, piperazin-1-yl, 4-isopropyl-piperazin-1-yl, 4-dimethylamino-piperidin-1-yl.

c) The definitions (cⁱ) for R² in increasing order of preference, starting with preferably (c¹) to particularly preferably (c²), are as follows:

(c¹): Preferably R² denotes hydrogen, fluorine, chlorine or methyl.

(c²): Particularly preferably R² denotes hydrogen.

d) The definitions (dⁱ) for M in increasing order of preference, starting with preferably (d¹), to particularly preferably (d²), are as follows:

(d¹): Preferably M is —N< or —CH<.

(d²): Preferably M is —N<.

e) The definitions (e$^i$) for L in increasing order of preference, starting with preferably (e$^1$), to particularly preferably (e$^2$), are as follows:
(e$^1$): Preferably L is —N< or —CH<.
(e$^2$): Preferably L is —N<.
f) The definitions (f$^i$) for T in increasing order of preference, starting with preferably (f$^1$), through particularly preferably (f$^2$) to particularly preferably (f$^3$), are as follows:
(f$^1$): Preferably T denotes a bond or C$_{1-2}$-alkylene.
(f$^2$): Particularly preferably T denotes a bond or methylene.
(f$^3$): Most particularly preferably T denotes a bond.
g) The definitions (g$^i$) for m in increasing order of preference, starting with preferably (g$^1$) to particularly preferably (g$^2$), are as follows:
(g$^1$): Preferably m denotes 0, 1 or 2.
(g$^2$): Particularly preferably m denotes 1 or 2.
(h$^1$): Preferably n is 1.
i) The definitions (i$^i$) for p in increasing order of preference, starting with preferably (i$^1$), through particularly preferably (i$^2$) to most particularly preferably (i$^3$), are as follows:
(i$^1$): Preferably p is 0, 1 or 2.
(i$^2$): Particularly preferably p is 0 or 1.
(i$^3$): Most particularly preferably p is 0.

Each a$^i$, b$^i$, c$^i$, d$^i$, e$^i$, f$^i$, g$^i$, h$^i$, represents a defined, individual embodiment of the respective group as shown above. According to the definitions shown hereinbefore each individual preferred embodiment is fully characterised by the expression (a$^i$b$^i$c$^i$d$^i$e$^i$f$^i$g$^i$h$^i$), while the index i in each case denotes an individual embodiment and the individual indices i are variable independently of one another. All the individual embodiments that are included by the expression in brackets, while the indices i may be varied and combined as desired according to the above definitions, should be encompassed by the present invention.

Table 1 that follows contains a list of the preferred embodiments E-1 to E-14 by way of example, in ascending order of preference from the first row to the last. Accordingly, embodiment E-14, shown in the last row of Table 1, has the highest preference.

TABLE 1

|      | Ar   | R$^1$ | R$^2$ | M    | L    | T    | m    | n    | p    |
|------|------|------|------|------|------|------|------|------|------|
| E-1  | a$^1$ | b$^1$ | c$^1$ | d$^1$ | e$^1$ | f$^1$ | g$^1$ | h$^1$ | i$^1$ |
| E-2  | a$^2$ | b$^1$ | c$^1$ | d$^1$ | e$^1$ | f$^2$ | g$^1$ | h$^1$ | i$^2$ |
| E-3  | a$^1$ | b$^1$ | c$^1$ | d$^1$ | e$^1$ | f$^1$ | g$^1$ | h$^1$ | i$^1$ |
| E-4  | a$^2$ | b$^2$ | c$^2$ | d$^1$ | e$^1$ | f$^2$ | g$^2$ | h$^1$ | i$^3$ |
| E-5  | a$^2$ | b$^2$ | c$^2$ | d$^1$ | e$^1$ | f$^2$ | g$^2$ | h$^1$ | i$^3$ |
| E-6  | a$^2$ | b$^3$ | c$^2$ | d$^2$ | e$^1$ | f$^3$ | g$^2$ | h$^1$ | i$^3$ |
| E-7  | a$^3$ | b$^2$ | c$^2$ | d$^2$ | e$^1$ | f$^3$ | g$^2$ | h$^1$ | i$^3$ |
| E-9  | a$^2$ | b$^3$ | c$^2$ | d$^1$ | e$^1$ | f$^2$ | g$^2$ | h$^1$ | i$^3$ |
| E-10 | a$^3$ | b$^2$ | c$^2$ | d$^1$ | e$^1$ | f$^2$ | g$^2$ | h$^1$ | i$^3$ |
| E-11 | a$^3$ | b$^3$ | c$^2$ | d$^2$ | e$^1$ | f$^2$ | g$^2$ | h$^1$ | i$^3$ |
| E-12 | a$^3$ | b$^3$ | c$^2$ | d$^2$ | e$^2$ | f$^3$ | g$^2$ | h$^1$ | i$^3$ |
| E-13 | a$^4$ | b$^3$ | c$^2$ | d$^2$ | e$^1$ | f$^2$ | g$^2$ | h$^1$ | i$^3$ |
| E-14 | a$^4$ | b$^3$ | c$^2$ | d$^2$ | e$^2$ | f$^3$ | g$^2$ | h$^1$ | i$^3$ | including the tautomers, the stereoisomers and the mixtures thereof.

The compounds of formula (I) described and claimed in the present application have proved particularly advantageous in two respects. On the one hand, they are comparatively readily soluble. On the other hand they inhibit the cytochrome P450 2C9-isoenzyme to a comparatively limited extent, which is generally accepted as an indication that the compounds described and claimed here have only a limited tendency, if any, to drug-drug interactions based on the cytochrome P450 2C9 isoenzyme. For example the following compounds are mentioned as preferred compounds:

1-methyl-7-[4-(1-methyl-piperidine-4-carbonyl)-piperazin-1-ylmethyl]-1H-indole-2-carboxylic acid (5-tert-butyl-3-methanesulphonylamino-2-methoxy-phenyl)-amide

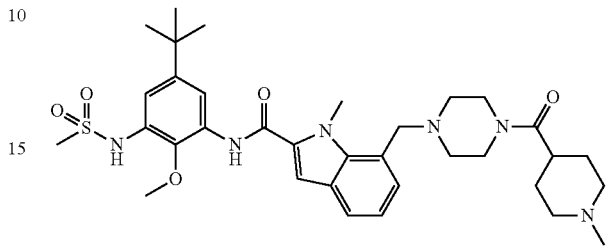

(S)-1-methyl-7-[4-(1-methyl-pyrrolidine-2-carbonyl)-piperazin-1-ylmethyl]-1H-indole-2-carboxylic acid (5-tert-butyl-3-methanesulphonylamino-2-methoxy-phenyl)-amide

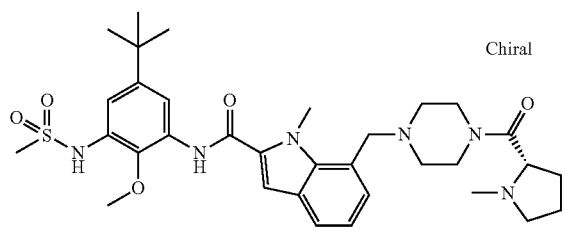 [SMILES: COc1c(NC(=O)c2cc3cccc(CN4CCN(C(=O)[C@@H]5CCCN5C)CC4)c3n2C)cc(C(C)(C)C)cc1NS(C)(=O)=O]

1-methyl-7-[4-(1-methyl-azetidine-3-carbonyl)-piperazin-1-ylmethyl]-1H-indole-2-carboxylic acid (5-tert-butyl-3-methanesulphonylamino-2-methoxy-phenyl)-amide

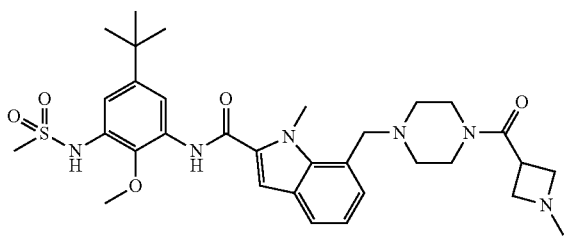

(R)-1-methyl-7-[4-(1-methyl-pyrrolidine-2-carbonyl)-piperazin-1-ylmethyl]-1H-indole-2-carboxylic acid (5-tert-butyl-3-methanesulphonylamino-2-methoxy-phenyl)-amide

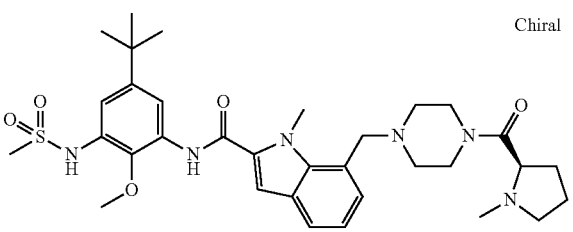 [SMILES: COc1c(NC(=O)c2cc3cccc(CN4CCN(C(=O)[C@H]5CCCN5C)CC4)c3n2C)cc(C(C)(C)C)cc1NS(C)(=O)=O]

27

(S)-1-methyl-7-[4-(pyrrolidine-2-carbonyl)-piperazin-1-ylmethyl]-1H-indole-2-carboxylic acid (5-tert-butyl-3-methanesulphonylamino-2-methoxyphenyl)-amide

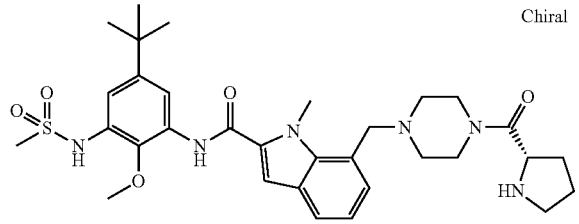 [SMILES: COc1c(NC(=O)c2cc3cccc(CN4CCN(C(=O)[C@@H]5CCCN5)CC4)c3n2C)cc(C(C)(C)C)cc1NS(C)(=O)=O]

1-methyl-7-[4-(1-methyl-azetidine-2-carbonyl)-piperazin-1-ylmethyl]-1H-indole-2-carboxylic acid (5-tert-butyl-3-methanesulphonylamino-2-methoxyphenyl)-amide

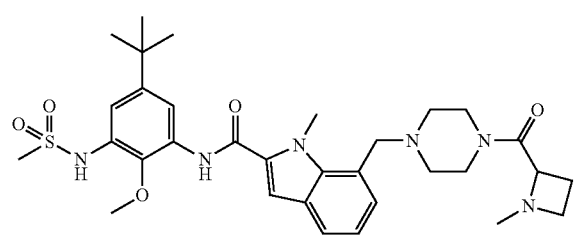 [SMILES: COc1c(NC(=O)c2cc3cccc(CN4CCN(C(=O)C5CCN5C)CC4)c3n2C)cc(C(C)(C)C)cc1NS(C)(=O)=O]

(R)-1-methyl-7-[1-(1-methyl-pyrrolidine-2-carbonyl)-piperidin-4-ylmethyl]-1H-indole-2-carboxylic acid (5-tert-butyl-3-methanesulphonylamino-2-methoxy-phenyl)-amide

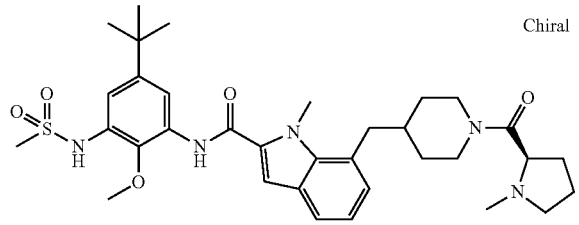 [SMILES: COc1c(NC(=O)c2cc3cccc(CC4CCN(C(=O)[C@H]5CCCN5C)CC4)c3n2C)cc(C(C)(C)C)cc1NS(C)(=O)=O]

(S)-1-methyl-7-[1-(1-methyl-pyrrolidine-2-carbonyl)-piperidin-4-ylmethyl]-1H-indole-2-carboxylic acid (5-tert-butyl-3-methanesulphonylamino-2-methoxy-phenyl)-amide

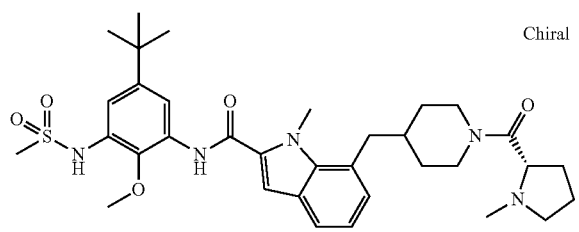 [SMILES: COc1c(NC(=O)c2cc3cccc(CC4CCN(C(=O)[C@@H]5CCCN5C)CC4)c3n2C)cc(C(C)(C)C)cc1NS(C)(=O)=O]

28

7-[4-((2S,4R)-4-hydroxy-1-methyl-pyrrolidine-2-carbonyl)-piperazin-1-ylmethyl]-1-methyl-1H-indole-2-carboxylic acid (5-tert-butyl-3-methanesulphonylamino-2-methoxy-phenyl)-amide

7-[4-((2R,4R)-4-methoxy-1-methyl-pyrrolidine-2-carbonyl)-piperazin-1-ylmethyl]-1-methyl-1H-indole-2-carboxylic acid (5-tert-butyl-3-methanesulphonylamino-2-methoxy-phenyl)-amide

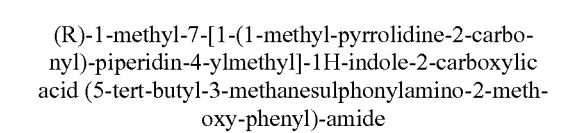

7-[4-((2R,4R)-4-hydroxy-1-methyl-pyrrolidine-2-carbonyl)-piperazin-1-ylmethyl]-1-methyl-1H-indole-2-carboxylic acid (5-tert-butyl-3-methanesulphonylamino-2-methoxy-phenyl)-amide

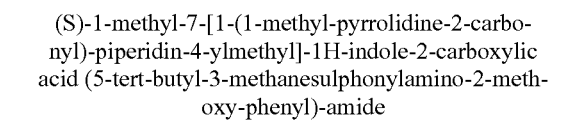

7-[4-((2R,4S)-4-hydroxy-1-methyl-pyrrolidine-2-carbonyl)-piperazin-1-ylmethyl]-1-methyl-1H-indole-2-carboxylic acid (5-tert-butyl-3-methanesulphonylamino-2-methoxy-phenyl)-amide

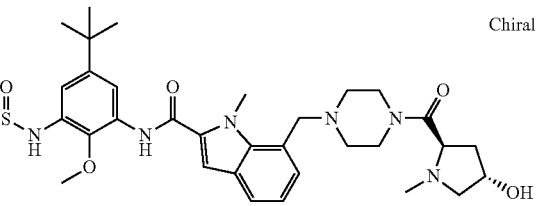

29

7-[4-((2S,4S)-4-hydroxy-1-methyl-pyrrolidine-2-carbonyl)-piperazin-1-ylmethyl]-1-methyl-1H-indole-2-carboxylic acid (5-tert-butyl-3-methanesulphonylamino-2-methoxy-phenyl)-amide

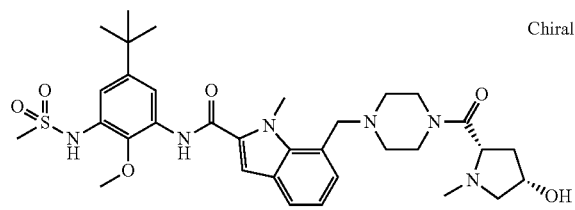 [SMILES: COc1c(NC(=O)c2cc3cccc(CN4CCN(C(=O)[C@@H]5C[C@H](O)CN5C)CC4)c3n2C)cc(C(C)(C)C)cc1NS(C)(=O)=O]

30

1-methyl-7-[4-(2-pyrrolidin-1-yl-propionyl)-piperazin-1-ylmethyl]-1H-indole-2-carboxylic acid-(5-tert-butyl-3-methanesulphonylamino-2-methoxy-phenyl)-amide

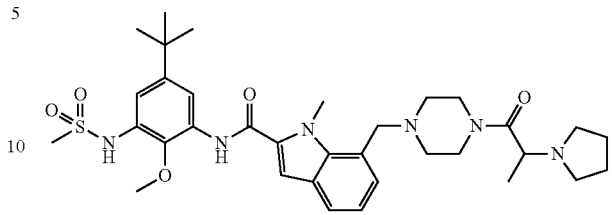

7-{4-[2-(4-isopropyl-piperazin-1-yl)-acetyl]-piperazin-1-ylmethyl}-1-methyl-1H-indole-2-carboxylic acid-(5-tert-butyl-3-methanesulphonylamino-2-methoxy-phenyl)-amide

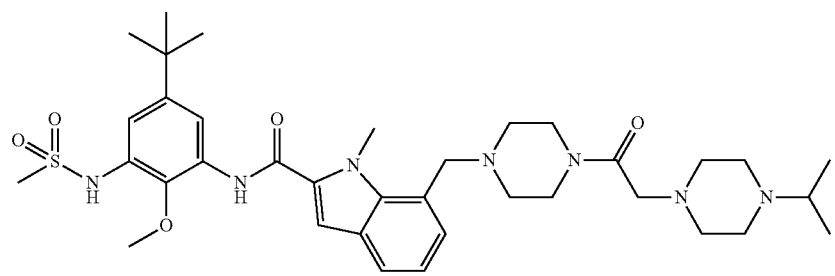

(S)-7-{4-[2-(3-hydroxy-pyrrolidin-1-yl)-acetyl]-piperazin-1-ylmethyl}-1-methyl-1H-indole-2-carboxylic acid-(5-tert-butyl-3-methanesulphonylamino-2-methoxy-phenyl)-amide

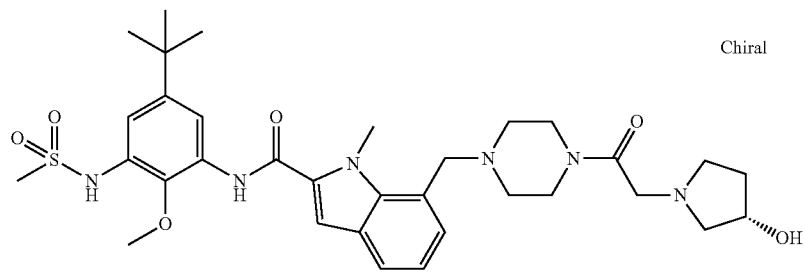 [SMILES: COc1c(NC(=O)c2cc3cccc(CN4CCN(C(=O)CN5CC[C@H](O)C5)CC4)c3n2C)cc(C(C)(C)C)cc1NS(C)(=O)=O]

1-methyl-7-[4-(2-pyrrolidin-1-yl-acetyl)-piperazin-1-ylmethyl]-1H-indole-2-carboxylic acid-(5-tert-butyl-3-methanesulphonylamino-2-methoxy-phenyl)-amide

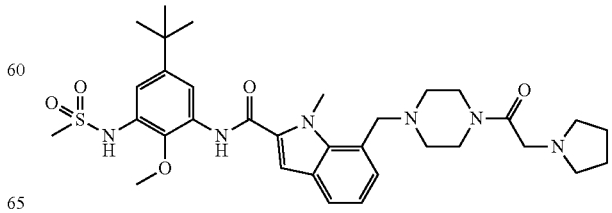

1-methyl-7-{4-[2-(4-methyl-piperazin-1-yl)-acetyl]-piperazin-1-ylmethyl}-1H-indole-2-carboxylic acid-(5-tert-butyl-3-methanesulphonylamino-2-methoxy-phenyl)-amide

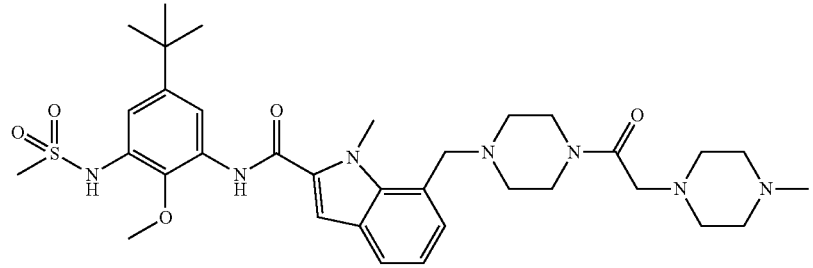

1-methyl-7-[1-((2S)-1-methyl-pyrrolidine-2-carbonyl)-azepan-4-ylmethyl]-1H-indole-2-carboxylic acid-(5-tert-butyl-3-methanesulphonylamino-2-methoxy-phenyl)-amide 1-methyl-7-[4-((2R)-1-methyl-pyrrolidine-2-carbonyl)-[1,4]diazepan-1-ylmethyl]-1H-indole-2-carboxylic acid-(5-tert-butyl-3-methanesulphonylamino-2-methoxy-phenyl)-amide

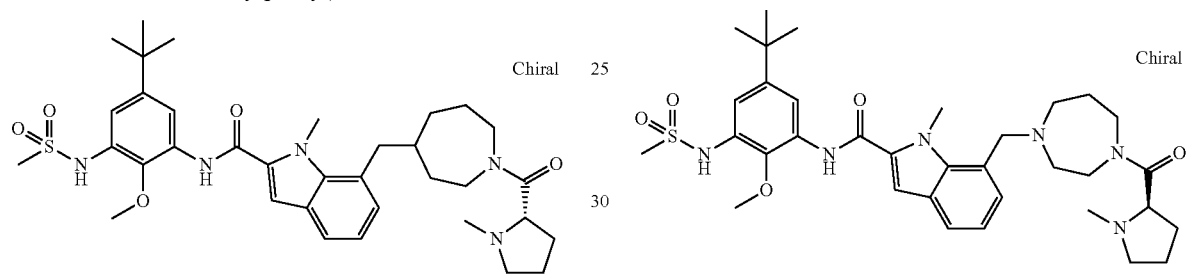

1-methyl-7-[1-(1-methyl-piperidine-4-carbonyl)-azepan-4-ylmethyl]-1H-indole-2-carboxylic acid-(5-tert-butyl-3-methanesulphonylamino-2-methoxy-phenyl)-amide 1-methyl-7-[4-(4-methyl-piperazine-1-carbonyl)-piperidin-1-ylmethyl]-1H-indole-2-carboxylic acid-(5-tert-butyl-3-methanesulphonylamino-2-methoxy-phenyl)-amide

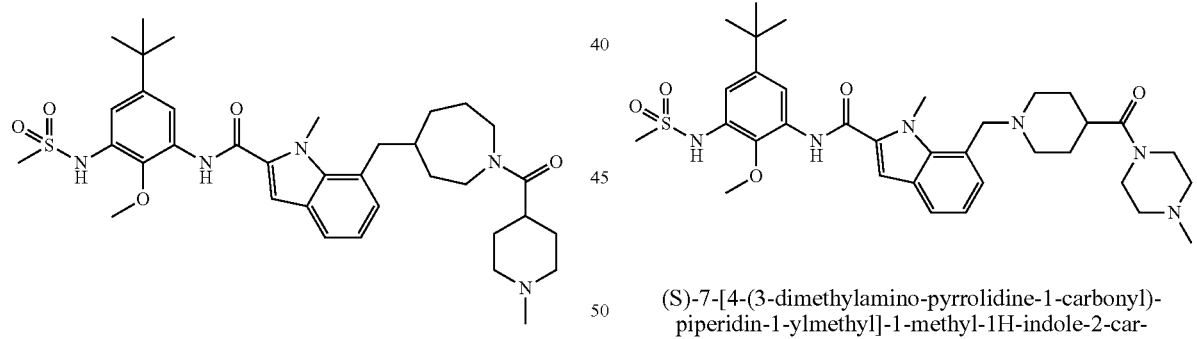

1-methyl-7-[1-((2R)-1-methyl-pyrrolidine-2-carbonyl)-azepan-4-ylmethyl]-1H-indole-2-carboxylic acid-(5-tert-butyl-3-methanesulphonylamino-2-methoxy-phenyl)-amide (S)-7-[4-(3-dimethylamino-pyrrolidine-1-carbonyl)-piperidin-1-ylmethyl]-1-methyl-1H-indole-2-carboxylic acid-(5-tert-butyl-3-methanesulphonylamino-2-methoxy-phenyl)-amide

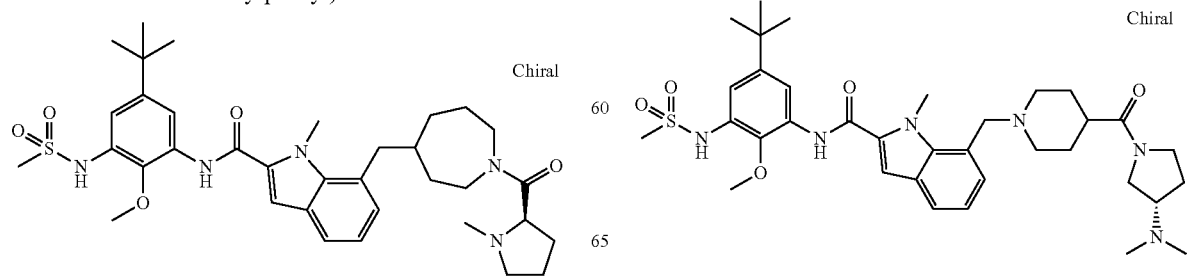

33

(R)-7-[4-(3-dimethylamino-pyrrolidine-1-carbonyl)-piperidin-1-ylmethyl]-1-methyl-1H-indole-2-carboxylic acid-(5-tert-butyl-3-methanesulphonylamino-2-methoxy-phenyl)-amide

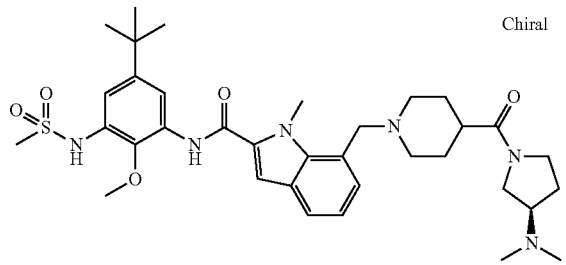

(S)-1-methyl-7-[4-(1-methyl-pyrrolidine-2-carbonyl)-piperazin-1-ylmethyl]-1H-indole-2-carboxylic acid-(3-morpholin-4-yl-phenyl)-amide

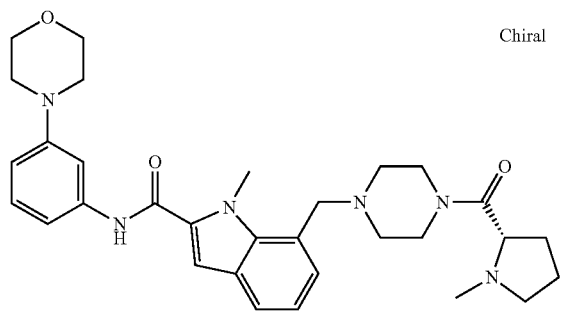 [SMILES: CN1CCC[C@H]1C(=O)N1CCN(Cc2cccc3cc(C(=O)Nc4cccc(N5CCOCC5)c4)n(C)c23)CC1]

(R)-7-[4-(3-dimethylamino-pyrrolidine-1-carbonyl)-piperazin-1-ylmethyl]-1-methyl-1H-indole-2-carboxylic acid (5-tert-butyl-3-methanesulphonylamino-2-methoxy-phenyl)-amide

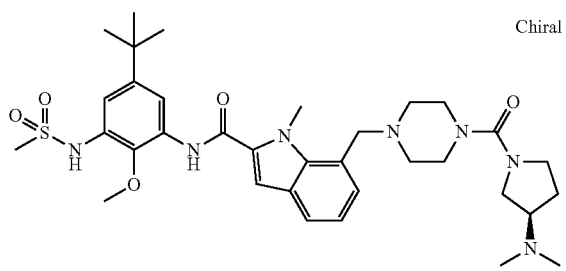

(S)-7-[4-(3-dimethylamino-pyrrolidine-1-carbonyl)-piperazin-1-ylmethyl]-1-methyl-1H-indole-2-carboxylic acid (5-tert-butyl-3-methanesulphonylamino-2-methoxy-phenyl)-amide

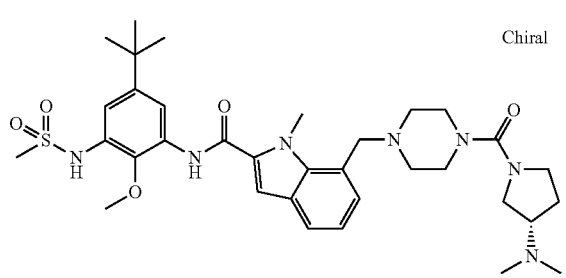

34

7-[4-(azetidine-3-carbonyl)-piperazin-1-ylmethyl]-1-methyl-1H-indole-2-carboxylic acid (5-tert-butyl-3-methanesulphonylamino-2-methoxy-phenyl)-amide

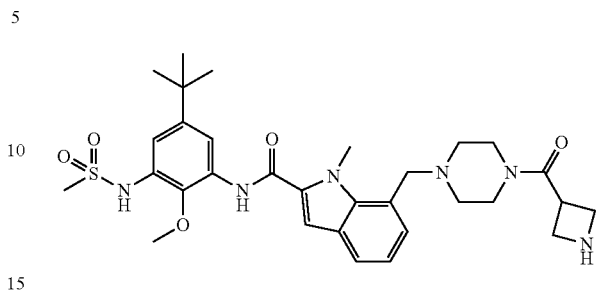

1-methyl-7-[4-(1-methyl-piperidine-3-carbonyl)-piperazin-1-ylmethyl]-1H-indole-2-carboxylic acid (5-tert-butyl-3-methanesulphonylamino-2-methoxy-phenyl)-amide

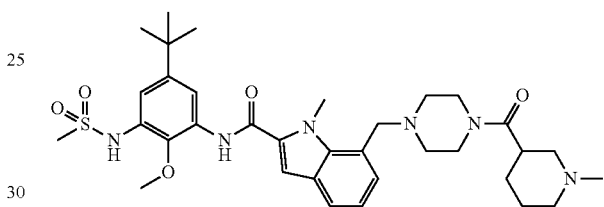

(S)-1-methyl-7-[4-(1-methyl-pyrrolidine-3-carbonyl)-piperazin-1-ylmethyl]-1H-indole-2-carboxylic acid (5-tert-butyl-3-methanesulphonylamino-2-methoxy-phenyl)-amide

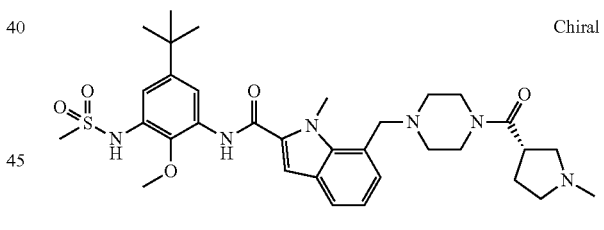

(S)-1-methyl-7-[4-(1-methyl-pyrrolidine-3-carbonyl)[1,4]diazepan-1-ylmethyl]-1H-indole-2-carboxylic acid-(5-tert-butyl-3-methanesulphonylamino-2-methoxy-phenyl)-amide

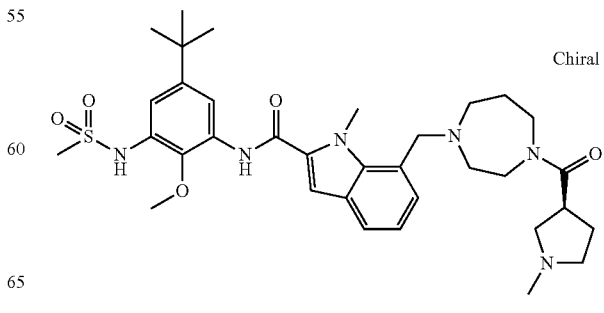

(R)-1-methyl-7-[4-(1-methyl-pyrrolidine-3-carbonyl)-[1,4]diazepan-1-ylmethyl]-1H-indole-2-carboxylic acid-(5-tert-butyl-3-methanesulphonylamino-2-methoxy-phenyl)-amide

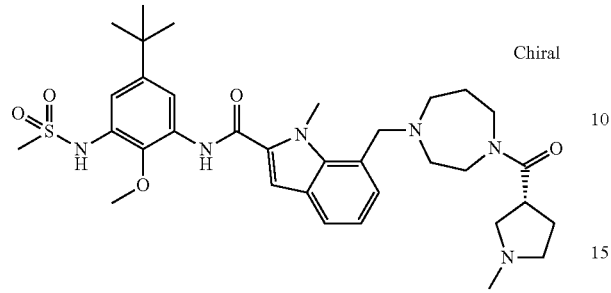

7-{4-[2-(4-dimethylamino-piperidin-1-yl)-acetyl]-piperazin-1-ylmethyl}-1-methyl-1H-indole-2-carboxylic acid-(5-tert-butyl-3-methanesulphonylamino-2-methoxy-phenyl)-amide

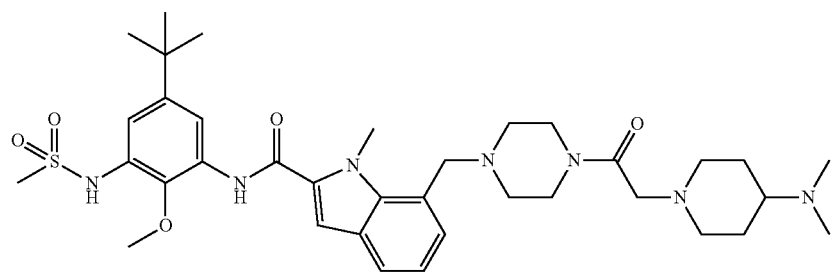

(R)-7-{4-[2-(3-hydroxy-pyrrolidin-1-yl)-acetyl]-piperazin-1-ylmethyl}-1-methyl-1H-indole-2-carboxylic acid-(5-tert-butyl-3-methanesulphonylamino-2-methoxy-phenyl)-amide

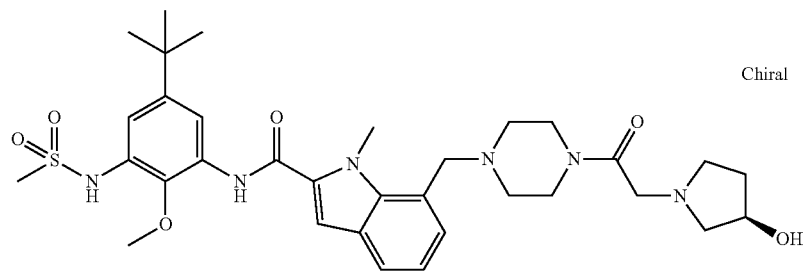 [SMILES: COc1c(NC(=O)c2cc3cccc(CN4CCN(C(=O)CN5CC[C@@H](O)C5)CC4)c3n2C)cc(C(C)(C)C)cc1NS(C)(=O)=O]

(R)-7-{4-[2-(3-dimethylamino-pyrrolidin-1-yl)-
acetyl]-piperazin-1-ylmethyl}-1-methyl-1H-indole-
2-carboxylic acid-(5-tert-butyl-3-methanesulphony-
lamino-2-methoxy-phenyl)-amide

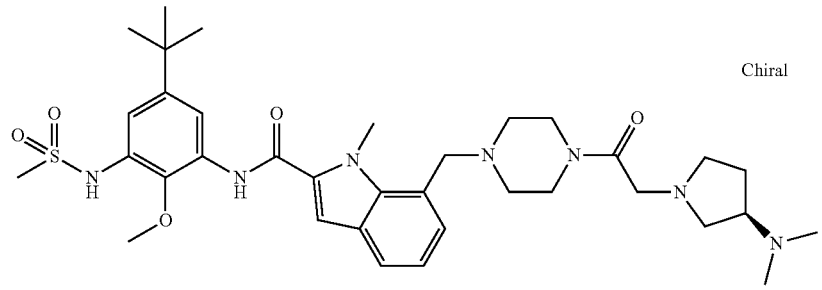

(S)-7-{4-[2-(3-dimethylamino-pyrrolidin-1-yl)-
acetyl]-piperazin-1-ylmethyl}-1-methyl-1H-indole-
2-carboxylic acid-(5-tert-butyl-3-methanesulphony-
lamino-2-methoxy-phenyl)-amide

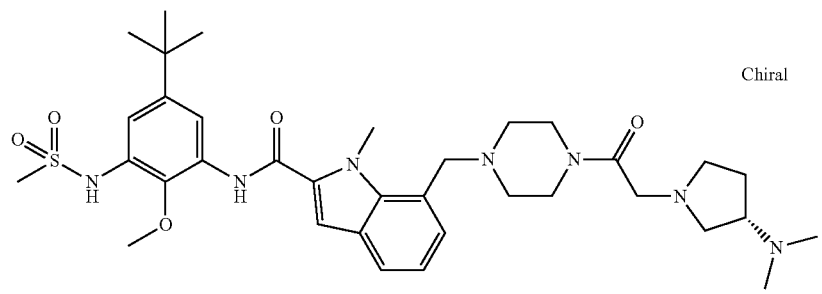

1-methyl-7-[4-(2-piperazin-1-yl-acetyl)-piperazin-1-
ylmethyl]-1H-indole-2-carboxylic acid-(5-tert-butyl-
3-methanesulphonylamino-2-methoxy-phenyl)-
amide

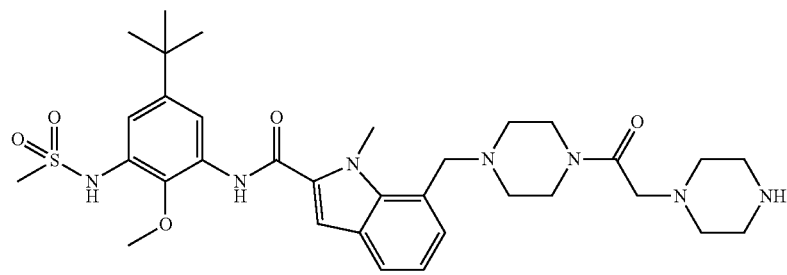 [SMILES: COc1c(NC(=O)c2cc3cccc(CN4CCN(C(=O)CN5CCNCC5)CC4)c3n2C)cc(C(C)(C)C)cc1NS(C)(=O)=O]

1-methyl-7-[4-((2S)-1-methyl-pyrrolidine-2-carbo-
nyl)-[1,4]diazepan-1-ylmethyl]-1H-indole-2-car-
boxylic acid-(5-tert-butyl-3-methanesulphony-
lamino-2-methoxy-phenyl)-amide

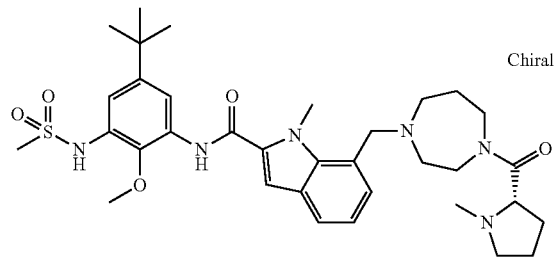 [SMILES: COc1c(NC(=O)c2cc3cccc(CN4CCCN(C(=O)[C@@H]5CCCN5C)CC4)c3n2C)cc(C(C)(C)C)cc1NS(C)(=O)=O]

1-methyl-7-[4-(1-methyl-piperidine-4-carbonyl)[1,4]
diazepan-1-ylmethyl]-1H-indole-2-carboxylic acid-
(5-tert-butyl-3-methanesulphonylamino-2-methoxy-
phenyl)-amide

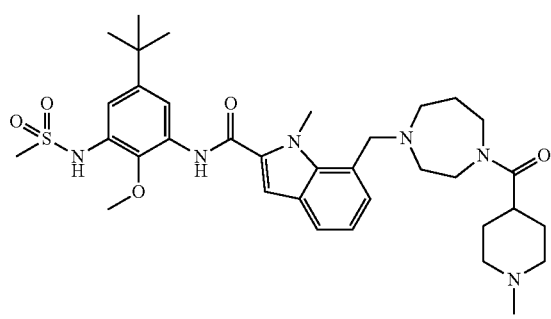 [SMILES: COc1c(NC(=O)c2cc3cccc(CN4CCCN(C(=O)C5CCN(C)CC5)CC4)c3n2C)cc(C(C)(C)C)cc1NS(C)(=O)=O]

(S)-1-methyl-7-[4-(1-methyl-pyrrolidine-2-carbo-
nyl)-piperazin-1-ylmethyl]-1H-indole-2-carboxylic
acid-(5-isobutyl-3-methanesulphonylamino-2-meth-
oxy-phenyl)-amide

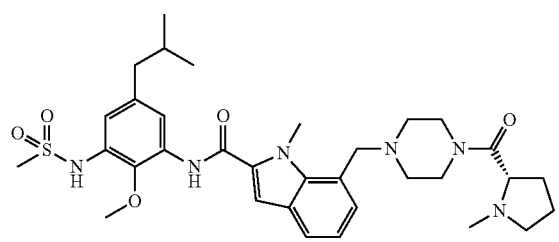

(S)-1-methyl-7-[4-(1-methyl-pyrrolidine-2-carbo-
nyl)-piperazin-1-ylmethyl]-1H-indole-2-carboxylic
acid-[5-tert-butyl-2-methoxy-3-(4-methyl-piperazin-
1-ylmethyl)-phenyl]-amide

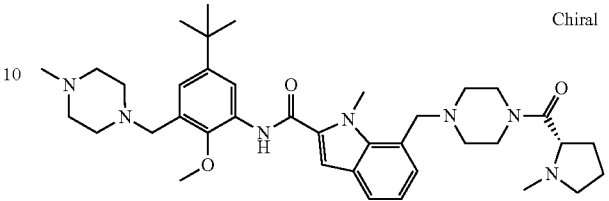

(S)-1-methyl-7-[4-(1-methyl-pyrrolidine-2-carbo-
nyl)-piperazin-1-ylmethyl]-1H-indole-2-carboxylic
acid-{5-tert-butyl-3-[(diisopropylamino)-methyl]-2-
methoxy-phenyl}-amide

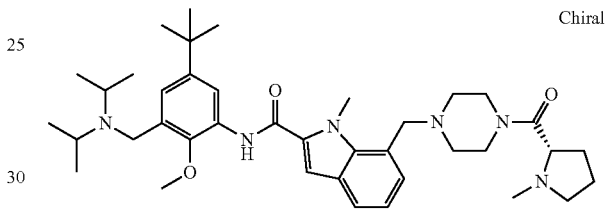

(S)-1-methyl-7-[4-(1-methyl-pyrrolidine-2-carbo-
nyl)-piperazin-1-ylmethyl]-1H-indole-2-carboxylic
acid-(5-tert-butyl-3-diethylaminomethyl-2-methoxy-
phenyl)-amide

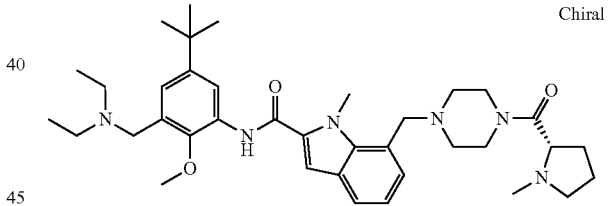

1-methyl-7-[4-((2S)-1-methyl-pyrrolidine-2-carbo-
nyl)-piperazin-1-ylmethyl]-1H-indole-2-carboxylic
acid-[5-tert-butyl-3-(3-dimethylamino-piperidin-1-
ylmethyl)-2-methoxy-phenyl]-amide

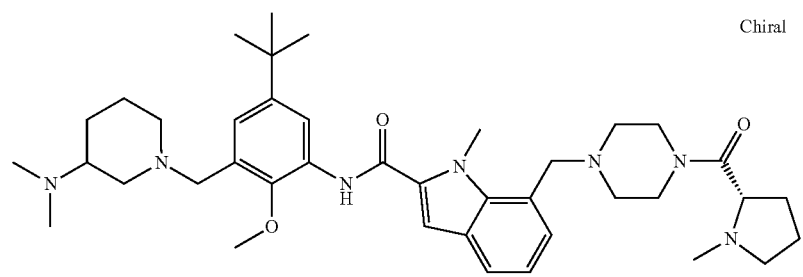 [SMILES: COc1c(CN2CCCC(N(C)C)C2)cc(C(C)(C)C)cc1NC(=O)c1cc2cccc(CN3CCN(C(=O)[C@@H]4CCCN4C)CC3)c2n1C]

1-methyl-7-[4-((2S)-1-methyl-pyrrolidine-2-carbonyl)-piperazin-1-ylmethyl]-1H-indole-2-carboxylic acid-[5-tert-butyl-3-(3-diethylamino-pyrrolidin-1-ylmethyl)-2-methoxy-phenyl]-amide

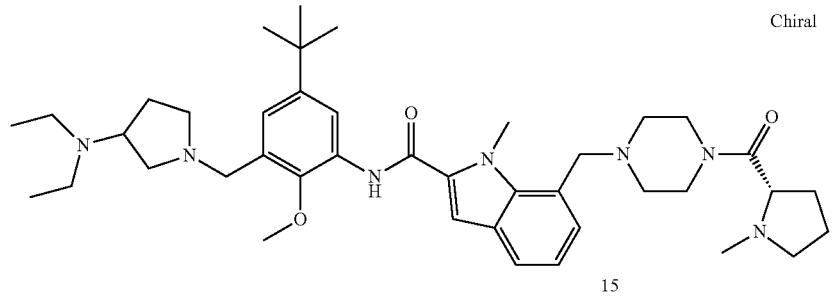

(S)-1-methyl-7-[4-(1-methyl-pyrrolidine-2-carbonyl)-piperazin-1-ylmethyl]-1H-indole-2-carboxylic acid-[5-tert-butyl-3-(4-dimethylamino-piperidin-1-ylmethyl)-2-methoxy-phenyl]-amide

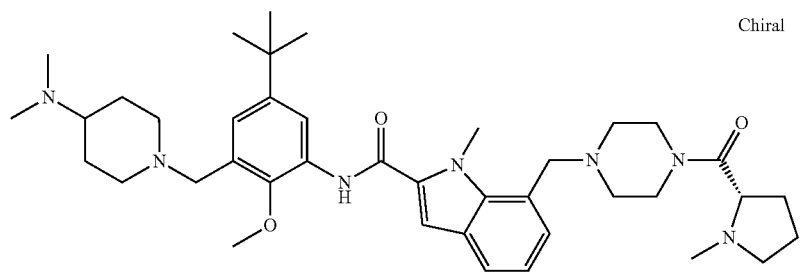 [SMILES: COc1c(CN2CCC(N(C)C)CC2)cc(C(C)(C)C)cc1NC(=O)c1cc2cccc(CN3CCN(C(=O)[C@@H]4CCCN4C)CC3)c2n1C]

(S)-1-methyl-7-[4-(1-methyl-pyrrolidine-2-carbonyl)-piperazin-1-ylmethyl]-1H-indole-2-carboxylic acid-[5-tert-butyl-3-(4-diethylamino-piperidin-1-ylmethyl)-2-methoxy-phenyl]-amide

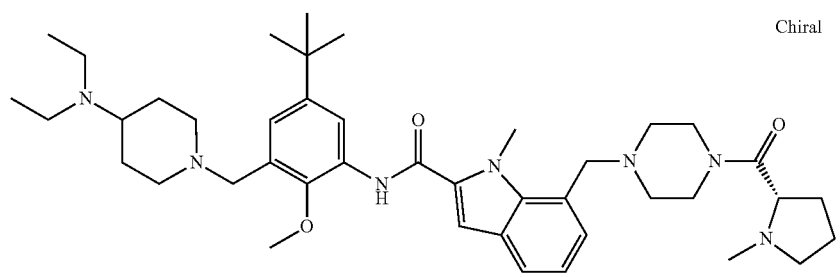 [SMILES: CCN(CC)C1CCN(Cc2cc(C(C)(C)C)cc(NC(=O)c3cc4cccc(CN5CCN(C(=O)[C@@H]6CCCN6C)CC5)c4n3C)c2OC)CC1]

(S)-1-methyl-7-[4-(1-methyl-pyrrolidine-2-carbonyl)-piperazin-1-ylmethyl]-1H-indole-2-carboxylic acid-[5-tert-butyl-3-(4-isopropyl-piperazin-1-ylmethyl)-2-methoxy-phenyl]-amide

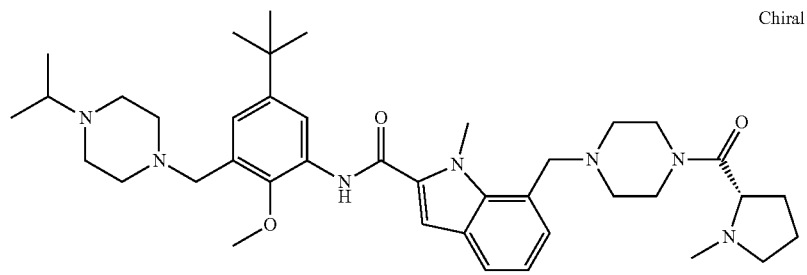 [SMILES: COc1c(CN2CCN(C(C)C)CC2)cc(C(C)(C)C)cc1NC(=O)c1cc2cccc(CN3CCN(C(=O)[C@@H]4CCCN4C)CC3)c2n1C]

43

(S)-1-methyl-7-[4-(1-methyl-pyrrolidine-2-carbonyl)-piperazin-1-ylmethyl]-1H-indole-2-carboxylic acid-(5-tert-butyl-3-cyclopropylcarbamoyl-2-methoxy-phenyl)-amide

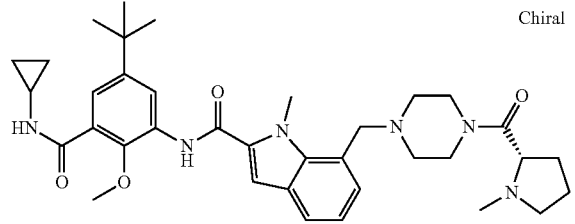 [SMILES: COc1c(NC(=O)c2cc3cccc(CN4CCN(C(=O)[C@@H]5CCCN5C)CC4)c3n2C)cc(C(C)(C)C)cc1C(=O)NC1CC1]

(S)-1-methyl-7-[4-(1-methyl-pyrrolidine-2-carbonyl)-piperazin-1-ylmethyl]-1H-indole-2-carboxylic acid-(5-tert-butyl-3-isopropylcarbamoyl-2-methoxy-phenyl)-amide

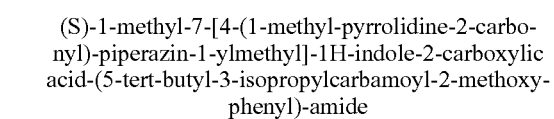

(S)-1-methyl-7-[4-(1-methyl-pyrrolidine-2-carbonyl)-piperazin-1-ylmethyl]-1H-indole-2-carboxylic acid-(5-tert-butyl-3-ethylcarbamoyl-2-methoxy-phenyl)-amide

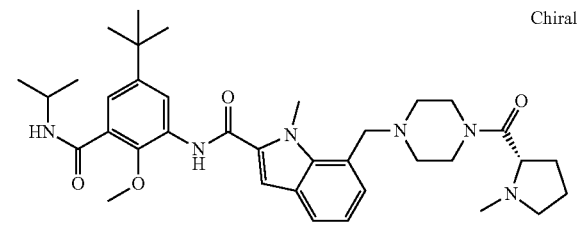 [SMILES: COc1c(NC(=O)c2cc3cccc(CN4CCN(C(=O)[C@@H]5CCCN5C)CC4)c3n2C)cc(C(C)(C)C)cc1C(=O)NC(C)C]

(S)-1-methyl-7-[4-(1-methyl-pyrrolidine-2-carbonyl)-piperazin-1-ylmethyl]-1H-indole-2-carboxylic acid-(5-tert-butyl-2-methoxy-3-methylcarbamoyl-phenyl)-amide

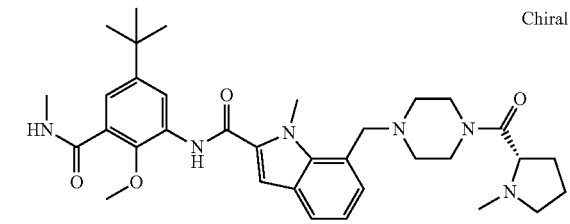 [SMILES: CNC(=O)c1cc(C(C)(C)C)cc(NC(=O)c2cc3cccc(CN4CCN(C(=O)[C@@H]5CCCN5C)CC4)c3n2C)c1OC]

44

(S)-1-methyl-7-[4-(1-methyl-pyrrolidine-2-carbonyl)-piperazin-1-ylmethyl]-1H-indole-2-carboxylic acid-(5-tert-butyl-3-carbamoyl-2-methoxy-phenyl)-amide

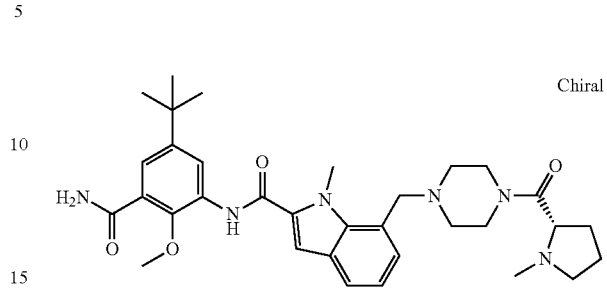

(S)-1-methyl-7-[4-(1-methyl-pyrrolidine-2-carbonyl)-piperazin-1-ylmethyl]-1H-indole-2-carboxylic acid-(5-tert-butyl-3-dimethylcarbamoyl-2-methoxy-phenyl)-amide

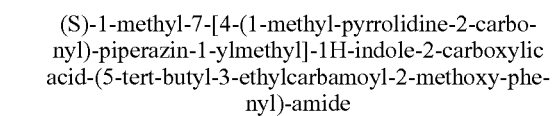

1-methyl-7-[4-((2S)-1-methyl-pyrrolidine-2-carbonyl)-piperazin-1-ylmethyl]-1H-indole-2-carboxylic acid-(5-sec-butyl-3-methanesulphonylamino-2-methoxy-phenyl)-amide

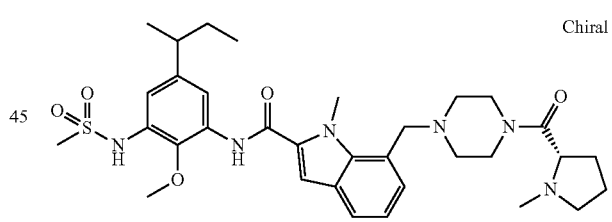

(S)-1-methyl-7-[4-(1-methyl-pyrrolidine-2-carbonyl)-piperazin-1-ylmethyl]-1H-indole-2-carboxylic acid-(5-isopropyl-3-methanesulphonylamino-2-methoxy-phenyl)-amide

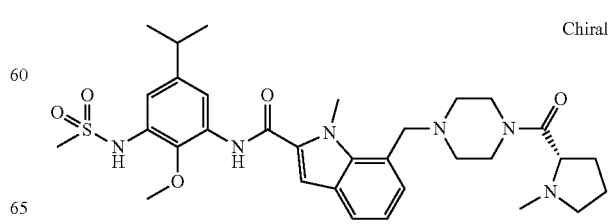

1-methyl-7-[4-((2S)-1-methyl-pyrrolidine-2-carbonyl)-piperazin-1-ylmethyl]-1H-indole-2-carboxylic acid-(5-tert-butyl-3-methanesulphinyl-2-methoxy-phenyl)-amide

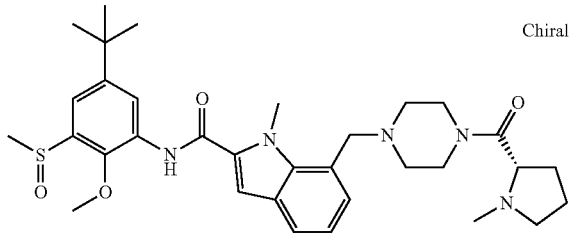 [SMILES: COc1c(NC(=O)c2cc3cccc(CN4CCN(C(=O)[C@@H]5CCCN5C)CC4)c3n2C)cc(C(C)(C)C)cc1S(C)=O]

(S)-1-methyl-7-[4-(1-methyl-pyrrolidine-2-carbonyl)-piperazin-1-ylmethyl]-1H-indole-2-carboxylic acid-(5-tert-butyl-3-methanesulphonyl-2-methoxy-phenyl)-amide

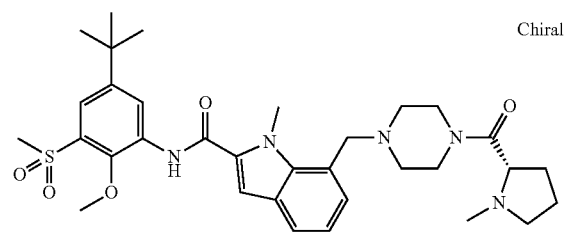 [SMILES: COc1c(NC(=O)c2cc3cccc(CN4CCN(C(=O)[C@@H]5CCCN5C)CC4)c3n2C)cc(C(C)(C)C)cc1S(C)(=O)=O]

(S)-1-methyl-7-[4-(1-methyl-pyrrolidine-2-carbonyl)-piperazin-1-ylmethyl]-1H-indole-2-carboxylic acid-(5-tert-butyl-3-methanesulphonylmethyl-2-methoxy-phenyl)-amide

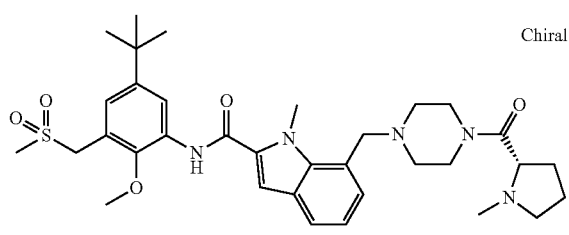 [SMILES: COc1c(CS(C)(=O)=O)cc(C(C)(C)C)cc1NC(=O)c1cc2cccc(CN3CCN(C(=O)[C@@H]4CCCN4C)CC3)c2n1C]

1-methyl-7-[4-((2S)-1-methyl-pyrrolidine-2-carbonyl)-piperazin-1-ylmethyl]-1H-indole-2-carboxylic acid-(5-tert-butyl-3-methanesulphinylmethyl-2-methoxy-phenyl)-amide

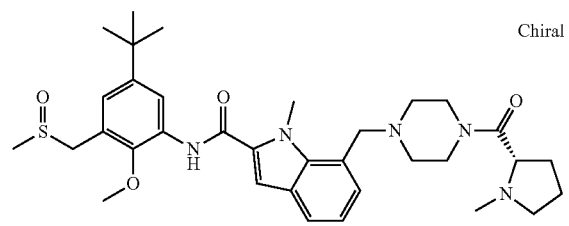 [SMILES: COc1c(CS(C)=O)cc(C(C)(C)C)cc1NC(=O)c1cc2cccc(CN3CCN(C(=O)[C@@H]4CCCN4C)CC3)c2n1C]

(S)-1-methyl-7-[4-(1-methyl-pyrrolidine-2-carbonyl)-piperazin-1-ylmethyl]-1H-indole-2-carboxylic acid-(5-tert-butyl-3-methanesulphonylamino-2-ethoxy-phenyl)-amide

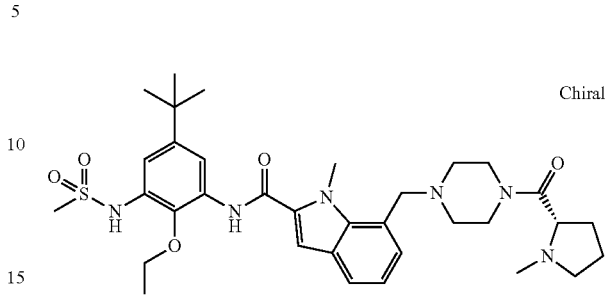

(S)-1-methyl-7-[4-(1-methyl-pyrrolidine-2-carbonyl)-piperazin-1-ylmethyl]-1H-indole-2-carboxylic acid-(5-tert-butyl-2-methoxy-3-propionylamino-phenyl)-amide

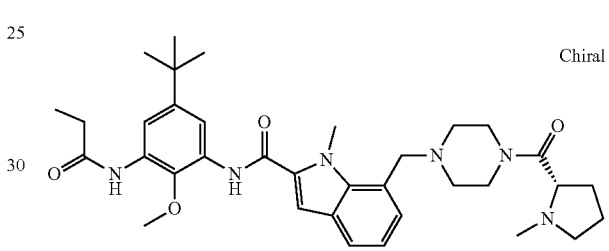

(S)-1-methyl-7-[4-(1-methyl-pyrrolidine-2-carbonyl)-piperazin-1-ylmethyl]-1H-indole-2-carboxylic acid-(5-tert-butyl-3-butyrylamino-2-methoxy-phenyl)-amide

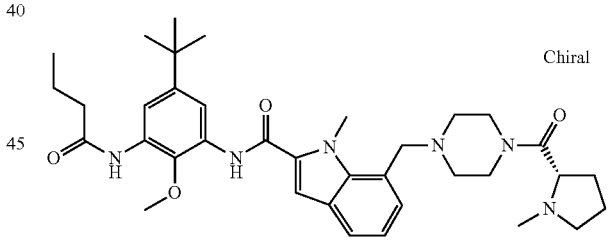

(S)-1-methyl-7-[4-(1-methyl-pyrrolidine-2-carbonyl)-piperazin-1-ylmethyl]-1H-indole-2-carboxylic acid-(3-acetylamino-5-tert-butyl-2-methoxy-phenyl)-amide

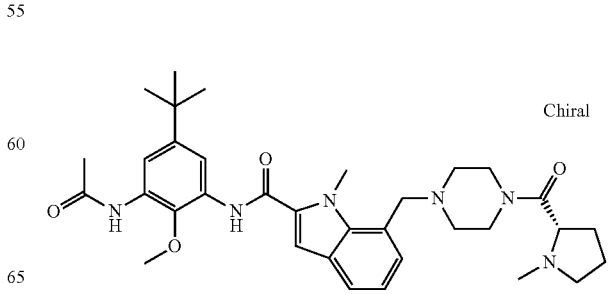

(S)-1-methyl-7-[4-(1-methyl-pyrrolidine-2-carbonyl)-piperazin-1-ylmethyl]-1H-indole-2-carboxylic acid-(5-tert-butyl-3-isobutyrylamino-2-methoxy-phenyl)-amide

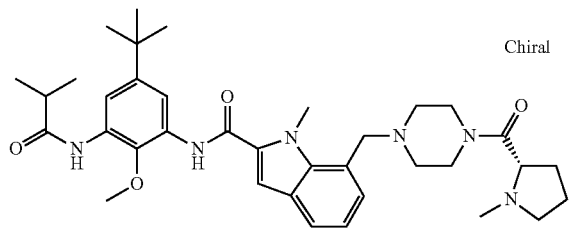 [SMILES: COc1c(NC(=O)c2cc3cccc(CN4CCN(C(=O)[C@@H]5CCCN5C)CC4)c3n2C)cc(C(C)(C)C)cc1NC(=O)C(C)C]

(S)-1-methyl-7-[4-(1-methyl-pyrrolidine-2-carbonyl)-piperazin-1-ylmethyl]-1H-indole-2-carboxylic acid-[5-tert-butyl-3-(cyclopropanecarbonyl-amino)-2-methoxy-phenyl]-amide

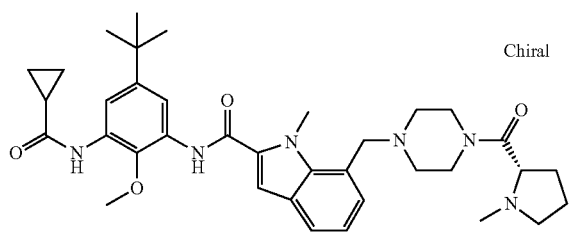 [SMILES: COc1c(NC(=O)c2cc3cccc(CN4CCN(C(=O)[C@@H]5CCCN5C)CC4)c3n2C)cc(C(C)(C)C)cc1NC(=O)C1CC1]

(S)-1-methyl-7-[4-(1-methyl-pyrrolidine-2-carbonyl)-piperazin-1-ylmethyl]-1H-indole-2-carboxylic acid-[5-tert-butyl-2-methoxy-3-(propane-1-sulphonylamino)-phenyl]-amide

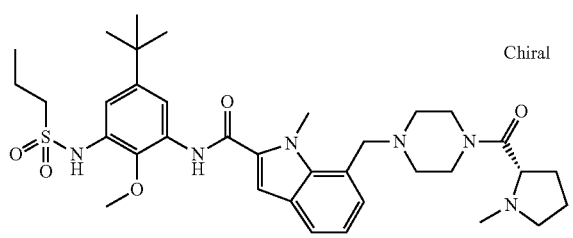 [SMILES: CCCS(=O)(=O)Nc1cc(C(C)(C)C)cc(NC(=O)c2cc3cccc(CN4CCN(C(=O)[C@@H]5CCCN5C)CC4)c3n2C)c1OC]

(S)-1-methyl-7-[4-(1-methyl-pyrrolidine-2-carbonyl)-piperazin-1-ylmethyl]-1H-indole-2-carboxylic acid-(5-tert-butyl-3-cyclopropanesulphonylamino-2-methoxy-phenyl)-amide

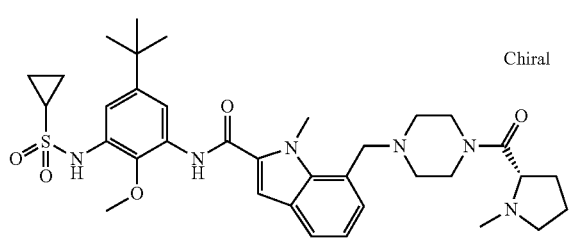 [SMILES: COc1c(NC(=O)c2cc3cccc(CN4CCN(C(=O)[C@@H]5CCCN5C)CC4)c3n2C)cc(C(C)(C)C)cc1NS(=O)(=O)C1CC1]

(S)-1-methyl-7-[4-(1-methyl-pyrrolidine-2-carbonyl)-piperazin-1-ylmethyl]-1H-indole-2-carboxylic acid-(3-methanesulphonylamino-2-methoxy-5-pentafluoroethyl-phenyl)-amide

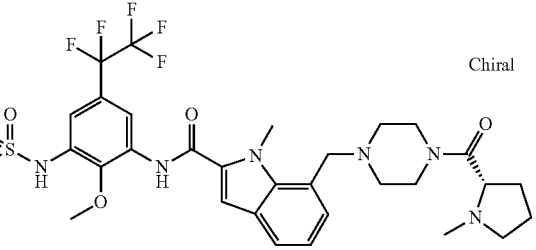

(S)-1-methyl-7-[4-(1-methyl-pyrrolidine-2-carbonyl)-piperazin-1-ylmethyl]-1H-indole-2-carboxylic acid-(3-methanesulphonylamino-2-methoxy-5-trifluoromethyl-phenyl)-amide

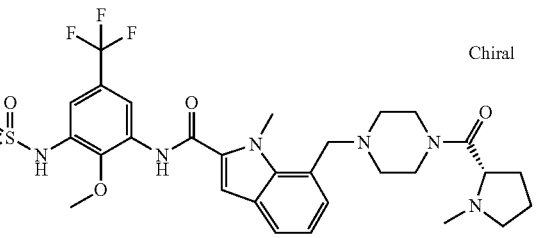

(S)-1-methyl-7-[4-(1-methyl-pyrrolidine-2-carbonyl)-piperazin-1-ylmethyl]-1H-indole-2-carboxylic acid-(5-tert-butyl-3-hydroxymethyl-2-methoxy-phenyl)-amide

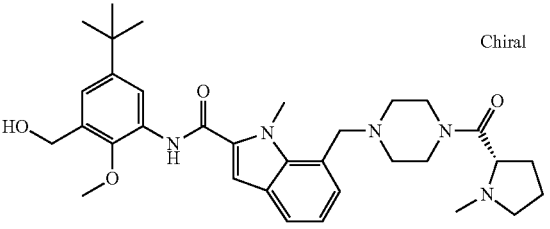 [SMILES: COc1c(CO)cc(C(C)(C)C)cc1NC(=O)c1cc2cccc(CN3CCN(C(=O)[C@@H]4CCCN4C)CC3)c2n1C]

including the tautomers, the stereoisomers and the mixtures thereof.

Terms that are used hereinbefore and hereinafter to describe the compounds according to the invention are defined in more detail below.

The term "substituted", as used herein, denotes that one or more hydrogen atom(s) is or are replaced at a particular atom (of a group/of a residue) by an atom (a group/a residue) selected from a specific group, provided that the possible valency number of the corresponding atom is not exceeded and the substitution leads to a stable compound.

The term halogen denotes an atom selected from among F, Cl, Br and I.

The term heteroatom denotes an atom selected from N, O, S or P. In equivalent manner, heteroalkyl, heteroaryl etc. denote alkyl or aryl structures in which carbon atoms have been replaced by heteroatoms.

The term $C_{1-n}$-alkyl, wherein n may have a value as specified hereinbefore, denotes a saturated, branched or unbranched hydrocarbon group with 1 to n C atoms. Examples of such groups include methyl, ethyl, n-propyl, i-propyl, butyl, i-butyl, sec.-butyl, tert.-butyl, n-pentyl, i-pentyl, neo-pentyl, tert.-pentyl, n-hexyl, i-hexyl, etc.

The term $C_{1-n}$-alkoxy or $C_{1-n}$-alkyloxy denotes a $C_{1-n}$-alkyl-O group, wherein $C_{1-n}$-alkyl is as hereinbefore defined. Examples of such groups include methoxy, ethoxy, n-propoxy, i-propoxy, n-butoxy, i-butoxy, sec.-butoxy, tert.-butoxy, n-pentoxy, i-pentoxy, neo-pentoxy, tert.-pentoxy, n-hexoxy, i-hexoxy etc.

The term $C_{1-n}$-alkylcarbonyl or $C_{1-n}$-alkyl-carbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, i-propylcarbonyl, n-butylcarbonyl, i-butylcarbonyl, sec.-butylcarbonyl, tert.-butylcarbonyl, n-pentylcarbonyl, i-pentylcarbonyl, neopentylcarbonyl, tert.-pentylcarbonyl, n-hexylcarbonyl, i-hexylcarbonyl, etc.

The term $C_{3-n}$-cycloalkyl, where n may assume values as specified hereinbefore, denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3,2,1]octyl, spiro[4,5]decyl, norpinyl, norbornyl, norcaryl, adamantyl, etc. Preferably the term $C_{3-7}$-cycloalkyl includes saturated monocyclic groups. Similarly cyclic groups are represented by the suffix "c-". For example, "c-hexyl" denotes cyclohexyl or "c-$C_{3-n}$-alkyl" denotes a cyclic alkyl group with 3-n ring atoms.

The term $C_{3-n}$-cycloalkylcarbonyl or $C_{3-n}$-cycloalkyl-carbonyl denotes a $C_{3-n}$-cycloalkyl-C(=O) group, wherein $C_{3-n}$-cycloalkyl is as hereinbefore defined.

The term $C_{3-n}$-cycloalkylsulphonyl or $C_{3-n}$-cycloalkyl-sulphonyl denotes a $C_{3-n}$-cycloalkyl-S(=O)$_2$ group, wherein $C_{3-n}$-cycloalkyl is as hereinbefore defined.

The term di-($C_{1-3}$-alkyl)amino includes amino groups that have identical or two different alkyl groups.

If alkyl groups occurring in groups, for example in $R^2$, $R^3$, $R^4$, $R^5$, $R^6$, or $R^7$, may be substituted, for example fluorinated, this includes not only alkyl groups in the groups that directly represent alkyl, but also in other definitions including alkyl groups, such as for example alkyloxy, alkylcarbonyl, alkoxyalkyl, etc. Thus, for example, $R^2$, $R^3$, $R^4$, $R^5$, $R^6$ or $R^7$ in the definition of alkyloxy or alkoxy, in which alkyl groups may be partly or completely fluorinated, also include difluoromethoxy and trifluoromethoxy.

The style used above and hereinafter, in which a bond of a substituent in a phenyl group or a heteroaryl group is shown towards the centre of the phenyl ring or heteroaryl ring, denotes, unless otherwise stated, that this substituent may be bound to any free position of the phenyl or heteroaryl ring bearing an H atom.

As already mentioned hereinbefore, the compounds of general formula I according to the invention and the physiologically acceptable salts thereof have valuable pharmacological properties, particularly an inhibitory effect on the enzyme p38 MAP-kinase.

The biological properties of the new compounds may be tested as follows:

The inhibition of the p38 MAP-kinase mediated signal transmission may be demonstrated for example by an enzymatic assay. In this, the amount of a substrate phosphorylated by the kinase is quantified. The test is carried out as follows:

Enzymatic Assay:

The kinase reaction is carried out in the presence of HEPES (20 mM, pH 7), MgCl2 (10 mM), DTT (1 mM) and TWEEN20 (0.01%). First, dimethylsulphoxide or inhibitor (final concentration: 1 μM) dissolved in dimethylsulphoxide are placed in a reaction vessel. Then the activated p38 MAP-kinase (final concentration 1 nM) is added and the mixture is incubated for 4 h at ambient temperature. Then a mixture of substrate (GST-tagged ATF2) and ATP is added and everything is incubated together for a further hour (final concentration ATP: 100 μM; final concentration ATF2: 10 nM).

The concentration of phosphorylated ATF2 is quantified by chemoluminescence-induced light emission. For this, a glutathione donor bead (final concentration: 5 μg/ml) which binds to the gluthathione on the ATF2 and phospho-ATF2 antibodies are added to the reaction mixture (final concentration: 3 nM; this binds the phosphate group added by the kinase reaction) to which a Protein A Acceptor Bead (final concentration: 5 μg/ml) binds. These components are dissolved in a buffer which contains 20 mM HEPES pH 7.0, 200 mM NaCL, 80 mM EDTA as well as 0.3% BSA. This reaction mixture is incubated in the dark for 1 hour at ambient temperature. When these beads come physically close, visible light is emitted which is measured in a photometer at 520-620 nm.

Evaluation:

To determine the inhibitory activity of the compounds according to the invention a calculation is made to determine the percentage by which the kinase activity is inhibited at a fixed inhibitor concentration of 1 μM. The maximum activity is determined by non-inhibited kinase. The minimum activity or nonspecific background activity is determined using a reaction mixture without kinase. The compounds of general formula I according to the invention exhibit inhibitory values of >50%, preferably >90%, for example.

Table 2 summarises the degree of inhibition of the enzyme p38 MAP-kinase—as described hereinbefore—mediated by the compounds according to the invention detailed in the section "Preparation of the final compounds".

Determining the Solubility:

Saturated solutions are prepared in suitable well dishes by adding 0.75 ml of a McIlvaine buffer (pH 7.4) to the well in question containing 0.75 mg of solid of an active substance. The wells are shaken for 2 hours and then filtration is carried out through a suitable filter membrane (typically polytetrafluoroethylene with a pore size of 0.45 μm). Filter absorption is prevented by discarding the first few drops of filtrate. The amount of active substance dissolved is determined by UV spectroscopy.

Determining the cyp2C9 Activity:

The inhibition of the cytochrome P450 2C9-isoenzyme catalysed O-demethylation of [O-methyl-$^{14}$C]-naproxen by the test compound at 37° C. with human recombinant cytochrome P450 2C9 is measured.

The assay is carried out in a robot system with 96-well plates. The final incubation volume is 200 μl of TRIS-Puffer (0.1 M), magnesium chloride (5 mM), recombinant protein (40 pmol/ml), $^{14}$C-labelled naproxen (80 μM) and the test compound in one of 4 concentrations (50 μM, 10 μM, 2 μM and 0.4 μM) as a duplicate in each case. After a short preincubation period the reactions are started by the addition of the cofactor (NADPH, 1 mM) and ended after 15 min by the addition of 50 μl of a 10% aqueous trichloroacetic acid solution. One aliquot of the incubate is transferred onto a 96-well solid phase extraction plate and extracted. The $^{14}$C-formaldehyde formed during the reaction is not retained on the solid phase extraction plate and is thus separated from the unmetabolised substrate by washing the solid phase extraction plate with water. One aliquot of the eluate is transferred into a well plate suitable for liquid scintillation. The rate of formation of $^{14}C$-formaldehyde in these incubations is compared with a control that does not contain any test compound. The $IC_{50}$ is determined by the least squares method using the following formula:

control activity=(100% control activity/(1+$(I/IC_{50})$ S))–B where
I=Inhibitor concentration
S=Pitch
B=Background activity When the inhibition of the reaction is >50% even at the lowest concentration of the test compound, the $IC_{50}$ is given as <0.4 μM.

Table 2. Inhibitory effect of compounds of general formula I according to the invention on the enzyme p38 MAP-kinase at an inhibitor concentration of 1 μM

TABLE 2

| Example | p38 (% Inh @ 1 μM) | CYP 2C9 IC50 (μM) | solubility at pH 7.4 (mg/ml) |
|---|---|---|---|
| 1(1) | 99.6 | 2.13 | 0.340 |
| 2 | 99.1 | 1.29 | 0.010 |
| 2(1) | 99.0 | 0.88 | 0.028 |
| 3 | 99.0 | 1.26 | 0.085 |
| 1(2) | 98.5 | 1.34 | 0.059 |
| 1(3) | 99.1 | 1.04 | 0.160 |
| 1(4) | 99.2 | 0.89 | 0.100 |
| 1(5) | 99.0 | 1.63 | 0.670 |
| 1(6) | 99.3 | 1.43 | 0.560 |
| 1 | 98.9 | 2.42 | 0.360 |
| 4 | 99.4 | 0.44 | 0.078 |
| 1(7) | 98.9 | 0.78 | 0.170 |
| 1(8) | 98.9 | 1.02 | 0.084 |
| 1(9) | 98.9 | 1.12 | 0.440 |
| 5 | 98.6 | 1.15 | 0.620 |
| 1(10) | 99.6 | 0.41 | 0.043 |
| 1(11) | 99.2 | 0.41 | 0.045 |
| 1(12) | 98.9 | 1.55 | 0.140 |
| 1(14) | 99.1 | 0.63 | 0.120 |
| 1(13) | 98.7 | 0.56 | 0.040 |
| 1(19) | 98.5 | 3.59 | 0.098 |
| 1(18) | 98.0 | 0.84 | 0.080 |
| 1(17) | 99.1 | 0.99 | 0.046 |
| 6(3) | 98.5 | 2.93 | 0.910 |
| 7 | 98.7 | 5.32 | 0.110 |
| 1(16) | 98.4 | 20.42 | 0.620 |
| 6(2) | 98.9 | 0.70 | >1.000 |
| 6(1) | 99.2 | 0.47 | 0.047 |
| 6 | 98.6 | 3.43 | >1.000 |
| 1(15) | 98.9 | 1.21 | 0.073 |
| 11(4) | 99.5 | 0.46 | 0.043 |
| 11 | 92.0 | 5.90 | 0.450 |
| 11(3) | 98.6 | 0.78 | 0.160 |
| 11(7) | 99.3 | 0.41 | 0.110 |
| 13(1) | 99.3 | 0.67 | 0.012 |
| 12(4) | 96.4 | 0.65 | 0.059 |
| 12(3) | 97.3 | 2.15 | 0.091 |
| 12(2) | 98.2 | 3.46 | 0.630 |
| 12(1) | 87.7 | 0.96 | 0.044 |
| 12 | 97.9 | 0.50 | 0.660 |
| 13 | 99.1 | 0.50 | 0.017 |
| 15 | 99.4 | 2.54 | 0.230 |
| 10(4) | 99.1 | 0.44 | 0.370 |
| 10(3) | 99.3 | 1.60 | 0.590 |
| 10(2) | 99.4 | 0.46 | 0.390 |
| 10(1) | 99.1 | 1.29 | 0.380 |
| 10 | 99.1 | 1.32 | 0.420 |
| 9(2) | 98.2 | 7.76 | 0.860 |
| 9(1) | 95.8 | 6.70 | 0.570 |

TABLE 2-continued

| Example | p38 (% Inh @ 1 μM) | CYP 2C9 IC50 (μM) | solubility at pH 7.4 (mg/ml) |
|---|---|---|---|
| 11(2) | 18.0 | 10.40 | >1.000 |
| 11(1) | 13.2 | 2.65 | >1.000 |
| 9 | 98.8 | 10.98 | >1.000 |
| 9(7) | 98.8 | 44.69 | 0.880 |
| 9(6) | 97.7 | 10.42 | 0.470 |
| 9(5) | 97.5 | 6.88 | 0.490 |
| 9(4) | 98.0 | 8.11 | 0.690 |
| 9(3) | 98.9 | 6.84 | 0.700 |
| 1(26) | 19.8 | 2.39 | 0.049 |
| 1(25) | 35.4 | 7.91 | 0.048 |
| 11(3) | 99.0 | 0.87 | 0.680 |
| 11(3) | 98.7 | 0.56 | >1.000 |
| 1(24) | 54.2 | 2.47 | 0.036 |
| 14(1) | 97.9 | 5.27 | 0.097 |
| 14 | 98.8 | 1.43 | 0.027 |
| 11(6) | 99.6 | 3.18 | 0.680 |
| 11(5) | 99.6 | 2.34 | 0.053 |
| 8(2) | 99.5 | 5.77 | 0.120 |
| 1(27) | 79.6 | 16.40 | 0.550 |
| 8(1) | 98.1 | 6.48 | 0.120 |
| 8 | 97.3 | 1.67 | 0.280 |
| 1(23) | 97.0 | 1.77 | 0.280 |
| 1(22) | 99.1 | 1.54 | 0.042 |
| 1(21) | 98.9 | 4.02 | 0.045 |
| 1(20) | 99.1 | 2.59 | 0.124 |
| 5(1) | 94.9 | 2.04 | 0.170 |
| 5(2) | 98.0 | 0.99 | 0.160 |
| Vc | 99.1 | <0.4 (BC) | <0.001 |
| Va | 98.8 | <0.4 (BC) | <0.001 |
| Vb | 99.1 | <0.4 (BC) | <0.001 |

Indications

In respect of their ability to inhibit the p38 MAP-kinase activity, the compounds of general formula I according to the invention and the corresponding pharmaceutically acceptable salts thereof are theoretically suitable for treating and/or preventatively treating all those conditions or ailments that are affected by an inhibition of the p38 MAP-kinase activity. The compounds according to the invention are suitable e.g. for improving an abnormal cytokine level mediated by p38 MAP-kinase, particularly for regulating the overproduction of the cytokines IL-1, IL-4, IL-8 and TNF-α. Therefore, the compounds according to the invention may be used for the prevention or treatment of diseases, particularly respiratory complaints, gastrointestinal diseases or complaints, inflammatory diseases (particularly of the airways, joints, skin or eyes), autoimmune diseases, destructive disorders of the bones, proliferation disorders, disorders of angiogenesis, neurodegenerative diseases, infectious diseases and viral diseases as well as diseases of the peripheral or central nervous system.

Preferential mention should be made of the prevention and treatment of diseases of the airways and of the lung which are accompanied by increased mucus production, inflammations and/or obstructive diseases of the airways, such as e.g. acute, allergic or chronic bronchitis, chronic obstructive bronchitis (COPD), cough, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, and alpha1-antitrypsin deficiency.

Also deserving special mention is the treatment of inflammatory diseases of the gastrointestinal tract, such as e.g. acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct and gall bladder, e.g. gallstones and conglomerates, inflammatory diseases of the joints such as rheumatoid arthritis or inflammatory diseases of the skin (e.g. psoriasis) and eyes.

Preferential mention should also be made of the prevention and treatment of diseases of the peripheral or central nervous system, such as e.g. Alzheimer's disease, Parkinson's disease, acute and chronic multiple sclerosis, acute and chronic pain as well as injuries to the brain caused by stroke, hypoxia or craniocerebral trauma.

The compounds according to the invention, including the physiologically acceptable salts thereof, are most particularly suitable for the prophylaxis or treatment of respiratory complaints, particularly COPD and asthma.

Combinations

By reason of their biological properties the compounds of general formula I according to the invention may be used on their own or in conjunction with other active substances of formula I according to the invention. Optionally the compounds of formula I may also be used in combination with one or more other pharmacologically active substances. For the treatment of respiratory complaints the compounds of general formula I according to the invention may be used on their own or in conjunction with other respiratory therapeutic agents, such as e.g. secretolytics (e.g. ambroxol, N-acetylcysteine, EGFR-inhibitors), broncholytics (e.g. tiotropium or ipratropium or fenoterol, salmeterol, salbutamol) and/or anti-inflammatories [e.g. theophylline or glucocorticoids (such as e.g., prednisolone, prednisone, butixocortpropionate, beclomethasone budesonide, fluticasone, mometasone, ciclesonide, dexamethasone, betamethasone), leukotrien receptor inhibitors or leukotriene biosynthesis inhibitors, antihistamines, PDE4 inhibitors (such as e.g. enprofyllin, theophyllin, roflumilast, ariflo (cilomilast), tofimilast, pumafentrin, lirimilast, arofyllin, atizoram)]. Moreover, these compounds may also be combined with non-steroidal antiinflammatory substances ("NSAID"; such as e.g. ibuprofen, celecoxib and rofecoxib), dopamine agonists, statins, antiviral active substances such as abacavir, PI3-kinase inhibitors, MRP4-inhibitors, PAF-antagonists and antiproliferative agents (e.g. methotrexats, leflunomide, FK506 (tacrolimus, prograf)). The combinations that contain one or more of the above mentioned compounds may be used together or successively, for simultaneous, sequential or separate administration. These compounds may be administered, either on their own or in combination with other active substances, by intravenous, subcutaneous, intramuscular, intraperitoneal, intranasal, inhalative, transdermal or oral route, while aerosol formulations are particularly suitable for inhalation.

For treating diseases in the region of the gastrointestinal tract, the compounds of general formula I according to the invention may also be administered on their own or in conjunction with substances having an effect on motility or secretion. These combinations may be administered either simultaneously or sequentially.

Moreover, the compounds according to the invention may be used in tumour therapy in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. These combinations may be administered either simultaneously or sequentially.

Formulations

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 0.01 to 100 mg/kg, preferably 0.01 to 10 mg/kg, by inhalation, and from 0.01 to 100 mg/kg, preferably 0.01 to 10 mg/kg by oral route, in each case administered 1 to 4 times a day. For this purpose, the compounds of formula (I) prepared according to the invention, optionally in conjunction with other active substances, may be formulated together with one or more inert conventional carriers, preservatives and/or diluents, e.g. with glucose, arabinose, lactose, saccharose, maltose, dextrane, maize starch, lactose, sucrose, microcrystalline cellulose, sorbitol, mannitol, xylitol, magnesium stearate, polyvinylpyrrolidone, citric acid, tartaric acid, malic acid, ascorbic acid, maleic acid, succinic acid, fumaric acid, acetic acid, sodium chlodie, calcium carbonate, water, water/ethanol, water/glycerol, water/sorbitol, water/polyethylene glycol, propylene glycol, cetylstearyl alcohol, carboxymethylcellulose or fatty substances such as hard fat or suitable mixtures thereof, cetylpyridinium chloride, benzalkonium chloride, benzoic acid, sodium benzoate, surfactants such as soya lecithin, oleic acid, polysorbate or polyvinylpyrrolidone, to produce conventional galenic preparations such as plain or coated tablets, capsules, powders, solutions, suspensions, suppositories, emulsions, inhalable powders or aerosols. To produce propellant-containing inhalation aerosols, propellent gases or mixtures of propellent gases such as e.g. n-propane, n-butane, isobutane, halogenated hydrocarbons such as fluorinated derivatives of methane, ethane [e.g. 1,1,1,2-tetrafluoroethane (TG134a)], propane [e.g. 1,1,1,2,3,3,3-heptafluoropropane(TG227)], butane, cyclopropane or cyclobutane are used.

The dosage for the above-mentioned combination partners is expediently ⅕ of the normally recommended minimum dose to 1/1 of the normally recommended dose.

Therefore, in another aspect this invention relates to the use of a compound according to the invention or a physiologically acceptable salt of such a compound in combination with at least one of the active substances described as a combination partner for preparing a medicament that is suitable for the treatment or prevention of diseases or conditions that can be influenced by inhibition of the enzyme p38 MAP-kinase. Preferably, this means a respiratory tract disease, particularly one of the above-mentioned diseases or conditions, most particularly COPD or asthma.

The use of the compound according to the invention, or a physiologically acceptable salt thereof, in combination with another active substance may take place simultaneously or at staggered times, but especially close together in time. When they are used simultaneously, the two active substances are given to the patient together; while if they are administered at staggered times the two active substances are given to the patient successively within a time span of less than or equal to 12 hours, but particularly less than or equal to 6 hours.

Consequently, the invention further relates to a medicament that comprises a compound according to the invention or a physiologically acceptable salt of such a compound as well as at least one of the active substances described hereinbefore as combination partners, optionally together with one or more inert carriers, preservatives and/or diluents.

The compound according to the invention, or a physiologically acceptable salt, and the additional active substance to be combined therewith may be present together in one formulation, e.g. a tablet, capsule, inhalable powder or aerosol, or separately in two identical or different formulations, e.g. as a so-called kit-of-parts.

Preparation Processes

The compounds according to the invention may be obtained using methods of synthesis that are known in principle. Preferably the compounds may be obtained using the methods of preparation according to the invention explained in more detail hereinafter.

The compounds of general formula I may be prepared according to process a) according to the invention as illustrated in Scheme 1, wherein Ar, m, T, $R^2$, p, and $R^1$ are as hereinbefore defined, A denotes nitrogen, $R^{13}$ denotes Br or I and denotes hydrogen, methyl or ethyl, starting from compounds of general formula V.

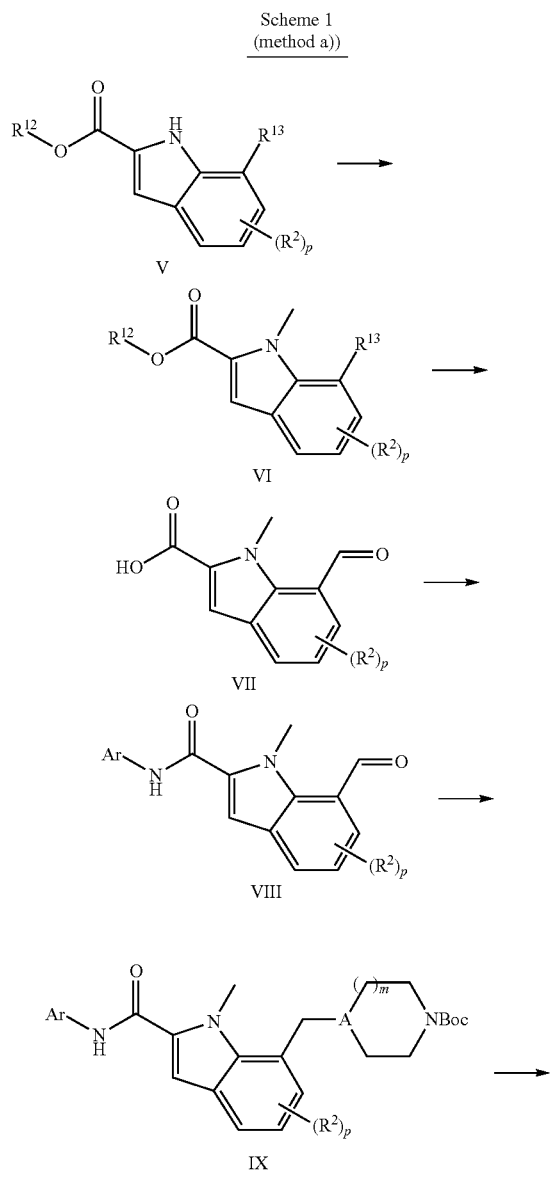

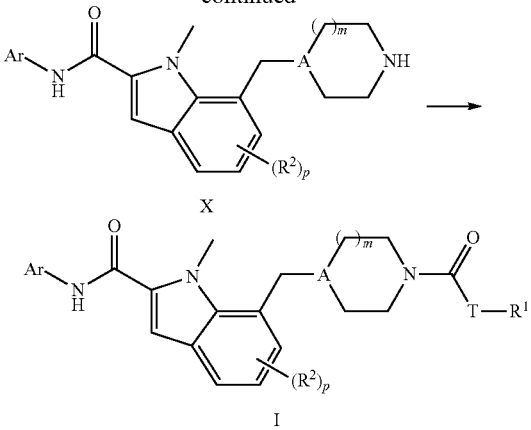

The compound of general formula V wherein $R^{13}$ denotes Br and $R^{12}$ denotes ethyl is described in *J. Org. Chem.* 2007, 72, 2978-2987. Compounds of general formula V may be converted into compounds of general formula VI by reacting with a methylating agent such as for example iodomethane, bromomethane, dimethylsulphate or dimethyl carbonate. The reaction is carried out in the presence of a base such as sodium hydride, potassium hydride, potassium-tert.-butoxide, sodium-tert.-butoxide, 1,4-diazabicyclo[2,2,2]octane, 1,8-diazabicyclo[5.4.0]undec-7-ene, potassium carbonate or caesium carbonate in a solvent such as tetrahydrofuran, 1,4-dioxane, acetonitrile, N,N-dimethylformamide or N-methylpyrrolidone at temperatures between −30° C. and 150° C., but preferably between 0° C. and 100° C. If compounds of general formula V wherein $R^{12}$ denotes hydrogen are used in this reaction, compounds of general formula VI are formed wherein $R^{12}$ denotes methyl. Compounds of general formula VI wherein $R^{12}$ denotes methyl or ethyl are converted into compounds of general formula VI wherein $R^{12}$ denotes hydrogen. This reaction is carried out hydrolytically in an aqueous solvent, e.g. in water, methanol/water, isopropanol/water, acetic acid/water, tetrahydrofuran/water or 1,4-dioxane/water, but preferably in methanol/water, in the presence of an acid such as trifluoroacetic acid, hydrochloric acid or sulphuric acid or in the presence of an alkali metal base such as lithium hydroxide, sodium hydroxide or potassium hydroxide, but preferably sodium hydroxide, or aprotically, e.g. in the presence of iodotrimethylsilane, at temperatures between 0 and 120° C., preferably at temperatures between 10 and 100° C.

Compounds of general formula VI wherein $R^{12}$ denotes hydrogen are then converted into compounds of general formula VII. In a halogen-metal exchange by reaction with n-butyllithium, sec.-butyllithium, tert.-butyllithium or isopropylmagnesium chloride/lithium chloride complex in an inert solvent such as for example diethyl ether, tetrahydrofuran or 1,4-dioxane, at temperatures between −90° C. and 0° C., but preferably between −78° C. and −20° C., optionally after the prior addition of a base such as sodium hydride or potassium hydride at temperatures between −50° C. and 50° C., first of all an organometallic species is produced. This is then reacted with an electrophile such as N,N-dimethylformamide, N-formylpiperidine or N-formylpyrrolidine at temperatures between −78° C. and −20° C. to form compounds of general formula VII.

Carboxylic acids of general formula VII are then reacted with an aniline to form the anilide of general formula VIII. For this, the carboxylic acid is activated in situ by the addition of N,N'-diisopropylcarbodiimide, N,N'-dicyclohexylcarbodiimide, N-(3-dimethylaminopropyl)-N'-ethyl-carbodiimide, O-(benzotriazol-1-yl)-N,N,N',N'-tetramethyluronium-tetrafluoroborate (TBTU), O-(benzotriazol-1-yl)-N,N,N',N'-tetramethyluronium-hexafluorophosphate (HBTU), O-(7-azabenzotriazol-1-yl)-N,N,N',N'-tetramethyluronium-hexafluorophosphate (HATU), (benzotriazol-1-yloxy)-tris-(dimethylamino)-phosphonium-hexafluorophosphate (BOP), (benzotriazol-1-yloxy)-tripyrrolidinophosphonium-hexafluorophosphate (PyBOP) or n-propylphosphonic anhydride and reacted in a dipolar aprotic solvent such as for example N,N-dimethylformamide, dimethylacetamide, tetrahydrofuran, acetonitrile, N-methylpyrrolidone or dimethylsulphoxide, but preferably in N,N-dimethylformamide or N-methylpyrrolidone with an aniline in the presence of a base such as triethylamine, N,N-diisopropyl-N-ethyl-amine and optionally a catalyst such as 4-N,N-dimethylaminopyridine at temperatures between −20° C. and 80° C., but preferably between 0° C. and 50° C.

Alternatively the carboxylic acid is first converted into an acid chloride. For this, the carboxylic acid is reacted with thionyl chloride, phosphorus oxychloride or oxalyl chloride optionally in a solvent such as toluene, benzene or dichloromethane at temperatures between 0° C. and 120° C. The acid chloride thus obtained is reacted with the aniline in a solvent such as dichloromethane, tetrahydrofuran, 1,4-dioxane or N,N-dimethylformamide at temperatures between −30° C. and 150° C., but preferably between 0° C. and 80° C. and optionally in the presence of a base such as triethylamine, N,N-diisopropyl-N-ethyl-amine and optionally in the presence of a catalyst such as 4-N,N-dimethylaminopyridine.

In addition, the carboxylic acid may be converted into an acid imidazolide. For this it is reacted with carbonyldiimidazole in a solvent such as dichloromethane, tetrahydrofuran or 1,4-dioxane at temperatures between 20° C. and 100° C. The acid imidazolide thus obtained is reacted with the aniline in a solvent such as dichloromethane, tetrahydrofuran, 1,4-dioxane or N,N-dimethylformamide, but preferably tetrahydrofuran, at temperatures between −30° C. and 150° C., but preferably between 0° C. and 80° C., and optionally in the presence of a base such as triethylamine, N,N-diisopropyl-N-ethyl-amine and optionally in the presence of a catalyst such as 4-N,N-dimethylaminopyridine.

Aldehydes of general formula VIII are reacted with N-Boc-piperazine in the presence of a reducing agent such as sodium triacetoxyborohydride or sodium cyanoborohydride as well as an acid such as for example acetic acid or trifluoroacetic acid in a solvent such as dichloromethane, 1,2-dichloroethane, methanol or ethanol at temperatures between 0° C. and 60° C. to form compounds of general formula IX.

The tert.-butyloxycarbonyl group in compounds of general formula IX is cleaved by treating with an acid such as trifluoroacetic acid or hydrochloric acid or by treating with iodotrimethylsilane, optionally using a solvent such as methylene chloride, 1,4-dioxane, methanol or diethyl ether.

The amines of general formula X thus obtained are then acylated to form compounds of general formula I. Acyl groups may be introduced by reacting a compound of general formula X with an acylating reagent such as for example an acid chloride or acid anhydride. The reaction may be carried out in the presence of a base such as sodium hydroxide, sodium hydride, sodium carbonate, potassium carbonate, caesium carbonate, triethylamine or N,N-diisopropyl-N-ethyl-amine as well as in a solvent such as dichloromethane, tetrahydrofuran, 1,4-dioxane or N,N-dimethylformamide at temperatures between −30° C. and 120° C., but preferably between 0° C. and 80° C.

Alternatively the reaction may be carried out by acylation with an acid. For this the acid is activated in situ by the addition of N,N'-diisopropylcarbodiimide, N,N'-dicyclohexylcarbodiimide, N-(3-dimethylaminopropyl)-N'-ethyl-carbodiimide, O-(benzotriazol-1-yl)-N,N,N',N'-tetramethyluronium-tetrafluoroborate (TBTU), O-(benzotriazol-1-yl)-N,N,N',N'-tetramethyluronium-hexafluorophosphate (HBTU), O-(7-azabenzotriazol-1-yl)-N,N,N',N'-tetramethyluronium-hexafluorophosphate (HATU), (benzotriazol-1-yloxy)-tris-(dimethylamino)-phosphonium-hexafluorophosphate (BOP), (benzotriazol-1-yloxy)-tripyrrolidinophosphonium-hexafluorophosphate (PyBOP) or n-propylphosphonic anhydride and reacted in a dipolar aprotic solvent such as for example N,N-dimethylformamide, dimethylacetamide, tetrahydrofuran, acetonitrile, N-methylpyrrolidone or dimethylsulphoxide, but preferably in N,N-dimethylformamide or N-methylpyrrolidone, with a compound of general formula X in the presence of a base such as triethylamine, N,N-diisopropyl-N-ethyl-amine and optionally a catalyst such as 4-N,N-dimethylaminopyridine at temperatures between −20° C. and 80° C., but preferably between 0° C. and 50° C.

Aminocarbonyl groups may be introduced by reacting with an isocyanate, optionally in the presence of a base such as for example sodium carbonate, potassium carbonate, caesium carbonate, triethylamine or N,N-diisopropyl-N-ethyl-amine in a solvent such as dichloromethane, tetrahydrofuran, 1,4-dioxane or N,N-dimethylformamide at temperatures between −30° C. and 150° C., but preferably between 0° C. and 100° C.

Alternatively aminocarbonyl groups are obtained by reacting a compound of general formula X with phosgene, diphosgene or triphosgene in a solvent such as dichloromethane, tetrahydrofuran or 1,4-dioxane in the presence of a base such as for example sodium carbonate, potassium carbonate, caesium carbonate, triethylamine or N,N-diisopropyl-N-ethyl-amine, but preferably N,N-diisopropyl-N-ethyl-amine and subsequently treating with an amine at temperatures between −20° C. and 100° C., but preferably between 0° C. and 50° C.

Compounds of general formula VII wherein $R^2$ denotes hydrogen may be prepared using method b) according to the invention illustrated in Scheme 2, starting from 1H-indole-7-carbaldehyde XI.

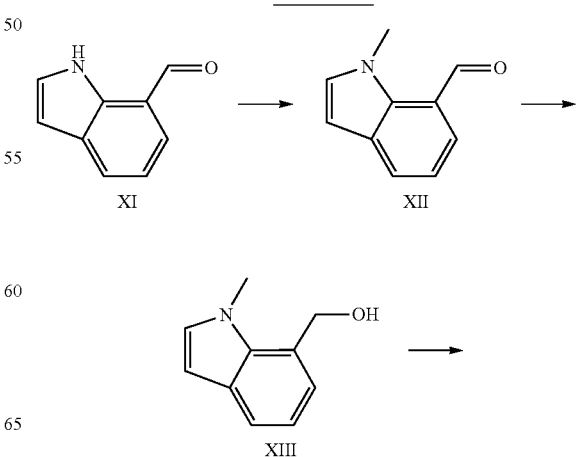

Scheme 2
(method b))

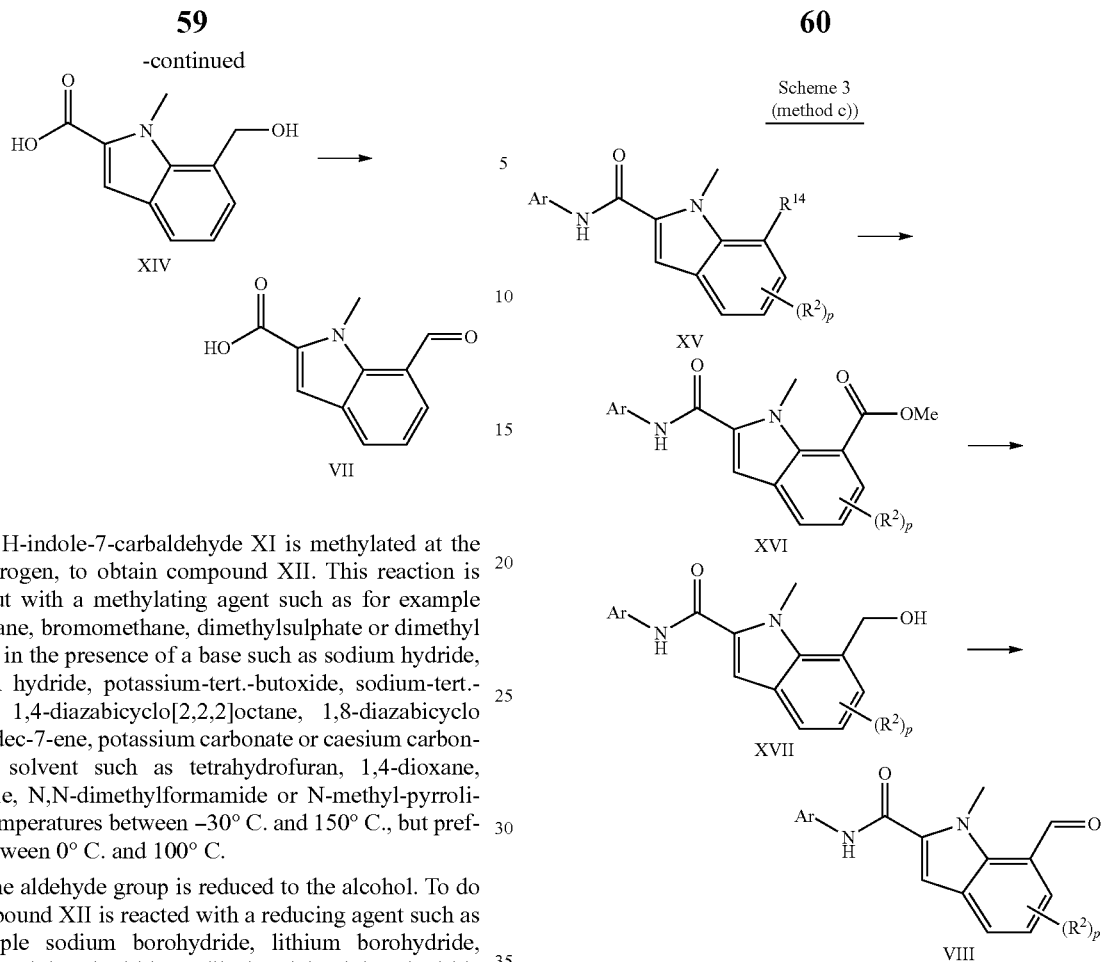

Here, 1H-indole-7-carbaldehyde XI is methylated at the indole nitrogen, to obtain compound XII. This reaction is carried out with a methylating agent such as for example iodomethane, bromomethane, dimethylsulphate or dimethyl carbonate in the presence of a base such as sodium hydride, potassium hydride, potassium-tert.-butoxide, sodium-tert.-butoxide, 1,4-diazabicyclo[2,2,2]octane, 1,8-diazabicyclo[5.4.0]undec-7-ene, potassium carbonate or caesium carbonate in a solvent such as tetrahydrofuran, 1,4-dioxane, acetonitrile, N,N-dimethylformamide or N-methyl-pyrrolidone at temperatures between −30° C. and 150° C., but preferably between 0° C. and 100° C.

Then the aldehyde group is reduced to the alcohol. To do this, compound XII is reacted with a reducing agent such as for example sodium borohydride, lithium borohydride, lithium aluminium hydride or diisobutylaluminium hydride in a solvent such as methanol, ethanol, diethyl ether, tetrahydrofuran, 1,4-dioxane or dichloromethane at temperatures between −78° C. and 80° C., but preferably between −40° C. and 50° C., to obtain compound XIII.

In order to introduce the carboxylic acid group compound XIII is metallised with an excess of a strong base such as for example n-butyllithium, sec.-butyllithium, tert.-butyllithium or 2,2,6,6-tetramethylpiperidin-1-yl-magnesium chloride/lithium chloride complex in an inert solvent such as for example diethyl ether, tetrahydrofuran, 1,4-dioxane or 1,2-dimethoxyethane at temperatures between −50° C. and 80° C., but preferably between −20° C. and 40° C. in the 2-position and then reacted with carbon dioxide to obtain the carboxylic acid XIV.

The alcohol group in XIV is oxidised to the aldehyde VII. This transformation may be carried out with Dess-Martin-Periodinane (*J. Chem. Soc.* 1983, 48, 4156), by Swern oxidation (*J. Org. Chem.* 1976, 41, 957), by Ley oxidation (*Synthesis* 1994, 639) or by a TEMPO-catalysed oxidation (*Tetrahedron Lett.* 1992, 5029).

The compound VII thus obtained may then be reacted by method a) shown in Scheme 1 to form the final compounds of general formula I, wherein $R^2$ denotes hydrogen and A denotes nitrogen.

Compounds of general formula VIII may also be prepared by method c) according to the invention shown in Scheme 3, wherein Ar, $R^2$ and p are as hereinbefore defined and $R^{14}$ denotes —OS(O)$_2$CF$_3$, Br or I, starting from compounds of general formula XV.

The compounds of general formula XV are converted into the methylesters XVI by reaction with carbon monoxide and methanol in the presence of catalytic amounts of palladium-II-acetate, catalytic amounts of a ligand such as for example 1,3-bis-(diphenylphosphino)-propane or 1,1'-bis-(diphenylphosphino)-ferrocene and a base such as triethylamine or N,N-diisopropyl-N-ethyl-amine.

These methyl esters are converted into the alcohols of general formula XVII by reaction with a reducing agent such as lithium aluminium hydride, diisobutylaluminium hydride or lithium borohydride, but preferably lithium aluminium hydride, in an inert solvent such as diethyl ether, tetrahydrofuran or 1,4-dioxane at temperatures between −30° C. and 80° C.

Oxidation of the compounds of general formula XVII into the aldehydes of general formula VIII may then be carried out with Dess-Martin-Periodinane (*J. Chem. Soc.* 1983, 48, 4156), by Swern oxidation (*J. Org. Chem.* 1976, 41, 957), by Ley oxidation (*Synthesis* 1994, 639) or by a TEMPO-catalysed oxidation (*Tetrahedron Lett.* 1992, 5029).

The compounds of general formula VIII thus prepared may then be reacted according to method a) shown in Scheme 1 to form the end compounds of general formula I.

Compounds of general formula XV may be prepared according to method d) according to the invention shown in Scheme 4, wherein Ar, $R^2$ and p are as hereinbefore defined, $R^{14}$ denotes —OS(O)$_2$CF$_3$ and $R^{15}$ represents hydrogen or methyl, starting from compounds of general formula XVIII.

Scheme 4
(method d))

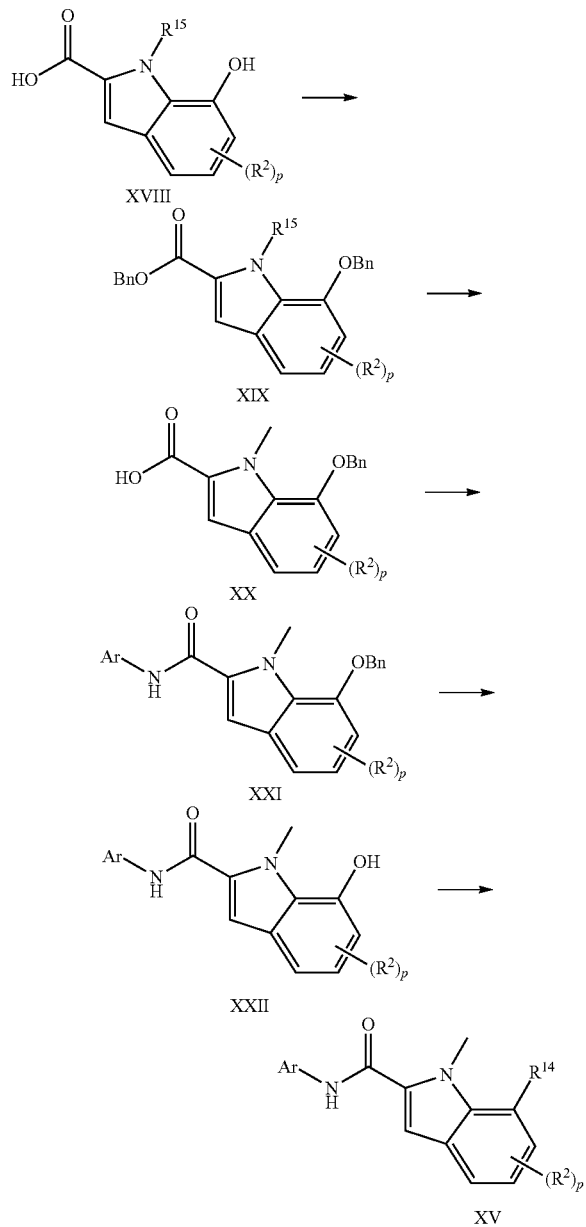

For this, compounds of general formula XVIII are converted into compounds of general formula XIX by reaction with benzyl chloride or benzylbromide in the presence of a base such as for example sodium hydride, potassium hydride, potassium-tert.-butoxide, sodium-tert.-butoxide, 1,4-diazabicyclo[2,2,2]octane, 1,8-diazabicyclo[5.4.0]undec-7-ene, triethylamine, N,N-diisopropyl-N-ethyl-amine, potassium carbonate or caesium carbonate in a solvent such as tetrahydrofuran, 1,4-dioxane, acetonitrile, N,N-dimethylformamide, N-methyl-pyrrolidone or dimethylsulphoxide, at temperatures between −50° C. and 120° C., but preferably between −20° C. and 80° C.

If compounds of general formula XVIII wherein $R^{15}$ denotes hydrogen are used, compounds of general formula XIX wherein $R^{15}$ denotes hydrogen are obtained. These may be converted into compounds of general formula XIX wherein $R^{15}$ denotes methyl. For this purpose, reaction is carried out with a methylating agent such as for example iodomethane, bromomethane, dimethylsulphate or dimethyl carbonate. The reaction is carried out in the presence of a base such as sodium hydride, potassium hydride, potassium-tert.-butoxide, sodium-tert.-butoxide, 1,4-diazabicyclo[2,2,2]octane, 1,8-diazabicyclo[5.4.0]undec-7-ene, potassium carbonate or caesium carbonate in a solvent such as tetrahydrofuran, 1,4-dioxane, acetonitrile, N,N-dimethylformamide or N-methyl-pyrrolidone at temperatures between −30° C. and 150° C., but preferably between 0° C. and 100° C.

Then the benzylester group in the compounds of general formula XIX is cleaved. This reaction is carried out hydrolytically in an aqueous solvent, e.g. in water, methanol/water, isopropanol/water, acetic acid/water, tetrahydrofuran/water or 1,4-dioxane/water, but preferably in methanol/water, in the presence of an acid such as trifluoroacetic acid, hydrochloric acid or sulphuric acid or in the presence of an alkali metal base such as lithium hydroxide, sodium hydroxide or potassium hydroxide, but preferably sodium hydroxide, or aprotically, e.g. in the presence of iodotrimethylsilane, at temperatures between 0 and 120° C., preferably at temperatures between 10 and 100° C.

The carboxylic acids of general formula XX thus obtained are then reacted with an aniline to form the anilide of general formula XXI. For this the carboxylic acid is activated in situ by the addition of N,N'-diisopropylcarbodiimide, N,N'-dicyclohexylcarbodiimide, N-(3-dimethylaminopropyl)-N'-ethyl-carbodiimide, O-(benzotriazol-1-yl)-N,N,N',N'-tetramethyluronium-tetrafluoroborate (TBTU), O-(benzotriazol-1-yl)-N,N,N',N'-tetramethyluronium-hexafluorophosphate (HBTU), O-(7-azabenzotriazol-1-yl)-N,N,N',N'-tetramethyluronium-hexafluorophosphate (HATU), (benzotriazol-1-yloxy)-tris-(dimethylamino)-phosphonium-hexafluorophosphate (BOP), (benzotriazol-1-yloxy)-tripyrrolidinophosphonium-hexafluorophosphate (PyBOP) or n-propylphosphonic anhydride and reacted in a dipolar aprotic solvent such as for example N,N-dimethylformamide, dimethylacetamide, tetrahydrofuran, acetonitrile, N-methylpyrrolidone or dimethylsulphoxide, but preferably in N,N-dimethylformamide or N-methylpyrrolidone with an aniline in the presence of a base such as triethylamine, N,N-diisopropyl-N-ethyl-amine and optionally a catalyst such as 4-N,N-dimethylaminopyridine at temperatures between −20° C. and 80° C., but preferably between 0° C. and 50° C.

Alternatively the carboxylic acid is first converted into an acid chloride. For this, the carboxylic acid is reacted with thionyl chloride, phosphorus oxychloride or oxalyl chloride optionally in a solvent such as toluene, benzene or dichloromethane at temperatures between 0° C. and 120° C. The acid chloride thus obtained is reacted with the aniline in a solvent such as dichloromethane, tetrahydrofuran, 1,4-dioxane or N,N-dimethylformamide at temperatures between −30° C. and 150° C., but preferably between 0° C. and 80° C. and optionally in the presence of a base such as triethylamine, N,N-diisopropyl-N-ethyl-amine and optionally in the presence of a catalyst such as 4-N,N-dimethylaminopyridine.

In addition, the carboxylic acid may be converted into an acid imidazolide. For this it is reacted with carbonyldiimidazole in a solvent such as dichloromethane, tetrahydrofuran or 1,4-dioxane at temperatures between 20° C. and 100° C. The acid imidazolide thus obtained is reacted with the aniline in a solvent such as dichloromethane, tetrahydrofuran, 1,4-dioxane or N,N-dimethylformamide, but preferably tetrahydrofuran, at temperatures between −30° C. and 150° C., but preferably between 0° C. and 80° C., and optionally in the presence of a base such as triethylamine, N,N-diisopropyl-N-ethyl-amine and optionally in the presence of a catalyst such as 4-N,N-dimethylaminopyridine.

The benzyl group in the compounds of general formula XXI is advantageously cleaved by hydrogenolysis, e.g. with hydrogen in the presence of a catalyst such as palladium on charcoal or palladium hydroxide on charcoal in a suitable solvent such as methanol, ethanol, tetrahydrofuran, 1,4-dioxane, ethyl acetate or glacial acetic acid, optionally with the addition of an acid such as hydrochloric acid at temperatures between 0 and 100° C., but preferably at temperatures between 20 and 60° C., and under a hydrogen pressure of 1 to 7 bar, but preferably from 1 to 3 bar, to obtain phenols of general formula XXII. The phenol of formula XXII wherein Ar denotes 5-tert.-butyl-3-methanesulphonyl-2-methoxyphenyl and $R^2$ denotes hydrogen, is described in US20040186114.

Then the phenols of general formula XXII thus obtained are converted into triflates of general formula XV by reaction with N-phenyl-trifluoromethanesulphonimide or trifluoromethanesulphonic acid anhydride in the presence of a base such as sodium hydride, potassium hydride, potassium-tert.-butoxide, sodium-tert.-butoxide, lithium-bis-(trimethylsilyl)-amide, sodium-bis-(trimethylsilyl)-amide, potassium-bis-(trimethylsilyl)-amide, 1,4-diazabicyclo[2,2,2]octane, 1,8-diazabicyclo[5.4.0]undec-7-ene, triethylamine, N,N-diisopropyl-N-ethyl-amine, pyridine, 2,6-lutidine, 4-N,N-dimethylaminopyridine, potassium carbonate or caesium carbonate, but preferably triethylamine or N,N-diisopropyl-N-ethyl-amine, in a solvent such as tetrahydrofuran, 1,4-dioxane, acetonitrile, N,N-dimethylformamide, N-methyl-pyrrolidone or dimethylsulphoxide at temperatures between −50° C. and 120° C., but preferably between −20° C. and 80° C.

The compounds of general formula XV thus prepared may then be reacted according to method c) illustrated in Scheme 3 to form the compounds of general formula VIII, which may then be converted into the end compounds of general formula I according to method a) shown in Scheme 1.

Compounds of general formula XV may be prepared according to method e) according to the invention shown in Scheme 5, wherein Ar, $R^2$ and p are as hereinbefore defined, $R^{14}$ denotes Br or I and $R^{15}$ denotes hydrogen or methyl, starting from compounds of general formula XXIII.

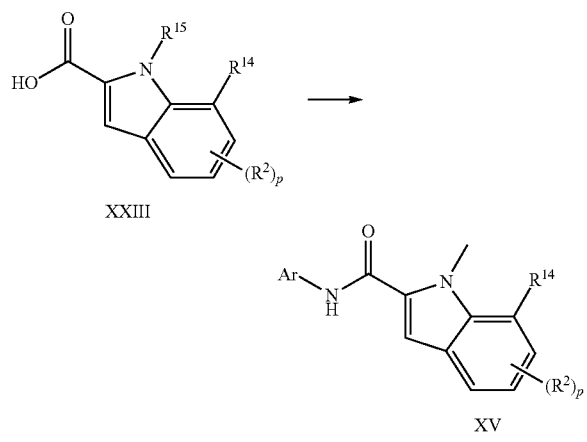

Scheme 5
(method e))

Compounds of general formula XXIII, wherein $R^{15}$ denotes hydrogen, may be converted into compounds of general formula XXIII, wherein $R^{15}$ denotes methyl. For this, they are reacted with a methylating agent such as for example iodomethane, bromomethane, dimethylsulphate or dimethyl carbonate. The reaction is carried out in the presence of a base such as sodium hydride, potassium hydride, potassium-tert.-butoxide, sodium-tert.-butoxide, 1,4-diazabicyclo[2,2,2]octane, 1,8-diazabicyclo[5.4.0]undec-7-ene, potassium carbonate or caesium carbonate in a solvent such as tetrahydrofuran, 1,4-dioxane, acetonitrile, N,N-dimethylformamide or N-methyl-pyrrolidone at temperatures between −30° C. and 150° C., but preferably between 0° C. and 100° C. The methyl ester obtained is then cleaved again. This reaction is carried out hydrolytically in an aqueous solvent, e.g. in water, methanol/water, isopropanol/water, acetic acid/water, tetrahydrofuran/water or 1,4-dioxane/water, but preferably in methanol/water, in the presence of an acid such as trifluoroacetic acid, hydrochloric acid or sulphuric acid or in the presence of an alkali metal base such as lithium hydroxide, sodium hydroxide or potassium hydroxide, but preferably sodium hydroxide, or aprotically, e.g. in the presence of iodotrimethylsilane, at temperatures between 0 and 120° C., preferably at temperatures between 10 and 100° C.

The carboxylic acids of general formula XXIII wherein $R^{15}$ denotes methyl are then reacted with an aniline to form the anilide of general formula XV. For this the carboxylic acid is activated in situ by the addition of N,N'-diisopropylcarbodiimide, N,N'-dicyclohexylcarbodiimide, N-(3-dimethylaminopropyl)-N'-ethyl-carbodiimide, O-(benzotriazol-1-yl)-N,N,N',N'-tetramethyluronium-tetrafluoroborate (TBTU), O-(benzotriazol-1-yl)-N,N,N',N'-tetramethyluronium-hexafluorophosphate (HBTU), O-(7-azabenzotriazol-1-yl)-N,N,N',N'-tetramethyluronium-hexafluorophosphate (HATU), (benzotriazol-1-yloxy)-tris-(dimethylamino)-phosphonium-hexafluorophosphate (BOP), (benzotriazol-1-yloxy)-tripyrrolidinophosphonium-hexafluorophosphate (PyBOP) or n-propylphosphonic anhydride and reacted with an aniline in a dipolar aprotic solvent such as for example N,N-dimethylformamide, dimethylacetamide, tetrahydrofuran, acetonitrile, N-methylpyrrolidone or dimethylsulphoxide, but preferably in N,N-dimethylformamide or N-methylpyrrolidone, in the presence of a base such as triethylamine, N,N-diisopropyl-N-ethyl-amine and optionally a catalyst such as 4-N,N-dimethylaminopyridine at temperatures between −20° C. and 80° C., but preferably between 0° C. and 50° C.

Alternatively the carboxylic acid is first converted into an acid chloride. For this, the carboxylic acid is reacted with thionyl chloride, phosphorus oxychloride or oxalyl chloride optionally in a solvent such as toluene, benzene or dichloromethane at temperatures between 0° C. and 120° C. The acid chloride thus obtained is reacted with the aniline in a solvent such as dichloromethane, tetrahydrofuran, 1,4-dioxane or N,N-dimethylformamide at temperatures between −30° C. and 150° C., but preferably between 0° C. and 80° C. and optionally in the presence of a base such as triethylamine, N,N-diisopropyl-N-ethyl-amine and optionally in the presence of a catalyst such as 4-N,N-dimethylaminopyridine.

In addition, the carboxylic acid may be converted into an acid imidazolide. For this it is reacted with carbonyldiimidazole in a solvent such as dichloromethane, tetrahydrofuran or 1,4-dioxane at temperatures between 20° C. and 100° C. The acid imidazolide thus obtained is reacted with the aniline in a solvent such as dichloromethane, tetrahydrofuran, 1,4-dioxane or N,N-dimethylformamide, but preferably tetrahydrofuran, at temperatures between −30° C. and 150° C., but preferably between 0° C. and 80° C., and optionally in the presence of a base such as triethylamine, N,N-diisopropyl-N-ethyl-amine and optionally in the presence of a catalyst such as 4-N,N-dimethylaminopyridine.

The compounds of general formula XV thus prepared may then be reacted according to method c) shown in Scheme 3 to form the compounds of general formula VIII, which may then be converted into the end compounds of general formula I according to method a) shown in Scheme 1.

Compounds of general formula IX may be prepared according to method f) according to the invention shown in Scheme 6, wherein Ar, $R^2$ and p are as hereinbefore defined, m denotes 1 or 2 and $R^{14}$ denotes —OS(O)$_2$CF$_3$, Br or I, starting from compounds of general formula XV.

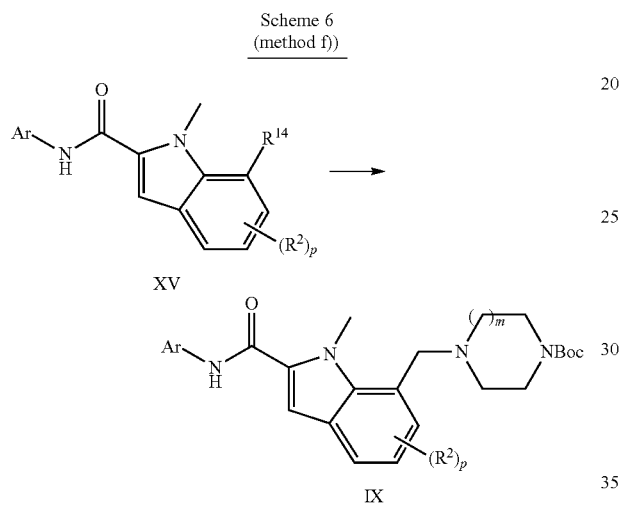

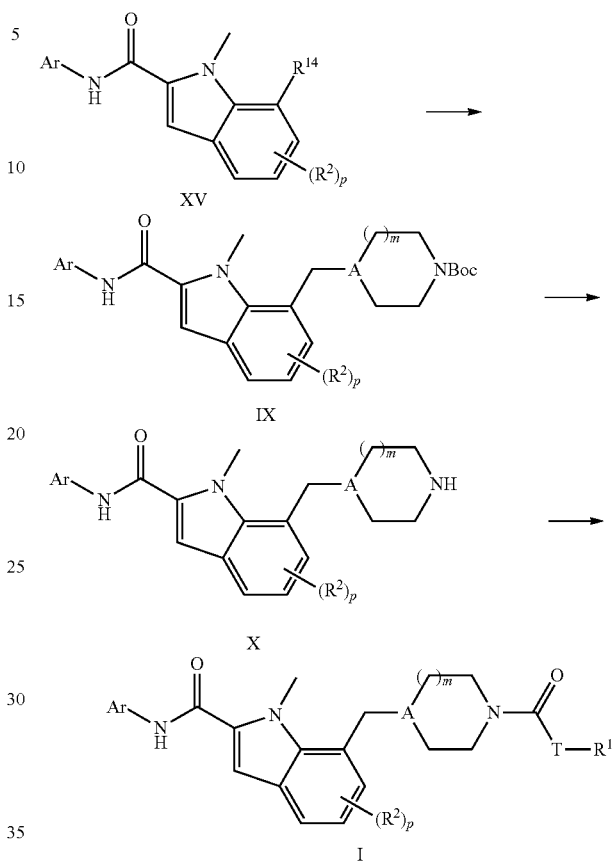

For this, compounds of general formula XV are reacted with potassium ((4-(tert.-butoxycarbonyl)-piperazin-1-yl)-methyl)-trifluoroborate (for preparation see: *Org. Lett.* 2007, 9, 1597-1600) or ((4-(tert.-butoxycarbonyl)-homopiperazin-1-yl)-methyl)-trifluoroborate in the presence of palladium-II-acetate as well as a ligand such as 2-dicyclohexylphosphino-2',4',6'-triisopropyl-1,1'-biphenyl (XPhos), tricyclohexylphosphine, tri-tert.-butylphosphine, 1,3-bis-(diphenylphosphino)-propane or 1,1'-bis-(diphenylphosphino)-ferrocene, but preferably 2-dicyclohexylphosphino-2',4',6'-triisopropyl-1,1'-biphenyl (XPhos), as well as a base such as sodium carbonate, potassium carbonate, caesium carbonate, triethylamine or N,N-diisopropyl-N-ethyl-amine, but preferably caesium carbonate, in a solvent such as tetrahydrofuran, 1,4-dioxane, cyclopentyl-methyl-ether, acetonitrile or N,N-dimethylformamide, but preferably in tetrahydrofuran or cyclopentyl-methyl-ether, optionally with the addition of water, at temperatures between 50° C. and 150° C., but preferably between 70° C. and 120° C., to obtain the compounds of general formula IX (cf. also *Org. Lett.* 2007, 9, 1597-1600).

The compounds of general formula IX thus prepared may then be reacted according to method a) shown in Scheme 1 to form the end compounds of general formula I.

Compounds of general formula I may also be prepared according to method g) according to the invention illustrated in Scheme 7, wherein Ar, T, $R^2$, p, m and $R^1$ are as hereinbefore defined, A denotes —C(H)<, $R^{14}$ denotes —OS(O)$_2$CF$_3$, Br or I, starting from compounds of general formula XV.

For this the compounds of general formula XV are reacted with tert.-butyl 4-(9-borabicyclo[3.3.1]nonan-9-ylmethyl)-piperidine-1-carboxylate (obtained from the reaction of tert-butyl 4-methylene-piperidine-1-carboxylate with 9-bora-bicyclo[3.3.1]nonane in tetrahydrofuran at reflux temperature) or tert-butyl 4-(9-bora-bicyclo[3.3.1]non-9-ylmethyl)-azepan-1-carboxylate (obtained from the reaction of tert-butyl 4-methylene-azepan-1-carboxylate with 9-bora-bicyclo [3.3.1]nonane in tetrahydrofuran at reflux temperature) in the presence of a catalyst such as [1,1'-bis(diphenylphosphino) ferrocene]-palladium-II-dichloride-dichloromethane complex, bis-tri-tert.-butylphosphine-palladium-(0), bis-tri-cyclohexylphosphine-palladium-(0), [1,2-bis (diphenylphosphino)ethane]palladium-II-dichloride or [1,3-bis(diphenylphosphino)propane]palladium-II-dichloride, but preferably [1,1'-bis(diphenylphosphino)ferrocene]-palladium-II-dichloride-dichloromethane complex, as well as a base such as for example sodium carbonate, potassium carbonate, caesium carbonate, triethylamine or N,N-diisopropyl-N-ethyl-amine, but preferably potassium carbonate, in a solvent such as tetrahydrofuran, 1,4-dioxane, acetonitrile or N,N-dimethylformamide, optionally with the addition of water, at temperatures between 30° C. and 150° C., but preferably between 50° C. and 120° C., to obtain the compounds of general formula IX.

The tert.-butyloxycarbonyl group in compounds of general formula IX is cleaved by treating with an acid such as trifluoroacetic acid or hydrochloric acid or by treating with iodotrimethylsilane optionally using a solvent such as methylene chloride, 1,4-dioxane, methanol or diethyl ether.

The amines of general formula X thus obtained are then acylated to form compounds of general formula I. Acyl groups may be introduced by reacting a compound of general formula X with an acylating reagent such as for example an acid chloride or acid anhydride. The reaction may be carried out in the presence of a base such as sodium hydroxide, sodium hydride, sodium carbonate, potassium carbonate, caesium carbonate, triethylamine or N,N-diisopropyl-N-ethyl-amine as well as in a solvent such as dichloromethane, tetrahydrofuran, 1,4-dioxane or N,N-dimethylformamide, at temperatures between −30° C. and 120° C., but preferably between 0° C. and 80° C.

Alternatively the reaction may be carried out by acylation with an acid. For this the acid is activated in situ by the addition of N,N'-diisopropylcarbodiimide, N,N'-dicyclohexylcarbodiimide, N-(3-dimethylaminopropyl)-N'-ethylcarbodiimide, O-(benzotriazol-1-yl)-N,N,N',N'-tetramethyluronium-tetrafluoroborate (TBTU), O-(benzotriazol-1-yl)-N,N,N',N'-tetramethyluronium-hexafluorophosphate (HBTU), O-(7-azabenzotriazol-1-yl)-N,N,N',N'-tetramethyluronium-hexafluorophosphate (HATU), (benzotriazol-1-yloxy)-tris-(dimethylamino)-phosphonium-hexafluorophosphate (BOP), (benzotriazol-1-yloxy)-tripyrrolidinophosphonium-hexafluorophosphate (PyBOP) or n-propylphosphonic anhydride and reacted in a dipolar aprotic solvent such as for example N,N-dimethylformamide, dimethylacetamide, tetrahydrofuran, acetonitrile, N-methylpyrrolidone or dimethylsulphoxide, but preferably in N,N-dimethylformamide or N-methylpyrrolidone, with a compound of general formula X in the presence of a base such as triethylamine or N,N-diisopropyl-N-ethyl-amine and optionally a catalyst such as 4-N,N-dimethylaminopyridine at temperatures between −20° C. and 80° C., but preferably between 0° C. and 50° C.

Aminocarbonyl groups may be introduced by reacting with an isocyanate, optionally in the presence of a base such as for example sodium carbonate, potassium carbonate, caesium carbonate, triethylamine or N,N-diisopropyl-N-ethyl-amine in a solvent such as dichloromethane, tetrahydrofuran, 1,4-dioxane or N,N-dimethylformamide at temperatures between −30° C. and 150° C., but preferably between 0° C. and 100° C.

Alternatively aminocarbonyl groups are obtained by reacting a compound of general formula X with phosgene, diphosgene or triphosgene in a solvent such as dichloromethane, tetrahydrofuran or 1,4-dioxane in the presence of a base such as for example sodium carbonate, potassium carbonate, caesium carbonate, triethylamine or N,N-diisopropyl-N-ethyl-amine, but preferably N,N-diisopropyl-N-ethyl-amine and subsequently treating with an amine at temperatures between −20° C. and 100° C., but preferably between 0° C. and 50° C.

Compounds of general formula I may also be prepared according to method h) according to the invention shown in Scheme 8, wherein Ar, A, $R^2$, p and m are as hereinbefore defined, T denotes —$CH_2$— and $R^1$ denotes an optionally substituted cyclic amine, starting from compounds of general formula X.

Scheme 8
(method h))

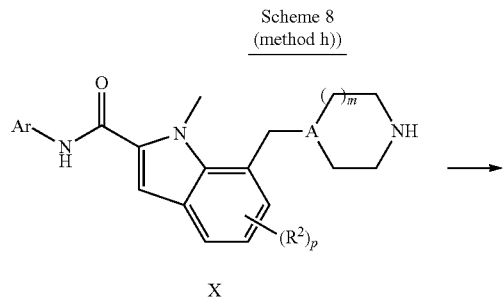

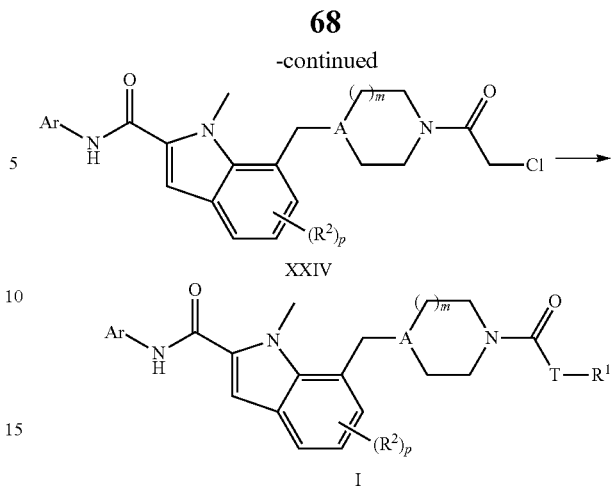

For this, the compounds of general formula X are reacted with chloroacetic acid chloride in a solvent such as dichloromethane, tetrahydrofuran or 1,4-dioxane in the presence of a base such as for example triethylamine or N,N-diisopropyl-N-ethyl-amine and optionally a catalyst such as 4-N,N-dimethylaminopyridine at temperatures between −20° C. and 80° C., but preferably between 0° C. and 50° C. to form compounds of general formula XXIV. These are then reacted with a suitable cyclic amine in a solvent such as dichloromethane, tetrahydrofuran, 1,4-dioxane or N,N-dimethylformamide, but preferably N,N-dimethylformamide, in the presence of a base such as for example sodium carbonate, potassium carbonate, caesium carbonate, triethylamine or N,N-diisopropyl-N-ethyl-amine, but preferably potassium carbonate, at temperatures between −30° C. and 100° C., but preferably between 0° C. and 80° C., to form compounds of general formula I.

In the reactions described hereinbefore, any reactive groups present such as carboxy, carbonyl, hydroxy, amino or alkylamino groups may be protected during the reaction by conventional protecting groups which are cleaved again after the reaction.

For example, a protecting group for a carboxy group may be a methyl, ethyl, tert.butyl or benzyl group.

For example, a protecting group for a carbonyl group of a ketone or aldehyde may be a ketal or acetal, e.g. derived from methanol, glycol or propane-1,3-diol.

For example, a protecting group for an aliphatic hydroxy group may be the trimethylsilyl, tert-butyldimethylsilyl, triisopropylsilyl, acetyl, pivaloyl, benzoyl, methyl, allyl, benzyl, 4-methoxybenzyl, trityl, methoxymethyl, ethoxymethyl, 2-trimethylsilylethoxymethyl or tetrahydropyranyl group.

Suitable protecting groups for a phenolic OH group, besides those already mentioned for the aliphatic hydroxy group, are methylsulphonyl, tosyl and trifluoromethylsulphonyl.

Suitable protecting groups for an amino or alkylamino group include for example the formyl, acetyl, trifluoroacetyl, ethoxycarbonyl, tert.-butoxycarbonyl, benzyloxycarbonyl, benzyl, 4-methoxybenzyl or 2,4-dimethoxybenzyl group.

A carboxymethyl or carboxyethyl unit may be cleaved hydrolytically, for example, in an aqueous solvent, e.g. in water, methanol/water, isopropanol/water, acetic acid/water, tetrahydrofuran/water or 1,4-dioxane/water, but preferably in methanol/water, in the presence of an acid such as trifluoroacetic acid, hydrochloric acid or sulphuric acid or in the presence of an alkali metal base such as lithium hydroxide, sodium hydroxide or potassium hydroxide, but preferably sodium hydroxide, or aprotically, e.g. in the presence of iodotrimethylsilane, at temperatures between 0 and 120° C., preferably at temperatures between 10 and 100° C.

A benzyl, methoxybenzyl or benzyloxycarbonyl group is advantageously cleaved hydrogenolytically, e.g. with hydrogen in the presence of a catalyst such as palladium on charcoal, palladium hydroxide or platinum oxide in a suitable solvent such as methanol, ethanol, ethyl acetate or glacial acetic acid, optionally with the addition of an acid such as hydrochloric acid at temperatures between 0 and 100° C., but preferably between 20 and 60° C., and under a hydrogen pressure of 1 to 7 bar, preferably 3 to 5 bar. Trimethylsilyl iodide, boron trichloride or boron trifluoride in the presence of a mopping up reagent, e.g. anisole, thioanisole or pentamethylbenzene, may also be used to cleave benzylethers including the substituted derivatives thereof. The cleaving of eletron-enriched benzyl groups, to such as e.g. 4-methoxybenzyl, may also be carried out oxidatively with e.g. 2,3-dichloro-5,6-dicyano-1,4-benzoquinone (DDQ) or cerium ammonium nitrate (CAN), preferably in alcoholic or aqueous solutions at between 10 and 120° C. The 2,4-dimethoxybenzyl group is preferably cleaved in trifluoroacetic acid in the presence of a mopping up reagent, e.g. anisole.

A tert.-butyl or tert.-butyloxycarbonyl group is preferably cleaved by treating with an acid such as trifluoroacetic acid or hydrochloric acid or by treating with iodotrimethylsilane, optionally using a solvent such as methylene chloride, 1,4-dioxane, methanol or diethyl ether.

Any acetal or ketal protecting group used is preferably cleaved in an aqueous solvent, e.g. water, isopropanol/water, tetrahydrofuran/water or 1,4-dioxane/water, in the presence of an acid, e.g. acetic acid, trifluoroacetic acid, hydrochloric acid or sulphuric acid, at temperatures between 0 and 120° C., preferably between 10 and 100° C.

A methyl group on a tertiary amine may be cleaved by treating with 1-chloroethylchloroformate. HBr or $BBr_3$ are particularly suitable for cleaving methyl ethers.

Moreover, the compounds of general formula (I) obtained, or intermediate products from the synthesis of compounds of general formula (I), as already mentioned hereinbefore, may be resolved into their enantiomers and/or diastereomers. Thus, for example, cis/trans mixtures may be resolved into their cis and trans isomers, and compounds with at least one stereocentre may be resolved into their enantiomers.

Thus, for example, the cis/trans mixtures obtained may be resolved by chromatography into their cis and trans isomers, the compounds of general formula (I) obtained, or intermediate products from the synthesis of compounds of general formula I, which occur as racemates may be separated by methods known per se (cf. N. L. Allinger and E. L. Eliel in "Topics in Stereochemistry", Vol. 6, Wiley Interscience, 1971) into their optical antipodes, and compounds of general formula (I), or intermediate products from the synthesis of compounds of general formula (I), with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by chromatography on chiral phases or by recrystallisation from an optically active solvent or by reacting with an optically active substance which forms salts or derivatives such as e.g. esters or amides with the racemic compound, and separating the diastereomeric mixture of salts or derivatives thus obtained, e.g. on the basis of their differences in solubility, whilst the free antipodes may be released from the pure diastereomeric salts or derivatives by the action of suitable agents. Examples of optically active substances include optically active acids and the activated derivatives or optically active alcohols thereof. Optically active acids in common use are e.g. the D- and L-forms of tartaric acid or dibenzoyltartaric acid, di-O-p-toluoyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of general formula (I) obtained, or intermediate products from the synthesis of compounds of general formula I, may be converted into the salts thereof, for pharmaceutical use in particular into the physiologically acceptable salts thereof with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the new compounds of general formula (I) obtained, or intermediate products from the synthesis of compounds of general formula I, if they contain a carboxy group, may, if desired, be converted into the salts thereof with inorganic or organic bases, for pharmaceutical use particularly into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae V, XI, XVIII and XXIII used as starting materials are known from the literature to some extent or may be prepared by methods known from the literature and analogously to the methods described in the Examples, optionally with the additional introduction of protecting groups.

Experimental Section

HPLC Methods:

Method 1:
Column: Merck Cromolith Speed ROD, RP18e, 50×4.6 mm; 1.5 ml/minute;
UV detection: 230 nm/254 nm; eluant A: water (0.1% formic acid), eluant B: acetonitrile (0.1% formic acid)

| gradient: | |
|---|---|
| time (min.) | % eluant B |
| 0.00 | 10 |
| 4.50 | 90 |
| 5.00 | 90 |
| 5.50 | 10 |

Method 2:
Column: Agilent Zorbax Bonus RP, 50×2.1 mm, 3.5 µm; 1.2 ml/minute;
UV detection: 230 nm/254 nm; eluant A: water (0.1% formic acid), eluant B: acetonitrile (0.1% formic acid)

| gradient: | |
|---|---|
| time (min.) | % eluant B |
| 0.00 | 10 |
| 4.50 | 99 |

-continued

| time (min.) | % eluant B |
|---|---|
| 5.00 | 99 |
| 5.50 | 10 |

Method 3: Preparative HPLC

Column: XBridge Prep C18, 225 g separating material, 300×50 mm, 5 μm;

120 ml/minute; UV detection: 230 nm/254 nm, eluant A: water (0.45% conc. ammonia), eluant B: acetonitrile

| time (min.) | % eluant B | flow rate |
|---|---|---|
| 0.00 | 10 | 60 ml/min. |
| 2.00 | 10 | 60 ml/min. |
| 3.00 | 10 | 120 ml/min. |
| 3.50 | 10 | 120 ml/min. |
| 22.00 | 100 | 120 ml/min. |
| 25.50 | 100 | 120 ml/min. |
| 26.50 | 10 | 120 ml/min. |
| 30.00 | 10 | 120 ml/min. |

Method 4: Preparative HPLC

Column: Waters Symmetrie C18, 150×50 mm, 7 μm;

120 ml/minute; mass-controlled fractionation (MS: Thermo Finnigan Surveyor MSQ); eluant A: water (0.14% formic acid), eluant B: acetonitrile

| time (min.) | % eluant B | flow rate |
|---|---|---|
| 0.00 | 10 | 120 ml/min. |
| 2.00 | 10 | 120 ml/min. |
| 9.00 | 95 | 120 ml/min. |
| 11.50 | 95 | 120 ml/min. |
| 12.00 | 5 | 120 ml/min. |
| 14.00 | 5 | 120 ml/min. |

Method 5:

Column: Waters Xbridge C18, 50×4.6 mm, 3.5 μm; 1.5 ml/minute;

UV detection: DAD 210-500 nm; eluant A: water (0.032% ammonia), eluant B: acetonitrile

| time (min.) | % eluant B |
|---|---|
| 0.00 | 0 |
| 2.00 | 100 |
| 3.00 | 100 |

Method 6:

Column: Waters Xbridge C18, 30×4.6 mm, 2.5 μm; 1.2 ml/minute; UV detection: DAD 190-400 nm; eluant A: water (0.1% ammonia), eluant B: acetonitrile

| time (min.) | % eluant B |
|---|---|
| 0.00 | 5 |
| 0.15 | 5 |
| 4.00 | 90 |
| 4.20 | 90 |
| 4.30 | 5 |
| 5.00 | 5 |

Method 7: Preparative HPLC

Column: Microsorb 100 C18, 225 g separating material, 250×41.4 mm, 8 μm; 120 ml/minute; UV detection: 230 nm/254 nm, eluant A: water (0.14% trifluoroacetic acid), eluant B: acetonitrile gradient: linear gradient (10% eluant B to 100% eluant B within 30 minutes.

Preparation of the Starting Compounds

Example I 1-methyl-1H-indole-7-carbaldehyde

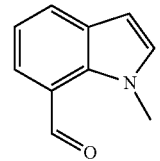

20 g 1H-indole-7-carbaldehyde are dissolved in 160 ml N,N-dimethylformamide and combined batchwise with 15.5 g potassium-tert.-butoxide under argon. After the addition has ended the mixture is left for 20 minutes with stirring and then 8.7 ml methyl iodide are added dropwise. Then the mixture is left for 12 hours at ambient temperature with stirring and then distributed between water and ethyl acetate. The aqueous phase is twice extracted with ethyl acetate and the combined organic phases are washed with saturated aqueous sodium chloride solution. After drying with magnesium sulphate the solvents are eliminated in vacuo. The residue is extracted from water. The solid thus obtained is suction filtered and dried in vacuo.

Yield: 20 g (91% of theory)

Mass spectrum (ESI$^+$): m/z=160 [M+H]$^+$

Example II (1-methyl-1H-indol-7-yl)-methanol

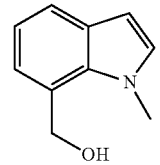

10.8 g 1-methyl-1H-indole-7-carbaldehyde are dissolved in 150 ml of ethanol, cooled to 0° C. and combined batchwise with 1.3 g sodium borohydride. After the addition has ended the cooling bath is removed and the mixture is stirred for another 2 hours at ambient temperature. Then 68 ml 1 M sodium hydroxide solution are added, the mixture is stirred for 10 minutes and then most of the ethanol is eliminated in vacuo. The residue is divided between water and ethyl acetate and the aqueous phase is extracted twice with ethyl acetate. The combined organic phases are washed with saturated aqueous sodium chloride solution and dried on magnesium sulphate. Then the solvents are eliminated in vacuo and the residue is dried in vacuo.

Yield: 10.5 mg (96% of theory)
HPLC (method 1): retention time=2.67 min.
Mass spectrum (ESI$^+$): m/z=162 [M+H]$^+$ Example III 7-hydroxymethyl-1-methyl-1H-indole-2-carboxylic acid

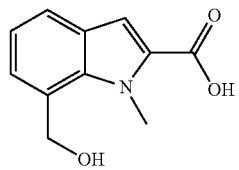

Under argon a solution of 4 g (1-methyl-1H-indol-7-yl)-methanol in 80 ml diethyl ether is added dropwise to 76 ml of a 1.6 M solution of n-butyllithium in hexane at 0° C., while the temperature does not exceed 35° C. Then the mixture is stirred for another 12 hours at ambient temperature and the solution thus obtained is poured onto 30 g of crushed dry ice in 100 ml diethyl ether. The mixture is stirred until all the dry ice has dissolved and the reaction is then stopped by the addition of 40 ml of water. The phases are separated and the organic phase is extracted twice with 20 ml of water. The combined aqueous phases are suction filtered and the filtrate is adjusted to pH 2 with concentrated hydrochloric acid. The solid precipitated is suction filtered and dried in vacuo.

Yield: 1.93 mg (47% of theory)
Mass spectrum (ESI$^-$): m/z=204 [M−H]$^-$

Example IV 7-formyl-1-methyl-1H-indole-2-carboxylic acid; salt with N-methyl-morpholine

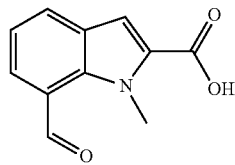

1.9 g 7-hydroxymethyl-1-methyl-1H-indole-2-carboxylic acid, 1.63 g N-methyl-morpholine-N-oxide and 400 mg molecular sieve (3 Å) are dissolved in 10 ml dichloromethane and combined with 260 mg tetra-n-propyl-ammonium-perrhutenate. The mixture is stirred for 12 hours at ambient temperature and the residue is chromatographed on silica gel with dichloromethane/methanol (95:1 to 80:20).

Yield: 1.45 g (51% of theory)
HPLC (method 2): retention time=2.75 min.
Mass spectrum (ESI$^+$): m/z=204 [M+H]$^+$ The following compound is obtained analogously to Example IV:

(1) 7-formyl-1-methyl-1H-indole-2-carboxylic acid-(5-tert-butyl-3-methanesulphonylamino-2-methoxy-phenyl)-amide

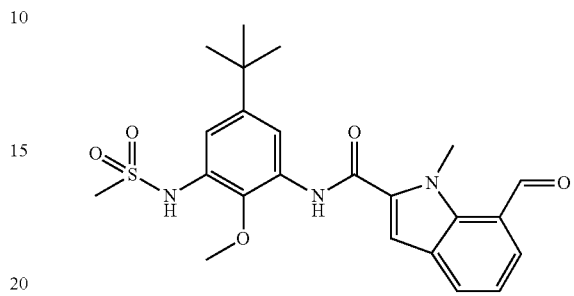

Mass spectrum (ESI$^+$): m/z=458 [M+H]$^+$

Example V 7-formyl-1-methyl-1H-indole-2-carboxylic acid(5-tert-butyl-3-methanesulphonylamino-2-methoxy-phenyl)-amide

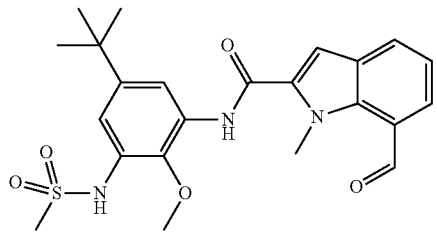 [SMILES: COc1c(NC(=O)c2cc3cccc(C=O)c3n2C)cc(C(C)(C)C)cc1NS(C)(=O)=O]

1.45 g 7-formyl-1-methyl-1H-indole-2-carboxylic acid (salt with N-methyl-morpholine) are dissolved in 8 ml N,N-dimethylformamide and combined with 2.72 g O-(7-azabenzotriazol-1-yl)-N,N,N',N'-tetramethyluronium-hexafluoro-phosphate (HATU), 2.45 ml N,N-diisopropyl-ethylamine (DIEA) as well as 324 mg 1-hydroxy-7-azabenzotriazole (HOAT). The mixture is left for 15 minutes at ambient temperature with stirring and then 1.47 g N-(3-amino-5-tert-butyl-2-methoxy-phenyl)-methanesulphonamide hydrochloride are added. The reaction is heated to 50° C. for 12 hours and then divided between water and ethyl acetate. The organic phase is washed successively with 1 N hydrochloric acid, water and saturated aqueous sodium chloride solution and dried on magnesium sulphate. After elimination of the solvents in vacuo the residue is chromatographed on silica gel with cyclohexane/ethyl acetate (70:30 to 20:80).

Yield: 1.43 g (66% of theory)
HPLC (method 2): retention time=3.37 min.
Mass spectrum (ESI$^+$): m/z=458 [M+H]$^+$

Example VI

Tert-butyl 4-[2-(5-tert-butyl-3-methanesulphony-lamino-2-methoxy-phenylcarbamoyl)-1-methyl-1H-indol-7-ylmethyl]-piperazine-1-carboxylate

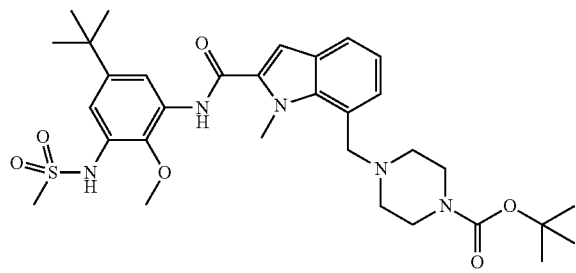 [SMILES: COc1c(NC(=O)c2cc3cccc(CN4CCN(C(=O)OC(C)(C)C)CC4)c3n2C)cc(C(C)(C)C)cc1NS(C)(=O)=O]

1.1 g 7-formyl-1-methyl-1H-indole-2-carboxylic acid(5-tert-butyl-3-methanesulphonylamino-2-methoxy-phenyl)-amide are dissolved in 50 ml 1,2-dichloroethane and combined with 2.63 ml glacial acetic acid as well as a solution of 4.48 g tert-butyl piperazine-1-carboxylate in 20 ml of 1,2-dichloroethane. The mixture is stirred for 30 minutes at ambient temperature and then 2.04 g sodium triacetoxyborohydride are added batchwise. Then the mixture is left for 4 hours with stirring and the reaction is stopped by the addition of saturated aqueous sodium hydrogen carbonate solution. A sufficient amount of ethyl acetate is added and the phases are separated. The aqueous phase is extracted twice with ethyl acetate and the combined organic phases are washed with saturated aqueous sodium chloride solution. After drying with magnesium sulphate, the solvents are eliminated in vacuo and the residue is chromatographed on silica gel with cyclohexane/ethyl acetate (80:20 to 20:80).

Yield: 1.13 g (75% of theory)
$R_f$ value: 0.30 (silica gel, cyclohexane/ethyl acetate 6:4)
Mass spectrum (ESI$^+$): m/z=628 [M+H]$^+$ The following compounds are obtained analogously to Example VI:

(1) tert-butyl 4-[2-(5-tert-butyl-3-methanesulphony-lamino-2-methoxy-phenylcarbamoyl)-1-methyl-1H-indol-7-ylmethyl]-[1,4]diazepan-1-carboxylate

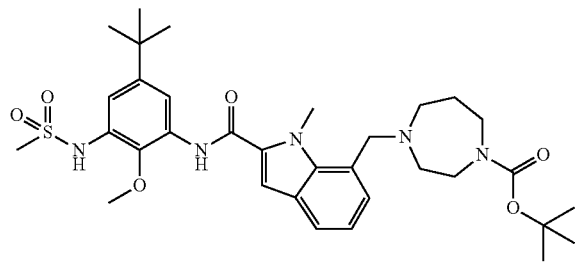 [SMILES: COc1c(NC(=O)c2cc3cccc(CN4CCCN(C(=O)OC(C)(C)C)CC4)c3n2C)cc(C(C)(C)C)cc1NS(C)(=O)=O]

$R_f$ value: 0.50 (silica gel, cyclohexane/ethyl acetate 1:1)
Mass spectrum (ESI$^+$): m/z=642 [M+H]$^+$ (2) tert-butyl 1-[2-(5-tert-butyl-3-methanesulphony-lamino-2-methoxy-phenylcarbamoyl)-1-methyl-1H-indol-7-ylmethyl]-piperidine-4-carboxylate

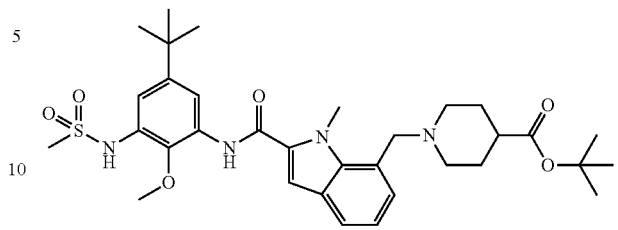

HPLC (method 1): retention time=3.22 min.
Mass spectrum (ESI$^+$): m/z=627 [M+H]$^+$ (3) (S)-1-methyl-7-[4-(1-methyl-pyrrolidine-2-carbo-nyl)-piperazin-1-ylmethyl]-1H-indole-2-carboxylic acid

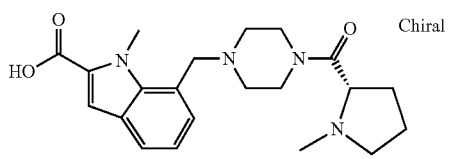 [SMILES: CN1CCC[C@H]1C(=O)N1CCN(Cc2cccc3cc(C(=O)O)n(C)c23)CC1]

7-formyl-1-methyl-1H-indole-2-carboxylic acid and (1-methyl-pyrrolidin-2-yl)-piperazin-1-yl-methanone are used as reaction partners. After the reaction has ended the solvents are eliminated in vacuo and the residue is taken up in a little dichloromethane/methanol 80:20. The solution is added to a short layer of silica gel and sucked into a vacuum suction flask by the application of reduced pressure. Then dichloromethane/methanol/water 1:1:0.1 is added in several small batches and again the solution is sucked into a vacuum suction flask by the application of reduced pressure. The fractions containing the product are combined and evaporated down in vacuo.

HPLC (method 6): retention time=1.99 min.
Mass spectrum (ESI$^+$): m/z=385 [M+H]$^+$

Example VII 1-methyl-7-piperazin-1-ylmethyl-1H-indole-2-car-boxylic acid(5-tert-butyl-3-methanesulphonylamino-2-methoxy-phenyl)-amide

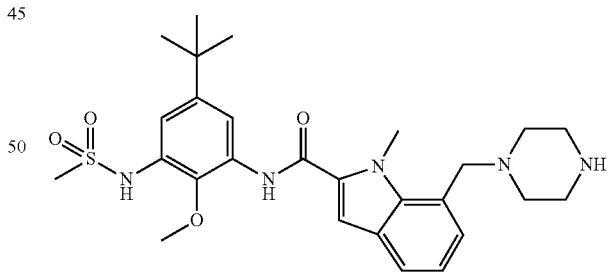

1.13 g tert-butyl 4-[2-(5-tert-butyl-3-methanesulphony-lamino-2-methoxy-phenylcarbamoyl)-1-methyl-1H-indol-7-ylmethyl]-piperazine-1-carboxylate are dissolved in 20 ml of a 5 M solution of HCl in isopropanol and stirred for 12 hours at ambient temperature. Then the mixture is adjusted to pH 9 with saturated aqueous sodium hydrogen carbonate solution and extracted twice with ethyl acetate. The combined organic phases are dried on magnesium sulphate and the solvent is eliminated in vacuo.

Yield: 955 mg (101% of theory)
HPLC (method 2): retention time=1.88 min.
Mass spectrum (ESI$^+$): m/z=528 [M+H]$^+$

Example VIII tert-butyl 3-{4-[2-(5-tert-butyl-3-methanesulphony-lamino-2-methoxy-phenylcarbamoyl)-1-methyl-1H-indol-7-ylmethyl]-piperazine-1-carbonyl}-azetidine-1-carboxylate

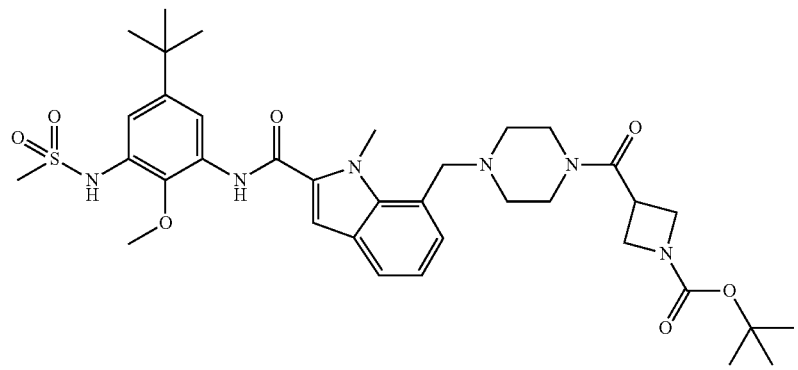 [SMILES: COc1c(NC(=O)c2cc3cccc(CN4CCN(C(=O)C5CN(C(=O)OC(C)(C)C)C5)CC4)c3n2C)cc(C(C)(C)C)cc1NS(C)(=O)=O]

153 mg 1-(tert.-butoxycarbonyl)-azetidine-3-carboxylic acid are dissolved in 3 ml N,N-dimethylformamide and combined with 244 mg O-(benzotriazol-1-yl)-N,N,N',N'-tetramethyluronium-tetrafluoroborate (TBTU) as well as 245 µl N,N-diisopropyl-ethylamine (DIEA). The mixture is left for 20 minutes with stirring, then 150 mg 1-methyl-7-piperazin-1-ylmethyl-1H-indole-2-carboxylic acid(5-tert-butyl-3-methanesulphonylamino-2-methoxy-phenyl)-amide are added and the mixture is stirred for 12 hours. It is then divided between water and ethyl acetate and the aqueous phase is extracted twice with ethyl acetate. The combined organic phases are washed with saturated aqueous sodium chloride solution and dried on magnesium sulphate. Then the solvents are eliminated in vacuo and the residue is chromatographed on silica gel with cyclohexane/ethyl acetate 70:30 to 0:100.

Yield: 243 mg (90% of theory)

$R_f$ value: 0.80 (silica gel, ethyl acetate)

Mass spectrum (ESI$^+$): m/z=711 [M+H]$^+$

The following compounds are obtained analogously to Example VIII:

(1) tert-butyl (S)-3-{4-[2-(5-tert-butyl-3-methane-sulphonylamino-2-methoxy-phenylcarbamoyl)-1-methyl-1H-indol-7-ylmethyl]-piperazine-1-carbonyl}-pyrrolidine-1-carboxylate

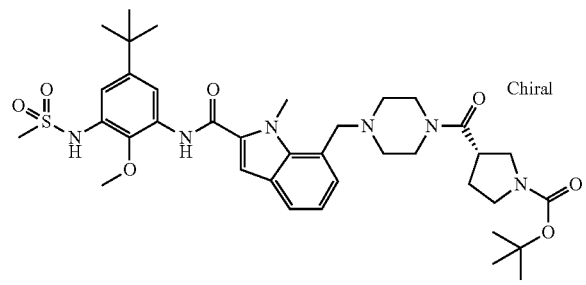 [SMILES: COc1c(NC(=O)c2cc3cccc(CN4CCN(C(=O)[C@H]5CCN(C(=O)OC(C)(C)C)C5)CC4)c3n2C)cc(C(C)(C)C)cc1NS(C)(=O)=O]

HPLC (method 1): retention time=3.40 min.

(2) tert-butyl (S)-3-{4-[2-(5-tert-butyl-3-methane-sulphonylamino-2-methoxy-phenylcarbamoyl)-1-methyl-1H-indol-7-ylmethyl]-[1,4]diazepan-1-carbonyl}-pyrrolidine-1-carboxylate

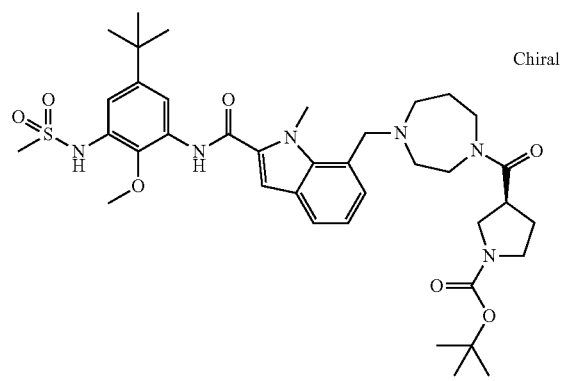 [SMILES: COc1c(NC(=O)c2cc3cccc(CN4CCCN(C(=O)[C@H]5CCN(C(=O)OC(C)(C)C)C5)CC4)c3n2C)cc(C(C)(C)C)cc1NS(C)(=O)=O]

$R_f$ value: 0.70 (silica gel, dichloromethane/methanol/(ammonia in methanol (saturated)) 95:5:0.1)

(3) tert-butyl (R)-3-{4-[2-(5-tert-butyl-3-methane-sulphonylamino-2-methoxy-phenylcarbamoyl)-1-methyl-1H-indol-7-ylmethyl]-[1,4]diazepan-1-carbonyl}-pyrrolidine-1-carboxylate

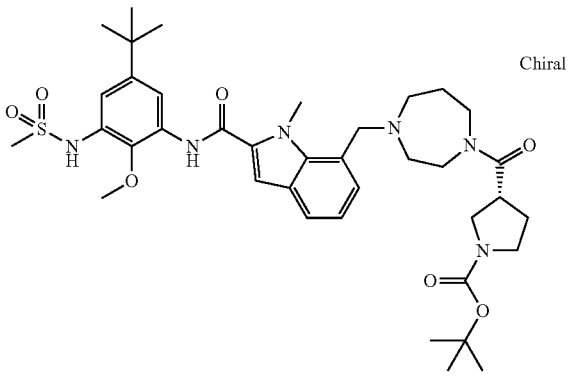 [SMILES: COc1c(NC(=O)c2cc3cccc(CN4CCCN(C(=O)[C@@H]5CCN(C(=O)OC(C)(C)C)C5)CC4)c3n2C)cc(C(C)(C)C)cc1NS(C)(=O)=O]

$R_f$ value: 0.73 (silica gel, dichloromethane/methanol/(ammonia in methanol (saturated)) 95:5:0.1)

Example IX

1-methyl-azetidine-3-carboxylic acid

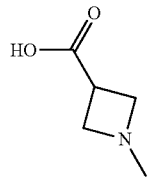

200 mg azetidine-3-carboxylic acid are dissolved in 10 ml of methanol, combined with 165 µl of a 37% solution of formaldehyde in water as well as 20 mg 10% palladium on charcoal and hydrogenated at 4 bar until the hydrogen uptake has ended. Then the catalyst is eliminated by suction filtering, the solvent is eliminated in vacuo, the residue is taken up in methanol and toluene and the solvents are again eliminated in vacuo.

Yield: 214 mg (94% of theory)
Mass spectrum (ESI$^+$): m/z=116 [M+H]$^+$

The following compounds are obtained analogously to Example IX:

(1) (R)-1-methyl-pyrrolidine-2-carboxylic acid

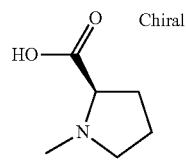

Mass spectrum (ESI$^+$): m/z=130 [M+H]$^+$ (2) 1-methyl-azetidine-2-carboxylic acid

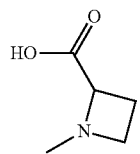

Mass spectrum (ESI$^+$): m/z=116 [M+H]$^+$ (3) (2S,4R)-4-hydroxy-1-methyl-pyrrolidine-2-carboxylic acid

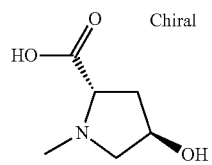

Mass spectrum (ESI$^+$): m/z=146 [M+H]$^+$ (4) (2R,4R)-4-methoxy-1-methyl-pyrrolidine-2-carboxylic acid hydrochloride

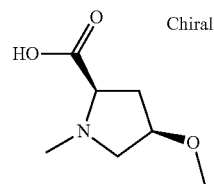

Mass spectrum (ESI$^+$): m/z=160 [M+H]$^+$ (5) (2R,4R)-4-hydroxy-1-methyl-pyrrolidine-2-carboxylic acid

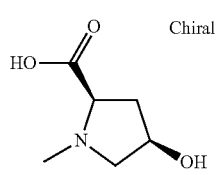

Mass spectrum (ESI$^+$): m/z=146 [M+H]$^+$ (6) (2R,4S)-4-hydroxy-1-methyl-pyrrolidine-2-carboxylic acid

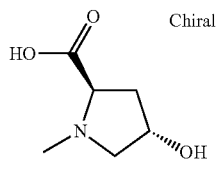

Mass spectrum (ESI$^+$): m/z=146 [M+H]$^+$ (7) (2S,4S)-4-hydroxy-1-methyl-pyrrolidine-2-carboxylic acid

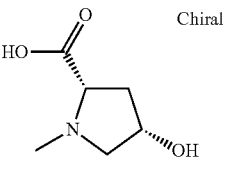

Mass spectrum (ESI$^+$): m/z=146 [M+H]$^+$

Example X

1-methyl-7-piperidin-4-ylmethyl-1H-indole-2-carboxylic acid(5-tert-butyl-3-methanesulphonyl-amino-2-methoxy-phenyl)-amide

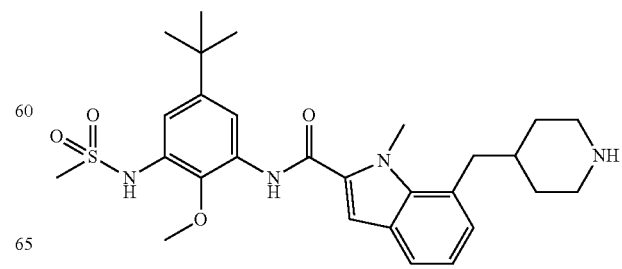

1.6 g tert-butyl 4-[2-(5-tert-butyl-3-methanesulphonylamino-2-methoxy-phenylcarbamoyl)-1-methyl-1H-indol-7-ylmethyl]-piperidine-1-carboxylate are dissolved in 10 ml dichloromethane, combined with 1.34 ml trifluoroacetic acid and stirred for 12 hours at ambient temperature. The solvents are eliminated in vacuo, the residue is taken up in methanol and adjusted to pH 12 with 1 N sodium hydroxide solution. The mixture is stirred for one hour, the methanol is eliminated in vacuo and the residue is divided between water and dichloromethane. Then the aqueous phase is extracted twice with dichloromethane. The combined organic phases are dried on magnesium sulphate and the solvents are eliminated in vacuo.

Yield: 1.6 g (119% of theory)

HPLC (method 1): retention time=2.83 min.

Example XI tert-butyl 4-[2-(5-tert-butyl-3-methanesulphonylamino-2-methoxy-phenylcarbamoyl)-1-methyl-1H-indol-7-ylmethyl]-piperidine-1-carboxylate

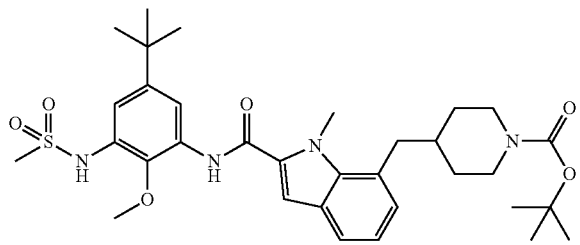 [SMILES: COc1c(NC(=O)c2cc3cccc(CC4CCN(C(=O)OC(C)(C)C)CC4)c3n2C)cc(C(C)(C)C)cc1NS(C)(=O)=O]

A mixture of 620 mg tert-butyl 4-methylene-piperidine-1-carboxylate and 6.3 ml of a 0.5 M solution of 9-borabicyclo[3.3.1]nonane in tetrahydrofuran is heated for one hour to 80° C. under argon. The solution thus prepared is added under argon to a mixture of 1.8 g 2-(5-tert-butyl-3-methanesulphonylamino-2-methoxy-phenylcarbamoyl)-1-methyl-1H-indol-7-yl trifluoro-methanesulphonate, 3.5 g potassium carbonate and 253 mg [1,1'-bis(diphenylphosphino)-ferrocen]dichloropalladium(II) complex with dichloromethane (1:1) in 12 ml N,N-dimethylformamide and 1.2 ml of water. The mixture is heated for 3 hours to 60° C., the solvents are eliminated in vacuo, taken up in ethyl acetate and the insoluble ingredients are filtered off. The filtrate is washed twice with water and once with saturated aqueous sodium chloride solution. After drying with magnesium sulphate the solvent is eliminated in vacuo and the residue is chromatographed on silica gel with cyclohexane/ethyl acetate 80:20 to 20:80.

Yield: 1.6 g (82% of theory)

HPLC (method 1): retention time=5.15 min.

Mass spectrum (ESI⁻): m/z=625 [M–H]⁻

The following compounds are obtained analogously to Example XI:

(1) tert-butyl 4-[2-(5-tert-butyl-3-methanesulphonylamino-2-methoxy-phenylcarbamoyl)-1-methyl-1H-indol-7-ylmethyl]-azepan-1-carboxylate

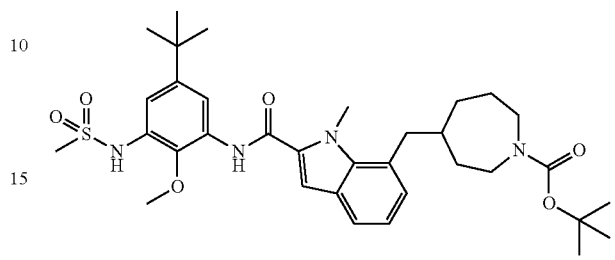

7-bromo-1-methyl-1H-indole-2-carboxylic acid-(5-tert-butyl-3-methanesulphonylamino-2-methoxy-phenyl)-amide is used instead of 2-(5-tert-butyl-3-methanesulphonylamino-2-methoxy-phenylcarbamoyl)-1-methyl-1H-indol-7-yl trifluoro-methanesulphonate and tert-butyl 4-methylene-azepan-1-carboxylate is used instead of tert-butyl 4-methylene-piperidine-1-carboxylate.

R$_f$ value: 0.40 (silica gel, dichloromethane/methanol 98:2)

Mass spectrum (ESI⁻): m/z=639 [M–H]⁻

(2) tert-butyl 4-[2-(5-tert-butyl-3-methanesulphonylamino-2-methoxy-phenylcarbamoyl)-1-methyl-1H-indol-7-ylmethyl]-piperidine-1-carboxylate

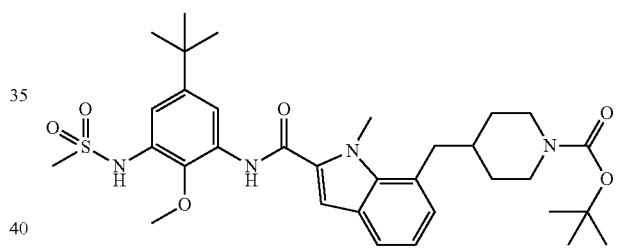

7-bromo-1-methyl-1H-indole-2-carboxylic acid-(5-tert-butyl-3-methanesulphonylamino-2-methoxy-phenyl)-amide is used instead of 2-(5-tert-butyl-3-methanesulphonylamino-2-methoxy-phenylcarbamoyl)-1-methyl-1H-indol-7-yl trifluoro-methanesulphonate.

HPLC (method 1): retention time=5.14 min.

Mass spectrum (ESI⁻): m/z=625 [M–H]⁻

Example XII 2-(5-tert-butyl-3-methanesulphonylamino-2-methoxy-phenyl-carbamoyl)-1-methyl-1H-indol-7-yl trifluoro-methanesulphonate

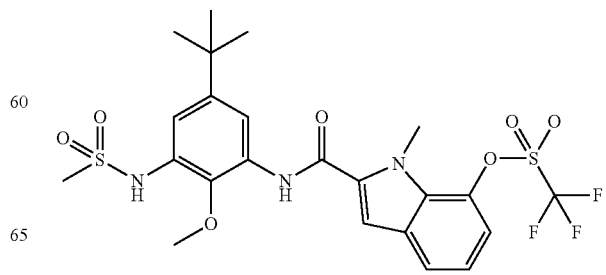

Under argon, 1.75 g 7-hydroxy-1-methyl-1H-indole-2-carboxylic acid(5-tert-butyl-3-methanesulphonylamino-2-methoxy-phenyl)-amide (for preparation see US20040186114) are dissolved in 30 ml of tetrahydrofuran, combined successively with 1.82 g N-phenyltrifluoromethanesulphonimide and 1.4 ml triethylamine and heated for 12 hours to 70° C. Then a further 700 mg N-phenyltrifluoromethanesulphonimide and 550 µl triethylamine are added and the mixture is heated for a further 12 hours to 70° C. Then the solvents are eliminated in vacuo and the residue is chromatographed on silica gel with cyclohexane/ethyl acetate 80:20 to 40:60.

Yield: 2 g (88% of theory)
HPLC (method 1): retention time=4.90 min.
Mass spectrum (ESI$^+$): m/z=578 [M+H]$^+$ Example XIII (S)-1-methyl-7-[4-(pyrrolidine-3-carbonyl)-piperazin-1-ylmethyl]-1H-indole-2-carboxylic acid(5-tert-butyl-3-methanesulphonylamino-2-methoxy-phenyl)-amide

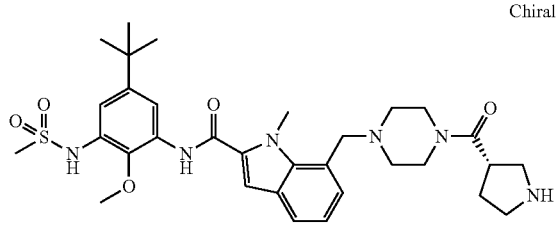 [SMILES: COc1c(NC(=O)c2cc3cccc(CN4CCN(C(=O)[C@H]5CCNC5)CC4)c3n2C)cc(C(C)(C)C)cc1NS(C)(=O)=O]

220 mg tert-butyl (S)-3-{4-[2-(5-tert-butyl-3-methanesulphonylamino-2-methoxy-phenylcarbamoyl)-1-methyl-1H-indol-7-ylmethyl]-piperazine-1-carbonyl}-pyrrolidine-1-carboxylate are dissolved in 5 ml dichloromethane, combined with 231 µl trifluoroacetic acid and stirred for 12 hours at ambient temperature. Then the solvents are eliminated in vacuo, divided between saturated aqueous sodium hydrogen carbonate solution and dichloromethane and stirred vigorously for 30 minutes. The phases are separated, the aqueous phase is extracted twice with dichloromethane and the combined organic phases are dried on magnesium sulphate. Then the solvents are eliminated in vacuo and the crude product is chromatographed on silica gel (dichloromethane/(methanol-conc. ammonia 9:1) 90:10 to 80:20).

Yield: 104 mg (55% of theory)
HPLC (method 1): retention time=2.36 min.
Mass spectrum (ESI$^+$): m/z=625 [M+H]$^+$ The following compounds are obtained analogously to Example XIII:

(1) 7-azepan-4-ylmethyl-1-methyl-1H-indole-2-carboxylic acid-(5-tert-butyl-3-methanesulphonylamino-2-methoxy-phenyl)-amide

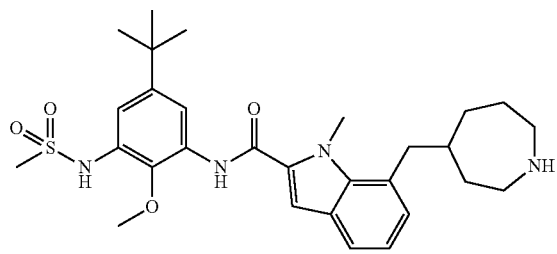 [SMILES: COc1c(NC(=O)c2cc3cccc(CC4CCCNCC4)c3n2C)cc(C(C)(C)C)cc1NS(C)(=O)=O]

Saturated sodium carbonate solution is used instead of saturated aqueous sodium hydrogen carbonate solution.
R$_f$ value: 0.20 (silica gel, dichloromethane/methanol/(ammonia in methanol (saturated)) 90:10:0.1)
Mass spectrum (ESI$^+$): m/z=541 [M+H]$^+$ (2) 7-[1,4]diazepan-1-ylmethyl-1-methyl-1H-indole-2-carboxylic acid-(5-tert-butyl-3-methanesulphonylamino-2-methoxy-phenyl)-amide

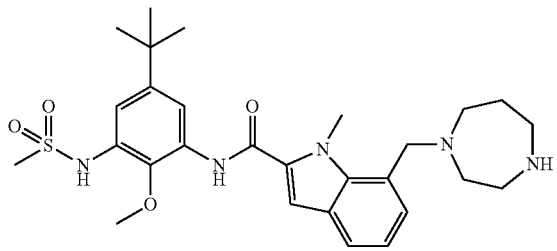 [SMILES: COc1c(NC(=O)c2cc3cccc(CN4CCCNCC4)c3n2C)cc(C(C)(C)C)cc1NS(C)(=O)=O]

Saturated sodium carbonate solution is used instead of saturated aqueous sodium hydrogen carbonate solution.
R$_f$ value: 0.10 (silica gel, dichloromethane/methanol/(ammonia in methanol (saturated)) 95:5:0.1)
Mass spectrum (ESI$^+$): m/z=542 [M+H]$^+$ (3) (S)-1-methyl-7-[4-(pyrrolidine-3-carbonyl)-[1,4]diazepan-1-ylmethyl]-1H-indole-2-carboxylic acid-(5-tert-butyl-3-methanesulphonylamino-2-methoxy-phenyl)-amide

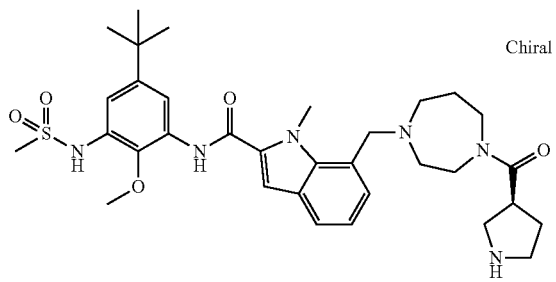 [SMILES: COc1c(NC(=O)c2cc3cccc(CN4CCCN(C(=O)[C@H]5CCNC5)CC4)c3n2C)cc(C(C)(C)C)cc1NS(C)(=O)=O]

Saturated sodium carbonate solution is used instead of saturated aqueous sodium hydrogen carbonate solution.
R$_f$ value: 0.10 (silica gel, dichloromethane/methanol/(ammonia in methanol (saturated)) 95:5:0.1)

(4) (R)-1-methyl-7-[4-(pyrrolidine-3-carbonyl)-[1,4]diazepan-1-ylmethyl]-1H-indole-2-carboxylic acid-(5-tert-butyl-3-methanesulphonylamino-2-methoxy-phenyl)-amide

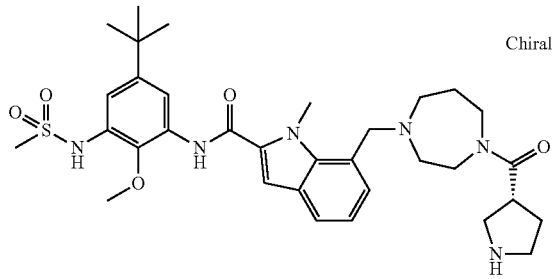 [SMILES: COc1c(NC(=O)c2cc3cccc(CN4CCCN(C(=O)[C@@H]5CCNC5)CC4)c3n2C)cc(C(C)(C)C)cc1NS(C)(=O)=O]

Saturated sodium carbonate solution is used instead of saturated aqueous sodium hydrogen carbonate solution.
R$_f$ value: 0.10 (silica gel, dichloromethane/methanol/(ammonia in methanol (saturated)) 95:5:0.1)

Example XIV (2R,4R)-4-methoxy-pyrrolidine-2-carboxylic acid hydrochloride

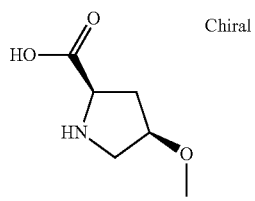

8.72 g 1-tert-butyl (2R,4R)-4-methoxy-pyrrolidine-1,2-dicarboxylate are dissolved in 60 ml of tetrahydrofuran, combined dropwise with 60 ml of a 6 M aqueous hydrochloric acid solution and stirred for 4 hours at ambient temperature. Then the solvents are eliminated in vacuo and the residue is taken up twice in 100 ml acetonitrile and the latter is in each case eliminated again in vacuo.

Yield: 6.91 g (107% of theory)
Mass spectrum (ESI$^+$): m/z=146 [M+H]$^+$

Example XV 1-tert-butyl (2R,4R)-4-methoxy-pyrrolidine-1,2-dicarboxylate

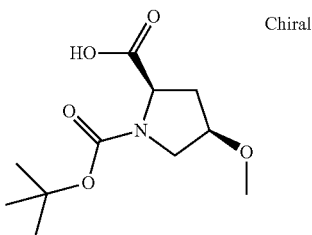 [SMILES: CO[C@@H]1C[C@H](C(=O)O)N(C(=O)OC(C)(C)C)C1]

13.72 g 1-tert-butyl (2R,4R)-4-hydroxy-pyrrolidine-1,2-dicarboxylate are dissolved in 150 ml of N,N-dimethylformamide, cooled to 0° C. and combined batchwise with 7.12 g of a 50% dispersion of sodium hydride in paraffin oil. The mixture is stirred for 20 minutes at ambient temperature and then 14.77 ml methyl iodide are added thereto. Then the mixture is left for 18 hours with stirring, a further 1.47 ml methyl iodide are added dropwise and the mixture is stirred for a further 6 hours. Then it is diluted with water, the aqueous phase is extracted twice with ethyl acetate and the combined organic phases are washed with saturated aqueous sodium chloride solution. After drying with magnesium sulphate the solvents are eliminated in vacuo. The residue is dissolved in 600 ml of methanol, combined with 74 ml of 4 M aqueous sodium hydroxide solution and stirred for 3 days at ambient temperature. After elimination of the methanol in vacuo the residue is diluted with water and acidified with saturated aqueous potassium hydrogen sulphate solution. It is extracted 3 times with ethyl acetate, then the combined organic phases are dried on sodium sulphate and then the solvents are eliminated in vacuo. The mixture is then taken up 500 ml of methanol once more, combined with 74 ml of 4 M aqueous sodium hydroxide solution and stirred for 12 hours. A further 74 ml of 4 M aqueous sodium hydroxide solution is added and the mixture is heated for 5 hours to 50° C. About 200 ml of methanol is eliminated in vacuo and the mixture is stirred for a further 12 hours. Then the remaining methanol is eliminated in vacuo, the residue is diluted with water and washed once with diethyl ether. The aqueous phase is acidified with saturated aqueous potassium hydrogen sulphate solution and extracted 4 times with ethyl acetate. The combined organic phases are dried on sodium sulphate and the solvents are eliminated in vacuo. The residue is purified by preparative HPLC (method 4; 500 mg per injection).

Yield: 7.97 g (55% of theory)
Mass spectrum (ESI$^-$): m/z=244 [M−H]$^-$

Example XVI tert-butyl 4-[2-(5-tert-butyl-3-methanesulphonylamino-2-methoxy-phenylcarbamoyl)-1-methyl-1H-indol-7-ylmethyl]-piperazine-1-carboxylate

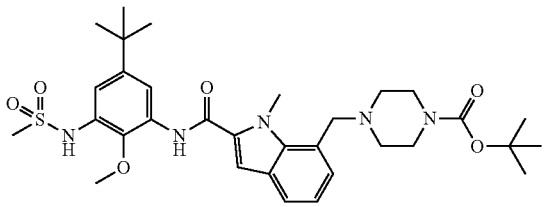 [SMILES: COc1c(NC(=O)c2cc3cccc(CN4CCN(C(=O)OC(C)(C)C)CC4)c3n2C)cc(C(C)(C)C)cc1NS(C)(=O)=O]

8.99 g 7-bromo-1-methyl-1H-indole-2-carboxylic acid-(5-tert-butyl-3-methanesulphonylamino-2-methoxy-phenyl)-amide and 5.95 g potassium ((4-(tert.-butoxycarbonyl)-piperazin-1-yl)-methyl)-trifluoroborate (for preparation see *Org. Lett.* 2007, 9, 1597-1600) are dissolved in 150 ml of tetrahydrofuran and 15 ml of water, combined with 17.3 g caesium carbonate and argon is piped through the resulting solution for 10 minutes. Then 120 mg palladium-II-acetate and 1.23 g 2-dicyclohexylphosphino-2',4',6'-triisopropyl-1,1'-biphenyl (XPhos) are added and the mixture is heated to 80° C. for 12 hours. Then it is divided between water and ethyl acetate and the organic phase is washed with saturated aqueous sodium chloride solution. After drying with magnesium sulphate the solvents are eliminated in vacuo. The crude product is further reacted directly.

Yield: 13.5 g (97% of theory)
HPLC (method 1): retention time=3.44 min.
Mass spectrum (ESI$^+$): m/z=628 [M+H]$^+$ The following compounds are obtained analogously to Example XVI:

(1) tert-butyl 4-[2-(5-isobutyl-3-methanesulphonylamino-2-methoxy-phenylcarbamoyl)-1-methyl-1H-indol-7-ylmethyl]-piperazine-1-carboxylate

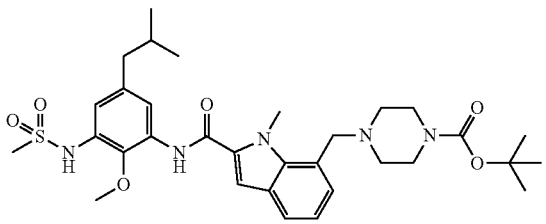 [SMILES: COc1c(NC(=O)c2cc3cccc(CN4CCN(C(=O)OC(C)(C)C)CC4)c3n2C)cc(CC(C)C)cc1NS(C)(=O)=O]

HPLC (method 1): retention time=3.55 min.
Mass spectrum (ESI$^+$): m/z=628 [M+H]$^+$

Example XVII 7-bromo-1-methyl-1H-indole-2-carboxylic acid-(5-tert-butyl-3-methanesulphonylamino-2-methoxy-phenyl)-amide

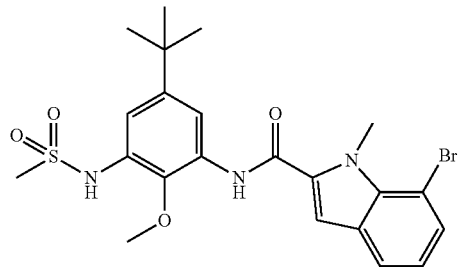 [SMILES: COc1c(NC(=O)c2cc3cccc(Br)c3n2C)cc(C(C)(C)C)cc1NS(C)(=O)=O]

to Under argon 6.15 g 7-bromo-1-methyl-1H-indole-2-carboxylic acid are dissolved in 60 ml of tetrahydrofuran, combined with 16.8 triethylamine as well as 19 ml of a 50% solution of n-propylphosphonic anhydride in ethyl acetate and stirred for 45 minutes at 0° C. Then 6.59 g N-(3-amino-5-tert-butyl-2-methoxy-phenyl)-methanesulphonamide are added batchwise. The mixture is left to come up to ambient temperature and stirred for a further 2.5 hours. Then the solvents are eliminated in vacuo and the residue is divided between saturated aqueous sodium hydrogen carbonate solution and ethyl acetate. A precipitate settles out, which is filtered off and dried (solid 1; 6.29 g). The phases are separated and the aqueous phase is extracted with ethyl acetate. The combined organic phases are washed with water and saturated aqueous sodium chloride solution and then dried on magnesium sulphate. The solvents are eliminated in vacuo and the residue is extracted from ethanol. The precipitate is filtered off, washed with a little ethanol and dried (solid 2; 2.7 g).

Yield: 8.99 g (73% of theory) (solid 1+2)
HPLC (method 1): retention time=4.80 min.
Mass spectrum (ESI$^+$): m/z=508 [M+H]$^+$ The following compounds are obtained analogously to Example XVII:

(1) benzyl (S)-4-(1-methyl-pyrrolidine-2-carbonyl)-piperazine-1-carboxylate

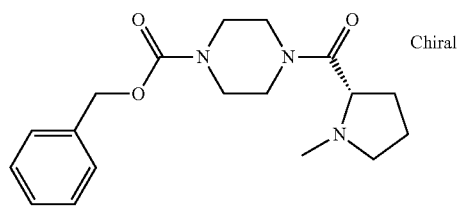 [SMILES: CN1CCC[C@H]1C(=O)N1CCN(C(=O)OCc2ccccc2)CC1]

Benzyl piperazine-1-carboxylate and (S)-1-methyl-pyrrolidine-2-carboxylic acid are used as reactants. After aqueous work up the crude product is obtained by evaporating the organic phase and further reacted directly.

R$_f$ value: 0.50 (silica gel, dichloromethane/methanol/(ammonia in methanol (saturated)) 90:10:0.1)
Mass spectrum (ESI$^+$): m/z=332 [M+H]$^+$

(2) 7-bromo-1-methyl-1H-indole-2-carboxylic acid-(5-isobutyl-3-methanesulphonylamino-2-methoxy-phenyl)-amide

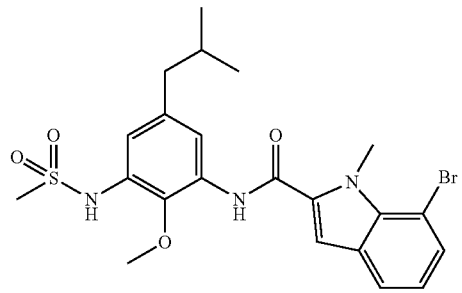 [SMILES: COc1c(NC(=O)c2cc3cccc(Br)c3n2C)cc(CC(C)C)cc1NS(C)(=O)=O]

HPLC (method 1): retention time=4.96 min.
Mass spectrum (ESI$^+$): m/z=508 [M+H]$^+$

Example XVIII 7-bromo-1-methyl-1H-indole-2-carboxylic acid

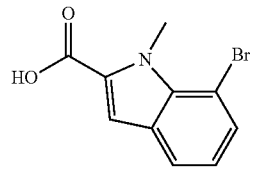

7.37 g ethyl 7-bromo-1H-indole-2-carboxylate are dissolved in 50 ml N,N-dimethylformamide, cooled to 0° C. and combined with 1.16 g sodium hydride (60% in mineral oil). The mixture is stirred for 20 minutes and then 1.78 ml methyl iodide are added dropwise. Then the mixture is allowed to come up to ambient temperature and stirred for 12 hours. Then 80 ml of methanol and 27.5 ml 2 N sodium hydroxide solution are added and the mixture is stirred for 3 hours at ambient temperature. The methanol is eliminated in vacuo, the residue is mixed with water and the precipitate is suction filtered. The filtrate is washed twice with ethyl acetate and the aqueous phase is combined with sufficient 2 N hydrochloric acid to give a pH of 2. The precipitated solid is suction filtered, washed with water and dried.

Yield: 4.26 g (61% of theory)
Mass spectrum (ESI$^-$): m/z=252 [M–H]$^-$

Example XIX

Ethyl 7-bromo-1H-indole-2-carboxylate

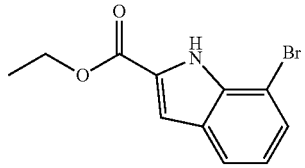

11.0 g 2-bromophenylhydrazine and 550 mg p-toluenesulphonic acid monohydrate are dissolved in 200 ml of toluene, combined with 6.74 ml ethyl pyruvate and refluxed for 2 hours using the water separator. The mixture is allowed to cool to 40° C. and combined with a solution that is obtained by dissolving 44.75 g p-toluenesulphonic acid monohydrate in 300 ml of toluene and refluxing for two hours using the water separator. Then the mixture is refluxed for 12 hours using the water separator. After cooling to ambient temperature the solvents are eliminated in vacuo, the residue is taken up in ethyl acetate and washed successively with water and saturated aqueous sodium hydrogen carbonate solution. After drying with magnesium sulphate the mixture is combined with activated charcoal, stirred for 15 minutes and filtered through kieselguhr. The process of adding activated charcoal, stirring and filtering is repeated twice more. The solvents are eliminated in vacuo and the residue is taken up in petroleum ether/dichloromethane 7:3. 30 g of silica gel are added, the mixture is stirred for 10 minutes and then suction filtered through kieselguhr. The suction filtered silica gel is washed with petroleum ether/dichloromethane 7:3. The solvents are eliminated in vacuo.

Yield: 7.37 g (47% of theory)

HPLC (method 1): retention time=3.82 min.

Mass spectrum (ESI$^+$): m/z=268 [M+H]$^+$

Example XX 2-bromophenylhydrazine

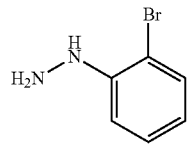

15 g 2-bromophenylhydrazine hydrochloride are suspended in 400 ml of toluene and combined with 240 ml of 1 N sodium hydroxide solution. The mixture is stirred for 1 hour and the phases are separated. The organic phase is dried on magnesium sulphate and the solvents are eliminated in vacuo. The crude product thus obtained is further reacted directly.

Yield: 12.12 g (99% of theory)

Mass spectrum (ESI$^+$): m/z=187 [M+H]$^+$

Example XXI

Tert-butyl 4-(2-{4-[2-(5-tert-butyl-3-methanesulphonylamino-2-methoxy-phenylcarbamoyl)-1-methyl-1H-indol-7-ylmethyl]-piperazin-1-yl}-2-oxo-ethyl)-piperazine-1-carboxylate

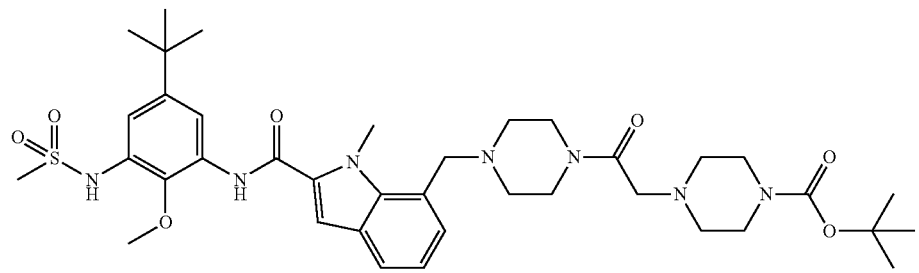 [SMILES: COc1c(NC(=O)c2cc3cccc(CN4CCN(C(=O)CN5CCN(C(=O)OC(C)(C)C)CC5)CC4)c3n2C)cc(C(C)(C)C)cc1NS(C)(=O)=O]

110 mg tert-butyl 4-carboxymethyl-piperazine-1-carboxylate are dissolved in 2 ml N,N-dimethylformamide, combined with 135 mg O-(benzotriazol-1-yl)-N,N,N',N'-tetramethyluronium-tetrafluoroborate (TBTU) as well as 270 µl N,N-diisopropyl-ethylamine (DIEA) and stirred for 20 minutes. Then 200 mg 1-methyl-7-piperazin-1-ylmethyl-1H-indole-2-carboxylic acid-(5-tert-butyl-3-methanesulphonylamino-2-methoxy-phenyl)-amide dihydrochloride are added, the mixture is stirred for 12 hours at ambient temperature and then divided between water and ethyl acetate. The organic phase is washed with saturated aqueous sodium chloride solution and dried on magnesium sulphate. The solvents are eliminated in vacuo and the residue is chromatographed on silica gel (dichloromethane/(methanol/conc. ammonia 9:1) 99:1 to 90:10).

Yield: 160 mg (64% of theory)

HPLC (method 1): retention time=2.79 min.

Mass spectrum (ESI$^+$): m/z=754 [M+H]$^+$

Example XXII 1-methyl-7-piperazin-1-ylmethyl-1H-indole-2-carboxylic acid(5-tert-butyl-3-methanesulphonylamino-2-methoxy-phenyl)-amide dihydrochloride

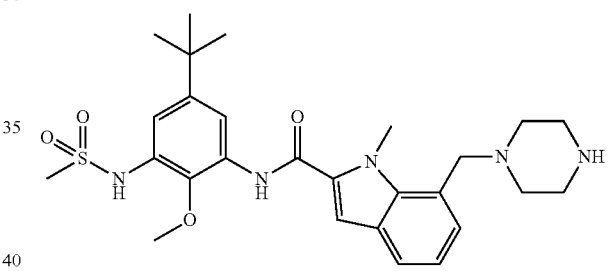

2.29 g tert-butyl 4-[2-(5-tert-butyl-3-methanesulphonylamino-2-methoxy-phenylcarbamoyl)-1-methyl-1H-indol-7-ylmethyl]-piperazine-1-carboxylate are dissolved in 25 ml of a 5 M solution of HCl in isopropanol and stirred for 12 hours at ambient temperature. Then the solvents are eliminated in vacuo and the residue is twice taken up with 20 ml of methanol and this is then eliminated again in vacuo.

Yield: 2.03 g (105% of theory)

Mass spectrum (ESI$^+$): m/z=528 [M+H]$^+$

Example XXIII

Tert-butyl 4-methylene-azepan-1-carboxylate

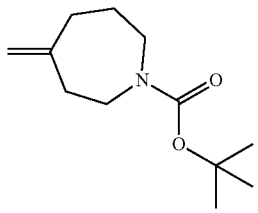

Under argon 12.56 g methyltriphenylphosphonium bromide are dissolved in 100 ml of tetrahydrofuran, cooled to −14° C. and within 45 minutes a 2 M solution of 17.58 ml n-butyllithium in hexane is added dropwise. The mixture is stirred for another 1 hour and then a solution of 5 g tert-butyl 4-oxo-azepan-1-carboxylate in 20 ml of tetrahydrofuran is added dropwise. Then the mixture is heated to ambient temperature and stirred for 12 hours. It is then divided between water and hexane and the aqueous phase is extracted twice with hexane. The combined organic phases are washed with saturated aqueous sodium chloride solution and dried on magnesium sulphate. The solvents are eliminated in vacuo and the residue is stirred with petroleum ether/tert.-butyl-methyl-ether. The solid is suction filtered and the mother liquor is evaporated down in vacuo. The residue is chromatographed on silica gel (petroleum ether/ethyl acetate 100:0, then 95:5).

Yield: 4.2 g (85% of theory)

$R_f$ value: 0.35 (silica gel, petroleum ether/ethyl acetate 95:5)

Mass spectrum (ESI$^+$): m/z=212 [M+H]$^+$

Example XXIV 7-hydroxymethyl-1-methyl-1H-indole-2-carboxylic acid-(5-tert-butyl-3-methanesulphonylamino-2-methoxy-phenyl)-amide

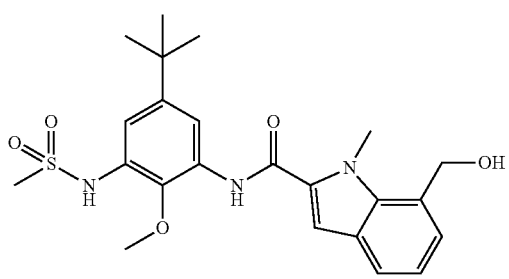 [SMILES: COc1c(NC(=O)c2cc3cccc(CO)c3n2C)cc(C(C)(C)C)cc1NS(C)(=O)=O]

Under argon 14.7 g of methyl 2-(5-tert-butyl-3-methanesulphonylamino-2-methoxy-phenylcarbamoyl)-1-methyl-1H-indole-7-carboxylate are dissolved in 120 ml of tetrahydrofuran, cooled to 0° C. and combined dropwise with 60 ml of a 1 M solution of lithium aluminium hydride in tetrahydrofuran. The mixture is stirred for 2 hours and then the reaction is stopped by the dropwise addition of 30 ml of 2 N sodium hydroxide solution. Then the mixture is stirred for 30 minutes, diluted with ethyl acetate and filtered through kieselguhr. The filter cake is taken up in 60 ml of tetrahydrofuran, stirred for 10 minutes and suction filtered through kieselguhr again. The combined organic phases are dried on magnesium sulphate and evaporated down in vacuo. The residue is extracted from methanol. The precipitated solid is filtered off and dried.

Yield: 8.2 g (59% of theory)

Mass spectrum (ESI$^-$): m/z=458 [M−H]$^-$

Example XXV

Methyl 2-(5-tert-butyl-3-methanesulphonylamino-2-methoxy-phenylcarbamoyl)-1-methyl-1H-indole-7-carboxylate

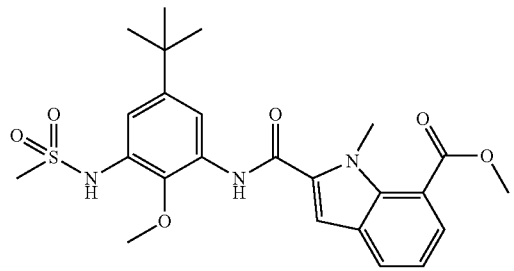

Argon is piped for 10 minutes through a suspension of 18.8 g 7-bromo-1-methyl-1H-indole-2-carboxylic acid-(5-tert-butyl-3-methanesulphonylamino-2-methoxy-phenyl)-amide in 250 ml of methanol and 50 ml N,N-dimethylformamide. Then 7.2 ml triethylamine and 2.3 g [1,1'-bis(diphenylphosphino)ferrocene]-palladium-II-dichloride-dichloromethane complex are added and 2 bar of carbon monoxide are compressed in for 15 hours at 80° C. Then the solvents are eliminated in vacuo, the residue is taken up in ethyl acetate and washed with 1 N hydrochloric acid, saturated aqueous sodium hydrogen carbonate solution and saturated aqueous sodium chloride solution. After drying with magnesium sulphate the solvent is eliminated in vacuo and the residue is extracted from methanol. The solid is suction filtered, washed with a little methanol and dried.

Yield: 14.7 g (81% of theory)

Mass spectrum (ESI$^+$): m/z=488 [M+H]$^+$

Example XXVI

N-(3-amino-5-tert-butyl-2-methoxy-phenyl)-methanesulphonamide

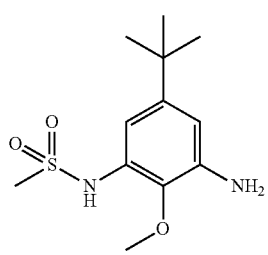 [SMILES: COc1c(N)cc(C(C)(C)C)cc1NS(C)(=O)=O]

50 g N-(3-amino-5-tert-butyl-2-methoxy-phenyl)-methanesulphonamid hydrochloride (*J. Med. Chem.* 2007, 50 (17), 4016-26) are suspended in 200 ml of water and 600 ml of ethyl acetate and sufficient 4 N sodium hydroxide solution is added with vigorous stirring to give a pH of 11. Then the phases are separated, the aqueous phase is extracted with ethyl acetate and the combined organic phases are dried on magnesium sulphate and evaporated down in vacuo. The solid thus obtained is further reacted directly.

Yield: 44 g (100% of theory)

Example XXVII (S)-1-methyl-7-[4-(1-methyl-pyrrolidine-2-carbonyl)-piperazin-1-ylmethyl]-1H-indole-2-carboxylic acid-(3-amino-5-tert-butyl-2-methoxy-phenyl)-amide trihydrochloride

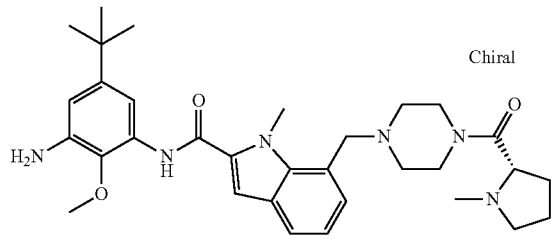 [SMILES: COc1c(N)cc(C(C)(C)C)cc1NC(=O)c1cc2cccc(CN3CCN(C(=O)[C@@H]4CCCN4C)CC3)c2n1C]

1.59 g tert-butyl [5-tert-butyl-2-methoxy-3-({1-methyl-7-[4-(1-methyl-pyrrolidine-2-carbonyl)-piperazin-1-ylmethyl]-1H-indole-2-carbonyl}-amino)-phenyl]-carbamate are dissolved in 15 ml dichloromethane, combined with 10 ml of a 5 M solution of hydrogen chloride in isopropanol and stirred for 3 hours at ambient temperature. Then the solvents are eliminated in vacuo. The product thus obtained is further reacted directly.

Yield: 1.80 mg (112% of theory)
HPLC (method 1): retention time=2.38 min.
Mass spectrum (ESI$^+$): m/z=561 [M+H]$^+$ The following compounds are obtained analogously to Example XXVII:

(1) 1-methyl-7-piperazin-1-ylmethyl-1H-indole-2-carboxylic acid-(5-isobutyl-3-methanesulphonylamino-2-methoxy-phenyl)-amide

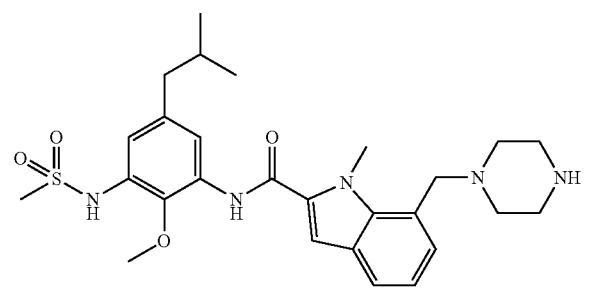 [SMILES: COc1c(NC(=O)c2cc3cccc(CN4CCNCC4)c3n2C)cc(CC(C)C)cc1NS(C)(=O)=O]

Tert-butyl 4-[2-(5-isobutyl-3-methanesulphonylamino-2-methoxy-phenylcarbamoyl)-1-methyl-1H-indol-7-ylmethyl]-piperazine-1-carboxylate is used instead of tert-butyl [5-tert-butyl-2-methoxy-3-({1-methyl-7-[4-(1-methyl-pyrrolidine-2-carbonyl)-piperazin-1-ylmethyl]-1H-indole-2-carbonyl}-amino)-phenyl]-carbamate. The crude product is divided between dichloromethane and saturated aqueous sodium hydrogen carbonate solution. The aqueous phase is extracted with dichloromethane. The combined organic phases are dried on magnesium sulphate and the solvents are eliminated in vacuo. The product thus obtained is further reacted directly.

HPLC (method 1): retention time=2.95 min.
Mass spectrum (ESI$^+$): m/z=528 [M+H]$^+$

Example XXVIII

1-[2-(5-tert-butyl-3-methanesulphonylamino-2-methoxy-phenylcarbamoyl)-1-methyl-1H-indol-7-ylmethyl]-piperidine-4-carboxylic acid

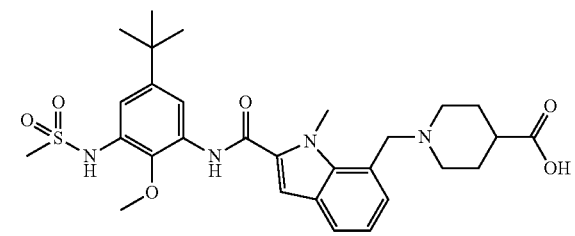 [SMILES: COc1c(NC(=O)c2cc3cccc(CN4CCC(C(=O)O)CC4)c3n2C)cc(C(C)(C)C)cc1NS(C)(=O)=O]

1.3 g tert-butyl 1-[2-(5-tert-butyl-3-methanesulphonylamino-2-methoxy-phenylcarbamoyl)-1-methyl-1H-indol-7-ylmethyl]-piperidine-4-carboxylate are dissolved in 20 ml dichloromethane, combined with 1.04 ml of a 4 M solution of hydrogen chloride in 1,4-dioxane and stirred for 12 hours. A further 2 ml of a 4 M solution of hydrogen chloride in 1,4-dioxane is added and the mixture is stirred for a further 24 hours. The solvents are eliminated in vacuo and the residue is taken up twice in dichloromethane and this is then eliminated in vacuo. The product thus obtained is further reacted directly.

Yield: 1.36 g (86% of theory)
HPLC (method 1): retention time=2.70 min.
Mass spectrum (ESI$^+$): m/z=571 [M+H]$^+$

Example XXIX 7-formyl-1-methyl-1H-indole-2-carboxylic acid

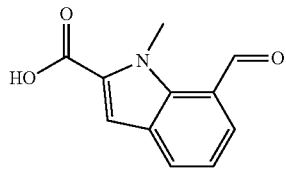

Under argon 4.14 g 7-bromo-1-methyl-1H-indole-2-carboxylic acid are dissolved in 36 ml of tetrahydrofuran and 5 ml 1,4-dioxane, cooled to −10° C. and combined dropwise with 37.6 ml of a 1.3 M solution of isopropylmagnesium chloride-lithium chloride complex in tetrahydrofuran. The mixture is slowly returned to ambient temperature and stirred for 12 hours. Then it is cooled to −10° C. and combined dropwise with 6.62 ml N,N-dimethylformamide. It is stirred for 30 minutes and the reaction is then ended by the addition of water. The organic solvents are mostly eliminated in vacuo and the pH value of the residue is adjusted to 2 by the addition of 4 N hydrochloric acid. The precipitated solid is suction filtered, taken up in tetrahydrofuran and dried on magnesium sulphate. The solvent is eliminated in vacuo and the solid thus obtained is further reacted directly.

Yield: 1.95 g (59% of theory)
HPLC (method 1): retention time=2.80 min.
Mass spectrum (ESI⁺): m/z=204 [M+H]⁺

Example XXX (S)-(1-methyl-pyrrolidin-2-yl)-piperazin-1-yl-methanone

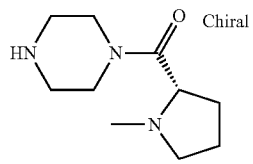

13.43 g benzyl (S)-4-(1-methyl-pyrrolidine-2-carbonyl)-piperazine-1-carboxylate are dissolved in 100 ml of methanol, combined with 1.4 g 10% palladium on charcoal and hydrogenated for 6 hours at ambient temperature and 3 bar hydrogen pressure. Then the catalyst is filtered off and the solvents are eliminated in vacuo. The product thus obtained is further reacted directly.

Yield: 7.95 g (99% of theory)
$R_f$ value: 0.20 (silica gel, dichloromethane/methanol/(ammonia in methanol (saturated)) 90:10:0.1)
Mass spectrum (ESI⁺): m/z=198 [M+H]⁺

Example XXXI (S)-1-methyl-7-[4-(1-methyl-pyrrolidine-2-carbonyl)-piperazin-1-ylmethyl]-1H-indole-2-carboxylic acid-(5-tert-butyl-3-formyl-2-methoxy-phenyl)-amide

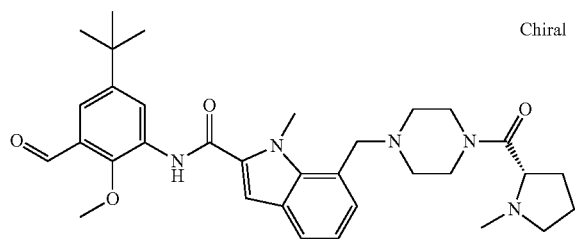 [SMILES: COc1c(C=O)cc(C(C)(C)C)cc1NC(=O)c1cc2cccc(CN3CCN(C(=O)[C@@H]4CCCN4C)CC3)c2n1C]

200 mg (S)-1-methyl-7-[4-(1-methyl-pyrrolidine-2-carbonyl)-piperazin-1-ylmethyl]-1H-indole-2-carboxylic acid-(5-tert-butyl-3-hydroxymethyl-2-methoxy-phenyl)-amide are dissolved in 5 ml dichloromethane, cooled to 0° C. and combined with 167 mg 1,1-dihydro-1,1,1-triacetoxy-1,2-benziodoxol-3(1H)-one (Dess-Martin-Periodinane). The mixture is stirred for 12 hours, while being heated to ambient temperature. Then it is divided between dichloromethane and a 10% aqueous potassium carbonate solution. A solid is precipitated which is filtered off. The liquid phases are separated and the organic phase is dried on magnesium sulphate. The solvents are then eliminated in vacuo. The product thus obtained is further reacted directly.

Yield: 220 mg (110% of theory)
HPLC (method 1): retention time=2.80 min.

Example XXXII (S)-1-methyl-7-[4-(1-methyl-pyrrolidine-2-carbonyl)-piperazin-1-ylmethyl]-1H-indole-2-carboxylic acid-(5-tert-butyl-3-hydroxymethyl-2-methoxy-phenyl)-amide

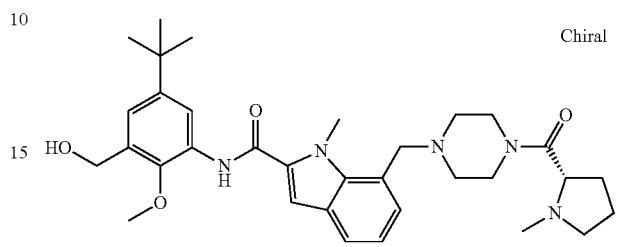

1.73 g (S)-1-methyl-7-[4-(1-methyl-pyrrolidine-2-carbonyl)-piperazin-1-ylmethyl]-1H-indole-2-carboxylic acid-(5-tert-butyl-2-methoxy-3-trimethylsilanyloxymethyl-phenyl)-amide are dissolved in 15 ml dichloromethane, combined with 5.34 ml of a 5 M solution of hydrogen chloride in isopropanol and stirred for 30 minutes at ambient temperature. The mixture is divided between dichloromethane and saturated aqueous sodium hydrogen carbonate solution, the aqueous phase is extracted twice with dichloromethane and the combined organic phases are washed with saturated aqueous sodium chloride solution. After drying with magnesium sulphate the solvents are eliminated in vacuo and the product thus obtained is further reacted directly.

Yield: 1.67 g (109% of theory)
Mass spectrum (ESI⁺): m/z=576 [M+H]⁺

Example XXXIII (S)-1-methyl-7-[4-(1-methyl-pyrrolidine-2-carbonyl)-piperazin-1-ylmethyl]-1H-indole-2-carboxylic acid-(5-tert-butyl-2-methoxy-3-trimethylsilanyloxymethyl-phenyl)-amide

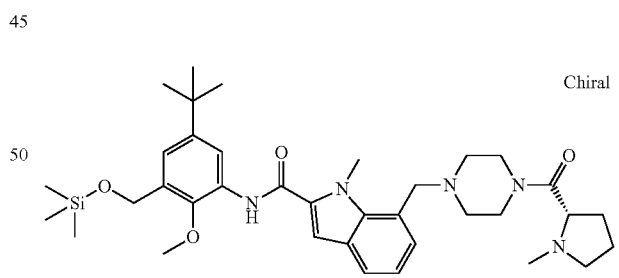

2 g (S)-1-methyl-7-[4-(1-methyl-pyrrolidine-2-carbonyl)-piperazin-1-ylmethyl]-1H-indole-2-carboxylic acid are dissolved in 20 ml acetonitrile, combined with 1.2 ml oxalyl chloride as well as 10 µl N,N-dimethylformamide and stirred for 2 hours. Then a further 450 µl oxalyl chloride are added and the mixture is stirred for a further hour. Then it is evaporated down in vacuo, taken up in dichloromethane and this is again eliminated in vacuo. The residue is taken up in 20 ml of 1,2-dichloroethane, combined with 2.85 ml triethylamine as well as 1.17 g 5-tert-butyl-2-methoxy-3-trimethylsilanyloxymethyl-phenylamine and stirred for 2 hours at ambient temperature. Then it is washed successively with water and saturated aqueous sodium chloride solution, dried on magnesium sulphate and the solvents are eliminated in vacuo. The residue is filtered through aluminium oxide with dichloromethane/ethyl acetate.

Yield: 1.73 g (64% of theory)
HPLC (method 1): retention time=2.43 min.
Mass spectrum (ESI$^+$): m/z=648 [M+H]$^+$ The following compounds are obtained analogously to Example XXXIII:

(1) methyl 5-tert-butyl-2-methoxy-3-({1-methyl-7-[4-(1-methyl-pyrrolidine-2-carbonyl)-piperazin-1-ylmethyl]-1H-indole-2-carbonyl}-amino)-benzoate

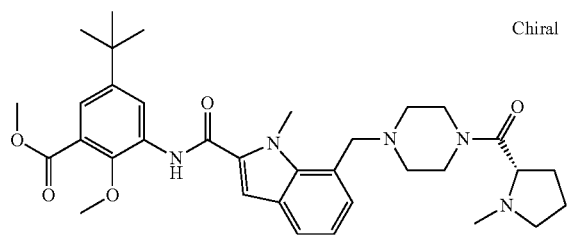 [SMILES: COC(=O)c1cc(C(C)(C)C)cc(NC(=O)c2cc3cccc(CN4CCN(C(=O)[C@@H]5CCCN5C)CC4)c3n2C)c1OC]

HPLC (method 1): retention time=2.90 min.
Mass spectrum (ESI$^+$): m/z=604 [M+H]$^+$ (2) tert-butyl (S)-[5-tert-butyl-2-methoxy-3-({1-methyl-7-[4-(1-methyl-pyrrolidine-2-carbonyl)-piperazin-1-ylmethyl]-1H-indole-2-carbonyl}-amino)-phenyl]-carbamate

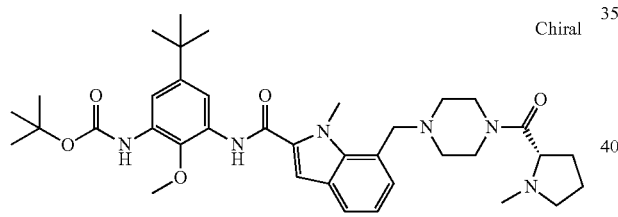

HPLC (method 1): retention time=3.20 min.
Mass spectrum (ESI$^+$): m/z=661 [M+H]$^+$ (3) (S)-1-methyl-7-[4-(1-methyl-pyrrolidine-2-carbonyl)-piperazin-1-ylmethyl]-1H-indole-2-carboxylic acid-(3-amino-2-methoxy-5-pentafluoroethyl-phenyl)-amide

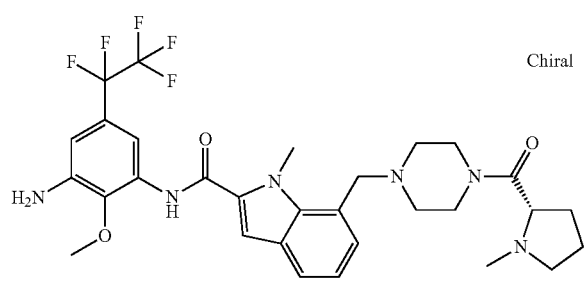 [SMILES: COc1c(N)cc(C(F)(F)C(F)(F)F)cc1NC(=O)c1cc2cccc(CN3CCN(C(=O)[C@@H]4CCCN4C)CC3)c2n1C]

The crude product is chromatographed on silica gel (dichloromethane/(methanol/ammonia in methanol (saturated) 9:1) 99:1 to 90:10) and the product thus obtained is purified by preparative HPLC (method 3).

HPLC (method 1): retention time=2.76 min.

(4) (S)-1-methyl-7-[4-(1-methyl-pyrrolidine-2-carbonyl)-piperazin-1-ylmethyl]-1H-indole-2-carboxylic acid-(3-amino-2-methoxy-5-trifluoromethyl-phenyl)-amide

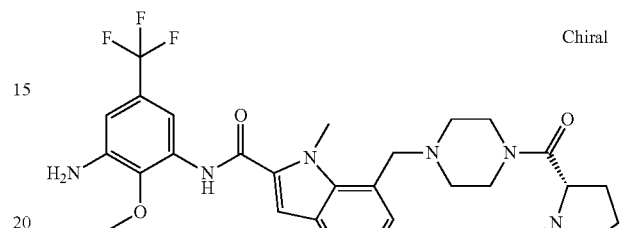

The crude product is chromatographed on silica gel (dichloromethane/(methanol/ammonia in methanol (saturated) 9:1) 99:1 to 90:10) and the product thus obtained is purified by preparative HPLC (method 3).

HPLC (method 6): retention time=4.00 min.
Mass spectrum (ESI$^+$): m/z=573 [M+H]$^+$ Example XXXIV 5-tert-butyl-2-methoxy-3-({1-methyl-7-[4-(1-methyl-pyrrolidine-2-carbonyl)-piperazin-1-ylmethyl]-1H-indole-2-carbonyl}-amino)-benzoic acid

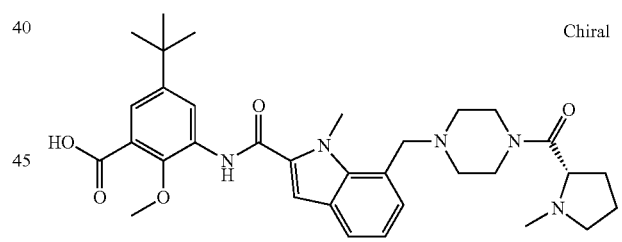

1.29 g methyl 5-tert-butyl-2-methoxy-3-({1-methyl-7-[4-(1-methyl-pyrrolidine-2-carbonyl)-piperazin-1-ylmethyl]-1H-indole-2-carbonyl}-amino)-benzoate are dissolved in 25 ml of tetrahydrofuran, combined with 4 ml of 4 N sodium hydroxide solution and heated for 2 hours to 40° C. Then the mixture is heated for 12 hours to 60° C., then a further 2 ml of 4 N sodium hydroxide solution are added and the mixture is heated for a further 12 hours to 60° C. It is then evaporated down in vacuo, the residue is taken up in water and the pH is adjusted to 5 by the addition of 4 N hydrochloric acid. It is extracted 5 times with dichloromethane/isopropanol 4:1 and the combined organic phases are dried on magnesium sulphate. The solvents are eliminated in vacuo and the product thus obtained is further reacted directly.

Yield: 1.3 g (103% of theory)
HPLC (method 1): retention time=2.48 min.
Mass spectrum (ESI$^+$): m/z=590 [M+H]$^+$

Example XXXV

Methyl 3-amino-5-tert-butyl-2-methoxy-benzoate

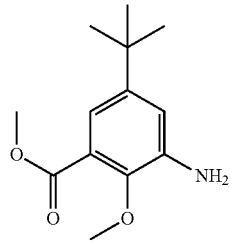 [SMILES: COC(=O)c1cc(C(C)(C)C)cc(N)c1OC]

2.7 g methyl 5-tert-butyl-2-methoxy-3-nitro-benzoate are dissolved in 120 ml of methanol, combined with 270 mg of 10% palladium on charcoal and hydrogenated for 12 hours at ambient temperature and 4 bar hydrogen pressure. Then the catalyst is filtered off, the solvents are eliminated in vacuo and the residue thus obtained is further reacted directly.

Yield: 2.24 g (94% of theory)

Mass spectrum (ESI$^+$): m/z=238 [M+H]$^+$

The following compounds are obtained analogously to Example XXXV:

(1) 3-amino-5-tert-butyl-2-methoxy-N,N-dimethyl-benzamide

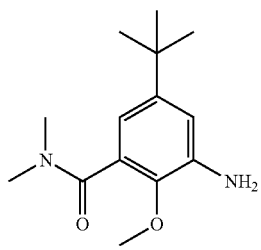 [SMILES: COc1c(N)cc(C(C)(C)C)cc1C(=O)N(C)C]

R$_f$ value: 0.20 (silica gel, petroleum ether/ethyl acetate 1:1)

(2) 5-tert-butyl-2-methoxy-1,3-diamino-benzene

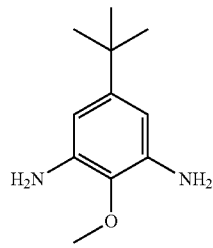

Mass spectrum (ESI$^+$): m/z=195 [M+H]$^+$ (3) 5-sec-butyl-2-methoxy-1,3-diamino-benzene

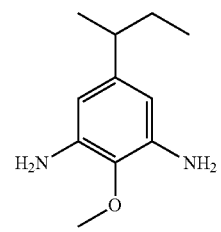

HPLC (method 1): retention time=1.81 min.
Mass spectrum (ESI$^+$): m/z=195 [M+H]$^+$ (4) 5-isopropyl-2-methoxy-1,3-diamino-benzene

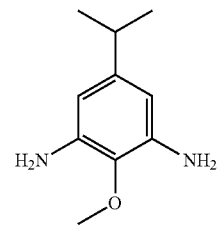

HPLC (method 1): retention time=3.81 min.

(5) 2-methoxy-5-pentafluoroethyl-1,3-diamino-benzene

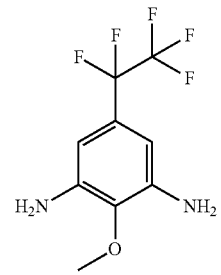 [SMILES: COc1c(N)cc(C(F)(F)C(F)(F)F)cc1N]

Raney nickel is used instead of 10% palladium on charcoal as hydrogenation catalyst.
Mass spectrum (ESI$^+$): m/z=257 [M+H]$^+$ (6) 2-methoxy-5-trifluoromethyl-1,3-diamino-benzene

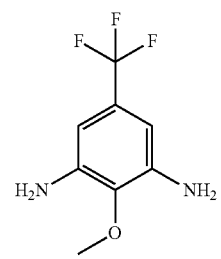

Raney nickel is used instead of 10% palladium on charcoal as hydrogenation catalyst. The crude product is further reacted directly.

(7) 5-tert-butyl-3-methanesulphonyl-2-methoxy-phenylamine

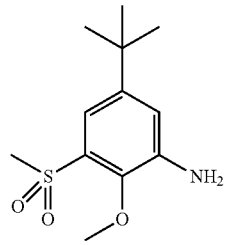 [SMILES: COc1c(N)cc(C(C)(C)C)cc1S(C)(=O)=O]

The crude product is extracted from n-pentane.
$R_f$ value: 0.30 (silica gel, petroleum ether/ethyl acetate 4:1)

(8) 5-tert-butyl-3-methanesulphonylmethyl-2-methoxy-phenylamine

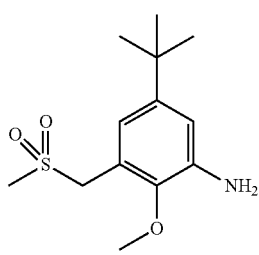 [SMILES: COc1c(N)cc(C(C)(C)C)cc1CS(C)(=O)=O]

HPLC (method 1): retention time=2.81 min.
Mass spectrum (ESI$^+$): m/z=272 [M+H]$^+$ (9) (3-amino-5-tert-butyl-2-methoxy-phenyl)-methanol

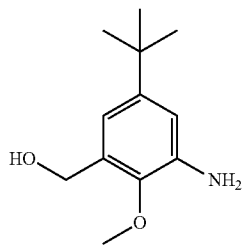

HPLC (method 1): retention time=2.06 min.
Mass spectrum (ESI$^+$): m/z=210 [M+H]$^+$

(10) 5-tert-butyl-3-methanesulphinylmethyl-2-methoxy-phenylamine

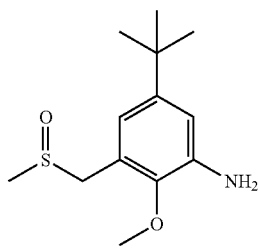 [SMILES: COc1c(N)cc(C(C)(C)C)cc1CS(C)=O]

HPLC (method 1): retention time=2.39 min.
Mass spectrum (ESI$^+$): m/z=256 [M+H]$^+$

(11) 5-tert-butyl-2-ethoxy-1,3-diamino-benzene

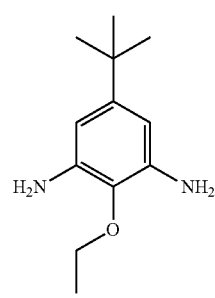

HPLC (method 1): retention time=1.94 min.
Mass spectrum (ESI$^+$): m/z=209 [M+H]$^+$

(12) 5-isobutyl-2-methoxy-1,3-diamino-benzene

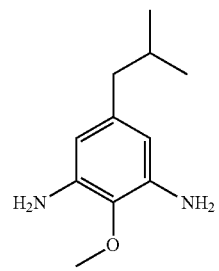

HPLC (method 1): retention time=1.96 min.
Mass spectrum (ESI$^+$): m/z=195 [M+H]$^+$ Example XXXVI Methyl 5-tert-butyl-2-methoxy-3-nitro-benzoate

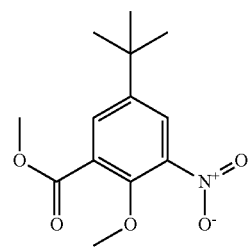 [SMILES: COC(=O)c1cc(C(C)(C)C)cc([N+](=O)[O-])c1OC]

5.4 g 5-tert-butyl-2-methoxy-3-nitro-benzoic acid are dissolved in 50 ml of methanol, cooled to 0° C. and combined dropwise with 2.32 ml of thionyl chloride. After the addition has ended the mixture is heated for 12 hours to 60° C. Then the solvents are eliminated in vacuo, the residue is divided between water and ethyl acetate and the aqueous phase is extracted twice with ethyl acetate. The combined organic phases are dried on magnesium sulphate and the solvent is eliminated in vacuo. The residue thus obtained is chromatographed on silica gel (cyclohexane/ethyl acetate (98:2 to 60:40).
Yield: 2.69 g (47% of theory)
HPLC (method 1): retention time=4.30 min.
Mass spectrum (ESI$^+$): m/z=268 [M+H]$^+$

Example XXXVII 5-tert-butyl-2-methoxy-3-nitro-benzoic acid

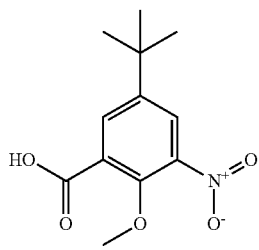 [SMILES: COc1c(C(=O)O)cc(C(C)(C)C)cc1[N+](=O)[O-]]

5 g 5-tert-butyl-2-methoxy-benzoic acid are dissolved in 15 ml sulphuric acid, cooled to 0° C. and combined dropwise with a solution of 2.3 ml nitric acid in 2.6 ml sulphuric acid. The mixture is stirred for 1.5 hours at 0° C. and for 1 hour at ambient temperature. Then it is added to ice water. The precipitate is filtered off, taken up in dichloromethane and dried on magnesium sulphate. The solvent is eliminated in vacuo and the product thus obtained is further reacted directly.

Yield: 5.4 g (89% of theory)

Example XXXVIII 5-tert-butyl-2-methoxy-N,N-dimethyl-3-nitro-benzamide

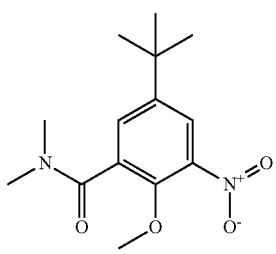 [SMILES: COc1c(C(=O)N(C)C)cc(C(C)(C)C)cc1[N+](=O)[O-]]

44 g 5-tert-butyl-2-methoxy-3-nitro-benzoic acid are dissolved in 400 ml of tetrahydrofuran, combined with 31 g carbonyldiimidazole and stirred for 2 hours at 50° C. The mixture is cooled to ambient temperature, combined with 173 ml of a 2 M solution of dimethylamine in tetrahydrofuran and stirred for a further 16 hours at 50° C. Then it is diluted with ethyl acetate and washed successively with 1 N hydrochloric acid, saturated aqueous sodium hydrogen carbonate solution and saturated aqueous sodium chloride solution. After drying with sodium sulphate the solvents are eliminated in vacuo and the residue is chromatographed on silica gel with chloroform.

Yield: 40 g (82% of theory)

$R_f$-value: 0.60 (silica gel, petroleum ether/ethyl acetate 1:1)

Example XXXIX

Tert-butyl(3-amino-5-tert-butyl-2-methoxy-phenyl)-carbamate

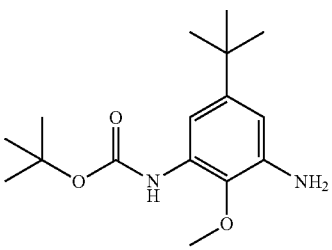 [SMILES: COc1c(N)cc(C(C)(C)C)cc1NC(=O)OC(C)(C)C]

3.2 g 5-tert-butyl-2-methoxy-1,3-diamino-benzene are dissolved in 50 ml acetonitrile, combined with 3.78 g di-tert.-butyl-dicarbonate and 20 mg 4-dimethylamino-pyridine and stirred for 12 hours at ambient temperature. The solvents are eliminated in vacuo and the residue is chromatographed on silica gel (cyclohexane/ethyl acetate 95:5 to 50:50).

Yield: 3.86 g (80% of theory)

Mass spectrum (ESI$^+$): m/z=295 [M+H]$^+$

Example XL 5-tert-butyl-2-methoxy-1,3-dinitro-benzene

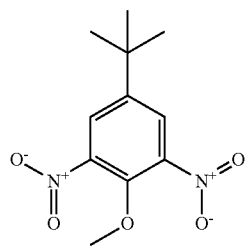 [SMILES: COc1c([N+](=O)[O-])cc(C(C)(C)C)cc1[N+](=O)[O-]]

3 g 4-tert.-butyl-anisol are dissolved in 100 ml acetonitrile, cooled to −30° C. and combined batchwise with 6.1 g nitronium-tetrafluoroborate. The mixture is allowed to come up to −15° C. within one hour, then cooled to −30° C. again, combined with another 1.0 g nitronium tetrafluoroborate and stirred for 30 minutes. It is then divided between saturated aqueous sodium hydrogen carbonate solution and ethyl acetate, the aqueous phase is extracted 3 times with ethyl acetate and the combined organic phases are washed with saturated aqueous sodium chloride solution. After drying with magnesium sulphate the solvents are eliminated in vacuo and the residue is extracted from isopropanol. The precipitated solid is filtered off and dried in vacuo.

Yield: 3.75 g (81% of theory)

HPLC (method 1): retention time=4.36 min.

The following compounds are obtained analogously to Example XL:

(1) 5-sec-butyl-2-methoxy-1,3-dinitro-benzene

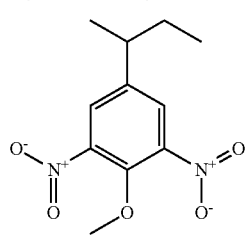

HPLC (method 1): retention time=4.40 min.
Mass spectrum (EI): m/z=254 [M]$^+$ (2) 5-isopropyl-2-methoxy-1,3-dinitro-benzene

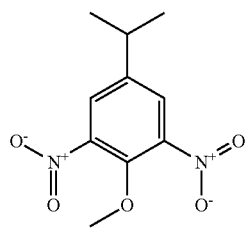

HPLC (method 1): retention time=4.17 min.

(3) 2-methoxy-1,3-dinitro-5-pentafluoroethyl-benzene

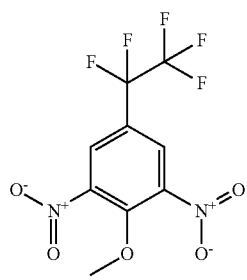

HPLC (method 1): retention time=4.24 min.

(4) 2-methoxy-1,3-dinitro-5-trifluoromethyl-benzene

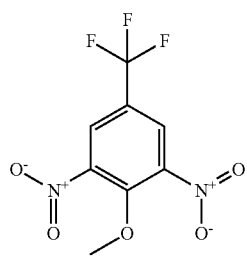

HPLC (method 1): retention time=3.70 min.

(5) 5-tert-butyl-2-hydroxy-3-nitro-benzaldehyde

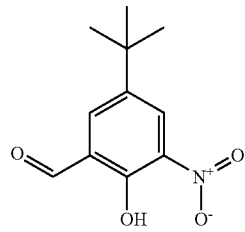 [SMILES: CC(C)(C)c1cc(C=O)c(O)c([N+](=O)[O-])c1]

Mass spectrum (ESI$^-$): m/z=222 [M–H]$^-$ (6) 4-tert-butyl-2,6-dinitro-phenol

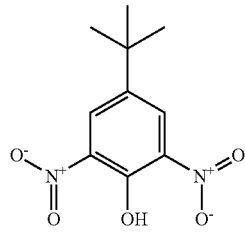 [SMILES: CC(C)(C)c1cc([N+](=O)[O-])c(O)c([N+](=O)[O-])c1]

HPLC (method 1): retention time=4.09 min.
Mass spectrum (ESI$^-$): m/z=239 [M–H]$^-$ (7) 5-isobutyl-2-methoxy-1,3-dinitro-benzene

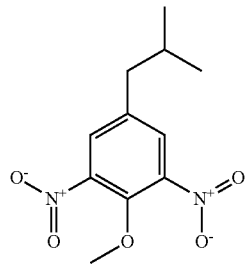 [SMILES: COc1c([N+](=O)[O-])cc(CC(C)C)cc1[N+](=O)[O-]]

The crude product is further reacted directly.

Example XLI

N-(3-amino-5-sec-butyl-2-methoxy-phenyl)-methanesulphonamide

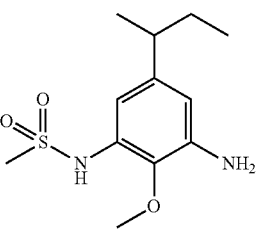 [SMILES: CCC(C)c1cc(N)c(OC)c(NS(C)(=O)=O)c1]

1.46 g of 5-sec-butyl-2-methoxy-1,3-diamino-benzene are dissolved in 20 ml dichloromethane, combined with 1.21 ml of pyridine and cooled to 0° C. 600 μl of methanesulphonic acid chloride are added, the mixture is allowed to come up to ambient temperature and stirred for 2 hours. The solvents are eliminated in vacuo and the residue is chromatographed on silica gel (cyclohexane/ethyl acetate 80:20 to 20:80).

Yield: 1.23 g (60% of theory)
HPLC (method 1): retention time=3.02 min.
Mass spectrum (ESI$^+$): m/z=273 [M+H]$^+$ The following compounds are obtained analogously to Example XLI:

(1) N-(3-amino-5-isopropyl-2-methoxy-phenyl)-methanesulphonamide

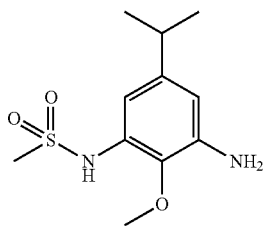 [SMILES: COc1c(N)cc(C(C)C)cc1NS(C)(=O)=O]

HPLC (method 1): retention time=2.63 min.
Mass spectrum (ESI$^+$): m/z=259 [M+H]$^+$ (2) N-(3-amino-5-tert-butyl-2-ethoxy-phenyl)-methanesulphonamide

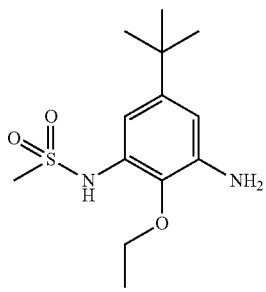 [SMILES: CCOc1c(N)cc(C(C)(C)C)cc1NS(C)(=O)=O]

HPLC (method 1): retention time=3.16 min.
Mass spectrum (ESI$^+$): m/z=287 [M+H]$^+$ (3) N-(3-amino-5-isobutyl-2-methoxy-phenyl)-methanesulphonamide

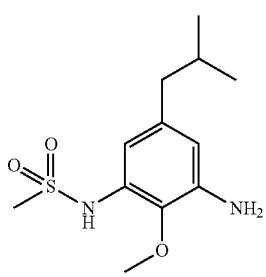 [SMILES: COc1c(N)cc(CC(C)C)cc1NS(C)(=O)=O]

HPLC (method 6): retention time=2.49 min.
Mass spectrum (ESI$^+$): m/z=273 [M+H]$^+$ Example XLII 4-sec-butyl-anisol

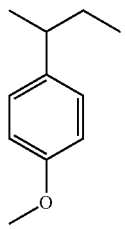

2 g 4-sec-butyl-phenol are dissolved in 15 ml N,N-dimethylformamide, combined with 2.2 g potassium carbonate, stirred for 30 minutes and then combined with 830 μl methyl iodide. The mixture is stirred for 12 hours and then a further 600 mg potassium carbonate and 300 μl methyl iodide are added. After stirring for 3 hours the mixture is divided between water and ethyl acetate and the organic phase is washed with saturated aqueous sodium chloride solution. It is dried with magnesium sulphate and the solvents are eliminated in vacuo. The product thus obtained is further reacted directly.

Yield: 2.14 g (98% of theory)

The following compounds are obtained analogously to Example XLII:

(1) 4-isopropyl-anisol

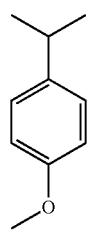

Mass spectrum (EI): m/z=150 [M]$^+$ (2) 5-tert-butyl-2-methoxy-3-nitro-benzaldehyde

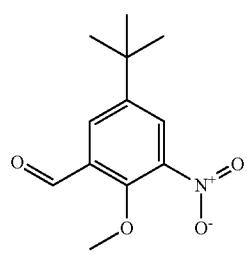 [SMILES: COc1c(C=O)cc(C(C)(C)C)cc1[N+](=O)[O-]]

Mass spectrum (EI): m/z=237 [M]$^+$ (3) 1-tert-butyl-4-propoxy-benzene

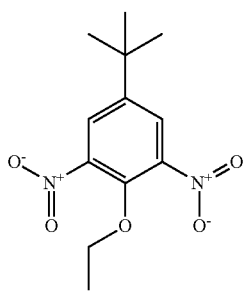

Ethyl iodide is used instead of methyl iodide.
HPLC (method 1): retention time=4.58 min.
Mass spectrum (EI): m/z=268 [M]$^+$ Example XLIII 4-pentafluoroethyl-anisol

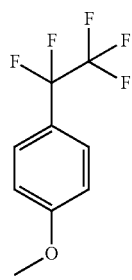

Under argon 1 g 4-iodo-anisol is dissolved in 7 ml N,N-dimethylformamide, and mixed with 1.2 g copper-(I)-iodide, 300 mg potassium fluoride and 1.0 g pentafluoroethyl-trimethyl-silane. The mixture is heated for 12 hours to 80° C., then another 1.0 g pentafluoroethyl-trimethyl-silane is added and the mixture is again heated for 12 hours to 80° C. It is diluted with a 2 M aqueous ammonia solution, stirred vigorously for 1 hour and the solid is filtered off. The filtrate is extracted 3 times with ethyl acetate and the combined organic phases are dried on magnesium sulphate. The solvents are eliminated in vacuo and the residue is taken up in petroleum ether/ethyl acetate 9:1. It is filtered through a short layer of silica gel and washed with petroleum ether/ethyl acetate 9:1. The solvents are eliminated in vacuo and the product thus obtained is further reacted directly.
Yield: 730 mg (76% of theory)
HPLC (method 1): retention time=4.42 min.

Example XLIV 5-tert-butyl-3-methanesulphinyl-2-methoxy-phenylamine

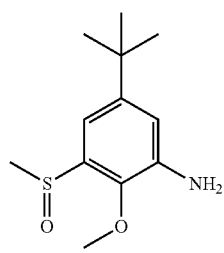 [SMILES: COc1c(N)cc(C(C)(C)C)cc1S(C)=O]

15.5 g 5-tert-butyl-1-methanesulphinyl-2-methoxy-3-nitro-benzene in 300 ml of ethyl acetate are added 3.0 g 10% palladium-(II)-hydroxide on charcoal and the mixture is hydrogenated for 16 hours at 3 bar hydrogen pressure. Then the hydrogenation catalyst is filtered off through kieselguhr and washed with 100 ml of ethyl acetate. The solvent is eliminated in vacuo and the residue is extracted from n-pentane.
Yield: 12.9 g (94% of theory)
R$_f$ value: 0.30 (silica gel, petroleum ether/ethyl acetate 1:1)

Example XLV 5-tert-butyl-1-methanesulphinyl-2-methoxy-3-nitro-benzene

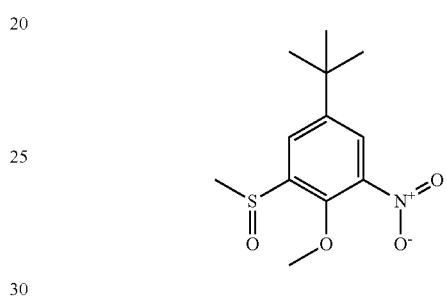

0.5 g of 5-tert-butyl-2-methoxy-1-methylsulphanyl-3-nitro-benzene are dissolved in 15 ml of 1,1,1,3,3,3-hexafluoroisopropanol, combined with 1.1 ml of a 9 M solution of hydrogen peroxide in water and stirred for 5 hours at ambient temperature. Then the mixture is cooled to 0° C. and diluted with 10% aqueous sodium thiosulphate solution. The mixture is extracted 3 times with ethyl acetate and the combined organic phases are washed with saturated aqueous sodium hydrogen carbonate solution and saturated aqueous sodium chloride solution. After drying with sodium sulphate the solvents are eliminated in vacuo and the residue is chromatographed on silica gel (petroleum ether/ethyl acetate 95:5).
Yield: 350 mg (66% of theory)
R$_f$ value: 0.20 (silica gel, petroleum ether/ethyl acetate 9:1)
The following compounds are obtained analogously to Example XLV:

(1) 5-tert-butyl-1-methanesulphinylmethyl-2-methoxy-3-nitro-benzene

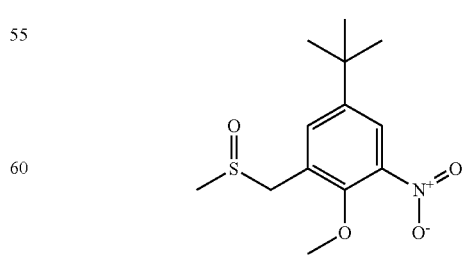

HPLC (method 1): retention time=3.28 min.
Mass spectrum (ESI$^+$): m/z=286 [M+H]$^+$

Example XLVI 5-tert-butyl-2-methoxy-1-methylsulphanyl-3-nitro-benzene

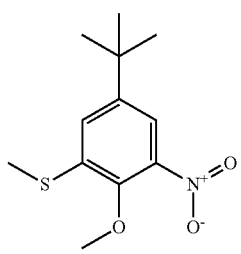 [SMILES: COc1c(SC)cc(C(C)(C)C)cc1[N+](=O)[O-]]

2 g 5-tert-butyl-2-methoxy-3-nitro-phenylamine are dissolved in 20 ml acetonitrile, combined successively with 3.6 ml isopentylnitrite as well as 2.4 ml dimethyldisulphide and refluxed for 2 h. The solvents are eliminated in vacuo and the residue is chromatographed on silica gel (petroleum ether/ethyl acetate 90:10).

Yield: 1.5 g (66% of theory)

$R_f$-value: 0.70 (silica gel, petroleum ether/ethyl acetate 9:1)

Example XLVII 5-tert-butyl-2-methoxy-3-nitro-phenylamine

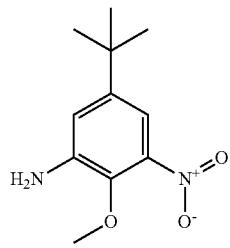 [SMILES: COc1c(N)cc(C(C)(C)C)cc1[N+](=O)[O-]]

2 g 5-tert-butyl-2-methoxy-1,3-dinitro-benzene are dissolved in 20 ml ethanol and combined with 2 ml of water and 100 mg of 10% palladium on charcoal. The mixture is refluxed, 1.9 ml of 4-methyl-1-cyclohexene are added and the mixture is refluxed for a further 2 hours. Then a further 1.0 ml of 4-methyl-1-cyclohexene are added dropwise and the mixture is refluxed for a further 16 hours. Then it is cooled to ambient temperature, the solvents are eliminated in vacuo and the residue is taken up in ethyl acetate. The mixture is washed with saturated aqueous sodium hydrogen carbonate solution, water, saturated aqueous sodium chloride solution and dried with sodium sulphate. The solvent is eliminated in vacuo and the product thus obtained is further reacted directly.

Yield: 1.7 g (96% of theory)

$R_f$-value: 0.20 (silica gel, petroleum ether/ethyl acetate 9:1)

Example XLVIII 5-tert-butyl-1-methanesulphonyl-2-methoxy-3-nitro-benzene

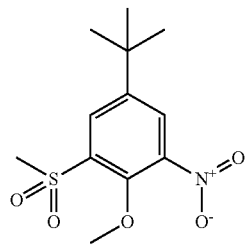 [SMILES: COc1c([N+](=O)[O-])cc(C(C)(C)C)cc1S(C)(=O)=O]

500 mg of 5-tert-butyl-2-methoxy-1-methylsulphanyl-3-nitro-benzene are dissolved in 10 ml dichloromethane, cooled to 0° C. and mixed with 850 mg metachloroperbenzoic acid. The mixture is allowed to come up to ambient temperature and stirred for 6 hours. Then it is diluted with dichloromethane and washed successively with saturated aqueous sodium hydrogen carbonate solution and saturated aqueous sodium chloride solution. After drying with sodium sulphate the solvents are eliminated in vacuo and the residue is chromatographed on silica gel (petroleum ether/ethyl acetate 9:1).

Yield: 350 mg (62% of theory)

$R_f$-value: 0.30 (silica gel, petroleum ether/ethyl acetate 9:1)

The following compounds are obtained analogously to Example XLVIII:

(1) 5-tert-butyl-1-methanesulphonylmethyl-2-methoxy-3-nitro-benzene

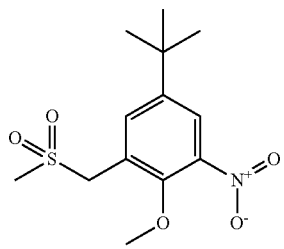 [SMILES: COc1c(CS(C)(=O)=O)cc(C(C)(C)C)cc1[N+](=O)[O-]]

HPLC (method 1): retention time=3.69 min.

Example XLIX 5-tert-butyl-2-methoxy-1-methylsulphanylmethyl-3-nitro-benzene

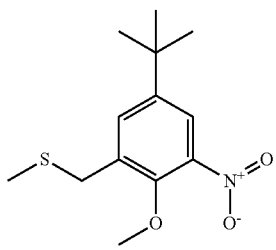 [SMILES: COc1c(CSC)cc(C(C)(C)C)cc1[N+](=O)[O-]]

4.64 g 5-tert-butyl-2-methoxy-3-nitro-benzyl methanesulphonate are dissolved in 50 ml of 1,4-dioxane, combined with 950 mg of sodium thiomethanolate and stirred for 12 hours at ambient temperature. A further 600 mg of sodium thiomethoxide are added and the mixture is stirred for 2 hours at 40° C. Then the solvents are eliminated in vacuo and the residue is chromatographed on silica gel (cyclohexane/ethyl acetate 98:2 to 60:40).

Yield: 2.91 g (87% of theory)
HPLC (method 1): retention time=4.74 min.

Example L 5-tert-butyl-2-methoxy-3-nitro-benzyl methanesulphonate

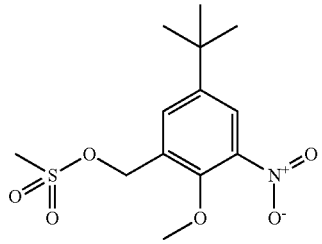 [SMILES: COc1c(COS(C)(=O)=O)cc(C(C)(C)C)cc1[N+](=O)[O-]]

3.43 g (5-tert-butyl-2-methoxy-3-nitro-phenyl)-methanol are dissolved in 30 ml dichloromethane, combined with 2.39 ml of triethylamine and cooled to 0° C. 1.2 g of methanesulphonic acid chloride are added dropwise and the mixture is stirred for 2 hours. Then it is diluted with dichloromethane and washed 3 times with water and once with saturated aqueous sodium chloride solution. After drying with magnesium sulphate the solvents are eliminated in vacuo and the product thus obtained is further reacted directly.

Yield: 4.67 g (87% of theory)
Mass spectrum (ESI$^+$): m/z=335 [M+NH$_4$]$^+$

Example LI 5-tert-butyl-2-methoxy-3-trimethylsilanyloxymethyl-phenylamine

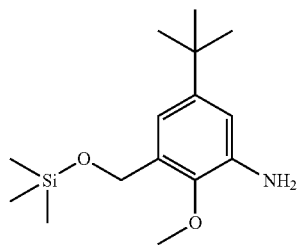 [SMILES: COc1c(N)cc(C(C)(C)C)cc1CO[Si](C)(C)C]

3.03 g (3-amino-5-tert-butyl-2-methoxy-phenyl)-methanol and 2.4 g imidazole are dissolved in 20 ml of tetrahydrofuran and 2.75 ml trimethylsilyl chloride are added dropwise thereto. The mixture is stirred for 2 hours at ambient temperature, the solvents are eliminated in vacuo and the residue is divided between 10% aqueous potassium carbonate solution and ethyl acetate. The aqueous phase is extracted with ethyl acetate and the combined organic phases are washed with saturated sodium chloride solution. After drying with magnesium sulphate the solvents are eliminated in vacuo and the residue is chromatographed on silica gel (cyclohexane/ethyl acetate 95:5 to 50:50).

Yield: 1.96 g (48% of theory)
Mass spectrum (ESI$^+$): m/z=282 [M+H]$^+$

Example LII (5-tert-butyl-2-methoxy-3-nitro-phenyl)-methanol

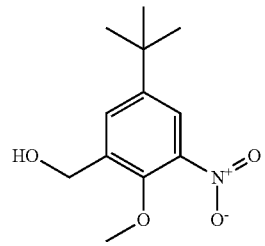 [SMILES: COc1c(CO)cc(C(C)(C)C)cc1[N+](=O)[O-]]

3.47 g 5-tert-butyl-2-methoxy-3-nitro-benzaldehyde are dissolved in 15 ml dichloromethane and 15 ml of methanol, cooled to 0° C. and combined with 600 mg sodium borohydride. The mixture is allowed to come up to ambient temperature and stirred for 2 hours. Then the solvents are eliminated in vacuo, the residue is taken up in water and combined with 6 ml acetic acid. It is stirred vigorously for 5 minutes and then extracted twice with ethyl acetate. The combined organic phases are washed with saturated aqueous sodium chloride solution, dried on magnesium sulphate and the solvents are eliminated in vacuo. The product thus obtained is further reacted directly.

Yield: 3.5 g (100% of theory)

Example LIII 1-isobutyl-4-methoxy-benzene

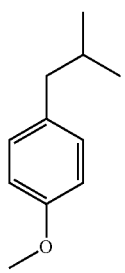

1.9 g 1-(4-methoxy-phenyl)-2-methyl-propan-1-ol are dissolved in 30 ml dissolved, cooled to 0° C. and mixed with 3.37 ml triethylsilane. The mixture is stirred for 10 minutes and then 1.62 ml trifluoroacetic acid are added. Within 1 hour the mixture is heated to 10° C., then the reaction is stopped by the addition of water and the phases are separated. The organic phase is washed with saturated aqueous sodium hydrogen carbonate solution and saturated aqueous sodium chloride solution and then dried on magnesium sulphate. The solvents are eliminated in vacuo and the residue is chromatographed on silica gel (cyclohexane/ethyl acetate 95:5 to 80:20).

Yield: 1.48 g (85% of theory)
HPLC (method 1): retention time=4.81 min.

Example LIV 1-(4-methoxy-phenyl)-2-methyl-propan-1-ol

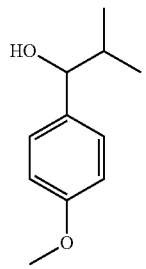

A solution of 1.5 ml 4-methoxy-benzaldehyde in 10 ml of toluene is added dropwise at 8° C. to 7.4 ml of a 2 M solution of isopropylmagnesium chloride in tetrahydrofuran. Then the mixture is allowed to come up to ambient temperature and stirred for 1 hour. Then the reaction is stopped by the addition of semisaturated aqueous ammonium chloride solution. The phases are separated and the aqueous phase is extracted with toluene. The combined organic phases are washed with semi-saturated aqueous ammonium chloride solution and dried on magnesium sulphate. The solvents are eliminated in vacuo and the product thus obtained is further reacted directly.

Yield: 2.12 g (95% of theory)
HPLC (method 1): retention time=3.22 min.

Preparation of the End Compounds

Example 1

1-methyl-7-[4-(1-methyl-piperidine-4-carbonyl)-piperazin-1-ylmethyl]-1H-indole-2-carboxylic acid (5-tert-butyl-3-methanesulphonylamino-2-methoxy-phenyl)-amide

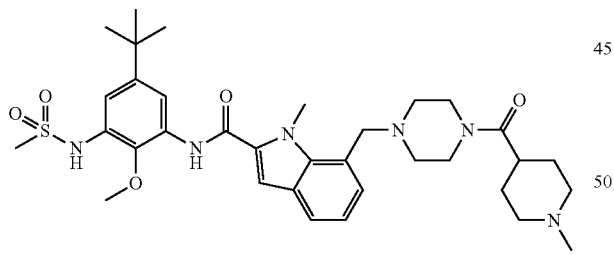

61 mg 1-methyl-piperidine-4-carboxylic acid are dissolved in 1 ml N,N-dimethylformamide and combined with 137 mg O-(benzotriazol-1-yl)-N,N,N',N'-tetramethyluronium-tetrafluoroborate (TBTU) and 138 µl N,N-diisopropylethylamine (DIEA). The mixture is stirred for 20 minutes, then 150 mg 1-methyl-7-piperazin-1-ylmethyl-1H-indole-2-carboxylic acid(5-tert-butyl-3-methanesulphonylamino-2-methoxy-phenyl)-amide are added and the mixture is stirred for 12 hours. Then it is divided between water and ethyl acetate and the aqueous phase is extracted twice with ethyl acetate. The combined organic phases are washed with saturated aqueous sodium chloride solution and dried on magnesium sulphate. Then the solvents are eliminated in vacuo and the residue is chromatographed on silica gel with dichloromethane/(methanol/ammonia 9:1) 99:1 to 90:10.

Yield: 118 mg (64% of theory)
HPLC (method 1): retention time=2.38 min.
Mass spectrum (ESI⁺): m/z=653 [M+H]⁺

The following compounds are obtained analogously to Example 1:

(1) (S)-1-methyl-7-[4-(1-methyl-pyrrolidine-2-carbonyl)-piperazin-1-ylmethyl]-1H-indole-2-carboxylic acid(5-tert-butyl-3-methanesulphonylamino-2-methoxy-phenyl)-amide

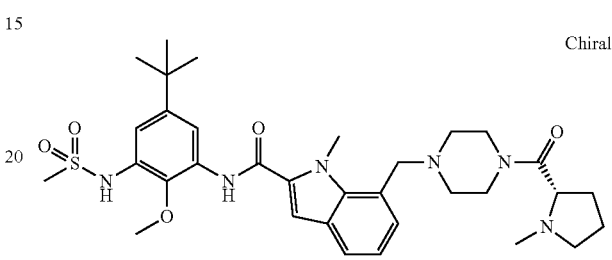

HPLC (method 2): retention time=1.54 min.
Mass spectrum (ESI⁺): m/z=639 [M+H]⁺

(2) 1-methyl-7-[4-(1-methyl-azetidine-3-carbonyl)-piperazin-1-ylmethyl]-1H-indole-2-carboxylic acid (5-tert-butyl-3-methanesulphonylamino-2-methoxy-phenyl)-amide

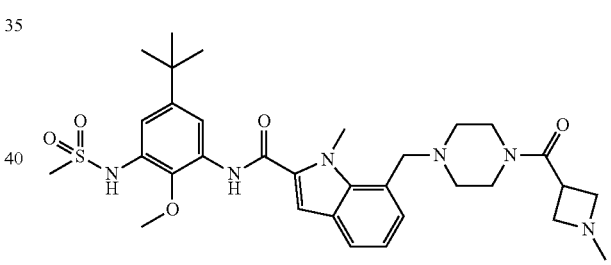

HPLC (method 1): retention time=2.39 min.
Mass spectrum (ESI⁺): m/z=625 [M+H]⁺

(3) (R)-1-methyl-7-[4-(1-methyl-pyrrolidine-2-carbonyl)-piperazin-1-ylmethyl]-1H-indole-2-carboxylic acid(5-tert-butyl-3-methanesulphonylamino-2-methoxy-phenyl)-amide

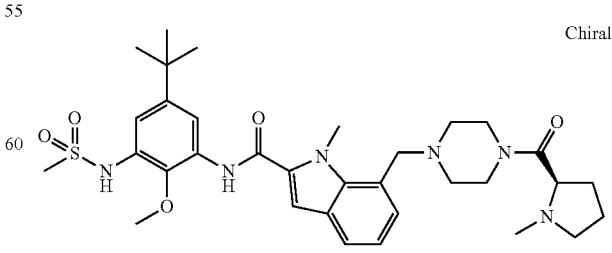

HPLC (method 1): retention time=2.45 min.
Mass spectrum (ESI⁺): m/z=639 [M+H]⁺

(4) (S)-1-methyl-7-[4-(pyrrolidine-2-carbonyl)-piperazin-1-ylmethyl]-1H-indole-2-carboxylic acid(5-tert-butyl-3-methanesulphonylamino-2-methoxy-phenyl)-amide

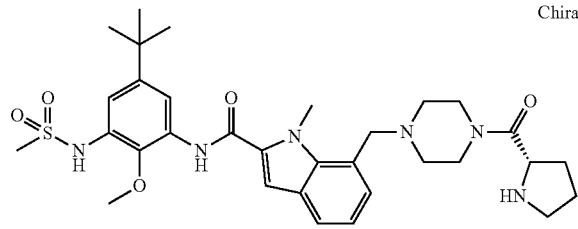

Mass spectrum (ESI⁺): m/z=625 [M+H]⁺

(5) 1-methyl-7-[4-(1-methyl-azetidine-2-carbonyl)-piperazin-1-ylmethyl]-1H-indole-2-carboxylic acid (5-tert-butyl-3-methanesulphonylamino-2-methoxyphenyl)-amide

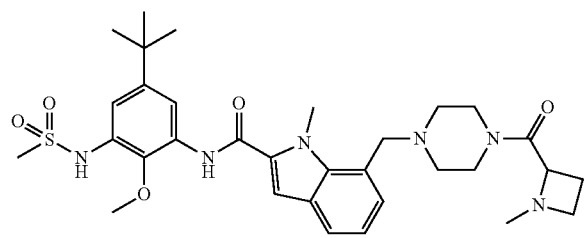 [SMILES: COc1c(NC(=O)c2cc3cccc(CN4CCN(C(=O)C5CCN5C)CC4)c3n2C)cc(C(C)(C)C)cc1NS(C)(=O)=O]

HPLC (method 1): retention time=2.41 min.
Mass spectrum (ESI⁺): m/z=625 [M+H]⁺

(6) (R)-1-methyl-7-[1-(1-methyl-pyrrolidine-2-carbonyl)-piperidin-4-ylmethyl]-1H-indole-2-carboxylic acid(5-tert-butyl-3-methanesulphonylamino-2-methoxy-phenyl)-amide

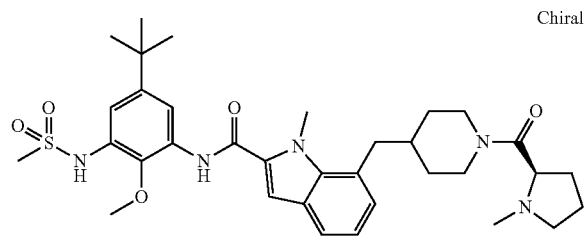 [SMILES: COc1c(NC(=O)c2cc3cccc(CC4CCN(C(=O)[C@H]5CCCN5C)CC4)c3n2C)cc(C(C)(C)C)cc1NS(C)(=O)=O]

HPLC (method 1): retention time=3.06 min.
Mass spectrum (ESI⁺): m/z=638 [M+H]⁺

(7) (S)-1-methyl-7-[1-(1-methyl-pyrrolidine-2-carbonyl)-piperidin-4-ylmethyl]-1H-indole-2-carboxylic acid(5-tert-butyl-3-methanesulphonylamino-2-methoxy-phenyl)-amide

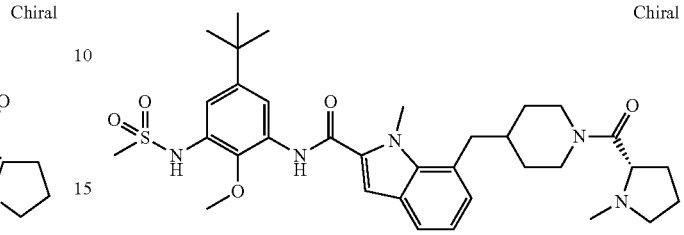

HPLC (method 1): retention time=3.09 min.
Mass spectrum (ESI⁺): m/z=638 [M+H]⁺

(8) 7-[4-((2S,4R)-4-hydroxy-1-methyl-pyrrolidine-2-carbonyl)-piperazin-1-ylmethyl]-1-methyl-1H-indole-2-carboxylic acid(5-tert-butyl-3-methanesulphonylamino-2-methoxy-phenyl)-amide

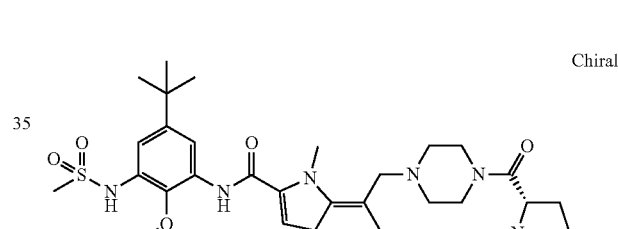

Mass spectrum (ESI⁺): m/z=655 [M+H]⁺

(9) 7-[4-((2R,4R)-4-methoxy-1-methyl-pyrrolidine-2-carbonyl)-piperazin-1-ylmethyl]-1-methyl-1H-indole-2-carboxylic acid(5-tert-butyl-3-methanesulphonylamino-2-methoxy-phenyl)-amide

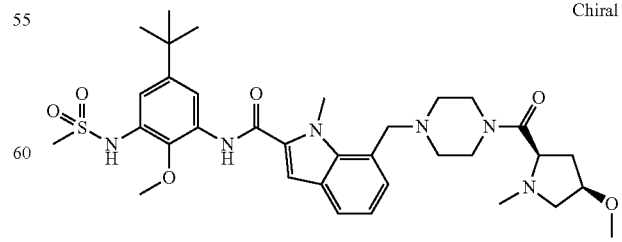

HPLC (method 1): retention time=2.48 min.
Mass spectrum (ESI⁺): m/z=669 [M+H]⁺

(10) 7-[4-((2R,4R)-4-hydroxy-1-methyl-pyrrolidine-2-carbonyl)-piperazin-1-ylmethyl]-1-methyl-1H-indole-2-carboxylic acid(5-tert-butyl-3-methane-sulphonylamino-2-methoxy-phenyl)-amide

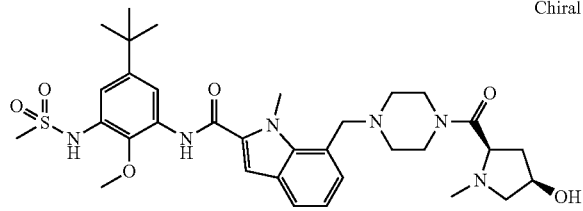 [SMILES: COc1c(NC(=O)c2cc3cccc(CN4CCN(C(=O)[C@H]5C[C@@H](O)CN5C)CC4)c3n2C)cc(C(C)(C)C)cc1NS(C)(=O)=O]

HPLC (method 1): retention time=2.42 min.
Mass spectrum (ESI⁺): m/z=655 [M+H]⁺

(11) 7-[4-((2R,4S)-4-hydroxy-1-methyl-pyrrolidine-2-carbonyl)-piperazin-1-ylmethyl]-1-methyl-1H-indole-2-carboxylic acid(5-tert-butyl-3-methane-sulphonylamino-2-methoxy-phenyl)-amide

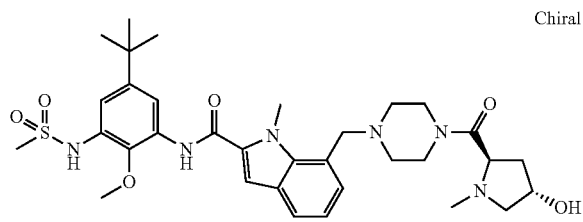 [SMILES: COc1c(NC(=O)c2cc3cccc(CN4CCN(C(=O)[C@H]5C[C@H](O)CN5C)CC4)c3n2C)cc(C(C)(C)C)cc1NS(C)(=O)=O]

HPLC (method 1): retention time=2.46 min.
Mass spectrum (ESI⁺): m/z=655 [M+H]⁺

(12) 7-[4-((2S,4S)-4-hydroxy-1-methyl-pyrrolidine-2-carbonyl)-piperazin-1-ylmethyl]-1-methyl-1H-indole-2-carboxylic acid(5-tert-butyl-3-methane-sulphonylamino-2-methoxy-phenyl)-amide

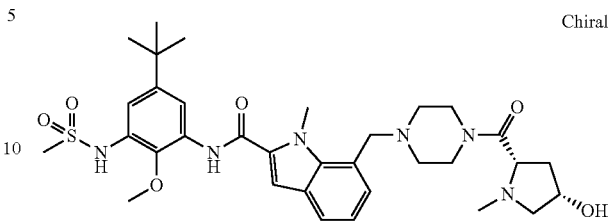

HPLC (method 1): retention time=2.43 min.
Mass spectrum (ESI⁺): m/z=655 [M+H]⁺

(13) 1-methyl-7-[4-(2-pyrrolidin-1-yl-propionyl)-piperazin-1-ylmethyl]-1H-indole-2-carboxylic acid-(5-tert-butyl-3-methanesulphonylamino-2-methoxy-phenyl)-amide

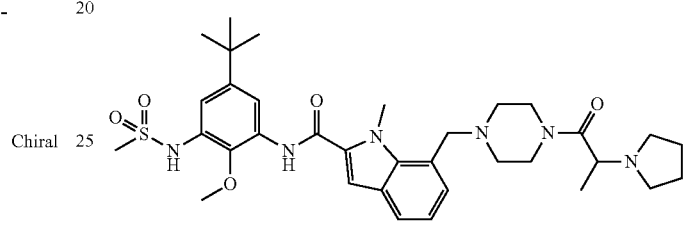

HPLC (method 1): retention time=2.52 min.
Mass spectrum (ESI⁺): m/z=653 [M+H]⁺

(14) 7-{4-[2-(4-isopropyl-piperazin-1-yl)-acetyl]-piperazin-1-ylmethyl}-1-methyl-1H-indole-2-carboxylic acid-(5-tert-butyl-3-methanesulphonylamino-2-methoxy-phenyl)-amide

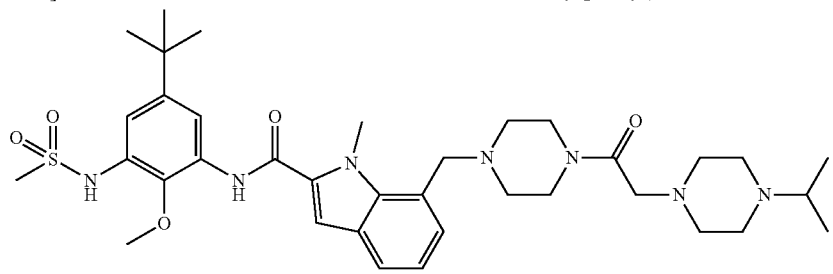

HPLC (method 1): retention time=2.32 min.
Mass spectrum (ESI⁺): m/z=696 [M+H]⁺

(15) (S)-7-{4-[2-(3-hydroxy-pyrrolidin-1-yl)-acetyl]-piperazin-1-ylmethyl}-1-methyl-1H-indole-2-carboxylic acid-(5-tert-butyl-3-methanesulphony-lamino-2-methoxy-phenyl)-amide

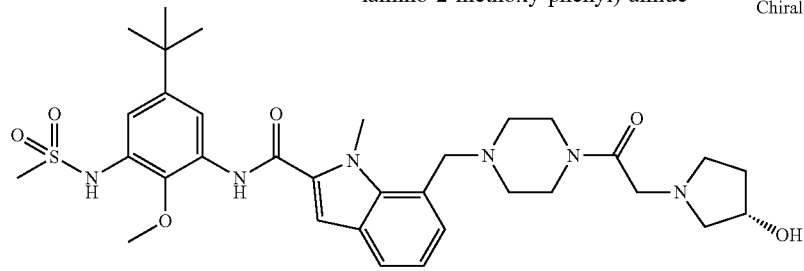 [SMILES: COc1c(NC(=O)c2cc3cccc(CN4CCN(C(=O)CN5CC[C@H](O)C5)CC4)c3n2C)cc(C(C)(C)C)cc1NS(C)(=O)=O]

HPLC (method 1): retention time=2.41 min.
Mass spectrum (ESI⁺): m/z=655 [M+H]⁺

(16) 1-methyl-7-[4-(2-pyrrolidin-1-yl-acetyl)-piperazin-1-ylmethyl]-1H-indole-2-carboxylic acid-(5-tert-butyl-3-methanesulphonylamino-2-methoxy-phenyl)-amide

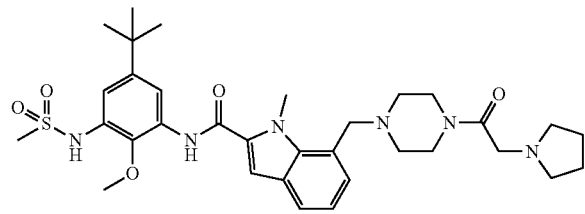 [SMILES: COc1c(NC(=O)c2cc3cccc(CN4CCN(C(=O)CN5CCCC5)CC4)c3n2C)cc(C(C)(C)C)cc1NS(C)(=O)=O]

HPLC (method 1): retention time=2.47 min.
Mass spectrum (ESI$^+$): m/z=639 [M+H]$^+$

(17) 1-methyl-7-{4-[2-(4-methyl-piperazin-1-yl)-acetyl]-piperazin-1-ylmethyl}-1H-indole-2-carboxylic acid-(5-tert-butyl-3-methanesulphonylamino-2-methoxy-phenyl)-amide

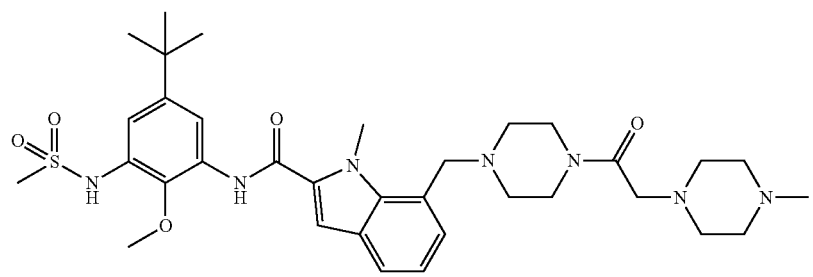

HPLC (method 1): retention time=2.32 min.
Mass spectrum (ESI$^+$): m/z=668 [M+H]$^+$

(18) 1-methyl-7-[1-((2S)-1-methyl-pyrrolidine-2-carbonyl)-azepan-4-ylmethyl]-1H-indole-2-carboxylic acid-(5-tert-butyl-3-methanesulphonylamino-2-methoxy-phenyl)-amide

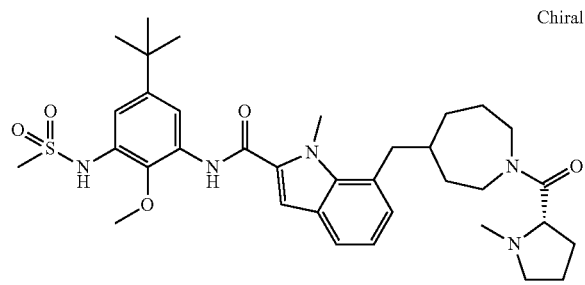 [SMILES: COc1c(NC(=O)c2cc3cccc(CC4CCCN(C(=O)[C@@H]5CCCN5C)CC4)c3n2C)cc(C(C)(C)C)cc1NS(C)(=O)=O]

$R_f$ value: 0.70 (silica gel, dichloromethane/methanol/(ammonia in methanol (saturated)) 90:10:0.1)
Mass spectrum (ESI$^+$): m/z=652 [M+H]$^+$

(19) 1-methyl-7-[1-(1-methyl-piperidine-4-carbonyl)-azepan-4-ylmethyl]-1H-indole-2-carboxylic acid-(5-tert-butyl-3-methanesulphonylamino-2-methoxy-phenyl)-amide $R_f$ value: 0.53 (silica gel, dichloromethane/methanol/(ammonia in methanol (saturated)) 90:10:0.1)
Mass spectrum (ESI$^+$): m/z=666 [M+H]$^+$

(20) 1-methyl-7-[1-((2R)-1-methyl-pyrrolidine-2-carbonyl)-azepan-4-ylmethyl]-1H-indole-2-carboxylic acid-(5-tert-butyl-3-methanesulphonylamino-2-methoxy-phenyl)-amide

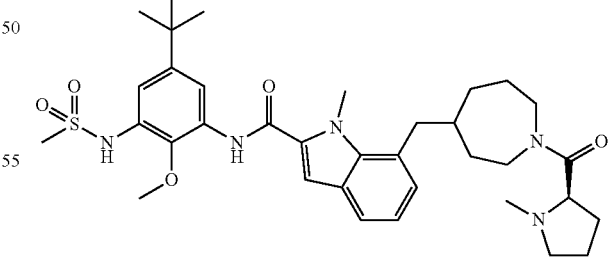

$R_f$ value: 0.70 (silica gel, dichloromethane/methanol/(ammonia in methanol (saturated)) 90:10:0.1)
Mass spectrum (ESI$^+$): m/z=652 [M+H]$^+$

(21) 1-methyl-7-[4-((2R)-1-methyl-pyrrolidine-2-carbonyl)-[1,4]diazepan-1-ylmethyl]-1H-indole-2-carboxylic acid-(5-tert-butyl-3-methanesulphonylamino-2-methoxy-phenyl)-amide

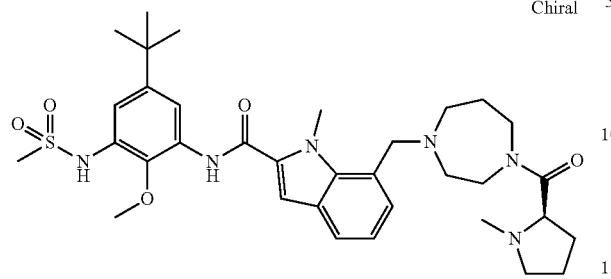

$R_f$ value: 0.76 (silica gel, dichloromethane/methanol/(ammonia in methanol (saturated)) 90:10:0.1)
Mass spectrum (ESI$^+$): m/z=653 [M+H]$^+$

(22) 1-methyl-7-[4-(4-methyl-piperazine-1-carbonyl)-piperidin-1-ylmethyl]-1H-indole-2-carboxylic acid-(5-tert-butyl-3-methanesulphonylamino-2-methoxy-phenyl)-amide

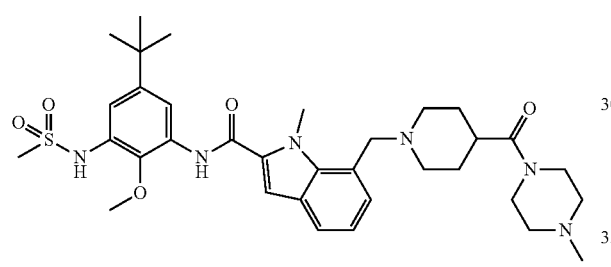

1-[2-(5-tert-butyl-3-methanesulphonylamino-2-methoxy-phenylcarbamoyl)-1-methyl-1H-indol-7-ylmethyl]-piperidine-4-carboxylic acid and 1-methylpiperazine are used as reactants. Tetrahydrofuran is used instead of N,N-dimethylformamide.
HPLC (method 1): retention time=2.27 min.
Mass spectrum (ESI$^+$): m/z=653 [M+H]$^+$

(23) (S)-7-[4-(3-dimethylamino-pyrrolidine-1-carbonyl)-piperidin-1-ylmethyl]-1-methyl-1H-indole-2-carboxylic acid-(5-tert-butyl-3-methanesulphonylamino-2-methoxy-phenyl)-amide

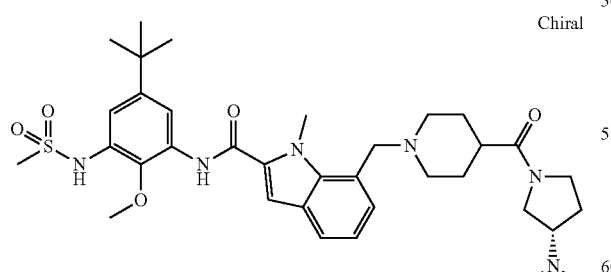

1-[2-(5-tert-butyl-3-methanesulphonylamino-2-methoxy-phenylcarbamoyl)-1-methyl-1H-indol-7-ylmethyl]-piperidine-4-carboxylic acid and (S)-3-dimethylamino-pyrrolidine are used as reactants.
HPLC (method 1): retention time=2.30 min.
Mass spectrum (ESI$^+$): m/z=667 [M+H]$^+$

(24) (R)-7-[4-(3-dimethylamino-pyrrolidine-1-carbonyl)-piperidin-1-ylmethyl]-1-methyl-1H-indole-2-carboxylic acid-(5-tert-butyl-3-methanesulphonylamino-2-methoxy-phenyl)-amide

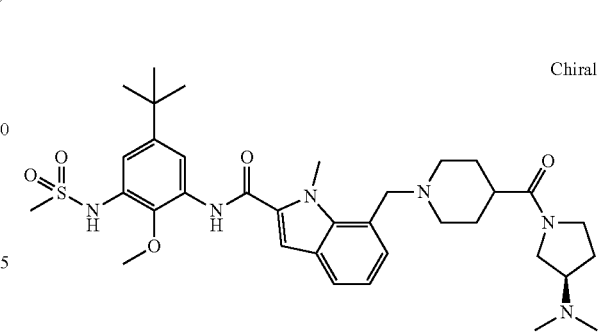

1-[2-(5-tert-butyl-3-methanesulphonylamino-2-methoxy-phenylcarbamoyl)-1-methyl-1H-indol-7-ylmethyl]-piperidine-4-carboxylic acid and (R)-3-dimethylamino-pyrrolidine are used as reactants.
HPLC (method 1): retention time=2.28 min.
Mass spectrum (ESI$^+$): m/z=667 [M+H]$^+$

(25) (S)-1-methyl-7-[4-(1-methyl-pyrrolidine-2-carbonyl)-piperazin-1-ylmethyl]-1H-indole-2-carboxylic acid-(3-morpholin-4-yl-phenyl)-amide

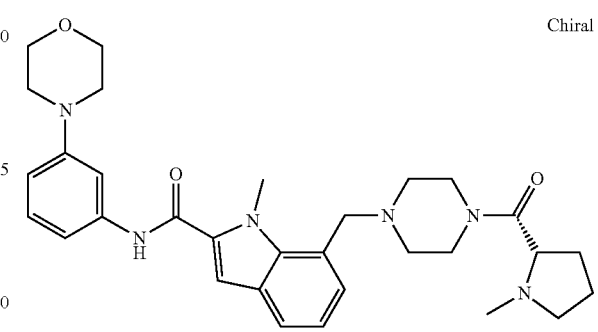

1-methyl-7-[4-(1-methyl-pyrrolidine-2-carbonyl)-piperazin-1-ylmethyl]-1H-indole-2-carboxylic acid and 3-morpholin-4-yl-phenylamine are used as reactants. O-(7-Azabenzotriazol-1-yl)-N,N,N',N'-tetramethyluronium-hexafluorophosphate (HATU) is used instead of O-(benzotriazol-1-yl)-N,N,N',N'-tetramethyluronium-tetrafluoroborate (TBTU).
HPLC (method 5): retention time=2.23 min.
Mass spectrum (ESI$^+$): m/z=545 [M+H]$^+$ Example 2

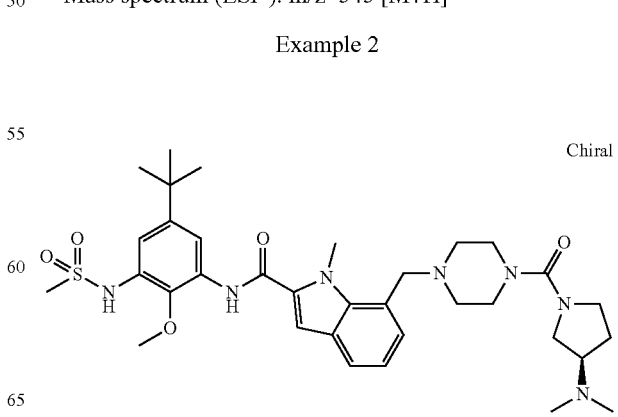

(R)-7-[4-(3-dimethylamino-pyrrolidine-1-carbonyl)-piperazin-1-ylmethyl]-1-methyl-1H-indole-2-carboxylic acid(5-tert-butyl-3-methanesulohonylamino-2-methoxy-phenyl)-amide 120 μl of a 20% solution of phosgene in toluene are dissolved in 2 ml of tetrahydrofuran, cooled to 0° C., and 173 μl N,N-diisopropyl-ethylamine (DIEA) and a solution of 100 mg of 1-methyl-7-piperazin-1-ylmethyl-1H-indole-2-carboxylic acid (5-tert-butyl-3-methanesulphonylamino-2-methoxy-phenyl)-amide in 1 ml of tetrahydrofuran are added dropwise successively. The mixture is stirred for 1 hour at 0° C. and then a solution of 26 μl (R)-dimethyl-pyrrolidin-3-yl-amine in 1 ml of tetrahydrofuran is added dropwise. The mixture is allowed to come up to ambient temperature and stirred for 1 hour. Then it is divided between water and ethyl acetate. The aqueous phase is extracted with ethyl acetate and the combined organic phases are washed with saturated aqueous sodium chloride solution. The solvents are eliminated in vacuo and the residue is chromatographed on silica gel with dichloromethane/methanol 100:0 to 90:10.

Yield: 44 mg (35% of theory)
Mass spectrum (ESI+): m/z=668 [M+H]+

The following compounds are obtained analogously to Example 2:

(1) (S)-7-[4-(3-dimethylamino-pyrrolidine-1-carbonyl)-piperazin-1-ylmethyl]-1-methyl-1H-indole-2-carboxylic acid (5-tert-butyl-3-methanesulphonylamino-2-methoxy-phenyl)-amide

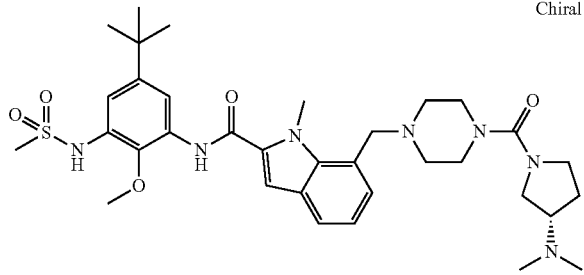

Chiral

Rf value: 0.50 (silica gel, dichloromethane/methanol 9:1)
Mass spectrum (ESI+): m/z=668 [m+H]+

Example 3

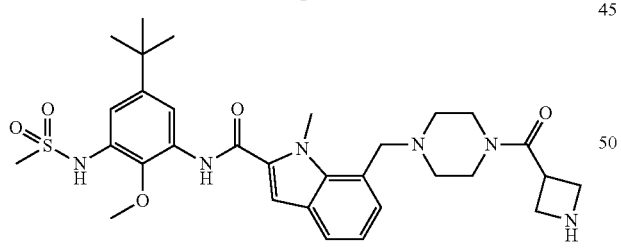

7-[4-(azetidine-3-carbonyl)-piperazin-1-ylmethyl]-1-methyl-1H-indole-2-carboxylic acid (5-tert-butyl-3-methanesulphonylamino-2-methoxy-phenyl)-amide 243 mg of tert-butyl 3-{4-[2-(5-tert-butyl-3-methanesulphonylamino-2-methoxy-phenylcarbamoyl)-1-methyl-1H-indol-7-ylmethyl]-piperazine-1-carbonyl}-azetidine-1-carboxylate are dissolved in 3 ml dichloromethane, cooled to 0° C. and combined with 261 μl trifluoroacetic acid. The mixture is allowed to come up to ambient temperature and stirred for 12 hours. Then a further 1.5 ml of trifluoroacetic acid are added and the mixture is stirred for 2 hours. Then it is diluted with dichloromethane and adjusted to pH 9 with 1 N sodium hydroxide solution. Saturated sodium chloride solution and saturated potassium carbonate solution are added and the phases are separated. The aqueous phase is extracted twice with dichloromethane. The combined organic phases are dried on magnesium sulphate and the solvents are eliminated in vacuo.

Yield: 83 mg (40% of theory)
Mass spectrum (ESI+): m/z=611 [M+H]+

Example 4

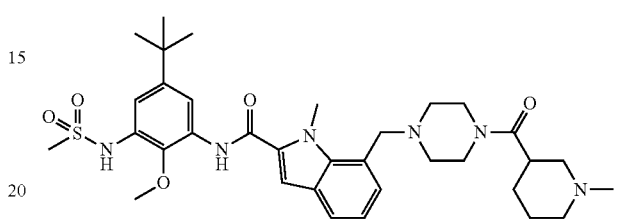

1-methyl-7-[4-(1-methyl-piperidine-3-carbonyl)-piperazin-1-ylmethyl]-1H-indole-2-carboxylic acid (5-tert-butyl-3-methanesulphonylamino-2-methoxy-phenyl)-amide 61 mg 1-methyl-piperidine-3-carboxylic acid are dissolved in 1 ml of tetrahydrofuran, combined with 69 mg carbonyldiimidazole and stirred for 20 minutes at 50° C. The mixture is left to cool to ambient temperature, 150 mg 1-methyl-7-piperazin-1-ylmethyl-1H-indole-2-carboxylic acid (5-tert-butyl-3-methanesulphonylamino-2-methoxy-phenyl)-amide are added and then the mixture is stirred for 12 hours at ambient temperature. Then a further 122 mg of 1-methyl-piperidine-3-carboxylic acid in 2 ml of tetrahydrofuran are combined with 138 mg carbonyldiimidazole, the mixture is stirred for 20 minutes at 50° C. and this solution is added to the reaction mixture. It is stirred for 2 hours at 50° C., then divided between water and ethyl acetate, the organic phase is washed with saturated aqueous sodium chloride solution, dried with magnesium sulphate and the solvents are eliminated in vacuo. The residue is chromatographed on silica gel with dichloromethane/(methanol/ammonia 9:1) 99:1 to 90:10. The product thus obtained is purified by preparative HPLC (HPLC method 3).

Yield: 102 mg (55% of theory)
HPLC (method 1): retention time=2.40 min.
Mass spectrum (ESI+): m/z=653 [M+H]+

Example 5

(S)-1-methyl-7-[4-(1-methyl-pyrrolidine-3-carbonyl)-piperazin-1-ylmethyl]-1H-indole-2-carboxylic acid (5-tert-butyl-3-methanesulphonylamino-2-methoxy-phenyl)-amide

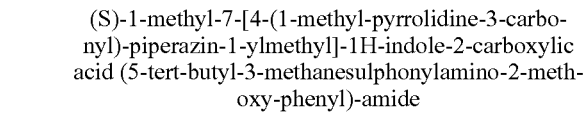

Chiral

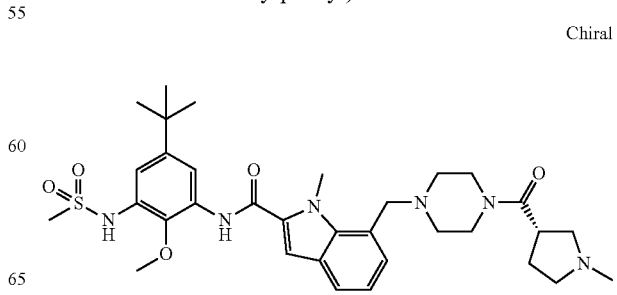

100 mg of (S)-1-methyl-7-[4-(pyrrolidine-3-carbonyl)-piperazin-1-ylmethyl]-1H-indole-2-carboxylic acid (5-tert-butyl-3-methanesulphonylamino-2-methoxy-phenyl)-amide are dissolved in 10 ml of methanol, combined with 14 µl of a 37% solution of formaldehyde in water and 20 mg of palladium on charcoal (10%) and hydrogenated for 4 hours at 4 bar. The catalyst is filtered off, the solvents are eliminated in vacuo and the residue is chromatographed on aluminium oxide (dichloromethane/methanol 95:5 to 80:20).

Yield: 81 mg (79% of theory)
HPLC (method 1): retention time=2.38 min.
Mass spectrum (ESI⁺): m/z=639 [M+H]⁺

The following compounds are obtained analogously to Example 5:

(1) (S)-1-methyl-7-[4-(1-methyl-pyrrolidine-3-carbonyl)-[1,4]diazepan-1-ylmethyl]-1H-indole-2-carboxylic acid-(5-tert-butyl-3-methanesulphonylamino-2-methoxy-phenyl)-amide

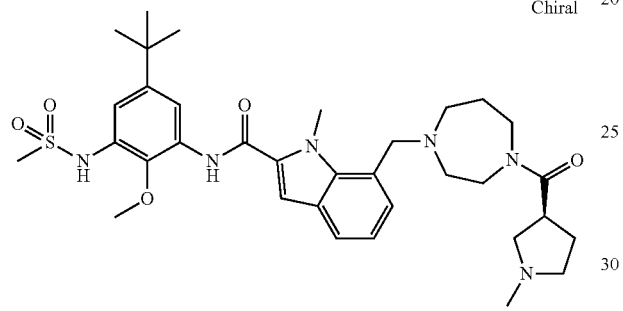

Chiral $R_f$ value: 0.27 (silica gel, dichloromethane/methanol/(ammonia in methanol (saturated)) 95:5:0.1
Mass spectrum (ESI⁺): m/z=653 [M+H]⁺

(2) (R)-1-methyl-7-[4-(1-methyl-pyrrolidine-3-carbonyl)-[1,4]diazepan-1-ylmethyl]-1H-indole-2-carboxylic acid-(5-tert-butyl-3-methanesulphonylamino-2-methoxy-phenyl)-amide

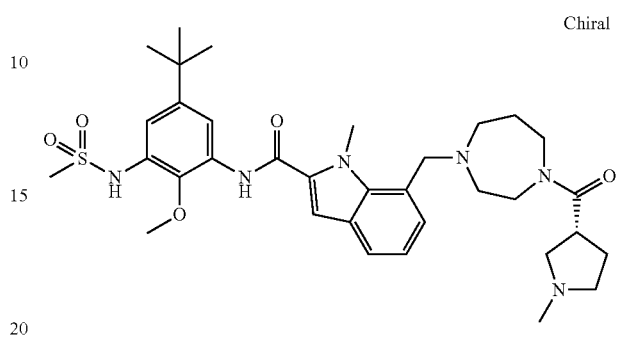

Chiral $R_f$ value: 0.30 (silica gel, dichloromethane/methanol/(ammonia in methanol (saturated)) 95:5:0.1)
Mass spectrum (ESI⁺): m/z=653 [M+H]⁺

Example 6

7-{4-[2-(4-dimethylamino-piperidin-1-yl)-acetyl]-piperazin-1-ylmethyl}-1-methyl-1H-indole-2-carboxylic acid-(5-tert-butyl-3-methanesulphonylamino-2-methoxy-phenyl)-amide

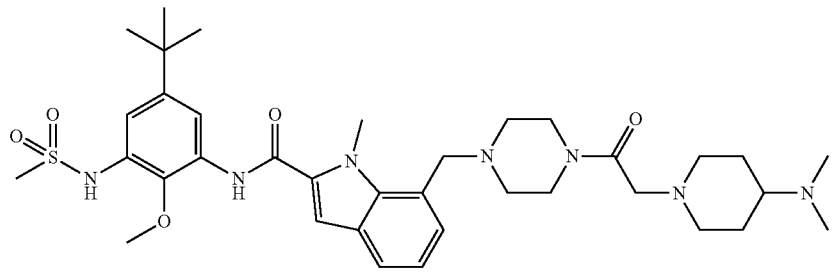

160 mg of 1-methyl-7-piperazin-1-ylmethyl-1H-indole-2-carboxylic acid (5-tert-butyl-3-methanesulphonylamino-2-methoxy-phenyl)-amide are dissolved in 5 ml dichloromethane, combined with 100 µL N,N-diisopropyl-ethylamine (DIEA) and cooled to 0° C. Then 30 µl of chloroacetic acid chloride are added dropwise, the mixture is heated to ambient temperature and stirred for 1 hour. The solvent is eliminated in vacuo and the residue is taken up in 2 ml N,N-dimethylformamide. Then 65 mg potassium carbonate and 55 µl 4-dimethylamino-piperidine are added successively. The mixture is stirred for 12 hours at ambient temperature, divided between water and ethyl acetate and the organic phase is washed with saturated aqueous sodium chloride solution. After drying with magnesium sulphate the solvents are eliminated in vacuo and the residue is chromatographed on silica gel (dichloromethane/(methanol/conc. ammonia 9:1) 99:1 to 85:15).

Yield: 90 mg (43% of theory)
HPLC (method 1): retention time=2.13 min.
Mass spectrum (ESI⁺): m/z=696 [M+H]⁺

The following compounds are obtained analogously to Example 6:

(1) (R)-7-{4-[2-(3-hydroxy-pyrrolidin-1-yl)-acetyl]-piperazin-1-ylmethyl}-1-methyl-1H-indole-2-carboxylic acid-(5-tert-butyl-3-methanesulphonylamino-2-methoxy-phenyl)-amide

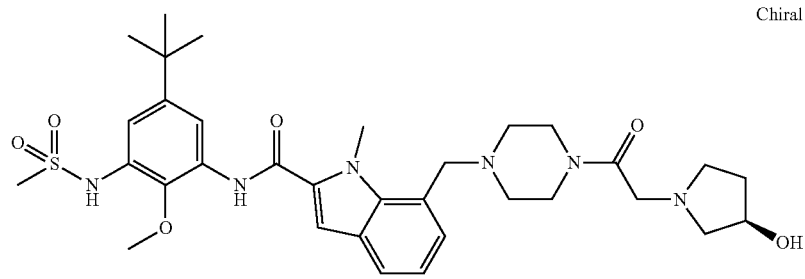 [SMILES: COc1c(NC(=O)c2cc3cccc(CN4CCN(C(=O)CN5CC[C@@H](O)C5)CC4)c3n2C)cc(C(C)(C)C)cc1NS(C)(=O)=O]

HPLC (method 1): retention time=2.34 min.
Mass spectrum (ESI⁺): m/z=655 [M+H]⁺

(2) (R)-7-{4-[2-(3-dimethylamino-pyrrolidin-1-yl)-acetyl]-piperazin-1-ylmethyl}-1-methyl-1H-indole-2-carboxylic acid-(5-tert-butyl-3-methanesulphonylamino-2-methoxy-phenyl)-amide

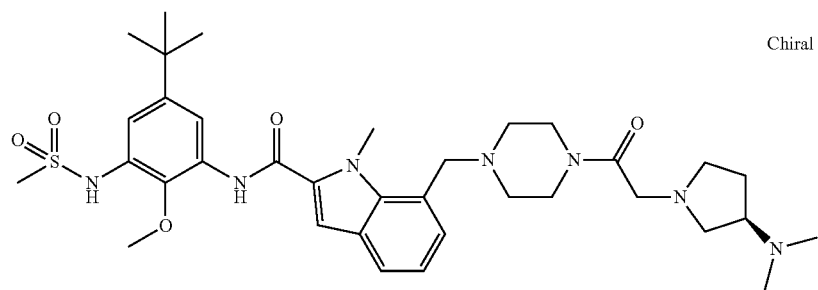

HPLC (method 1): retention time=2.18 min.
Mass spectrum (ESI⁺): m/z=682 [M+H]⁺

(3) (S)-7-{4-[2-(3-dimethylamino-pyrrolidin-1-yl)-acetyl]-piperazin-1-ylmethyl}-1-methyl-1H-indole-2-carboxylic acid-(5-tert-butyl-3-methanesulphonylamino-2-methoxy-phenyl)-amide

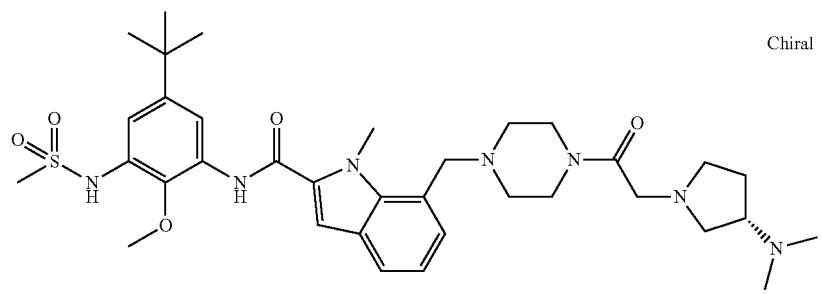

HPLC (method 1): retention time=2.17 min.
Mass spectrum (ESI⁺): m/z=682 [M+H]⁺

Example 7

1-methyl-7-[4-(2-piperazin-1-yl-acetyl)-piperazin-1-ylmethyl]-1H-indole-2-carboxylic acid-(5-tert-butyl-3-methanesulphonylamino-2-methoxy-phenyl)-amide

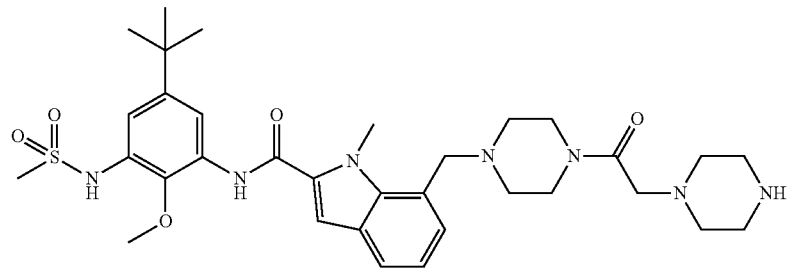 [SMILES: COc1c(NC(=O)c2cc3cccc(CN4CCN(C(=O)CN5CCNCC5)CC4)c3n2C)cc(C(C)(C)C)cc1NS(C)(=O)=O]

160 mg tert-butyl 4-(2-{4-[2-(5-tert-butyl-3-methanesulphonylamino-2-methoxy-phenylcarbamoyl)-1-methyl-1H-indol-7-ylmethyl]-piperazin-1-yl}-2-oxo-ethyl)-piperazine-1-carboxylate are dissolved in 5 ml dichloromethane, combined with 1 ml of a 5 M solution of hydrogen chloride in isopropanol and stirred for 12 hours at ambient temperature. Then the solvents are eliminated in vacuo and the residue is divided between saturated aqueous sodium hydrogen carbonate solution and ethyl acetate. The organic phase is washed with saturated aqueous sodium chloride solution and then dried on magnesium sulphate. The solvent is eliminated in vacuo and the residue is chromatographed on aluminium oxide (dichloromethane/methanol 100:0 to 95:5).

Yield: 80 mg (58% of theory)
HPLC (method 1): retention time=2.26 min.
Mass spectrum (ESI$^+$): m/z=654 [M+H]$^+$

Example 8

1-methyl-7-[4-((2S)-1-methyl-pyrrolidine-2-carbonyl)-[1,4]diazepan-1-ylmethyl]-1H-indole-2-carboxylic acid-(5-tert-butyl-3-methanesulphonylamino-2-methoxy-phenyl)-amide

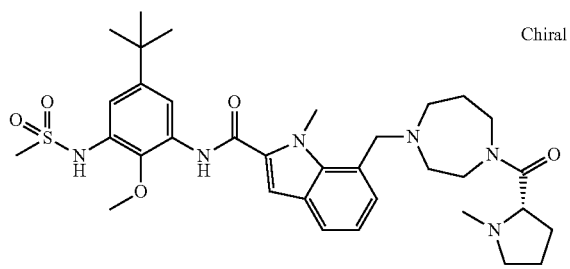 [SMILES: COc1c(NC(=O)c2cc3cccc(CN4CCCN(C(=O)[C@@H]5CCCN5C)CC4)c3n2C)cc(C(C)(C)C)cc1NS(C)(=O)=O]

Chiral

Under nitrogen, 90 mg of 7-[1,4]diazepan-1-ylmethyl-1-methyl-1H-indole-2-carboxylic acid-(5-tert-butyl-3-methanesulphonylamino-2-methoxy-phenyl)-amide and 28 mg of (S)-1-methyl-pyrrolidine-2-carboxylic acid are dissolved in 2 ml of tetrahydrofuran. 140 µl triethylamine and 160 µl of a 50% solution of n-propylphosphonic anhydride in ethyl acetate are added one after the other and the mixture is stirred for 48 hours at ambient temperature. Then it is diluted with ethyl acetate and washed with saturated aqueous sodium hydrogen carbonate solution and saturated aqueous sodium chloride solution. After drying with magnesium sulphate the solvents are eliminated in vacuo and the residue is chromatographed on silica gel (dichloromethane/methanol/(ammonia in methanol (saturated)) 97:3:0 to 93:6:1). The product thus obtained is dissolved in a little diethyl ether and crystallised out by the addition of n-hexane. The solid is suction filtered and dried.

Yield: 38 mg (35% of theory)
R$_f$ value: 0.76 (silica gel, dichloromethane/methanol/(ammonia in methanol (saturated)) 90:10:0.1)
Mass spectrum (ESI$^+$): m/z=653 [M+H]$^+$ The following compounds are obtained analogously to Example 8:

(1) 1-methyl-7-[4-(1-methyl-piperidine-4-carbonyl)-[1,4]diazepan-1-ylmethyl]-1H-indole-2-carboxylic acid-(5-tert-butyl-3-methanesulphonylamino-2-methoxy-phenyl)-amide

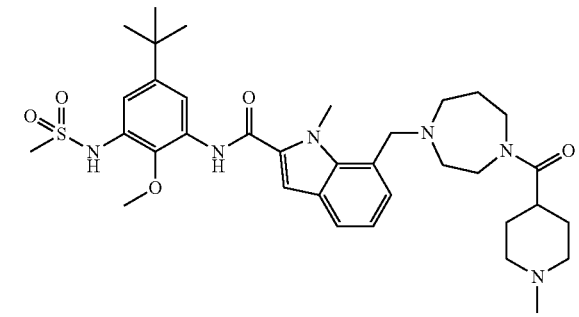 [SMILES: COc1c(NC(=O)c2cc3cccc(CN4CCCN(C(=O)C5CCN(C)CC5)CC4)c3n2C)cc(C(C)(C)C)cc1NS(C)(=O)=O]

R$_f$ value: 0.60 (silica gel, dichloromethane/methanol/(ammonia in methanol (saturated)) 90:10:0.1)
Mass spectrum (ESI$^+$): m/z=667 [M+H]$^+$ (2) (S)-1-methyl-7-[4-(1-methyl-pyrrolidine-2-carbonyl)-piperazin-1-ylmethyl]-1H-indole-2-carboxylic acid-(5-isobutyl-3-methanesulphonylamino-2-methoxy-phenyl)-amide

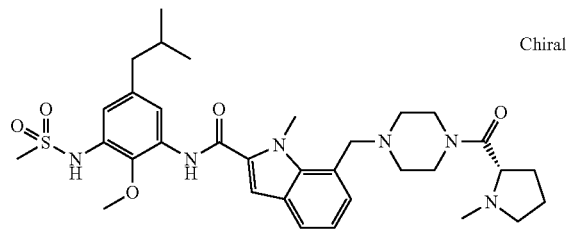 [SMILES: COc1c(NC(=O)c2cc3cccc(CN4CCN(C(=O)[C@@H]5CCCN5C)CC4)c3n2C)cc(CC(C)C)cc1NS(C)(=O)=O]

HPLC (method 1): retention time=2.65 min.
Mass spectrum (ESI⁺): m/z=639 [M+H]⁺

Example 9

(S)-1-methyl-7-[4-(1-methyl-pyrrolidine-2-carbonyl)-piperazin-1-ylmethyl]-1H-indole-2-carboxylic acid-[5-tert-butyl-2-methoxy-3-(4-methyl-piperazin-1-ylmethyl)-phenyl]-amide

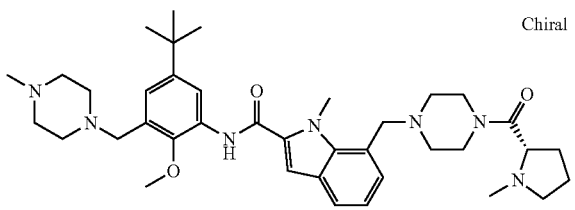 [SMILES: COc1c(CN2CCN(C)CC2)cc(C(C)(C)C)cc1NC(=O)c1cc2cccc(CN3CCN(C(=O)[C@@H]4CCCN4C)CC3)c2n1C]

160 mg of (S)-1-methyl-7-[4-(1-methyl-pyrrolidine-2-carbonyl)-piperazin-1-ylmethyl]-1H-indole-2-carboxylic acid-(5-tert-butyl-3-formyl-2-methoxy-phenyl)-amide are dissolved in 2 ml of 1,2-dichloroethane, combined successively with 40 µl acetic acid and 45 µl of 1-methylpiperazine and stirred for 1 hour at ambient temperature. Then 70 mg of sodium triacetoxyborohydride are added and the mixture is stirred for 5 hours. Then it is divided between dichloromethane and saturated aqueous sodium hydrogen carbonate solution and the organic phase is washed with saturated aqueous sodium chloride solution. After drying with magnesium sulphate the solvents are eliminated in vacuo and the residue is purified by preparative HPLC (method 7).
Yield: 45 mg (31% of theory)
HPLC (method 1): retention time=2.01 min.
Mass spectrum (ESI⁺): m/z=658 [M+H]⁺

The following compounds are obtained analogously to Example 9:

(1) (S)-1-methyl-7-[4-(1-methyl-pyrrolidine-2-carbonyl)-piperazin-1-ylmethyl]-1H-indole-2-carboxylic acid-{5-tert-butyl-3-[(diisopropylamino)-methyl]-2-methoxy-phenyl}-amide

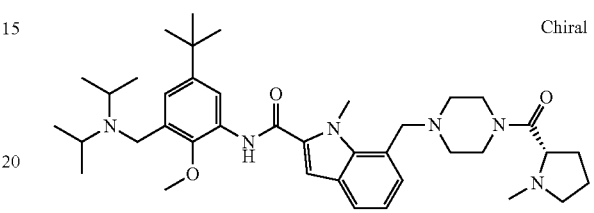

HPLC (method 1): retention time=2.18 min.
Mass spectrum (ESI⁺): m/z=659 [M+H]⁺

(2) (S)-1-methyl-7-[4-(1-methyl-pyrrolidine-2-carbonyl)-piperazin-1-ylmethyl]-1H-indole-2-carboxylic acid-(5-tert-butyl-3-diethylaminomethyl-2-methoxy-phenyl)-amide

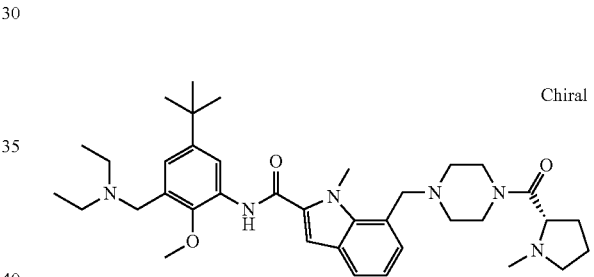

HPLC (method 1): retention time=2.06 min.
Mass spectrum (ESI⁺): m/z=631 [M+H]⁺

(3) 1-methyl-7-[4-((2S)-1-methyl-pyrrolidine-2-carbonyl)-piperazin-1-ylmethyl]-1H-indole-2-carboxylic acid-[5-tert-butyl-3-(3-dimethylamino-piperidin-1-ylmethyl)-2-methoxy-phenyl]-amide

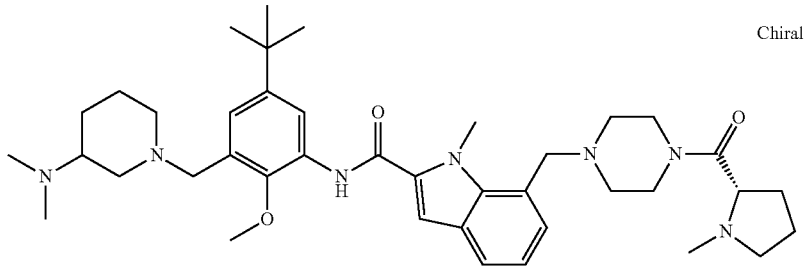 [SMILES: COc1c(CN2CCCC(N(C)C)C2)cc(C(C)(C)C)cc1NC(=O)c1cc2cccc(CN3CCN(C(=O)[C@@H]4CCCN4C)CC3)c2n1C]

HPLC (method 1): retention time=1.80 min.
Mass spectrum (ESI⁺): m/z=686 [M+H]⁺

(4) 1-methyl-7-[4-((2S)-1-methyl-pyrrolidine-2-carbonyl)-piperazin-1-ylmethyl]-1H-indole-2-carboxylic acid-[5-tert-butyl-3-(3-diethylamino-pyrrolidin-1-ylmethyl)-2-methoxy-phenyl]-amide

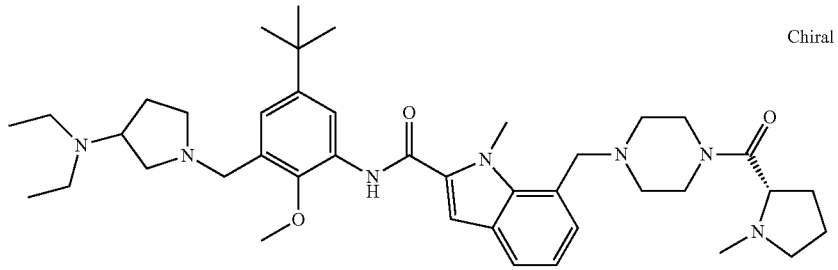 [SMILES: CCN(CC)C1CCN(Cc2cc(C(C)(C)C)cc(NC(=O)c3cc4cccc(CN5CCN(C(=O)[C@@H]6CCCN6C)CC5)c4n3C)c2OC)C1]

HPLC (method 1): retention time=1.81 min.
Mass spectrum (ESI$^+$): m/z=700 [M+H]$^+$ (5) (S)-1-methyl-7-[4-(1-methyl-pyrrolidine-2-carbonyl)-piperazin-1-ylmethyl]-1H-indole-2-carboxylic acid-[5-tert-butyl-3-(4-dimethylamino-piperidin-1-ylmethyl)-2-methoxy-phenyl]-amide

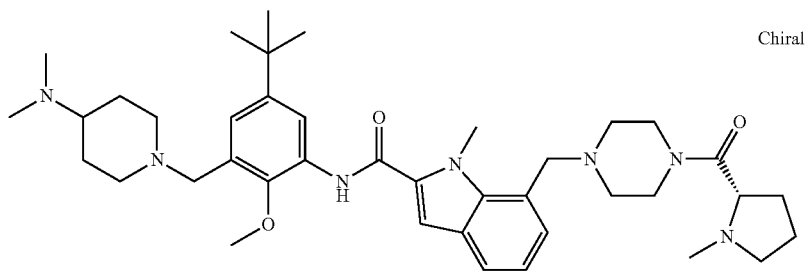 [SMILES: COc1c(CN2CCC(N(C)C)CC2)cc(C(C)(C)C)cc1NC(=O)c1cc2cccc(CN3CCN(C(=O)[C@@H]4CCCN4C)CC3)c2n1C]

HPLC (method 1): retention time=1.76 min.
Mass spectrum (ESI$^+$): m/z=686 [M+H]$^+$ (6) (S)-1-methyl-7-[4-(1-methyl-pyrrolidine-2-carbonyl)-piperazin-1-ylmethyl]-1H-indole-2-carboxylic acid-[5-tert-butyl-3-(4-diethylamino-piperidin-1-ylmethyl)-2-methoxy-phenyl]-amide

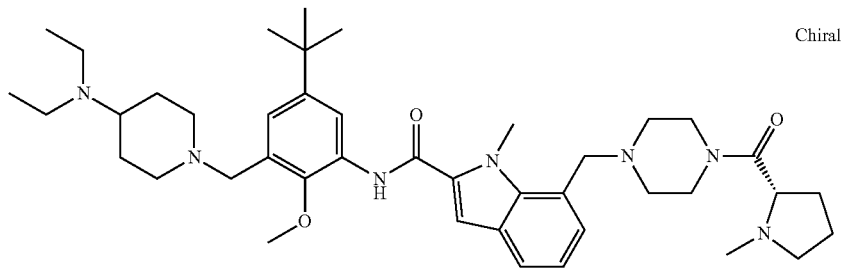 [SMILES: CCN(CC)C1CCN(Cc2cc(C(C)(C)C)cc(NC(=O)c3cc4cccc(CN5CCN(C(=O)[C@@H]6CCCN6C)CC5)c4n3C)c2OC)CC1]

HPLC (method 1): retention time=1.79 min.
Mass spectrum (ESI$^+$): m/z=714 [M+H]$^+$-

(7) (S)-1-methyl-7-[4-(1-methyl-pyrrolidine-2-carbonyl)-piperazin-1-ylmethyl]-1H-indole-2-carboxylic acid-[5-tert-butyl-3-(4-isopropyl-piperazin-1-ylmethyl)-2-methoxy-phenyl]-amide

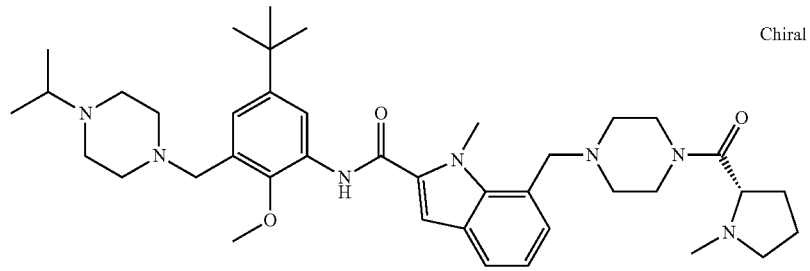 [SMILES: COc1c(CN2CCN(C(C)C)CC2)cc(C(C)(C)C)cc1NC(=O)c1cc2cccc(CN3CCN(C(=O)[C@@H]4CCCN4C)CC3)c2n1C]

HPLC (method 1): retention time=2.06 min.
Mass spectrum (ESI⁺): m/z=686 [M+H]⁺

Example 10

(S)-1-methyl-7-[4-(1-methyl-pyrrolidine-2-carbonyl)-piperazin-1-ylmethyl]-1H-indole-2-carboxylic acid-(5-tert-butyl-3-cyclopropylcarbamoyl-2-methoxy-phenyl)-amide

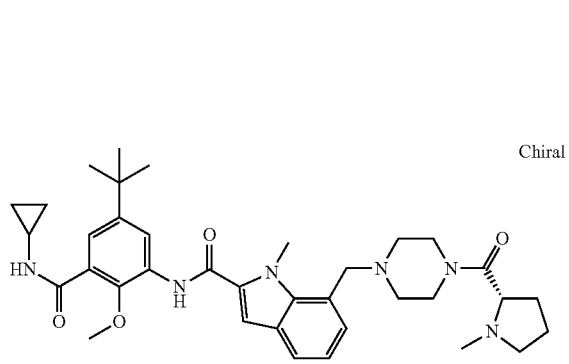 [SMILES: COc1c(NC(=O)c2cc3cccc(CN4CCN(C(=O)[C@@H]5CCCN5C)CC4)c3n2C)cc(C(C)(C)C)cc1C(=O)NC1CC1]

150 mg of 5-tert-butyl-2-methoxy-3-({1-methyl-7-[4-(1-methyl-pyrrolidine-2-carbonyl)-piperazin-1-ylmethyl]-1H-indole-2-carbonyl}-amino)-benzoic acid are dissolved in 2 ml of N,N-dimethylformamide and combined with 105 mg O-(benzotriazol-1-yl)-N,N,N',N'-tetramethyluronium-tetrafluoroborate (TBTU) and 120 µl N,N-diisopropyl-ethylamine (DIEA). The mixture is stirred for 20 minutes, then 21 µl of cyclopropylamine are added and the mixture is stirred for 12 hours. A further 21 µl of cyclopropylamine are added and the mixture is stirred for 30 minutes. Then the solvents are eliminated in vacuo and the residue is purified by preparative HPLC (method 3).

Yield: 97 mg (61% of theory)
HPLC (method 1): retention time=2.52 min.
Mass spectrum (ESI⁺): m/z=629 [M+H]⁺

The following compounds are obtained analogously to Example 10:

(1) (S)-1-methyl-7-[4-(1-methyl-pyrrolidine-2-carbonyl)-piperazin-1-ylmethyl]-1H-indole-2-carboxylic acid-(5-tert-butyl-3-isopropylcarbamoyl-2-methoxy-phenyl)-amide

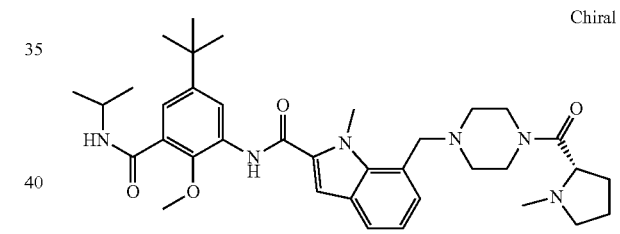

HPLC (method 1): retention time=2.66 min.
Mass spectrum (ESI⁺): m/z=631 [M+H]⁺

(2) (S)-1-methyl-7-[4-(1-methyl-pyrrolidine-2-carbonyl)-piperazin-1-ylmethyl]-1H-indole-2-carboxylic acid-(5-tert-butyl-3-ethylcarbamoyl-2-methoxy-phenyl)-amide

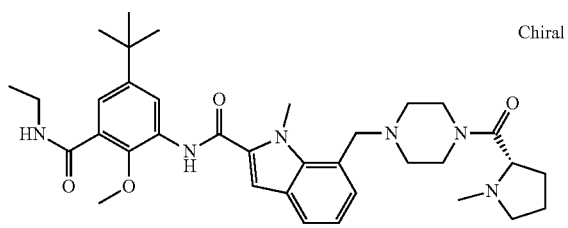 [SMILES: CCNC(=O)c1cc(C(C)(C)C)cc(NC(=O)c2cc3cccc(CN4CCN(C(=O)[C@@H]5CCCN5C)CC4)c3n2C)c1OC]

HPLC (method 6): retention time=4.00 min.
Mass spectrum (ESI⁺): m/z=617 [M+H]⁺

(3) (S)-1-methyl-7-[4-(1-methyl-pyrrolidine-2-carbonyl)-piperazin-1-ylmethyl]-1H-indole-2-carboxylic acid-(5-tert-butyl-2-methoxy-3-methylcarbamoyl-phenyl)-amide

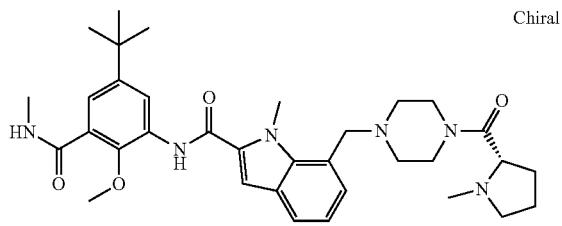 [SMILES: CNC(=O)c1cc(C(C)(C)C)cc(NC(=O)c2cc3cccc(CN4CCN(C(=O)[C@@H]5CCCN5C)CC4)c3n2C)c1OC]

HPLC (method 6): retention time=3.81 min.
Mass spectrum (ESI$^+$): m/z=603 [M+H]$^+$ (4) (S)-1-methyl-7-[4-(1-methyl-pyrrolidine-2-carbonyl)-piperazin-1-ylmethyl]-1H-indole-2-carboxylic acid-(5-tert-butyl-3-carbamoyl-2-methoxy-phenyl)-amide

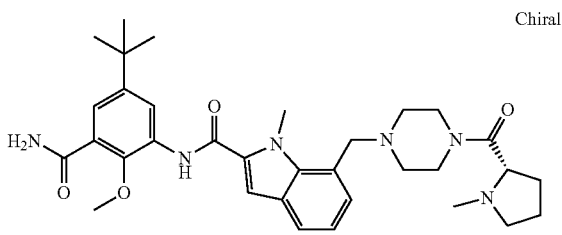 [SMILES: COc1c(NC(=O)c2cc3cccc(CN4CCN(C(=O)[C@@H]5CCCN5C)CC4)c3n2C)cc(C(C)(C)C)cc1C(N)=O]

HPLC (method 1): retention time=2.33 min.
Mass spectrum (ESI$^+$): m/z=589 [M+H]$^+$ Example 11

(S)-1-methyl-7-[4-(1-methyl-pyrrolidine-2-carbonyl)-piperazin-1-ylmethyl]-1H-indole-2-carboxylic acid-(5-tert-butyl-3-dimethylcarbamoyl-2-methoxy-phenyl)-amide

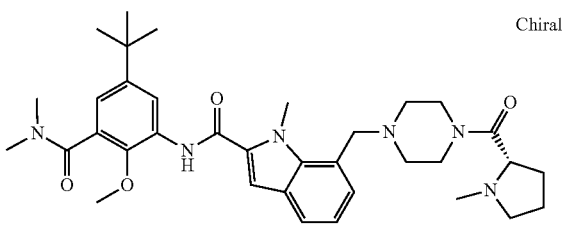 [SMILES: COc1c(NC(=O)c2cc3cccc(CN4CCN(C(=O)[C@@H]5CCCN5C)CC4)c3n2C)cc(C(C)(C)C)cc1C(=O)N(C)C]

150 mg of (S)-1-methyl-7-[4-(1-methyl-pyrrolidine-2-carbonyl)-piperazin-1-ylmethyl]-1H-indole-2-carboxylic acid are dissolved in 2 ml acetonitrile, mixed with 113 µl oxalyl chloride and 10 µl of N,N-dimethylformamide and stirred for 1 hour. Then the mixture is evaporated down in vacuo, taken up in dichloromethane and the latter is eliminated in vacuo. The residue is taken up in 2 ml of 1,2-dichloroethane, combined with 130 µl triethylamine and 78 mg of 3-amino-5-tert-butyl-2-methoxy-N,N-dimethyl-benzamide and stirred for 2 hours at ambient temperature. Then it is divided between water and dichloromethane, the aqueous phase is extracted twice with dichloromethane and the combined organic phases are dried on magnesium sulphate. The solvents are eliminated in vacuo and the residue is chromatographed on silica gel (dichloromethane/(methanol/ammonia in methanol (saturated) 9:1) 99:1 to 90:10).

Yield: 115 mg (60% of theory)
HPLC (method 1): retention time=2.50 min.
Mass spectrum (ESI$^+$): m/z=617 [M+H]$^+$ The following compounds are obtained analogously to Example 11:

(1) 1-methyl-7-[4-((2S)-1-methyl-pyrrolidine-2-carbonyl)-piperazin-1-ylmethyl]-1H-indole-2-carboxylic acid-(5-sec-butyl-3-methanesulphonylamino-2-methoxy-phenyl)-amide

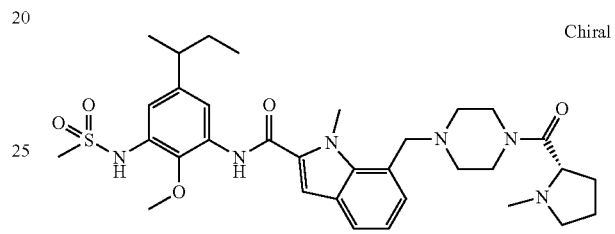

The crude product is purified by preparative HPLC (method 3).
HPLC (method 1): retention time=2.74 min.
Mass spectrum (ESI$^+$): m/z=639 [M+H]$^+$ (2) (S)-1-methyl-7-[4-(1-methyl-pyrrolidine-2-carbonyl)-piperazin-1-ylmethyl]-1H-indole-2-carboxylic acid-(5-isopropyl-3-methanesulphonylamino-2-methoxy-phenyl)-amide

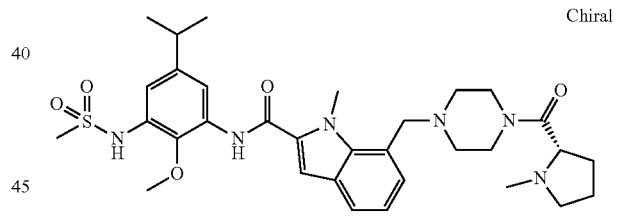

The crude product is purified by preparative HPLC (method 3).
HPLC (method 1): retention time=2.44 min.
Mass spectrum (ESI$^+$): m/z=625 [M+H]$^+$ (3) 1-methyl-7-[4-((2S)-1-methyl-pyrrolidine-2-carbonyl)-piperazin-1-ylmethyl]-1H-indole-2-carboxylic acid-(5-tert-butyl-3-methanesulphinyl-2-methoxy-phenyl)-amide

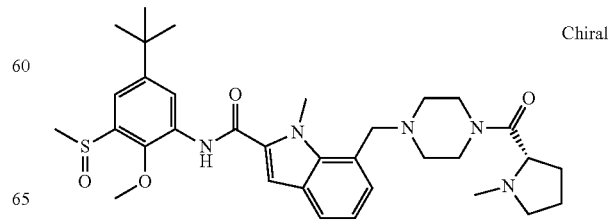

The product is purified by preparative HPLC (method 7). The product fractions are combined, the acetonitrile is eliminated in vacuo and the aqueous phase is diluted with saturated aqueous sodium hydrogen carbonate solution. The mixture is extracted 3 times with dichloromethane, dried with magnesium sulphate and the solvents are eliminated in vacuo.

HPLC (method 1): retention time=2.33 min.

Mass spectrum (ESI$^+$): m/z=608 [M+H]$^+$

The two diastereomers are separated by preparative HPLC as follows:

Column: twice Daicel ASH; 250×10 mm; 10 ml/minute; UV detection 220 nm; eluant: $CO_2$/(0.2% diethylamine in isopropanol) 60:40 (isocratic)

Diastereomer 1:

retention time: 14.2 minutes

Mass spectrum (ESI$^+$): m/z=608 [M+H]$^+$

Diastereomer 2:

retention time: 21.8 minutes

Mass spectrum (ESI$^+$): m/z=608 [M+H]$^+$ (4) (S)-1-methyl-7-[4-(1-methyl-pyrrolidine-2-carbonyl)-piperazin-1-ylmethyl]-1H-indole-2-carboxylic acid-(5-tert-butyl-3-methanesulphonyl-2-methoxy-phenyl)-amide

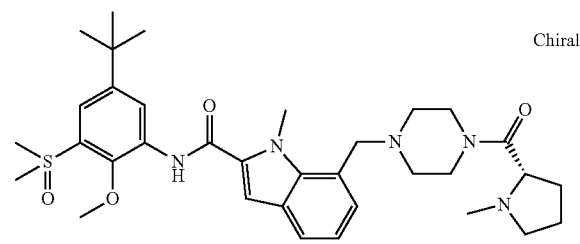

HPLC (method 1): retention time=2.58 min.

Mass spectrum (ESI$^+$): m/z=624 [M+H]$^+$ (5) (S)-1-methyl-7-[4-(1-methyl-pyrrolidine-2-carbonyl)-piperazin-1-ylmethyl]-1H-indole-2-carboxylic acid-(5-tert-butyl-3-methanesulphonylmethyl-2-methoxy-phenyl)-amide

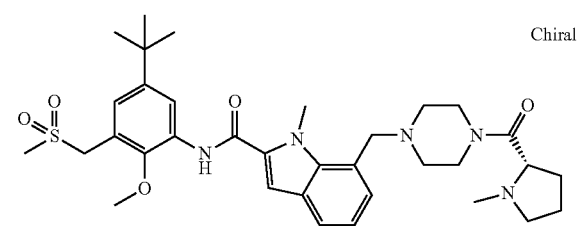 [SMILES: COc1c(CS(C)(=O)=O)cc(C(C)(C)C)cc1NC(=O)c1cc2cccc(CN3CCN(C(=O)[C@@H]4CCCN4C)CC3)c2n1C]

HPLC (method 1): retention time=2.51 min.

Mass spectrum (ESI$^+$): m/z=638 [M+H]$^+$ (6) 1-methyl-7-[4-((2S)-1-methyl-pyrrolidine-2-carbonyl)-piperazin-1-ylmethyl]-1H-indole-2-carboxylic acid-(5-tert-butyl-3-methanesulphinylmethyl-2-methoxy-phenyl)-amide

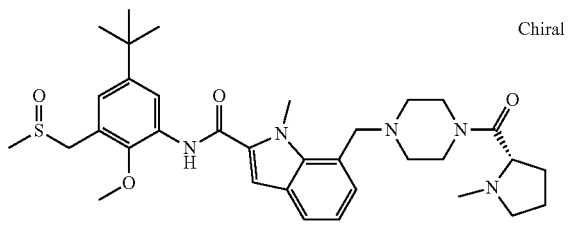 [SMILES: COc1c(CS(C)=O)cc(C(C)(C)C)cc1NC(=O)c1cc2cccc(CN3CCN(C(=O)[C@@H]4CCCN4C)CC3)c2n1C]

HPLC (method 1): retention time=2.38 min.

Mass spectrum (ESI$^+$): m/z=622 [M+H]$^+$ (7) (S)-1-methyl-7-[4-(1-methyl-pyrrolidine-2-carbonyl)-piperazin-1-ylmethyl]-1H-indole-2-carboxylic acid-(5-tert-butyl-3-methanesulphonylamino-2-ethoxy-phenyl)-amide

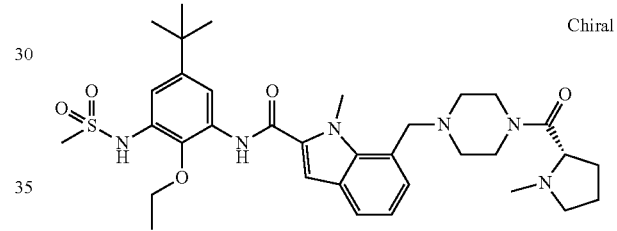

HPLC (method 1): retention time=2.67 min.

Mass spectrum (ESI$^+$): m/z=653 [M+H]$^+$

Example 12

(S)-1-methyl-7-[4-(1-methyl-pyrrolidine-2-carbonyl)-piperazin-1-ylmethyl]-1H-indole-2-carboxylic acid-(5-tert-butyl-2-methoxy-3-propionylamino-phenyl)-amide

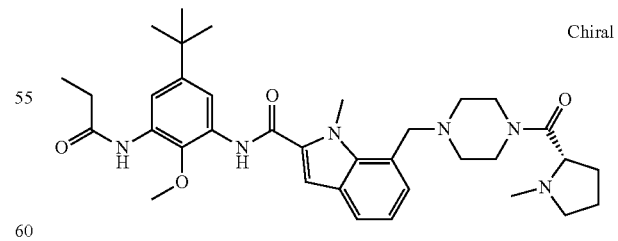

150 mg of 1-methyl-7-[4-(1-methyl-pyrrolidine-2-carbonyl)-piperazin-1-ylmethyl]-1H-indole-2-carboxylic acid-(3-amino-5-tert-butyl-2-methoxy-phenyl)-amide trihydrochloride are dissolved in 2 ml of dichloromethane and combined successively with 160 μl triethylamine as well as 25 μl propionyl chloride. The mixture is stirred for 2 hours at ambient temperature, the solvents are eliminated in vacuo and the residue is purified by preparative HPLC (method 3).

Yield: 54 mg (39% of theory)
HPLC (method 1): retention time=2.51 min.
Mass spectrum (ESI$^+$): m/z=617 [M+H]$^+$ The following compounds are obtained analogously to Example 12:

(1) (S)-1-methyl-7-[4-(1-methyl-pyrrolidine-2-carbonyl)-piperazin-1-ylmethyl]-1H-indole-2-carboxylic acid-(5-tert-butyl-3-butyrylamino-2-methoxy-phenyl)-amide

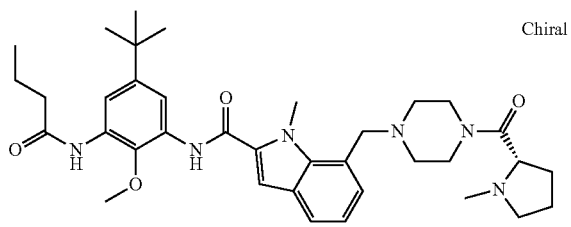 [SMILES: CCCC(=O)Nc1cc(C(C)(C)C)cc(NC(=O)c2cc3cccc(CN4CCN(C(=O)[C@@H]5CCCN5C)CC4)c3n2C)c1OC]

HPLC (method 6): retention time=4.22 min.
Mass spectrum (ESI$^+$): m/z=631 [M+H]$^+$ (2) (S)-1-methyl-7-[4-(1-methyl-pyrrolidine-2-carbonyl)-piperazin-1-ylmethyl]-1H-indole-2-carboxylic acid-(3-acetylamino-5-tert-butyl-2-methoxy-phenyl)-amide

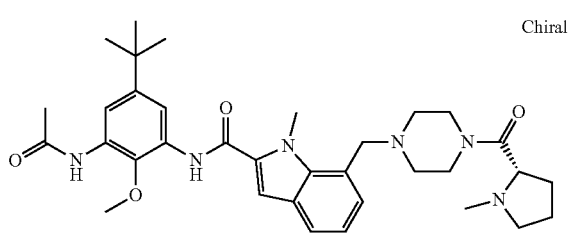 [SMILES: COc1c(NC(C)=O)cc(C(C)(C)C)cc1NC(=O)c1cc2cccc(CN3CCN(C(=O)[C@@H]4CCCN4C)CC3)c2n1C]

HPLC (method 1): retention time=2.42 min.
Mass spectrum (ESI$^+$): m/z=603 [M+H]$^+$ (3) (S)-1-methyl-7-[4-(1-methyl-pyrrolidine-2-carbonyl)-piperazin-1-ylmethyl]-1H-indole-2-carboxylic acid-(5-tert-butyl-3-isobutyrylamino-2-methoxy-phenyl)-amide

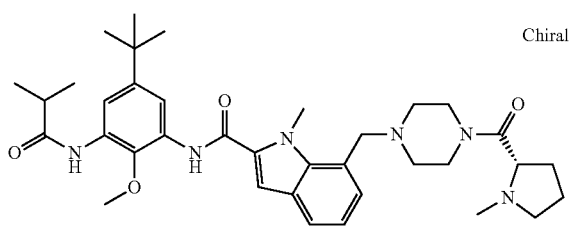 [SMILES: COc1c(NC(=O)c2cc3cccc(CN4CCN(C(=O)[C@@H]5CCCN5C)CC4)c3n2C)cc(C(C)(C)C)cc1NC(=O)C(C)C]

HPLC (method 1): retention time=2.69 min.
Mass spectrum (ESI$^+$): m/z=631 [M+H]$^+$ (4) (S)-1-methyl-7-[4-(1-methyl-pyrrolidine-2-carbonyl)-piperazin-1-ylmethyl]-1H-indole-2-carboxylic acid-[5-tert-butyl-3-(cyclopropanecarbonyl-amino)-2-methoxy-phenyl]-amide

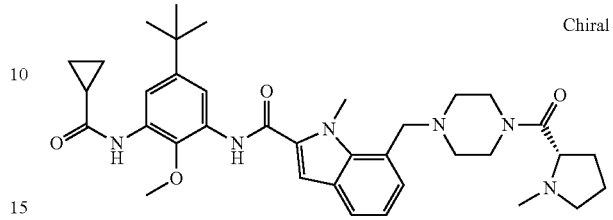

HPLC (method 1): retention time=2.65 min.
Mass spectrum (ESI$^+$): m/z=629 [M+H]$^+$ Example 13

(S)-1-methyl-7-[4-(1-methyl-pyrrolidine-2-carbonyl)-piperazin-1-ylmethyl]-1H-indole-2-carboxylic acid-[5-tert-butyl-2-methoxy-3-(propane-1-sulphonylamino)-phenyl]-amide

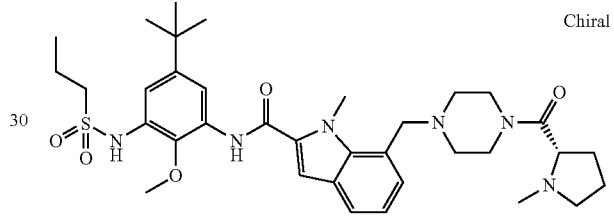

200 mg of 1-methyl-7-[4-(1-methyl-pyrrolidine-2-carbonyl)-piperazin-1-ylmethyl]-1H-indole-2-carboxylic acid-(3-amino-5-tert-butyl-2-methoxy-phenyl)-amide trihydrochloride are dissolved in 2 ml dichloromethane and mixed successively with 210 µl triethylamine, 80 µl propylsulphonic acid chloride and 70 µl pyridine. The mixture is stirred for 2 hours at ambient temperature, a further 80 µl of propylsulphonic acid chloride are added and the mixture is stirred for a further 12 hours. The solvents are eliminated in vacuo and the residue is purified by preparative HPLC (method 3).

Yield: 110 mg (55% of theory)
HPLC (method 1): retention time=2.79 min.
Mass spectrum (ESI$^+$): m/z=667 [M+H]$^+$ The following compounds are obtained analogously to Example 13:

(1) (S)-1-methyl-7-[4-(1-methyl-pyrrolidine-2-carbonyl)-piperazin-1-ylmethyl]-1H-indole-2-carboxylic acid-(5-tert-butyl-3-cyclopropanesulphonylamino-2-methoxy-phenyl)-amide

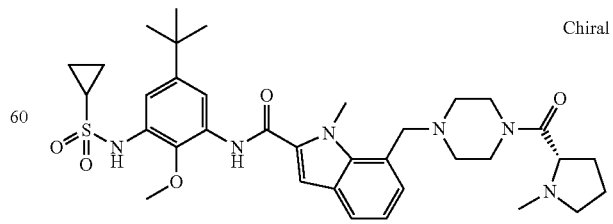

HPLC (method 1): retention time=2.69 min.
Mass spectrum (ESI$^+$): m/z=665 [M+H]$^+$

Example 14

(S)-1-methyl-7-[4-(1-methyl-pyrrolidine-2-carbonyl)-piperazin-1-ylmethyl]-1H-indole-2-carboxylic acid-(3-methanesulphonylamino-2-methoxy-5-pentafluoroethyl-phenyl)-amide

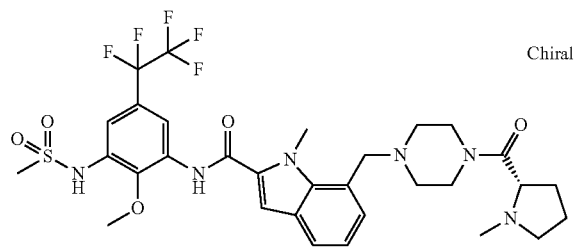 [SMILES: COc1c(NC(=O)c2cc3cccc(CN4CCN(C(=O)[C@@H]5CCCN5C)CC4)c3n2C)cc(C(F)(F)C(F)(F)F)cc1NS(C)(=O)=O]

70 mg (S)-1-methyl-7-[4-(1-methyl-pyrrolidine-2-carbonyl)-piperazin-1-ylmethyl]-1H-indole-2-carboxylic acid-(3-amino-2-methoxy-5-pentafluoroethyl-phenyl)-amide are dissolved in 2 ml dichloromethane, combined with 36 µl triethylamine, and 20 µl methanesulphonic acid chloride are added dropwise to this mixture. It is stirred for 2 hours, a further 20 µl methanesulphonic acid chloride and 36 µl triethylamine are added and then it is stirred for 1.5 hours. Then 2 ml of methanol and 600 µl of 2 N sodium hydroxide solution are added. The mixture is stirred for 2 hours, the solvents are eliminated in vacuo and the residue is chromatographed on silica gel (dichloromethane/(methanol/ammonia in methanol (saturated) 9:1) 99:1 to 85:15).

Yield: 48 mg (61% of theory)

HPLC (method 6): retention time=2.75 min.

Mass spectrum (ESI$^+$): m/z=701 [M+H]$^+$

The following compounds are obtained analogously to Example 14:

(1) (S)-1-methyl-7-[4-(1-methyl-pyrrolidine-2-carbonyl)-piperazin-1-ylmethyl]-1H-indole-2-carboxylic acid-(3-methanesulphonylamino-2-methoxy-5-trifluoromethyl-phenyl)-amide

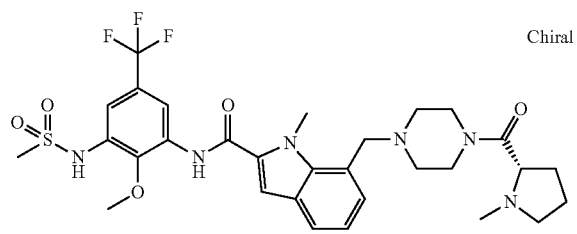 [SMILES: COc1c(NC(=O)c2cc3cccc(CN4CCN(C(=O)[C@@H]5CCCN5C)CC4)c3n2C)cc(C(F)(F)F)cc1NS(C)(=O)=O]

HPLC (method 6): retention time=2.70 min.

Mass spectrum (ESI$^+$): m/z=651 [M+H]$^+$

Example 15

(S)-1-methyl-7-[4-(1-methyl-pyrrolidine-2-carbonyl)-piperazin-1-ylmethyl]-1H-indole-2-carboxylic acid-(5-tert-butyl-3-hydroxymethyl-2-methoxy-phenyl)-amide

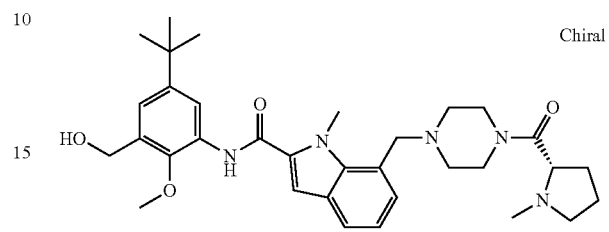

270 mg of (S)-1-methyl-7-[4-(1-methyl-pyrrolidine-2-carbonyl)-piperazin-1-ylmethyl]-1H-indole-2-carboxylic acid-(5-tert-butyl-2-methoxy-3-trimethylsilanyloxymethyl-phenyl)-amide are dissolved in 5 ml dichloromethane, mixed with 833 µl of a 5 M solution of hydrogen chloride in isopropanol and stirred for 30 minutes at ambient temperature. The mixture is divided between dichloromethane and saturated aqueous sodium hydrogen carbonate solution, the aqueous phase is extracted twice with dichloromethane and the combined organic phases are washed with saturated aqueous sodium chloride solution. After drying with magnesium sulphate the solvents are eliminated in vacuo and the product thus obtained is purified by preparative HPLC (method 3).

Yield: 75 mg (31% of theory)

HPLC (method 6): retention time=4.09 min.

Mass spectrum (ESI$^+$): m/z=576 [M+H]$^+$

The following are examples of formulations, in which the term "active substance" denotes one or more compounds according to the invention, including the salts thereof. In the case of one of the combinations described hereinbefore having one or more additional active substances, the term "active substance" also includes the additional active substances.

Example A

Coated tablets containing 75 mg active substance
Composition:

| 1 table core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

Example B

Tablets containing 100 mg of active substance
Composition

| 1 tablet contains: | |
| --- | --- |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

Example C

Tablets containing 150 mg of active substance
Composition

| 1 tablet contains: | |
| --- | --- |
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

Example D

Hard gelatine capsules containing 150 mg of active substance
Composition

| 1 capsule contains: | |
| --- | --- |
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

Example E

Suppositories containing 150 mg of active substance
Composition

| 1 suppository contains: | |
| --- | --- |
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example F

Suspension containing 50 mg of active substance
Composition

| 100 ml of suspension contain: | |
| --- | --- |
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

Example G

Ampoules containing 10 mg active substance
Composition

| active substance | 10.0 mg |
|---|---|
| 0.01N hydrochloric acid | q.s. |
| double-distilled water | ad 2.0 ml |

Preparation:
The active substance is dissolved in the necessary amount of 0.01 N HCl, made isotonic with common salt, filtered sterile and transferred into 2 ml ampoules.

Example H

Ampoules containing 50 mg of active substance
Composition

| active substance | 50.0 mg |
|---|---|
| 0.01N hydrochloric acid | q.s. |
| double-distilled water | ad 10.0 ml |

Preparation:
The active substance is dissolved in the necessary amount of 0.01 N HCl, made isotonic with common salt, filtered sterile and transferred into 10 ml ampoules.

Example I

Capsules for powder inhalation containing 5 mg of active substance

| 1 capsule contains: | |
|---|---|
| active substance | 5.0 mg |
| lactose for inhalation | 15.0 mg |
| | 20.0 mg |

Preparation:
The active substance is mixed with lactose for inhalation. The mixture is packed into capsules in a capsule-making machine (weight of the empty capsule approx. 50 mg).
weight of capsule: 70.0 mg
size of capsule: 3

Example J

Solution for inhalation for hand-held nebulisers containing 2.5 mg active substance

| 1 spray contains: | |
|---|---|
| active substance | 2.500 mg |
| benzalkonium chloride | 0.001 mg |
| 1N hydrochloric acid q.s. | |
| ethanol/water (50/50) | ad 15.000 mg |

Preparation:
The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).
Contents of the container: 4.5 g

The invention claimed is:
1. A compound of the formula I

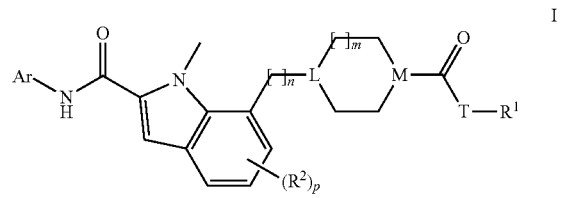

wherein
Ar denotes a substituent of formula (II), (III) or (IV)

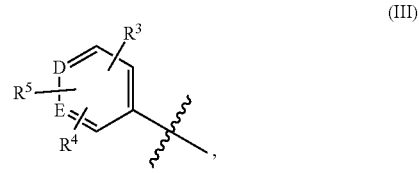

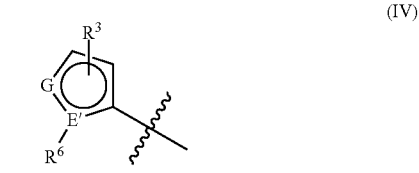

wherein $R^3$ denotes $C_{1-6}$-alkyl, $C_{3-6}$-cycloalkyl, $C_{1-4}$-alkoxy, $C_{1-2}$-perfluoroalkyl, 3-methyl-oxetan-3-yl, $C_{1-2}$-perfluoroalkoxy, morpholinyl,
wherein the cycloalkyl group may optionally be substituted by $C_{1-3}$-alkyl,
wherein $R^4$ denotes H, $C_{1-4}$-alkyl, $C_{1-4}$-alkoxy,
wherein $R^5$ denotes H, $C_{1-5}$-alkyl-sulphonyl-amino, $C_{3-6}$-cycloalkyl-sulphonyl-amino, ($C_{1-5}$-alkyl-sulphonyl)-(methyl)-amino, ($C_{3-6}$-cycloalkyl-sulphonyl)-(methyl)-amino, $C_{1-5}$-alkyl-carbonyl-amino, $C_{3-6}$-cycloalkyl-carbonyl-amino, ($C_{1-5}$-alkyl-carbonyl)-(methyl)-amino, ($C_{3-6}$-cycloalkyl-carbonyl)-(methyl)-amino, aminocarbonyl, $C_{1-5}$-alkyl-aminocarbonyl, $C_{3-6}$-cycloalkyl-amino-carbonyl, di-($C_{1-3}$-alkyl)-amino-carbonyl, di-($C_{1-3}$-alkyl)-amino-$C_{1-2}$-alkyl, di-($C_{1-3}$-alkyl)-amino-pyrrolidin-1-yl-$C_{1-2}$-alkyl, 4-$C_{1-5}$-alkyl-piperazin-1-yl-$C_{1-2}$-alkyl, 4-di-($C_{1-3}$-alkyl)-amino-piperidin-1-yl-$C_{1-2}$-alkyl, 3-di-($C_{1-3}$-alkyl)-amino-piperidin-1-yl-$C_{1-2}$-alkyl, $C_{1-5}$-alkyl-sulphinyl, $C_{3-6}$-cycloalkyl-sulphinyl, $C_{1-5}$-alkyl-sulphonyl, $C_{3-6}$-cycloalkyl-sulphonyl, hydroxy-$C_{1-2}$-alkyl, $C_{1-5}$-alkyl-sulphinyl-methyl, $C_{1-5}$-alkyl-sulphonyl-methyl, wherein $R^6$ denotes $C_{1-3}$-alkyl or phenyl,
  wherein the $C_{1-3}$-alkyl group may optionally be substituted by hydroxy or di-($C_{1-3}$-alkyl)-amino and the phenyl group may optionally be substituted by fluorine or $C_{1-3}$-alkyl,
wherein D or E represents nitrogen,
wherein G and E' independently of one another represent nitrogen or oxygen,
wherein $R^6$ is only bound to E' if E' denotes nitrogen,
$R^1$ denotes a $C_{4-6}$-cycloalkyl system, which contains 1 to 2 nitrogen atoms that may optionally be 1- to 2-substituted by $R^7$,
  wherein $R^7$ may be $C_{1-3}$-alkyl, hydroxy, $C_{1-3}$-alkoxy, amino, $C_{1-3}$-alkyl-amino, di-($C_{1-3}$-alkyl)-amino,
$R^2$ denotes hydrogen, halogen or $C_{1-4}$-alkyl,
L denotes —C(H)< or —N<,
M denotes —C(H)< or —N<,
T denotes a bond or $C_{1-4}$-alkylene,
  while the $C_{1-4}$-alkylene group may be substituted by $C_{1-2}$-alkyl,
m denotes 0, 1, 2 or 3,
n denotes 1, 2 or 3,
p denotes 0, 1, 2 or 3,
while, unless stated otherwise, the above-mentioned alkyl groups may be straight-chain or branched,
the tautomers, the stereoisomers, the mixtures and the physiologically acceptable salts thereof.

2. The compound of the formula (I) according to claim 1, wherein
Ar is a substituent according to general formula (II')

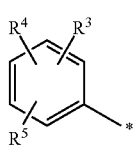

(II')

wherein $R^3$ denotes —$C_1$-$C_6$-alkyl, —$C_3$-$C_6$-cycloalkyl, —$CF_3$, —$CF_2CF_3$ or

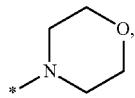

while the —$C_3$-$C_6$-cycloalkyl group may be substituted by —$C_1$-$C_3$-alkyl,
wherein $R^4$ denotes —H, —$C_1$-$C_4$-alkyl or —O—$C_1$-$C_4$-alkyl,
wherein $R^5$ is selected from
—NH—S(O)$_2$—$C_1$-$C_4$-alkyl;
—NH—S(O)$_2$—$C_3$-$C_5$-cycloalkyl;
—N(CH$_3$)—S(O)$_2$—$C_1$-$C_4$-alkyl;
—N(CH$_3$)—S(O)$_2$—$C_3$-$C_5$-cycloalkyl;
—NH—C(O)—$C_1$-$C_4$-alkyl;
—NH—C(O)—$C_3$-$C_5$-cycloalkyl;
—N(CH$_3$)—C(O)—$C_1$-$C_4$-alkyl;
—N(CH$_3$)—C(O)—$C_3$-$C_5$-cycloalkyl;
—C(O)—NH$_2$;
—C(O)—NH—$C_1$-$C_4$-alkyl;
—C(O)—N(di-$C_1$-$C_4$-alkyl);
—C(O)—NH—$C_3$-$C_5$-cycloalkyl;
—C(O)—N($C_1$-$C_4$-alkyl)($C_3$-$C_5$-cycloalkyl);
—S(O)—$C_1$-$C_4$-alkyl;
—S(O)—$C_3$-$C_5$-cycloalkyl;
—S(O)$_2$—$C_1$-$C_4$-alkyl;
—S(O)$_2$—$C_3$-$C_5$-cycloalkyl;
—$C_1$-$C_4$-alkyl-OH
—CH$_2$—S(O)—$C_1$-$C_4$-alkyl;
—CH$_2$—S(O)—$C_3$-$C_5$-cycloalkyl;
—CH$_2$—S(O)$_2$—$C_1$-$C_4$-alkyl;
—CH$_2$—S(O)$_2$—$C_3$-$C_5$-cycloalkyl;
—$C_1$-$C_4$-alkylene-N($R^8$,$R^{8'}$);
wherein $R^1$ denotes —$C_4$-$C_6$-cycloalkyl, which contains 1 to 2 nitrogen atoms in the ring,
  wherein $R^1$ is optionally substituted by a group selected from —$C_1$-$C_4$-alkyl,
  —OH, —O—$C_1$-$C_4$-alkyl, and —N($R^9$,$R^{9'}$),
wherein $R^2$ is selected from —H, -halogen and $C_1$-$C_4$-alkyl,
wherein in each case $R^8$, $R^{8'}$, $R^9$ and $R^{9'}$ independently of one another are selected from —H and —$C_1$-$C_5$-alkyl,
wherein the two groups $R^8$ and $R^{8'}$ together with the nitrogen to which they are bound, may form a 4- to 6-membered ring system, which may be substituted by —OH or —N($R^{10}$,$R^{10'}$),
wherein in each case $R^{10}$ and $R^{10'}$ independently of one another are selected from —H and —$C_1$-$C_5$-alkyl,
wherein L and M independently of one another are selected from —CH< and —N<,
wherein T is selected from a bond and —$C_1$-$C_3$-alkylene,
  while the $C_{1-3}$-alkylene group may be substituted by methyl,
wherein m may be 0-3,
wherein n may be 1-3,
wherein p may be 0-3,
optionally in the form of the individual optical isomers thereof, mixtures of these isomers, racemates, optionally in the form of the acid addition salts thereof with pharmacologically acceptable acids.

3. The compound of the formula (I) according to claim 2, wherein
Ar is a substituent according to general formula (II")

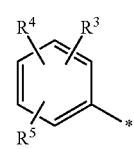

(II")

wherein $R^3$ is selected from —CH$_3$, —C$_2$H$_5$, -n-C$_3$H$_7$, -i-C$_3$H$_7$, —C(CH$_3$)$_3$, -n-C$_4$H$_9$, —CH$_2$-i-C$_3$H$_7$, —CH(CH$_3$)(C$_2$H$_5$), -n-C$_5$H$_{11}$, —CH$_2$—CH$_2$-i-C$_3$H$_7$, —CH$_2$—C(CH$_3$)$_3$, —CF$_3$, —CF$_2$CF$_3$ or

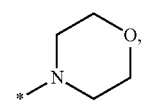

wherein $R^4$ is selected from H, —O—CH$_3$, —O—C$_2$H$_5$,
wherein $R^5$ is selected from H, —NH—S(O)$_2$—CH$_3$, —NH—S(O)$_2$—C$_2$H$_5$, —NH—S(O)$_2$-n-C$_3$H$_7$, —NH—S(O)$_2$-i-C$_3$H$_7$, NH—S(O)$_2$-c-C$_3$H$_5$, —NH—S(O)$_2$-n-C$_4$H$_9$, —NH—S(O)$_2$—CH$_2$-i-C$_3$H$_7$, —NH—S(O)$_2$—C(CH$_3$)$_3$, —NH—S(O)$_2$-c-

$C_4H_7$, —NH—S(O)$_2$-n-C$_5$H$_{11}$, —NH—S(O)$_2$—(CH$_2$)$_2$-i-C$_3$H$_7$, —NH—S(O)$_2$—CH$_2$—C(CH$_3$)$_3$, —NH—S(O)$_2$-c-C$_5$H$_9$, —NH—C(O)—CH$_3$, —NH—C(O)—C$_2$H$_5$, —NH—C(O)-n-C$_3$H$_7$, —NH—C(O)-i-C$_3$H$_7$, —NH—C(O)-c-C$_3$H$_5$, —NH—C(O)-n-C$_4$H$_9$, —NH—C(O)—CH$_2$-i-C$_3$H$_7$, —NH—C(O)—C(CH$_3$)$_3$, —NH—C(O)-c-C$_4$H$_7$, —NH—C(O)-n-C$_5$H$_{11}$, —NH—C(O)—(CH$_2$)$_2$-i-C$_3$H$_7$, —NH—C(O)—CH$_2$—C(CH$_3$)$_3$, —NH—C(O)-c-C$_5$H$_9$, —C(O)—NH$_2$, —C(O)—NH—CH$_3$, —C(O)—N(CH$_3$)$_2$, —C(O)—NH—C$_2$H$_5$, —C(O)—N(C$_2$H$_5$)$_2$, —C(O)—NH-n-C$_3$H$_7$, —C(O)—N(C$_3$H$_7$)$_2$, —C(O)—NH-i-C$_3$H$_7$, —C(O)—N(i-C$_3$H$_7$)$_2$, —C(O)—NH-c-C$_3$H$_5$, —C(O)—NH-n-C$_4$H$_9$, —C(O)—N(n-C$_4$H$_9$)$_2$, —C(O)—NH—CH$_2$-i-C$_3$H$_7$, —C(O)—N(CH$_2$-i-C$_3$H$_7$)$_2$, —C(O)—NH-c-C$_4$H$_7$, —CH$_2$—N(CH$_3$)$_2$, —CH$_2$—N(C$_2$H$_5$)$_2$, —CH$_2$—N(n-C$_3$H$_7$)$_2$, —CH$_2$—N(i-C$_3$H$_7$)$_2$, —CH$_2$—N(n-C$_4$H$_9$)$_2$, —CH$_2$—N(CH$_2$-i-C$_3$H$_7$)$_2$,

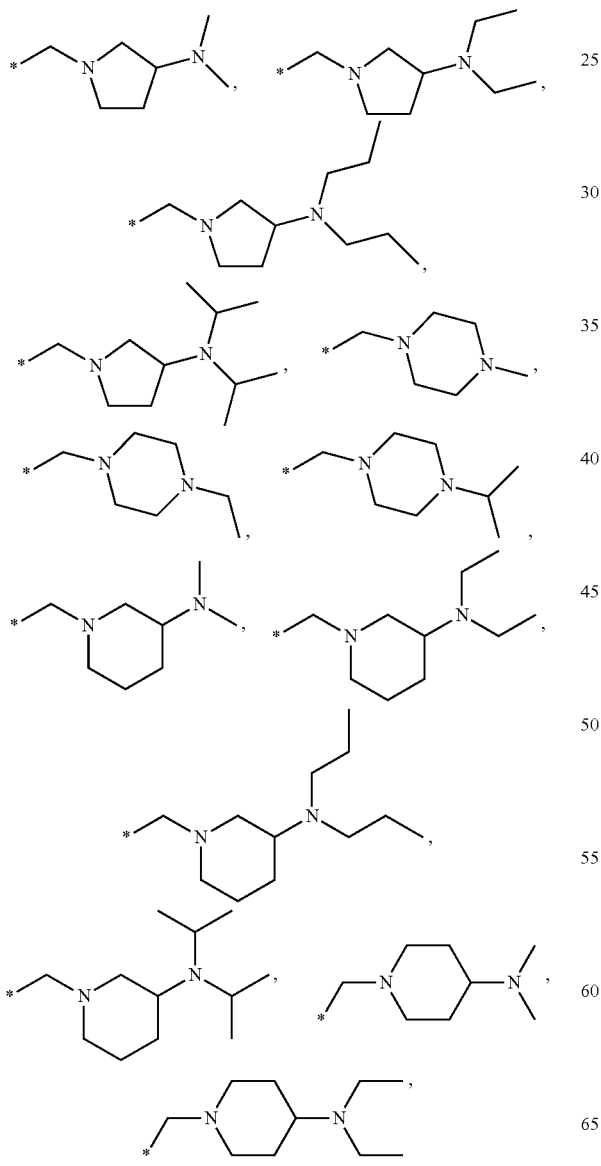

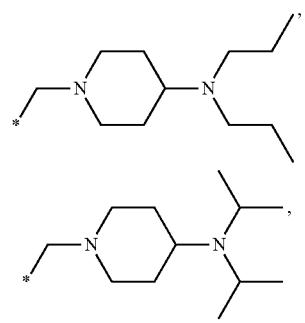

—S(O)—CH$_3$, —S(O)$_2$—CH$_3$, —S(O)—C$_2$H$_5$, —S(O)$_2$—C$_2$H$_5$, —CH$_2$—OH, —CH$_2$—S(O)—CH$_3$, —CH$_2$—S(O)$_2$—CH$_3$, —CH$_2$—S(O)—C$_2$H$_5$ or —CH$_2$—S(O)$_2$—C$_2$H$_5$, wherein R$^1$ is selected from

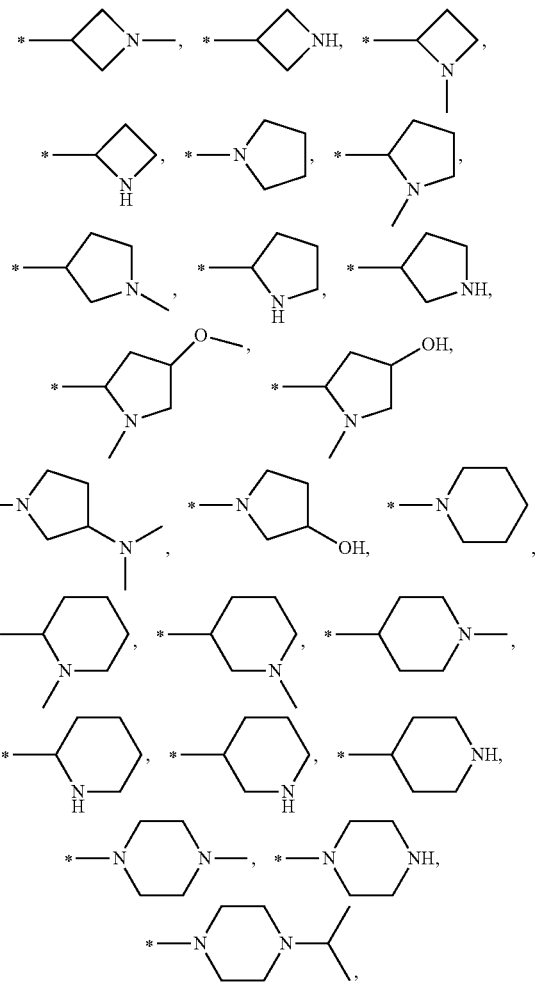

wherein R$^2$ denotes H,
wherein L is selected from —CH< or —N<,
wherein M denotes —N< or —CH<,
wherein T is selected from a bond or —CH$_2$—,
  while the —CH$_2$— group may be substituted by methyl,
wherein m may be 1 or 2
wherein n may be 1 or 2, optionally in the form of the individual optical isomers thereof, mixtures of these isomers, racemates, optionally in the form of the acid addition salts thereof with pharmacologically acceptable acids.

4. The compound of the formula (I) according to claim 3, wherein

Ar is a substituent according to general formula (II''')

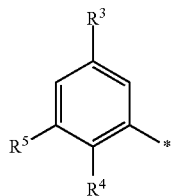
(II''')

wherein R³ denotes —C(CH₃)₃, —CH(CH₃)(C₂H₅), -i-C₃H₇, —CH₂-i-C₃H₇, —CF₃ or —CF₂CF₃,
wherein R⁴ denotes —O—CH₃ or —O—C₂H₅,
wherein R⁵ is selected from —NH—S(O)₂—CH₃, —NH—S(O)₂-n-C₃H₇, —NH—S(O)₂-c-C₃H₅, —NH—C(O)—CH₃, —NH—C(O)—C₂H₅, —NH—C(O)-n-C₃H₇, —NH—C(O)-i-C₃H₇, —NH—C(O)-c-C₃H₅, —C(O)—NH₂, —C(O)—NH—CH₃, —C(O)—NH—C₂H₅, —C(O)—NH-i-C₃H₇, —C(O)—NH-c-C₃H₅, —C(O)—N(CH₃)₂, —CH₂—N(CH₃)₂, —CH₂—N(C₂H₅)₂, —CH₂—N(i-C₃H₇)₂,

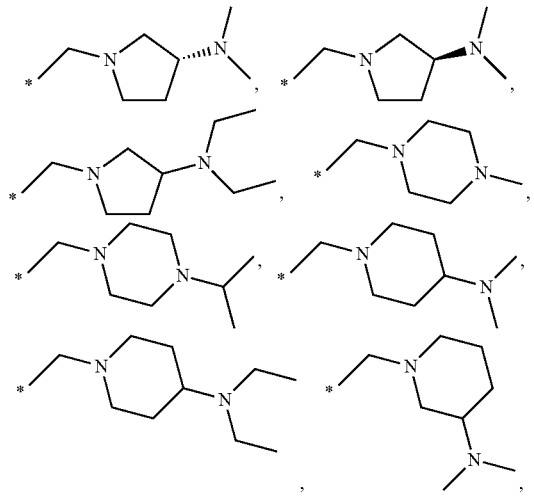

—S(O)—CH₃, —S(O)₂—CH₃, —CH₂—OH, —CH₂—S(O)—CH₃ or —CH₂—S(O)₂—CH₃,
wherein R¹ is selected from,

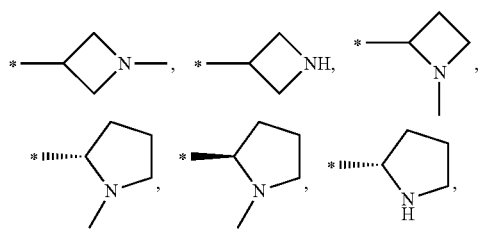

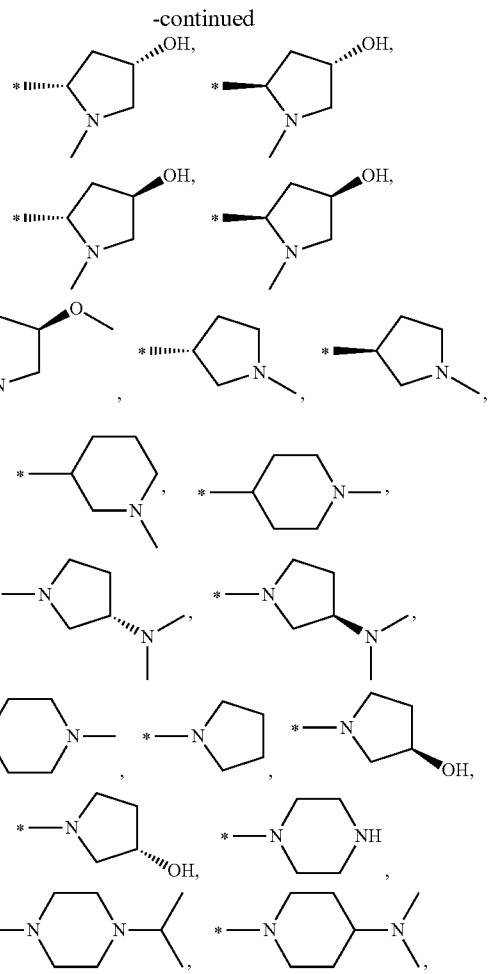

wherein R² denotes —H,
wherein L is selected from —CH< and —N<,
wherein M denotes —N<,
wherein T denotes a bond,
wherein m denotes 1,
wherein n denotes 1,
optionally in the form of the individual optical isomers thereof, mixtures of these isomers, racemates, optionally in the form of the acid addition salts thereof with pharmacologically acceptable acids.

5. The compound of the formula (I) according to claim 4, wherein

Ar is a substituent according to one of general formulae (IIa), (IIIa) or (IVa),

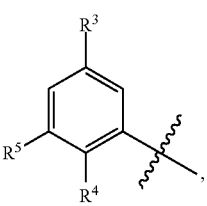
(IIa)

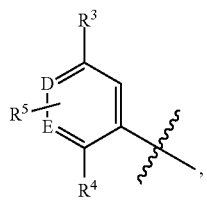

(IIIa)

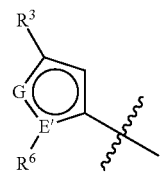

(IVa)

wherein $R^3$ denotes $C_{1-6}$-alkyl, $C_{3-6}$-cycloalkyl, $C_{1-4}$-alkoxy, $C_{1-2}$-perfluoroalkyl, 3-methyl-oxetan-3-yl, $C_{1-2}$-perfluoroalkoxy, morpholinyl,
  wherein the cycloalkyl group may optionally be substituted by $C_{1-3}$-alkyl,
wherein $R^4$ denotes H, $C_{1-4}$-alkyl, $C_{1-4}$-alkoxy,
wherein $R^5$ denotes H, $C_{1-5}$-alkyl-sulphonyl-amino, $C_{3-6}$-cycloalkyl-sulphonyl-amino, ($C_{1-5}$-alkyl-sulphonyl)-(methyl)-amino, ($C_{3-6}$-cycloalkyl-sulphonyl)-(methyl)-amino, $C_{1-5}$-alkyl-carbonyl-amino, $C_{3-6}$-cycloalkyl-carbonyl-amino, ($C_{1-5}$-alkyl-carbonyl)-(methyl)-amino, ($C_{3-6}$-cycloalkyl-carbonyl)-(methyl)-amino, aminocarbonyl, $C_{1-5}$-alkyl-amino-carbonyl, $C_{3-6}$-cycloalkyl-amino-carbonyl, di-($C_{1-3}$-alkyl)-amino-carbonyl, di-($C_{1-3}$-alkyl)-amino-$C_{1-2}$-alkyl, di-($C_{1-3}$-alkyl)-amino-pyrrolidin-1-yl-$C_{1-2}$-alkyl, 4-$C_{1-5}$-alkyl-piperazin-1-yl-$C_{1-2}$-alkyl, 4-di-($C_{1-3}$-alkyl)-amino-piperidin-1-yl-$C_{1-2}$-alkyl, 3-di-($C_{1-3}$-alkyl)-amino-piperidin-1-yl-$C_{1-2}$-alkyl, $C_{1-5}$-alkyl-sulphinyl, $C_{3-6}$-cycloalkyl-sulphinyl, $C_{1-5}$-alkyl-sulphonyl, $C_{3-6}$-cycloalkyl-sulphonyl, hydroxy-$C_{1-2}$-alkyl, $C_{1-5}$-alkyl-sulphinyl-methyl, $C_{1-5}$-alkyl-sulphonyl-methyl,
wherein $R^6$ denotes $C_{1-3}$-alkyl or phenyl,
  while the $C_{1-3}$-alkyl group may optionally be substituted by hydroxy or di-($C_{1-3}$-alkyl)-amino and
  the phenyl group may optionally be substituted by fluorine or $C_{1-3}$-alkyl,
wherein D or E represents nitrogen,
wherein G and E' independently of one another represent nitrogen or oxygen,
wherein $R^6$ is only bound to E' if E' denotes nitrogen,
optionally in the form of the individual optical isomers thereof, mixtures of these isomers, racemates, optionally in the form of the acid addition salts thereof with pharmacologically acceptable acids.

6. The compound of the formula (I) according to claim 5, wherein
Ar denotes a substituent of formula (IIa) or (IIIa),

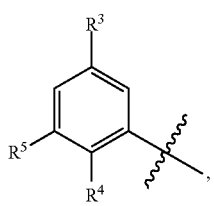

(IIa)

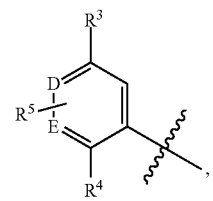

(IIIa)

wherein $R^3$ denotes methyl, ethyl, n-propyl, i-propyl, n-butyl, i-butyl, sec.-butyl, tert-butyl, n-pentyl, i-pentyl, neo-pentyl, 1-methyl-cyclopropyl, methoxy, trifluoromethyl, pentafluoroethyl, 3-methyl-oxetan-3-yl, trifluoromethoxy, morpholin-4-yl,
wherein $R^4$ denotes H, methyl, ethyl, n-propyl, methoxy, ethoxy, n-propyloxy, i-propyloxy,
wherein $R^5$ denotes H, methyl-sulphonyl-amino, ethyl-sulphonyl-amino, n-propyl-sulphonyl-amino, i-propyl-sulphonyl-amino, n-butyl-sulphonyl-amino, i-butyl-sulphonyl-amino, sec-butyl-sulphonyl-amino, tert.-butyl-sulphonyl-amino, n-pentyl-sulphonyl-amino, i-pentyl-sulphonyl-amino, neo-pentyl-sulphonyl-amino, cyclopropyl-sulphonyl-amino, cyclobutyl-sulphonyl-amino, cyclopentyl-sulphonyl-amino, acetyl-amino, ethyl-carbonyl-amino, n-propyl-carbonyl-amino, i-propyl-carbonyl-amino, cyclopropyl-carbonyl-amino, n-butyl-carbonyl-amino, i-butyl-carbonyl-amino, sec-butyl-carbonyl-amino, tert.-butyl-carbonyl-amino, cyclobutyl-carbonyl-amino, n-pentyl-carbonyl-amino, i-pentyl-carbonyl-amino, neo-pentyl-carbonyl-amino, cyclopentyl-carbonyl-amino, amino-carbonyl, methylamino-carbonyl, ethylamino-carbonyl, n-propylamino-carbonyl, i-propylamino-carbonyl, n-butylamino-carbonyl, i-butylamino-carbonyl, sec-butylamino-carbonyl, tert.-butylamino-carbonyl, n-pentylamino-carbonyl, i-pentylamino-carbonyl, neo-pentylamino-carbonyl, cyclopropylamino-carbonyl, cyclobutylamino-carbonyl, cyclopentylamino-carbonyl, dimethylamino-carbonyl, diethylamino-carbonyl, di-n-propylamino-carbonyl, di-i-propylamino-carbonyl, dimethylamino-methyl, diethylamino-methyl, di-n-propylamino-methyl, di-i-propylamino-methyl,
3-dimethylamino-pyrrolidin-1-yl-methyl, 3-diethylamino-pyrrolidin-1-yl-methyl, 3-di-n-propylamino-pyrrolidin-1-yl-methyl, 3-di-i-propylamino-pyrrolidin-1-yl-methyl, 4-methyl-piperazin-1-yl-methyl, 4-ethyl-piperazin-1-yl-methyl, 4-n-propyl-piperazin-1-yl-methyl, 4-i-propyl-piperazin-1-yl-methyl, 4-n-butyl-piperazin-1-yl-methyl, 4-sec-but-yl-piperazin-1-yl-methyl, 4-i-butyl-piperazin-1-yl-methyl, 4-tert-butyl-piperazin-1-yl-methyl, 4-dimethylamino-piperidin-1-yl-methyl, 4-diethylamino-piperidin-1-yl-methyl, 4-di-n-propylamino-piperidin-1-yl-methyl, 4-di-i-propylamino-piperidin-1-yl-methyl, 3-dimethylamino-piperidin-1-yl-methyl, 3-diethylamino-piperidin-1-yl-methyl, 3-di-n-propylamino-piperidin-1-yl-methyl, 3-di-i-propylamino-piperidin-1-yl-methyl, methyl-sulphinyl, ethyl-sulphinyl, n-propyl-sulphinyl, i-propyl-sulphinyl, cyclopropyl-sulphinyl, methyl-sulphonyl, ethyl-sulphonyl, n-propyl-sulphonyl, i-propyl-sulphonyl, cyclopropyl-sulphonyl, hydroxy-methyl, methyl-sulphinyl-methyl, methyl-sulphonyl-methyl,
wherein D or E represents nitrogen,
optionally in the form of the individual optical isomers thereof, mixtures of these isomers, racemates, optionally in the form of the acid addition salts thereof with pharmacologically acceptable acids.

7. The compound of the formula (I) according to claim 6, wherein
Ar denotes a substituent of formula (IIa),

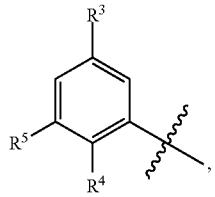

(IIa)

wherein R³ denotes i-propyl, i-butyl, sec.-butyl, tert.-butyl, 1-methyl-cyclopropyl, methoxy, trifluoromethyl, pentafluoroethyl, trifluoromethoxy,
wherein R⁴ denotes methoxy, ethoxy,
wherein R⁵ denotes methyl-sulphonyl-amino, ethyl-sulphonyl-amino, n-propyl-sulphonyl-amino, i-propyl-sulphonyl-amino, cyclopropyl-sulphonyl-amino, acetyl-amino, ethyl-carbonyl-amino, n-propyl-carbonyl-amino, i-propyl-carbonyl-amino, cyclopropyl-carbonyl-amino, amino-carbonyl, methylamino-carbonyl, ethylamino-carbonyl, i-propylamino-carbonyl, cyclopropylamino-carbonyl, dimethylamino-carbonyl, diethylamino-carbonyl, di-n-propylamino-carbonyl, di-i-propylamino-carbonyl, dimethylamino-methyl, diethylamino-methyl, di-n-propylamino-methyl, di-i-propylamino-methyl, 3-dimethylamino-pyrrolidin-1-yl-methyl, 3-diethylamino-pyrrolidin-1-yl-methyl, 3-di-n-propylamino-pyrrolidin-1-yl-methyl, 3-di-i-propylamino-pyrrolidin-1-yl-methyl, 4-methyl-piperazin-1-yl-methyl, 4-ethyl-piperazin-1-yl-methyl, 4-n-propyl-piperazin-1-yl-methyl, 4-i-propyl-piperazin-1-yl-methyl, 4-dimethylamino-piperidin-1-yl-methyl, 4-diethylamino-piperidin-1-yl-methyl, 4-di-n-propylamino-piperidin-1-yl-methyl, 4-di-i-propylamino-piperidin-1-yl-methyl,
3-dimethylamino-piperidin-1-yl-methyl, 3-diethylamino-piperidin-1-yl-methyl, 3-di-n-propylamino-piperidin-1-yl-methyl, 3-di-i-propylamino-piperidin-1-yl-methyl, methyl-sulphinyl, ethyl-sulphinyl, n-propyl-sulphinyl, i-propyl-sulphinyl, cyclopropyl-sulphinyl, methyl-sulphonyl, ethyl-sulphonyl, n-propyl-sulphonyl, i-propyl-sulphonyl, cyclopropyl-sulphonyl, hydroxy-methyl, methyl-sulphinyl-methyl, methyl-sulphonyl-methyl,
optionally in the form of the individual optical isomers thereof, mixtures of these isomers, racemates, optionally in the form of the acid addition salts thereof with pharmacologically acceptable acids.

8. The compound of the formula (I) according to claim 7, wherein
Ar denotes a substituent of formula (IIa),

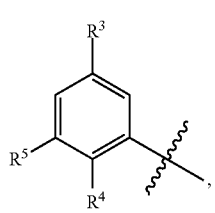

(IIa)

wherein R³ denotes tert.-butyl, sec-butyl, i-propyl, i-butyl, trifluoromethyl, pentafluoroethyl,
wherein R⁴ denotes methoxy, ethoxy,
wherein R⁵ denotes methyl-sulphonyl-amino, n-propyl-sulphonyl-amino, cyclopropyl-sulphonyl-amino, acetyl-amino, ethyl-carbonyl-amino, n-propyl-carbonyl-amino, i-propyl-carbonyl-amino, cyclopropyl-carbonyl-amino, amino-carbonyl, methylamino-carbonyl, ethylamino-carbonyl, i-propylamino-carbonyl, cyclopropylamino-carbonyl, dimethylamino-carbonyl, dimethylamino-methyl, diethylamino-methyl, di-i-propylamino-methyl, (R)-3-dimethylamino-pyrrolidin-1-yl-methyl, (S)-3-dimethylamino-pyrrolidin-1-yl-methyl, 3-diethylamino-pyrrolidin-1-yl-methyl, 4-methyl-piperazin-1-yl-methyl, 4-i-propyl-piperazin-1-yl-methyl, 4-dimethylamino-piperidin-1-yl-methyl, 4-diethylamino-piperidin-1-yl-methyl, 3-dimethylamino-piperidin-1-yl-methyl, methyl-sulphinyl, methyl-sulphonyl, hydroxy-methyl, methyl-sulphinyl-methyl, methyl-sulphonyl-methyl,
optionally in the form of the individual optical isomers thereof, mixtures of these isomers, racemates, optionally in the form of the acid addition salts thereof with pharmacologically acceptable acids.

9. The compound of the formula (I) according to claim 1, wherein
Ar is a substituent according to general formula (II')

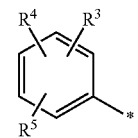

(II')

wherein R³ denotes —C₁-C₆-alkyl, —C₃-C₆-cycloalkyl, —CF₃, —CF₂CF₃ or

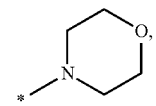

while the —C₃-C₆-cycloalkyl group may be substituted by —C₁-C₃-alkyl,
wherein R⁴ denotes —H, —C₁-C₄-alkyl or —O—C₁-C₄-alkyl,
wherein R⁵ is selected from
—NH—S(O)₂—C₁-C₄-alkyl;
—NH—S(O)₂—C₃-C₅-cycloalkyl;
—N(CH₃)—S(O)₂—C₁-C₄-alkyl;
—N(CH₃)—S(O)₂—C₃-C₅-cycloalkyl;
—NH—C(O)—C₁-C₄-alkyl;
—NH—C(O)—C₃-C₅-cycloalkyl;
—N(CH₃)—C(O)—C₁-C₄-alkyl;
—N(CH₃)—C(O)—C₃-C₅-cycloalkyl;
—C(O)—NH₂;
—C(O)—NH—C₁-C₄-alkyl;
—C(O)—N(di-C₁-C₄-alkyl);
—C(O)—NH—C₃-C₅-cycloalkyl;
—C(O)—N(C₁-C₄-alkyl)(C₃-C₅-cycloalkyl);
—S(O)—C₁-C₄-alkyl;
—S(O)—C₃-C₅-cycloalkyl;
—S(O)₂—C₁-C₄-alkyl;
—S(O)₂—C₃-C₅-cycloalkyl;
—C₁-C₄-alkyl-OH —CH₂—S(O)—C₁-C₄-alkyl;
—CH₂—S(O)—C₃-C₅-cycloalkyl;
—CH₂—S(O)₂—C₁-C₄-alkyl;
—CH₂—S(O)₂—C₃-C₅-cycloalkyl;
—C₁-C₄-alkylene-N(R⁸,R⁸');
wherein R⁸ and R⁸' are each selected independently of one another from —H and —C₁-C₅-alkyl,
wherein the two groups R⁸ and R⁸' together with the nitrogen to which they are bound may form a 4- to 6-membered ring system, which may be substituted by —OH or —N(R¹⁰,R¹⁰'),
wherein R¹⁰ and R¹⁰' are each selected independently of one another from —H and —C₁-C₅-alkyl,
optionally in the form of the individual optical isomers thereof, mixtures of these isomers, racemates, optionally in the form of the acid addition salts thereof with pharmacologically acceptable acids.

10. The compound of the formula (I) according to claim 1, wherein
Ar is a substituent according to general formula (II")

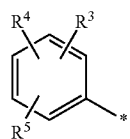

(II")

wherein R³ is selected from —CH₃, —C₂H₅, -n-C₃H₇, -i-C₃H₇, —C(CH₃)₃, -n-C₄H₉, —CH₂-i-C₃H₇, —CH(CH₃)(C₂H₅), -n-C₅H₁₁, —CH₂—CH₂-i-C₃H₇, —CH₂—C(CH₃)₃, —CF₃, —CF₂CF₃ or

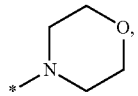

wherein R⁴ is selected from H, —O—CH₃ or —O—C₂H₅,
wherein R⁵ is selected from H, —NH—S(O)₂—CH₃, —NH—S(O)₂—C₂H₅, —NH—S(O)₂-n-C₃H₇, —NH—S(O)₂-i-C₃H₇, NH—S(O)₂-c-C₃H₅, —NH—S(O)₂-n-C₄H₉, —NH—S(O)₂—CH₂-i-C₃H₇, —NH—S(O)₂—C(CH₃)₃, —NH—S(O)₂-c-C₄H₇, —NH—S(O)₂-n-C₅H₁₁, —NH—S(O)₂—(CH₂)₂-i-C₃H₇, —NH—S(O)₂—CH₂—C(CH₃)₃, —NH—S(O)₂-c-C₅H₉,
—NH—C(O)—CH₃, —NH—C(O)—C₂H₅, —NH—C(O)-n-C₃H₇, —NH—C(O)-i-C₃H₇, —NH—C(O)-c-C₃H₅, —NH—C(O)-n-C₄H₉, —NH—C(O)—CH₂-i-C₃H₇, —NH—C(O)—C(CH₃)₃, —NH—C(O)-c-C₄H₇, —NH—C(O)-n-C₅H₁₁, —NH—C(O)—(CH₂)₂-i-C₃H₇, —NH—C(O)—CH₂—C(CH₃)₃, —NH—C(O)-c-C₅H₉,
—C(O)—NH₂, —C(O)—NH—CH₃, —C(O)—N(CH₃)₂, —C(O)—NH—C₂H₅, —C(O)—N(C₂H₅)₂, —C(O)—NH-n-C₃H₇, —C(O)—N(C₃H₇)₂, —C(O)—NH-i-C₃H₇, —C(O)—N(i-C₃H₇)₂, —C(O)—NH-c-C₃H₅, —C(O)—NH-n-C₄H₉, —C(O)—N(n-C₄H₉)₂, —C(O)—NH—CH₂-i-C₃H₇, —C(O)—N(CH₂-i-C₃H₇)₂, —C(O)—NH-c-C₄H₇,
—CH₂—N(CH₃)₂, —CH₂—N(C₂H₅)₂, —CH₂—N(n—C₃H₇)₂, —CH₂—N(i-C₃H₇)₂, —CH₂—N(n-C₄H₉)₂, —CH₂—N(CH₂-i-C₃H₇)₂,

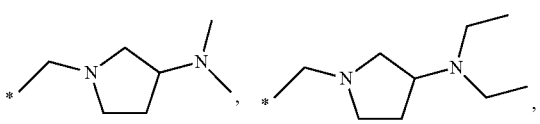

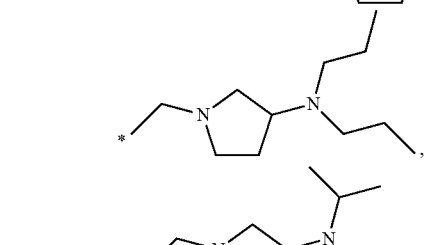

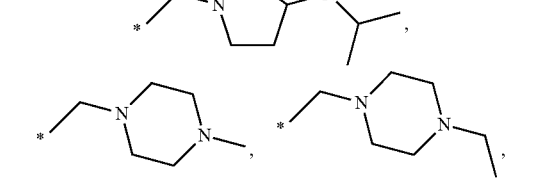

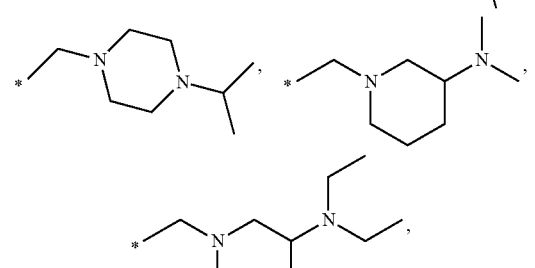

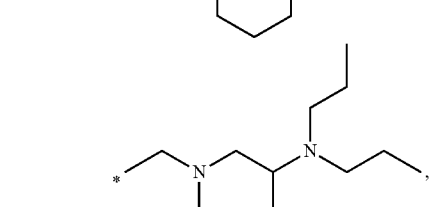

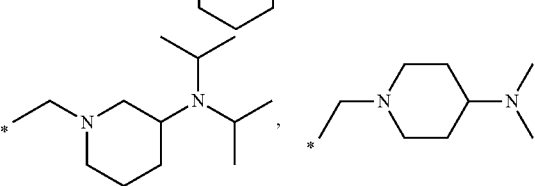

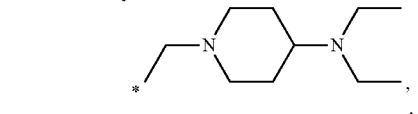

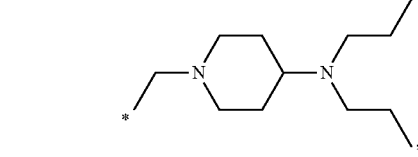

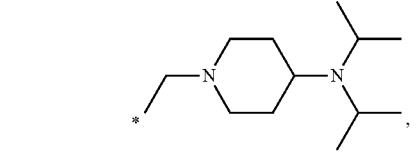

—S(O)—CH₃, —S(O)₂—CH₃, —S(O)—C₂H₅, —S(O)₂—C₂H₅, —CH₂—OH, —CH₂—S(O)—CH₃, —CH₂—S(O)₂—CH₃, —CH₂—S(O)—C₂H₅ or —CH₂—S(O)₂—C₂H₅, optionally in the form of the individual optical isomers thereof, mixtures of these isomers, racemates, optionally in the form of the acid addition salts thereof with pharmacologically acceptable acids.

11. The compound of the formula (I) according to claim 1, wherein

Ar is a substituent according to general formula (II''')

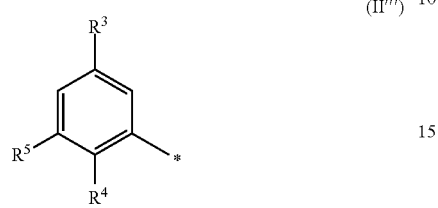

wherein R³ denotes —C(CH₃)₃, —CH(CH₃)(C₂H₅), -i-C₃H₇, —CH₂-i-C₃H₇, —CF₃ or —CF₂CF₃, wherein R⁴ denotes —O—CH₃ or —O—C₂H₅, wherein R⁵ is selected from —NH—S(O)₂—CH₃, —NH—S(O)₂-n-C₃H₇, —NH—S(O)₂-c-C₃H₅, —NH—C(O)—CH₃, —NH—C(O)—C₂H₅, —NH—C(O)-n-C₃H₇, —NH—C(O)-i-C₃H₇, —NH—C(O)-c-C₃H₅, —C(O)—NH₂, —C(O)—NH—CH₃, —C(O)—NH—C₂H₅, —C(O)—NH-i-C₃H₇, —C(O)—NH-c-C₃H₅, —C(O)—N(CH₃)₂, —CH₂—N(CH₃)₂, —CH₂—N(C₂H₅)₂, —CH₂—N(i-C₃H₇)₂,

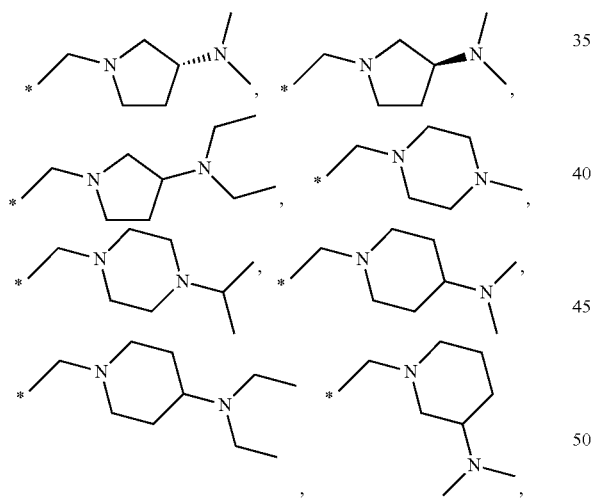

→S(O)—CH₃, —S(O)₂—CH₃, —CH₂—OH, —CH₂—S(O)—CH₃ or —CH₂—S(O)₂—CH₃, optionally in the form of the individual optical isomers thereof, mixtures of these isomers, racemates, optionally in the form of the acid addition salts thereof with pharmacologically acceptable acids.

12. The compound of the formula (I) according to claim 8, wherein

R¹ denotes a C₄₋₆-cycloalkyl system, which contains 1 to 2 nitrogen atoms that may optionally be 1- to 2-substituted by R⁷, wherein R⁷ may be C₁₋₃-alkyl, hydroxy, C₁₋₃-alkoxy, amino, C₁₋₃-alkyl-amino, di-(C₁₋₃-alkyl)-amino, optionally in the form of the individual optical isomers thereof, mixtures of these isomers, racemates, optionally in the form of the acid addition salts thereof with pharmacologically acceptable acids.

13. The compound of the formula (I) according to claim 12, wherein

R¹ denotes azetidin-2-yl, azetidin-3-yl, 1-methyl-azetidin-2-yl, 1-methyl-azetidin-3-yl, 1-ethyl-azetidin-2-yl, 1-ethyl-azetidin-3-yl, pyrrolidin-1-yl, pyrrolidin-2-yl, pyrrolidin-3-yl, 3-hydroxy-pyrrolidin-1-yl, 3-amino-pyrrolidin-1-yl, 3-methylamino-pyrrolidin-1-yl, 3-dimethylamino-pyrrolidin-1-yl, 3-ethylamino-pyrrolidin-1-yl, 3-diethylamino-pyrrolidin-1-yl, 1-methyl-pyrrolidin-2-yl, 1-methyl-pyrrolidin-3-yl, 1-ethyl-pyrrolidin-2-yl, 1-ethyl-pyrrolidin-3-yl, 1-methyl-4-hydroxy-pyrrolidin-2-yl, 1-methyl-4-methoxy-pyrrolidin-2-yl, piperidin-1-yl, piperidin-2-yl, piperidin-3-yl, piperidin-4-yl, 4-amino-piperidin-1-yl, 4-methylamino-piperidin-1-yl, 4-dimethylamino-piperidin-1-yl, 4-ethylamino-piperidin-1-yl, 4-diethylamino-piperidin-1-yl, 1-methyl-piperidin-2-yl, 1-methyl-piperidin-3-yl, 1-methyl-piperidin-4-yl, 1-ethyl-piperidin-2-yl, 1-ethyl-piperidin-3-yl, 1-ethyl-piperidin-4-yl, piperazin-1-yl, 4-methyl-piperazin-1-yl, 4-ethyl-piperazin-1-yl, 4-isopropyl-piperazin-1-yl, optionally in the form of the individual optical isomers thereof, mixtures of these isomers, racemates, optionally in the form of the acid addition salts thereof with pharmacologically acceptable acids.

14. The compound of the formula (I) according to claim 13, wherein

R¹ denotes 1-methyl-azetidin-3-yl, azetidin-3-yl, (2RS)-1-methyl-azetidin-2-yl, (2S)-1-methyl-pyrrolidin-2-yl, (2R)-1-methyl-pyrrolidin-2-yl, (2S)-pyrrolidin-2-yl, (2S,4S)-1-methyl-4-hydroxy-pyrrolidin-2-yl, (2R,4S)-1-methyl-4-hydroxy-pyrrolidin-2-yl, (2S,4R)-1-methyl-4-hydroxy-pyrrolidin-2-yl, (2R,4R)-1-methyl-4-hydroxy-pyrrolidin-2-yl, (2R,4R)-1-methyl-4-methoxy-pyrrolidin-2-yl, (3S)-1-methyl-pyrrolidin-3-yl, (3R)-1-methyl-pyrrolidin-3-yl, 1-methyl-piperidin-3-yl, 1-methyl-piperidin-4-yl, (3S)-3-dimethylamino-pyrrolidin-1-yl, (3R)-3-dimethylamino-pyrrolidin-1-yl, 4-methyl-piperazin-1-yl, pyrrolidin-1-yl, (3R)-3-hydroxy-pyrrolidin-1-yl, (3S)-3-hydroxy-pyrrolidin-1-yl, piperazin-1-yl, 4-isopropyl-piperazin-1-yl, 4-dimethylamino-piperidin-1-yl, optionally in the form of the individual optical isomers thereof, mixtures of these isomers, racemates, optionally in the form of the acid addition salts thereof with pharmacologically acceptable acids.

15. The compound of the formula (I) according to claim 8, wherein

R¹ is selected from —C₄-C₆-cycloalkyl, which contains 1 to 2 nitrogen atoms in the ring, wherein R¹ is optionally substituted by a group selected from —C₁-C₄-alkyl, —OH, —O—C₁-C₄-alkyl, and —N(R⁹,R⁹'), wherein R⁹, R⁹' have the meanings given above, optionally in the form of the individual optical isomers thereof, mixtures of these isomers, racemates, optionally in the form of the acid addition salts thereof with pharmacologically acceptable acids.

16. The compound of the formula (I) according to claim 8, wherein
R¹ is selected from

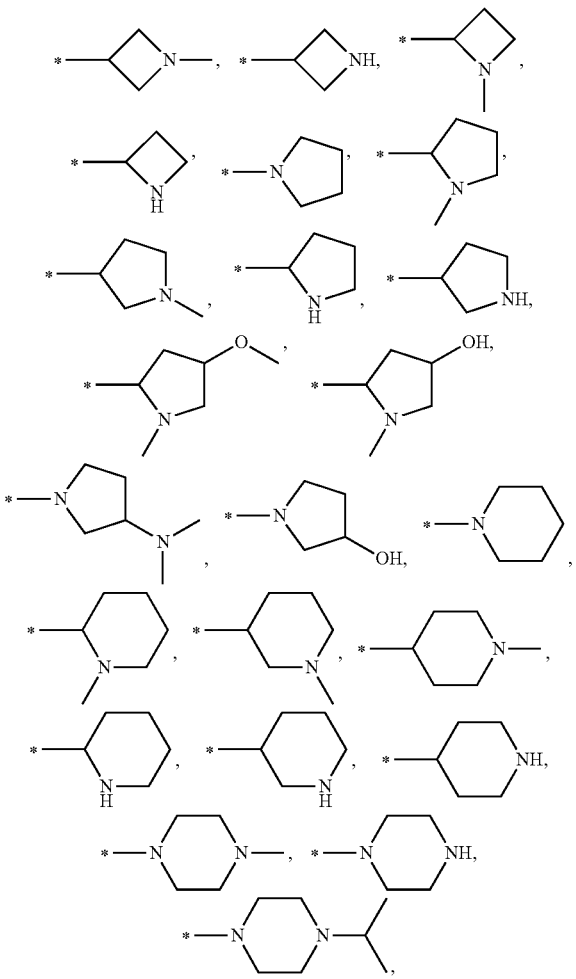

optionally in the form of the individual optical isomers thereof, mixtures of these isomers, racemates, optionally in the form of the acid addition salts thereof with pharmacologically acceptable acids.

17. The compound of the formula (I) according to claim 8, wherein
R¹ is selected from

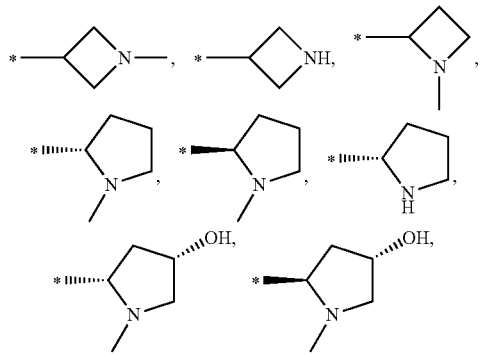

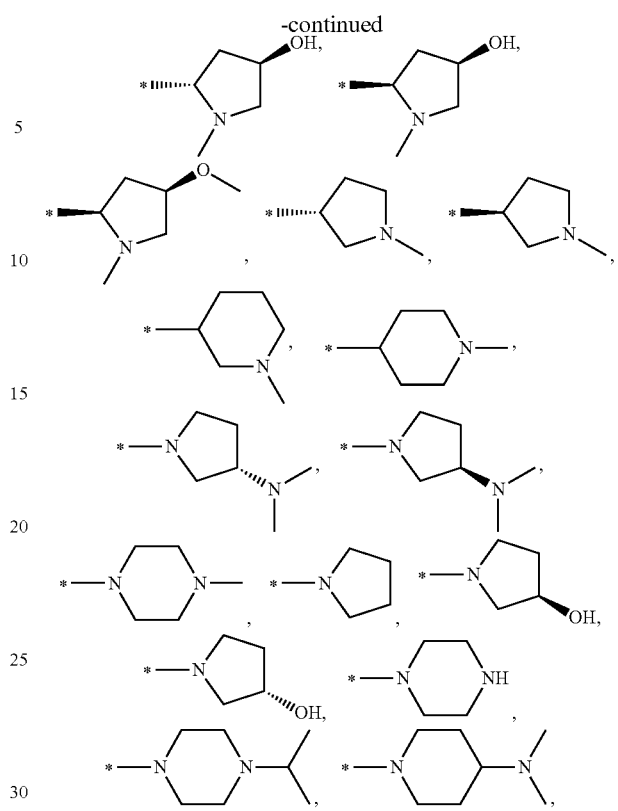

optionally in the form of the individual optical isomers thereof, mixtures of these isomers, racemates, optionally in the form of the acid addition salts thereof with pharmacologically acceptable acids.

18. The compound of the formula (I) according to claim 8, wherein
R² is selected from —H, —F, —Cl and —CH₃,
and wherein
p is selected from 0, 1, 2 or 3
optionally in the form of the individual optical isomers thereof, mixtures of these isomers, racemates, optionally in the form of the acid addition salts thereof with pharmacologically acceptable acids.

19. The compound of the formula (I) according to claim 8, wherein
R² is H,
optionally in the form of the individual optical isomers thereof, mixtures of these isomers, racemates, optionally in the form of the acid addition salts thereof with pharmacologically acceptable acids.

20. The compound of the formula (I) according to claim 8, wherein
L and M independently of one another are selected from —CH< and —N<,
optionally in the form of the individual optical isomers thereof, mixtures of these isomers, racemates, optionally in the form of the acid addition salts thereof with pharmacologically acceptable acids.

21. The compound of the formula (I) according to claim 8, wherein
M denotes —N<,
optionally in the form of the individual optical isomers thereof, mixtures of these isomers, racemates, optionally in the form of the acid addition salts thereof with pharmacologically acceptable acids.

22. The compound of the formula (I) according to claim 8, wherein

T is selected from a bond and —C$_1$-C$_3$-alkylene,
while the —C$_1$-C$_3$-alkylene group may be substituted by methyl, optionally in the form of the individual optical isomers thereof, mixtures of these isomers, racemates, optionally in the form of the acid addition salts thereof with pharmacologically acceptable acids.

23. The compound of the formula (I) according to claim 8, wherein

T is selected from a bond, and —CH$_2$—,
while the —CH$_2$— group may be substituted by methyl, optionally in the form of the individual optical isomers thereof, mixtures of these isomers, racemates, optionally in the form of the acid addition salts thereof with pharmacologically acceptable acids.

24. The compound of the formula (I) according to claim 8, wherein

T denotes a bond, optionally in the form of the individual optical isomers thereof, mixtures of these isomers, racemates, optionally in the form of the acid addition salts thereof with pharmacologically acceptable acids.

25. A compound chosen from

1-Methyl-7-[4-(1-methyl-piperidine-4-carbonyl)-piperazin-1-ylmethyl]-1H-indole-2-carboxylic acid (5-tert-butyl-3-methanesulphonylamino-2-methoxy-phenyl)-amide, (S)-1-methyl-7-[4-(1-methyl-pyrrolidine-2-carbonyl)-piperazin-1-ylmethyl]-1H-indole-2-carboxylic acid (5-tert-butyl-3-methanesulphonylamino-2-methoxy-phenyl)-amide, 1-methyl-7-[4-(1-methyl-azetidine-3-carbonyl)-piperazin-1-ylmethyl]-1H-indole-2-carboxylic acid (5-tert-butyl-3-methanesulphonylamino-2-methoxy-phenyl)-amide, (R)-1-methyl-7-[4-(1-methyl-pyrrolidine-2-carbonyl)-piperazin-1-ylmethyl]-1H-indole-2-carboxylic acid (5-tert-butyl-3-methanesulphonylamino-2-methoxy-phenyl)-amide, (S)-1-methyl-7-[4-(pyrrolidine-2-carbonyl)-piperazin-1-ylmethyl]-1H-indole-2-carboxylic acid (5-tert-butyl-3-methanesulphonylamino-2-methoxy-phenyl)-amide, 1-methyl-7-[4-(1-methyl-azetidine-2-carbonyl)-piperazin-1-ylmethyl]-1H-indole-2-carboxylic acid (5-tert-butyl-3-methanesulphonylamino-2-methoxy-phenyl)-amide, (R)-1-methyl-7-[1-(1-methyl-pyrrolidine-2-carbonyl)-piperidin-4-ylmethyl]-1H-indole-2-carboxylic acid (5-tert-butyl-3-methanesulphonylamino-2-methoxy-phenyl)-amide.

(S)-1-methyl-7-[1-(1-methyl-pyrrolidine-2-carbonyl)-piperidin-4-ylmethyl]-1H-indole-2-carboxylic acid (5-tert-butyl-3-methanesulphonylamino-2-methoxy-phenyl)-amide, 7-[4-((2S,4R)-4-hydroxy-1-methyl-pyrrolidine-2-carbonyl)-piperazin-1-ylmethyl]-1-methyl-1H-indole-2-carboxylic acid (5-tert-butyl-3-methanesulphonylamino-2-methoxyphenyl)-amide, 7-[4-((2R,4R)-4-methoxy-1-methyl-pyrrolidine-2-carbonyl)-piperazin-1-ylmethyl]-1-methyl-1H-indole-2-carboxylic acid (5-tert-butyl-3-methanesulphonylamino-2-methoxyphenyl)-amide, 7-[4-((2R,4R)-4-hydroxy-1-methyl-pyrrolidine-2-carbonyl)-piperazin-1-ylmethyl]-1-methyl-1H-indole-2-carboxylic acid (5-tert-butyl-3-methanesulphonylamino-2-methoxyphenyl)-amide, 7-[4-((2R,4S)-4-hydroxy-1-methyl-pyrrolidine-2-carbonyl)-piperazin-1-ylmethyl]-1-methyl-1H-indole-2-carboxylic acid (5-tert-butyl-3-methanesulphonylamino-2-methoxyphenyl)-amide, 7-[4-((2S,4S)-4-hydroxy-1-methyl-pyrrolidine-2-carbonyl)-piperazin-1-ylmethyl]-1-methyl-1H-indole-2-carboxylic acid (5-tert-butyl-3-methanesulphonylamino-2-methoxyphenyl)-amide, 1-methyl-7-[4-(2-pyrrolidin-1-yl-propionyl)-piperazin-1-ylmethyl]-1H-indole-2-carboxylic acid-(5-tert-butyl-3-methanesulphonylamino-2-methoxy-phenyl)-amide, 7-{4-[2-(4-isopropyl-piperazin-1-yl)-acetyl]-piperazin-1-ylmethyl}-1-methyl-1H-indole-2-carboxylic acid-(5-tert-butyl-3-methanesulphonylamino-2-methoxy-phenyl)-amide, (S)-7-{4-[2-(3-hydroxy-pyrrolidin-1-yl)-acetyl]-piperazin-1-ylmethyl}-1-methyl-1H-indole-2-carboxylic acid-(5-tert-butyl-3-methanesulphonylamino-2-methoxy-phenyl)-amide, 1-methyl-7-[4-(2-pyrrolidin-1-yl-acetyl)-piperazin-1-ylmethyl]-1H-indole-2-carboxylic acid-(5-tert-butyl-3-methanesulphonylamino-2-methoxy-phenyl)-amide, 1-methyl-7-{4-[2-(4-methyl-piperazin-1-yl)-acetyl]-piperazin-1-ylmethyl}-1H-indole-2-carboxylic acid-(5-tert-butyl-3-methanesulphonylamino-2-methoxy-phenyl)-amide, 1-methyl-7-[1-((2S)-1-methyl-pyrrolidine-2-carbonyl)-azepan-4-ylmethyl]-1H-indole-2-carboxylic acid-(5-tert-butyl-3-methanesulphonylamino-2-methoxy-phenyl)-amide, 1-methyl-7-[1-(1-methyl-piperidine-4-carbonyl)-azepan-4-ylmethyl]-1H-indole-2-carboxylic acid-(5-tert-butyl-3-methanesulphonylamino-2-methoxy-phenyl)-amide, 1-methyl-7-[1-((2R)-1-methyl-pyrrolidine-2-carbonyl)-azepan-4-ylmethyl]-1H-indole-2-carboxylic acid-(5-tert-butyl-3-methanesulphonylamino-2-methoxy-phenyl)-amide, 1-methyl-7-[4-((2R)-1-methyl-pyrrolidine-2-carbonyl)-[1,4]diazepan-1-ylmethyl]-1H-indole-2-carboxylic acid-(5-tert-butyl-3-methanesulphonylamino-2-methoxy-phenyl)-amide, 1-methyl-7-[4-(4-methyl-piperazine-1-carbonyl)-piperidin-1-ylmethyl]-1H-indole-2-carboxylic acid-(5-tert-butyl-3-methanesulphonylamino-2-methoxy-phenyl)-amide, (S)-7-[4-(3-dimethylamino-pyrrolidine-1-carbonyl)-piperidin-1-ylmethyl]-1-methyl-1H-indole-2-carboxylic acid-(5-tert-butyl-3-methanesulphonylamino-2-methoxy-phenyl)-amide, (R)-7-[4-(3-dimethylamino-pyrrolidine-1-carbonyl)-piperidin-1-ylmethyl]-1-methyl-1H-indole-2-carboxylic acid-(5-tert-butyl-3-methanesulphonylamino-2-methoxy-phenyl)-amide, (S)-1-methyl-7-[4-(1-methyl-pyrrolidine-2-carbonyl)-piperazin-1-ylmethyl]-1H-indole-2-carboxylic acid-(3-morpholin-4-yl-phenyl)-amide, (R)-7-[4-(3-dimethylamino-pyrrolidine-1-carbonyl)-piperazin-1-ylmethyl]-1-methyl-1H-indole-2-carboxylic acid (5-tert-butyl-3-methanesulphonylamino-2-methoxy-phenyl)-amide, (S)-7-[4-(3-dimethylamino-pyrrolidine-1-carbonyl)-piperazin-1-ylmethyl]-1-methyl-1H-indole-2-carboxylic acid (5-tert-butyl-3-methanesulphonylamino-2-methoxy-phenyl)-amide, 7-[4-(azetidine-3-carbonyl)-piperazin-1-ylmethyl]-1-methyl-1H-indole-2-carboxylic acid (5-tert-butyl-3-methanesulphonylamino-2-methoxy-phenyl)-amide, 1-methyl-7-[4-(1-methyl-piperidine-3-carbonyl)-piperazin-1-ylmethyl]-1H-indole-2-carboxylic acid (5-tert-butyl-3-methanesulphonylamino-2-methoxy-phenyl)-amide, (S)-1-methyl-7-[4-(1-methyl-pyrrolidine-3-carbonyl)-piperazin-1-ylmethyl]-1H-indole-2-carboxylic acid (5-tert-butyl-3-methanesulphonylamino-2-methoxy-phenyl)-amide, (S)-1-methyl-7-[4-(1-methyl-pyrrolidine-3-carbonyl)-[1,4]diazepan-1-ylmethyl]-1H-indole-2-carboxylic acid-(5-tert-butyl-3-methanesulphonylamino-2-methoxy-phenyl)-amide, (R)-1-methyl-7-[4-(1-methyl-pyrrolidine-3-carbonyl)-[1,4]diazepan-1-ylmethyl]-1H-indole-2-carboxylic acid-(5-tert-butyl-3-methanesulphonylamino-2-methoxy-phenyl)-amide, 7-{4-[2-(4-dimethylamino-piperidin-1-yl)-acetyl]-piperazin-1-ylmethyl}-1-methyl-1H-indole-2-carboxylic acid-(5-tert-butyl-3-methanesulphonylamino-2-methoxy-phenyl)-amide, (R)-7-{4-[2-(3-hydroxy-pyrrolidin-1-yl)-acetyl]-piperazin-1-ylmethyl}-1-methyl-1H-indole-2-carboxylic acid-(5-tert-butyl-3-methanesulphonylamino-2-methoxy-phenyl)-amide, (R)-7-{4-[2-(3-dimethylamino-pyrrolidin-1-yl)-acetyl]-piperazin-1-ylmethyl}-1-methyl-1H-indole-2-carboxylic acid-(5-tert-butyl-3-methanesulphonylamino-2-methoxy-phenyl)-amide, (S)-7-{4-[2-(3-dimethylamino-pyrrolidin-1-yl)-acetyl]-piperazin-1-ylmethyl}-1-methyl-1H-indole-2-carboxylic acid-(5-tert-butyl-3-methanesulphonylamino-2-methoxy-phenyl)-amide, 1-methyl-7-[4-(2-piperazin-1-yl-acetyl)-piperazin-1-ylmethyl]-1H-indole-2-carboxylic acid-(5-tert-butyl-3-methanesulphonylamino-2-methoxy-phenyl)-amide 1-methyl-7-[4-((2S)-1-methyl-pyrrolidine-2-carbonyl)-[1,4]diazepan-1-ylmethyl]-1H-indole-2-carboxylic acid-(5-tert-butyl-3-methanesulphonylamino-2-methoxy-phenyl)-amide, 1-methyl-7-[4-(1-methyl-piperidine-4-carbonyl)-[1,4]diazepan-1-ylmethyl]-1H-indole-2-carboxylic acid-(5-tert-butyl-3-methanesulphonylamino-2-methoxy-phenyl)-amide, (S)-1-methyl-7-[4-(1-methyl-pyrrolidine-2-carbonyl)-piperazin-1-ylmethyl]-1H-indole-2-carboxylic acid-(5-isobutyl-3-methanesulphonylamino-2-methoxy-phenyl)-amide, (S)-1-methyl-7-[4-(1-methyl-pyrrolidine-2-carbonyl)-piperazin-1-ylmethyl]-1H-indole-2-carboxylic acid-[5-tert-butyl-2-methoxy-3-(4-methyl-piperazin-1-ylmethyl)-phenyl]-amide, (S)-1-methyl-7-[4-(1-methyl-pyrrolidine-2-carbonyl)-piperazin-1-ylmethyl]-1H-indole-2-carboxylic acid-[5-tert-butyl-3-[(diisopropylamino)-methyl]-2-methoxy-phenyl]-amide (S)-1-methyl-7-[4-(1-methyl-pyrrolidine-2-carbonyl)-piperazin-1-ylmethyl]-1H-indole-2-carboxylic acid-(5-tert-butyl-3-diethylaminomethyl-2-methoxy-phenyl)-amide, 1-methyl-7-[4-((2S)-1-methyl-pyrrolidine-2-carbonyl)-piperazin-1-ylmethyl]-1H-indole-2-carboxylic acid-[5-tert-butyl-3-(3-dimethylamino-piperidin-1-ylmethyl)-2-methoxy-phenyl]-amide, 1-methyl-7-[4-((2S)-1-methyl-pyrrolidine-2-carbonyl)-piperazin-1-ylmethyl]-1H-indole-2-carboxylic acid-[5-tert-butyl-3-(3-diethylamino-pyrrolidin-1-ylmethyl)-2-methoxy-phenyl]-amide, (S)-1-methyl-7-[4-(1-methyl-pyrrolidine-2-carbonyl)-piperazin-1-ylmethyl]-1H-indole-2-carboxylic acid-[5-tert-butyl-3-(4-dimethylamino-piperidin-1-ylmethyl)-2-methoxy-phenyl]-amide, (S)-1-methyl-7-[4-(1-methyl-pyrrolidine-2-carbonyl)-piperazin-1-ylmethyl]-1H-indole-2-carboxylic acid-[5-tert-butyl-3-(4-diethylamino-piperidin-1-ylmethyl)-2-methoxy-phenyl]-amide, (S)-1-methyl-7-[4-(1-methyl-pyrrolidine-2-carbonyl)-piperazin-1-ylmethyl]-1H-indole-2-carboxylic acid-[5-tert-butyl-3-(4-isopropyl-piperazin-1-ylmethyl)-2-methoxy-phenyl]-amide, (S)-1-methyl-7-[4-(1-methyl-pyrrolidine-2-carbonyl)-piperazin-1-ylmethyl]-1H-indole-2-carboxylic acid-(5-tert-butyl-3-cyclopropylcarbamoyl-2-methoxy-phenyl)-amide, (S)-1-methyl-7-[4-(1-methyl-pyrrolidine-2-carbonyl)-piperazin-1-ylmethyl]-1H-indole-2-carboxylic acid-(5-tert-butyl-3-isopropylcarbamoyl-2-methoxy-phenyl)-amide, (S)-1-methyl-7-[4-(1-methyl-pyrrolidine-2-carbonyl)-piperazin-1-ylmethyl]-1H-indole-2-carboxylic acid-(5-tert-butyl-3-ethylcarbamoyl-2-methoxy-phenyl)-amide (S)-1-methyl-7-[4-(1-methyl-pyrrolidine-2-carbonyl)-piperazin-1-ylmethyl]-1H-indole-2-carboxylic acid-(5-tert-butyl-2-methoxy-3-methylcarbamoyl-phenyl)-amide, (S)-1-methyl-7-[4-(1-methyl-pyrrolidine-2-carbonyl)-piperazin-1-ylmethyl]-1H-indole-2-carboxylic acid-(5-tert-butyl-3-carbamoyl-2-methoxy-phenyl)-amide, (S)-1-methyl-7-[4-(1-methyl-pyrrolidine-2-carbonyl)-piperazin-1-ylmethyl]-1H-indole-2-carboxylic acid-(5-tert-butyl-3-dimethylcarbamoyl-2-methoxy-phenyl)-amide, 1-methyl-7-[4-((2S)-1-methyl-pyrrolidine-2-carbonyl)-piperazin-1-ylmethyl]-1H-indole-2-carboxylic acid-(5-sec-butyl-3-methanesulphonylamino-2-methoxy-phenyl)-amide, (S)-1-methyl-7-[4-(1-methyl-pyrrolidine-2-carbonyl)-piperazin-1-ylmethyl]-1H-indole-2-carboxylic acid-(5-isopropyl-3-methanesulphonylamino-2-methoxy-phenyl)-amide, 1-methyl-7-[4-((2S)-1-methyl-pyrrolidine-2-carbonyl)-piperazin-1-ylmethyl]-1H-indole-2-carboxylic acid-(5-tert-butyl-3-methanesulphinyl-2-methoxy-phenyl)-amide, (S)-1-methyl-7-[4-(1-methyl-pyrrolidine-2-carbonyl)-piperazin-1-ylmethyl]-1H-indole-2-carboxylic acid-(5-tert-butyl-3-methanesulphonyl-2-methoxy-phenyl)-amide, (S)-1-methyl-7-[4-(1-methyl-pyrrolidine-2-carbonyl)-piperazin-1-ylmethyl]-1H-indole-2-carboxylic acid-(5-tert-butyl-3-methanesulphonylmethyl-2-methoxy-phenyl)-amide, 1-methyl-7-[4-((2S)-1-methyl-pyrrolidine-2-carbonyl)-piperazin-1-ylmethyl]-1H-indole-2-carboxylic acid-(5-tert-butyl-3-methanesulphinylmethyl-2-methoxy-phenyl)-amide, (S)-1-methyl-7-[4-(1-methyl-pyrrolidine-2-carbonyl)-piperazin-1-ylmethyl]-1H-indole-2-carboxylic acid-(5-tert-butyl-3-methanesulphonylamino-2-ethoxy-phenyl)-amide, (S)-1-methyl-7-[4-(1-methyl-pyrrolidine-2-carbonyl)-piperazin-1-ylmethyl]-1H-indole-2-carboxylic acid-(5-tert-butyl-2-methoxy-3-propionylamino-phenyl)-amide, (S)-1-methyl-7-[4-(1-methyl-pyrrolidine-2-carbonyl)-piperazin-1-ylmethyl]-1H-indole-2-carboxylic acid-(5-tert-butyl-3-butyrylamino-2-methoxy-phenyl)-amide, (S)-1-methyl-7-[4-(1-methyl-pyrrolidine-2-carbonyl)-piperazin-1-ylmethyl]-1H-indole-2-carboxylic acid-(3-acetylamino-5-tert-butyl-2-methoxy-phenyl)-amide, (S)-1-methyl-7-[4-(1-methyl-pyrrolidine-2-carbonyl)-piperazin-1-ylmethyl]-1H-indole-2-carboxylic acid-(5-tert-butyl-3-isobutyrylamino-2-methoxy-phenyl)-amide, (S)-1-methyl-7-[4-(1-methyl-pyrrolidine-2-carbonyl)-piperazin-1-ylmethyl]-1H-indole-2-carboxylic acid-[5-tert-butyl-3-(cyclopropanecarbonyl-amino)-2-methoxy-phenyl]-amide, (S)-1-methyl-7-[4-(1-methyl-pyrrolidine-2-carbonyl)-piperazin-1-ylmethyl]-1H-indole-2-carboxylic acid-[5-tert-butyl-2-methoxy-3-(propane-1-sulphonylamino)-phenyl]-amide, (S)-1-methyl-7-[4-(1-methyl-pyrrolidine-2-carbonyl)-piperazin-1-ylmethyl]-1H-indole-2-carboxylic acid-(5-tert-butyl-3-cyclopropanesulphonylamino-2-methoxy-phenyl)-amide, (S)-1-methyl-7-[4-(1-methyl-pyrrolidine-2-carbonyl)-piperazin-1-ylmethyl]-1H-indole-2-carboxylic acid-(3-methanesulphonylamino-2-methoxy-5-pentafluoroethyl-phenyl)-amide, (S)-1-methyl-7-[4-(1-methyl-pyrrolidine-2-carbonyl)-piperazin-1-ylmethyl]-1H-indole-2-carboxylic acid-(3-methanesulphonylamino-2-methoxy-5-trifluoromethyl-phenyl)-amide, and (S)-1-methyl-7-[4-(1-methyl-pyrrolidine-2-carbonyl)-piperazin-1-ylmethyl]-1H-indole-2-carboxylic acid-(5-tert-butyl-3-hydroxymethyl-2-methoxy-phenyl)-amide, the tautomers, the stereoisomers and the mixtures thereof.

26. A pharmaceutical composition comprising a therapeutically effective amount of a compound according to claim 1 or a physiologically acceptable salt thereof and one or more inert carriers, preservatives and/or diluents.

27. A method of treating COPD and asthma comprising administering to a patient a therapeutically effective amount of a compound according to claim 1 or a physiologically acceptable salt thereof.

* * * * *

UNITED STATES PATENT AND TRADEMARK OFFICE
CERTIFICATE OF CORRECTION

PATENT NO. : 8,686,022 B2  Page 1 of 1
APPLICATION NO. : 13/060504
DATED : April 1, 2014
INVENTOR(S) : Wagner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 354 days.

Signed and Sealed this
Twenty-ninth Day of September, 2015

Michelle K. Lee
*Director of the United States Patent and Trademark Office*